(12) United States Patent
Dasseux et al.

(10) Patent No.: US 6,713,507 B2
(45) Date of Patent: Mar. 30, 2004

(54) ETHER COMPOUNDS AND COMPOSITIONS FOR CHOLESTEROL MANAGEMENT AND RELATED USES

(75) Inventors: Jean-Louis Henri Dasseux, Brighton, MI (US); Carmen Daniela Oniciu, Ann Arbor, MI (US)

(73) Assignee: Esperion Therapeutics, Inc., Ann Arbor, MI (US)

( * ) Notice: Subject to any disclaimer, the term of this patent is extended or adjusted under 35 U.S.C. 154(b) by 36 days.

(21) Appl. No.: 09/976,867

(22) Filed: Oct. 11, 2001

(65) Prior Publication Data

US 2003/0018013 A1 Jan. 23, 2003

Related U.S. Application Data

(60) Provisional application No. 60/239,482, filed on Oct. 11, 2000.

(51) Int. Cl.$^7$ .................... A61K 31/351; C07D 309/04
(52) U.S. Cl. .................... 514/451; 549/427; 549/500; 549/502; 549/292; 549/294; 549/320; 548/243; 548/250; 548/311.1; 548/317.1; 546/114; 514/301; 514/380; 514/381; 514/386; 514/461; 514/473
(58) Field of Search ................. 514/451, 461, 514/301, 380, 381, 386, 460; 549/427, 500, 502, 292, 294, 320; 546/114; 548/243, 250, 311.1, 317.1

(56) References Cited

U.S. PATENT DOCUMENTS

| | | |
|---|---|---|
| 3,773,946 A | 11/1973 | Creger |
| 3,930,024 A | 12/1975 | Creger |
| 4,287,200 A | 9/1981 | Kawamatsu et al. |
| 4,584,321 A | 4/1986 | Manghisi et al. |
| 4,613,593 A | 9/1986 | Yamatsu et al. |
| 4,634,719 A | 1/1987 | Takaishi et al. |
| 4,689,344 A | 8/1987 | Bar-Tana |
| 4,711,896 A | 12/1987 | Bar-Tana et al. |
| 5,502,198 A | 3/1996 | Picard et al. |
| 5,504,073 A | 4/1996 | Homan |
| 5,578,639 A | 11/1996 | Homan |
| 5,633,287 A | 5/1997 | Lee et al. |
| 5,648,387 A | 7/1997 | Bisgaier et al. |
| 5,750,569 A | 5/1998 | Bisgaier et al. |
| 5,756,344 A | 5/1998 | Onda et al. |
| 5,756,544 A | 5/1998 | Bisgaier et al. |
| 5,783,600 A | 7/1998 | Bisgaier et al. |
| 5,968,963 A | 10/1999 | Homan |
| 5,981,595 A | 11/1999 | Picard et al. |
| 6,017,905 A | 1/2000 | Roark et al. |
| 6,093,719 A | 7/2000 | Bocan |
| 6,093,744 A | 7/2000 | Lee et al. |
| 6,124,309 A | 9/2000 | Bocan |
| 6,143,755 A | 11/2000 | Bocan |

FOREIGN PATENT DOCUMENTS

| | | |
|---|---|---|
| WO | WO 96/30328 | 10/1996 |
| WO | WO 98/30530 | 7/1998 |
| WO | WO 99/00116 | 1/1999 |

OTHER PUBLICATIONS

Acton et al., 1996, "Identification of scavenger receptor SR–BI as a high density lipoprotein receptor", Science 271:518–520.

Badimon et al., 1992, "Role of high density lipoproteins in the regression of atherosclerosis", Circulation 86(Suppl. III):86–94.

Barrans et al., 1996, "Pre–beta HDL: structure and metabolism", Biochem. Biophys Acta 1300:73–85.

Bisgaier et al., 1998, "A novel compound that elevates high density lipoprotein and activates the preoxisome proliferator activated receptor", J. Lipid Res. 39:17–30; erratum at 39:1317 (1998).

Brown and Goldstein, 1990, "Drugs used in the treatment of hyperlipoproteinemias", In; The Pharmacological Basis of Therapeutics, 8$^{th}$ Ed., Goodman & Gilman, eds., Pergamon Press, Ch. 36, pp. 874–896.

Bruce et al., 1998, "Plasma lipid transfer proteins, high–density lipoproteins, and reverse cholesterol transport", Annu. Rev. Nutr. 18:297–330.

Dansky and Fisher, 1999, "High–density lipoprotein and plaque regression: the good cholesterol gets even better", Circulation 100:1762–1763.

Decossin et al., 1997, "Subclasses of LpA–I in coronary artery disease: distribution and cholesterol efflux ability", Eur. J. Clin. Invest. 27:299–307.

Fielding and Fielding, 1995, "Molecular physiology of reverse cholesterol transport", J. Lipid Res. 36:211–228.

Gearing et al., 1993, "Interaction of the peroxisome–proliferator–activated receptor and retinoid X receptor", Proc. Natl. Acad. Sci. USA 90:1440–1444.

(List continued on next page.)

Primary Examiner—C. S. Aulakh
(74) Attorney, Agent, or Firm—Pennie & Edmonds LLP

(57) ABSTRACT

The present invention relates to novel ether compounds, compositions comprising ether compounds, and methods useful for treating and preventing cardiovascular diseases, dyslipidemias, dysproteinemias, and glucose metabolism disorders comprising administering a composition comprising an ether compound. The compounds, compositions, and methods of the invention are also useful for treating and preventing Alzheimer's Disease, Syndrome X, peroxisome proliferator activated receptor-related disorders, septicemia, thrombotic disorders, obesity, pancreatitis, hypertension, renal disease, cancer, inflammation, and impotence. In certain embodiments, the compounds, compositions, and methods of the invention are useful in combination therapy with other therapeutics, such as hypocholesterolemic and hypoglycemic agents.

19 Claims, 1 Drawing Sheet

OTHER PUBLICATIONS

Figure 1:
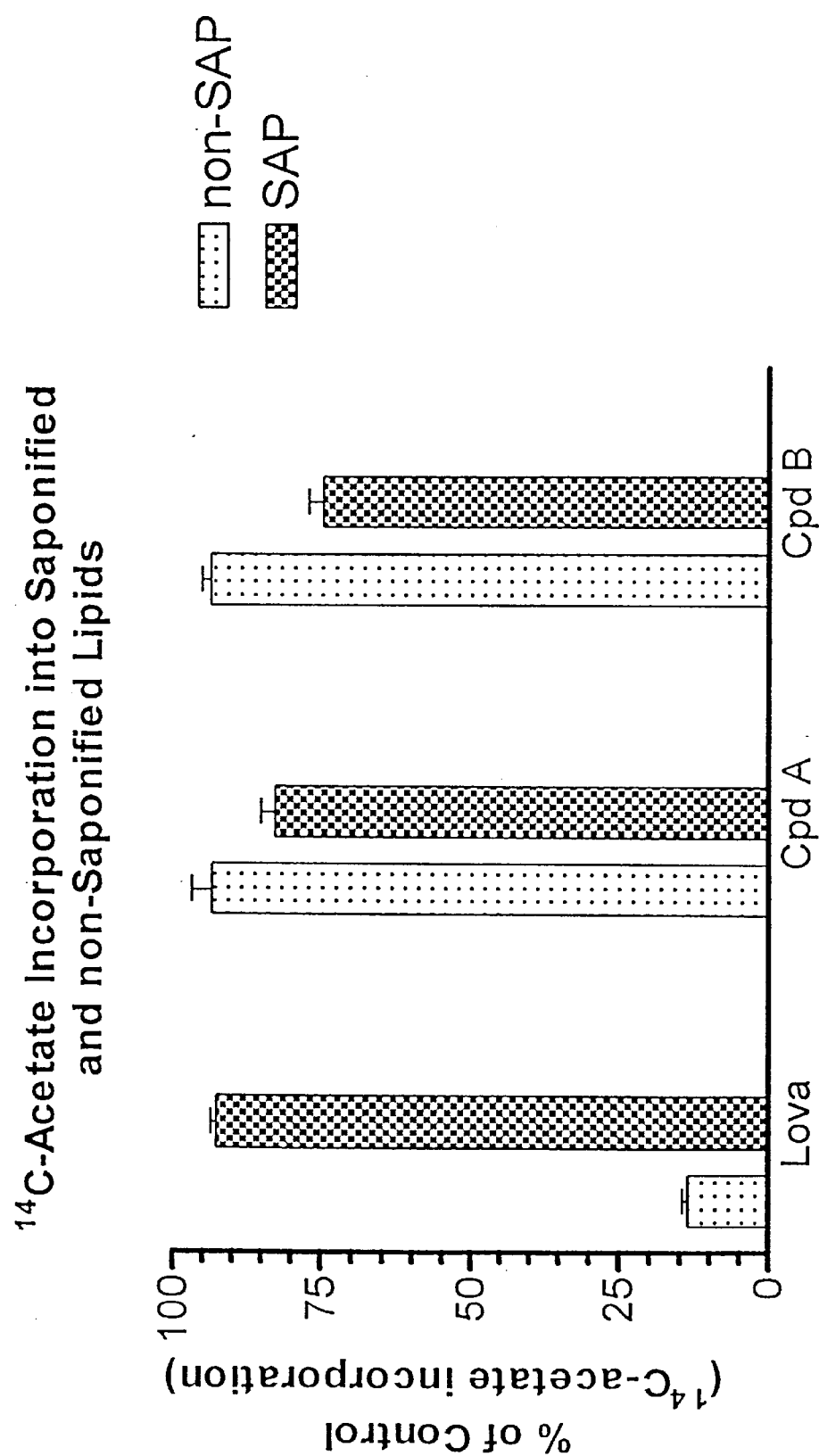

Harris and Kletzien, 1994, "Localization of a pioglitazone response element in the adipocyte fatty acid–binding protein gene", Mol. Pharmacol. 45:439–445.

Heyman et al., 1992, "9–cis retinoic acid is a high affinity ligand for the retinoid X receptor", Cell 68:397–406.

Hidaka and Fidge, 1992, "Affinity purification of the hepatic high–density lipoprotein receptor identifies two acidic glycoproteins and enables further characterization of their binding properties", Biochem, J. 284:161–167.

Hirano et al., 1997, "Genetic cholesteryl ester transfer protein deficiency is extremely frequent in the Omagari area of Japan. Marked hyperalphalipoproteinemia caused by CETP gene mutation is not associated with longevity", Arterioscler. Thromb. Vasc. Biol. 17:1053–1059.

Issemann and Green, 1990, "Activation of a member of the steroid hormone receptor superfamily by peroxisome proliferators"Nature 347:645–650.

Keller and Wahli, 1993, "Peroxisome proliferator–activated receptors—a link between endocrinology and nutrition", TEM 4:291–296.

Keller et al., 1993, "Fatty acids retinoids control lipid metabolism through activation of peroxisome proliferator–activated receptor–retinoid X receptor heterodimers", Proc. Natl. Acad. Sci. USA 90:2160–2164.

Kliewer et al., 1992, "Convergence of 9–cis retinoic acid and peroxisome proliferator signalling pathways through heterodimer formation of their receptors", Nature 358:771–774.

Kurata et al., 1998, "A candidate high density lipoprotein (HDL) receptor, $HB_2$, with possible multiple functions shows sequence homology with adhesion molecules", J. Atheroscler, and Thromb. 4:112–117.

Lagrost et al., 1996, "Opposite effects of cholesteryl ester transfer protein and phospholipid transfer protein on the size distribution of plasma high density lipoproteins. Physiological relevance in alcoholic patients", J. Biol. Chem. 271:19058–19065.

Landschulz et al., 1996, "Regulation of scavenger receptor, class B, type I, a high density lipoprotein receptor, in liver and steroidogenic tissues of the rat", J. Clin. Invest. 98:984–995.

Lazarow and Fujiki, 1985, "Biogenesis of peroxisomes", Annu. Rev. Biol. 1:489–530.

Levin et al., 1992, "9–cis retinoic acid stereoisomer binds and activates the nuclear receptor RXRα", Nature 355:359–361.

Nemali et al., 1988, "Comparison of constitutive and inducible levels of expression of peroxisomal β–oxidation and catalase genes in liver and extrahepatic tissues of rat", Cancer Res. 48:5316–5324.

Parra et al., 1992, "A case–control study of lipoprotein particles in two populations at contrasting risk for coronary heart disease. The ECTIM Study", Arterioscler. Thromb. 12:701–707.

Reaven, 1993, "Role of insulin resistance in human disease (syndrome X): an expanded definition", Annu. Rev. Med. 44:121–131.

Reddy and Lalwani, 1983, "Carcinogenesis by hepatic peroxisome proliferators: evaluation of the risk of hypolipidemic drugs and industrial plasticizers to humans", Crit. Rev. Toxicol. 12:1–58.

Rigotti et al., 1996, "Regulation by adrenocorticotropic hormone of the in vivo expression of scavenger receptor class B type I (SR–BI), a high density lipoprotein receptor, in steroidogenic cells of the murine adrenal gland", J. Biol. Chem. 271–33545–33549.

Robins and Fasulo, 1997, "High density lipoproteins, but not other lipoproteins, provide a vehicle for sterol transport to bile", J. Clin. Invest. 99:380–384.

Staels and Auwerx, 1998, "Regulation of apo–A–I gene expression by fibrates", Atherosclerosis 137(Suppl.):S19–S23.

Tontonoz et al., 1994, "Adipocyte–specific transcription factor ARF6 is a heterodimeric complex of two nuclear hormone receptors, PPARγ and RXRα", Nucl. Acids Res. 22:5628–5634.

Vamecq and Draye, 1989, "Pathophysiology of peroxisomal β–oxidation", Essays Biochem, 24: 115–225.

ETHER COMPOUNDS AND COMPOSITIONS FOR CHOLESTEROL MANAGEMENT AND RELATED USES

This application claims the benefit of U.S. Provisional Application No. 60/239,482, filed Oct. 11, 2000, hereby expressly incorporated by reference herein.

1. FIELD OF THE INVENTION

The present invention relates to ether compounds, compositions comprising the ether compounds, and methods for treating or preventing a disease or disorder, for example, cardiovascular disease, dyslipidemia; dyslipoproteinemia; a disorder of glucose metabolism; Alzheimer's Disease; Syndrome X; a peroxisome proliferator activated receptor-associated disorder; septicemia; a thrombotic disorder; obesity; pancreatitis; hypertension; renal disease; cancer; inflammation; and impotence. The compound of the invention can also treat or prevent inflammatory processes and diseases like gastrointestinal disease, irritable bowel syndrome (IBS), inflammatory bowel disease (Crohn's Disease, ulcerative colitis), arthritis (rheumatoid arthritis, osteoarthritis), autoimmune disease (systemic lupus erythematosus, etc.), scleroderna, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. The ether compounds and compositions of the invention may also be used to reduce the fat content of meat in livestock and reduce the cholesterol content of eggs.

2. BACKGROUND OF THE INVENTION

Obesity, hyperlipidemia, and diabetes have been shown to play a casual role in atherosclerotic cardiovascular diseases, which currently account for a considerable proportion of morbidity in Western society. Further, one human disease, termed "Syndrome X" or "Metabolic Syndrome", is manifested by defective glucose metabolism (insulin resistance), elevated blood pressure (hypertension), and a blood lipid imbalance (dyslipidemia). See e.g. Reaven, 1993, Annu. Rev. Med. 44:121–131.

The evidence linking elevated serum cholesterol to coronary heart disease is overwhelming. Circulating cholesterol is carried by plasma lipoproteins, which are particles of complex lipid and protein composition that transport lipids in the blood. Low density lipoprotein (LDL) and high density lipoprotein (HDL) are the major cholesterol-carrier proteins. LDL is believed to be responsible for the delivery of cholesterol from the liver, where it is synthesized or obtained from dietary sources, to extrahepatic tissues in the body. The term "reverse cholesterol transport" describes the transport of cholesterol from extrahepatic tissues to the liver, where it is catabolized and eliminated. It is believed that plasma HDL particles play a major role in the reverse transport process, acting as scavengers of tissue cholesterol. HDL is also responsible for the removal of non-cholesterol lipid, oxidized cholesterol and other oxidized products from the bloodstream.

Atherosclerosis, for example, is a slowly progressive disease characterized by the accumulation of cholesterol within the arterial wall. Compelling evidence supports the belief that lipids deposited in atherosclerotic lesions are derived primarily from plasma apolipoprotein B (apo B)-containing lipoproteins, which include chylomicrons, VLDL, IDL and LDL. The apo B-containing lipoprotein, and in particular LDL, has popularly become known as the "bad" cholesterol. In contrast, HDL serum levels correlate inversely with coronary heart disease. Indeed, high serum levels of HDL is regarded as a negative risk factor. It is hypothesized that high levels of plasma HDL are not only protective against coronary artery disease, but may actually induce regression of atherosclerotic plaque (e.g., see Badimon et al., 1992, Circulation 86:(Suppl. 111)86–94; Dansky and Fisher, 1999, Circulation 100: 1762–3.). Thus, HDL has popularly become known as the "good" cholesterol.

2.1. Cholesterol Transport

The fat-transport system can be divided into two pathways: an exogenous one for cholesterol and triglycerides absorbed from the intestine and an endogenous one for cholesterol and triglycerides entering the bloodstream from the liver and other non-hepatic tissue.

In the exogenous pathway, dietary fats are packaged into lipoprotein particles called chylomicrons, which enter the bloodstream and deliver their triglycerides to adipose tissue for storage and to muscle for oxidation to supply energy. The remnant of the chylomicron, which contains cholesteryl esters, is removed from the circulation by a specific receptor found only on liver cells. This cholesterol then becomes available again for cellular metabolism or for recycling to extrahepatic tissues as plasma lipoproteins.

In the endogenous pathway, the liver secretes a large, very-low-density lipoprotein particle (VLDL) into the bloodstream. The core of VLDL consists mostly of triglycerides synthesized in the liver, with a smaller amount of cholesteryl esters either synthesized in the liver or recycled from chylomicrons. Two predominant proteins are displayed on the surface of VLDL, apolipoprotein B-100 (apo B-100) and apolipoprotein E (apo E), although other apolipoproteins are present, such as apolipoprotein CM (apo CIII) and apolipoprotein CII (apo CII). When a VLDL reaches the capillaries of adipose tissue or of muscle, its triglyceride is extracted. This results in the formation of a new kind of particle called intermediate-density lipoprotein (IDL) or VLDL remnant, decreased in size and enriched in cholesteryl esters relative to a VLDL, but retaining its two apoproteins.

In human beings, about half of the IDL particles are removed from the circulation quickly, generally within two to six hours of their formation. This is because IDL particles bind tightly to liver cells, which extract IDL cholesterol to make new VLDL and bile acids. The IDL not taken up by the liver is catabolized by the hepatic lipase, an enzyme bound to the proteoglycan on liver cells. Apo E dissociates from IDL as it is transformed to LDL. Apo B-100 is the sole protein of LDL.

Primarily, the liver takes up and degrades circulating cholesterol to bile acids, which are the end products of cholesterol metabolism. The uptake of cholesterol-containing particles is mediated by LDL receptors, which are present in high concentrations on hepatocytes. The LDL receptor binds both apo E and apo B-100 and is responsible for binding and removing both IDL and LDL from the circulation. In addition, remnant receptors are responsible for clearing chylomicrons and VLDL remnants (i.e., LDL). However, the affinity of apo E for the LDL receptor is greater than that of apo B-100. As a result, the LDL particles have a much longer circulating life span than LDL particles; LDL circulates for an average of two and a half days before binding to the LDL receptors in the liver and other tissues. High serum levels of LDL, the "bad" cholesterol, are positively associated with coronary heart disease. For example, in atherosclerosis, cholesterol derived from circulating LDL accumulates in the walls of arteries. This accumulation forms bulky plaques that inhibit the flow of blood until a clot eventually forms, obstructing an artery and causing a heart attack or stroke.

Ultimately, the amount of intracellular cholesterol liberated from the LDL controls cellular cholesterol metabolism. The accumulation of cellular cholesterol derived from VLDL and LDL controls three processes. First, it reduces the cell's ability to make its own cholesterol by turning off the synthesis of HMGCoA reductase, a key enzyme in the cholesterol biosynthetic pathway. Second, the incoming LDL-derived cholesterol promotes storage of cholesterol by the action of ACAT, the cellular enzyme that converts cholesterol into cholesteryl esters that are deposited in storage droplets. Third, the accumulation of cholesterol within the cell drives a feedback mechanism that inhibits cellular synthesis of new LDL receptors. Cells, therefore, adjust their complement of LDL receptors so that enough cholesterol is brought in to meet their metabolic needs, without overloading (for a review, see Brown & Goldstein, In, The Pharmacological Basis Of Therapeutics, 8th Ed., Goodman & Gilman, Pergamon Press, New York, 1990, Ch. 36, pp. 874–896).

High levels of apo B-containing lipoproteins can be trapped in the subendothelial space of an artery and undergo oxidation. The oxidized lipoprotein is recognized by scavenger receptors on macrophages. Binding of oxidized lipoprotein to the scavenger receptors can enrich the macrophages with cholesterol and cholesteryl esters independently of the LDL receptor. Macrophages can also produce cholesteryl esters by the action of ACAT. LDL can also be complexed to a high molecular weight glycoprotein called apolipoprotein(a), also known as apo(a), through a disulfide bridge. The LDL-apo(a) complex is known as Lipoprotein (a) or Lp(a). Elevated levels of Lp(a) are detrimental, having been associated with atherosclerosis, coronary heart disease, myocardial infarction, stroke, cerebral infarction, and restenosis following angioplasty.

2.2. Reverse Cholesterol Transport

Peripheral (non-hepatic) cells predominantly obtain their cholesterol from a combination of local synthesis and uptake of preformed sterol from VLDL and LDL. Cells expressing scavenger receptors, such as macrophages and smooth muscle cells, can also obtain cholesterol from oxidized apo B-containing lipoproteins. In contrast, reverse cholesterol transport (RCT) is the pathway by which peripheral cell cholesterol can be returned to the liver for recycling to extrahepatic tissues, hepatic storage, or excretion into the intestine in bile. The RCT pathway represents the only means of eliminating cholesterol from most extrahepatic tissues and is crucial to maintenance of the structure and function of most cells in the body.

The enzyme in blood involved in the RCT pathway, lecithin:cholesterol acyltransferase (LCAT), converts cell-derived cholesterol to cholesteryl esters, which are sequestered in HDL destined for removal. LCAT is produced mainly in the liver and circulates in plasma associated with the HDL fraction. Cholesterol ester transfer protein (CETP) and another lipid transfer protein, phospholipid transfer protein (PLTP), contribute to further remodeling the circulating HDL population (see for example Bruce et al., 1998, Annu. Rev. Nutr. 18:297–330). PLTP supplies lecithin to HDL, and CETP can move cholesteryl ester made by LCAT to other lipoproteins, particularly apoB-containing lipoproteins, such as VLDL. HDL triglyceride can be catabolized by the extracellular hepatic triglyceride lipase, and lipoprotein cholesterol is removed by the liver via several mechanisms.

Each HDL particle contains at least one molecule, and usually two to four molecules, of apolipoprotein (apo A-I). Apo A-I is synthesized by the liver and small intestine as preproapolipoprotein which is secreted as a proprotein that is rapidly cleaved to generate a mature polypeptide having 243 amino acid residues. Apo A-I consists mainly of a 22 amino acid repeating segment, spaced with helix-breaking proline residues. Apo A-I forms three types of stable structures with lipids: small, lipid-poor complexes referred to as pre-beta-1 HDL; flattened discoidal particles, referred to as pre-beta-2 HDL, which contain only polar lipids (e.g., phospholipid and cholesterol); and spherical particles containing both polar and nonpolar lipids, referred to as spherical or mature HDL ($HDL_3$ and $HDL_2$). Most HDL in the circulating population contains both apo A-I and apo A-II, a second major HDL protein. This apo A-I- and apo A-II-containing fraction is referred to herein as the AI/AII-HDL fraction of HDL. But the fraction of HDL containing only apo A-I, referred to herein as the AI-HDL fraction, appears to be more effective in RCT. Certain epidemiologic studies support the hypothesis that the AI-HDL fraction is anti-artherogenic (Parra et al., 1992, Arterioscler. Thromb. 12:701–707; Decossin et al., 1997, Eur. J Clin. Invest. 27:299–307).

Although the mechanism for cholesterol transfer from the cell surface is unknown, it is believed that the lipid-poor complex, pre-beta-1 HDL, is the preferred acceptor for cholesterol transferred from peripheral tissue involved in RCT. Cholesterol newly transferred to pre-beta-1 HDL from the cell surface rapidly appears in the discoidal pre-beta-2 HDL. PLTP may increase the rate of disc formation (Lagrost et al., 1996, J Biol. Chem. 271:19058–19065), but data indicating a role for PLTP in RCT is lacking. LCAT reacts preferentially with discoidal and spherical HDL, transferring the 2-acyl group of lecithin or phosphatidylethanolamine to the free hydroxyl residue of fatty alcohols, particularly cholesterol, to generate cholesteryl esters (retained in the HDL) and lysolecithin. The LCAT reaction requires an apolipoprotein such apo A-I or apo A-IV as an activator. ApoA-I is one of the natural cofactors for LCAT. The conversion of cholesterol to its HDL-sequestered ester prevents re-entry of cholesterol into the cell, resulting in the ultimate removal of cellular cholesterol. Cholesteryl esters in the mature HDL particles of the AI-HDL fraction are removed by the liver and processed into bile more effectively than those derived from the AI/AII-HDL fraction. This may be due, in part, to the more effective binding of AI-HDL to the hepatocyte membrane. Several HDL receptors have been identified, the most well characterized of which is the scavenger receptor class B, type I (SR-BI) (Acton et al., 1996, Science 271:518–520). The SR-BI is expressed most abundantly in steroidogenic tissues (e.g., the adrenals), and in the liver (Landshulz et al., 1996, J Clin. Invest. 98:984–995; Rigotti etal., 1996, J Biol. Chem. 271:33545–33549). Other proposed HDL receptors include HB1 and HB2 (Hidaka and Fidge, 1992, Biochem J. 15:161–7; Kurata et al., 1998, J Atherosclerosis and Thrombosis 4:112–7).

While there is a consensus that CETP is involved in the metabolism of VLDL- and LDL-derived lipids, its role in RCT remains controversial. However, changes in CETP activity or its acceptors, VLDL and LDL, play a role in "remodeling" the HDL population. For example, in the absence of CETP, the HDL becomes enlarged particles that are poorly removed from the circulation (for reviews on RCT and HDL, see Fielding & Fielding, 1995, *J. Lipid Res.* 36:211–228; Barrans et al., 1996, *Biochem. Biophys. Acta.* 1300:73–85; Hirano et al., 1997, *Arterioscler. Thromb. Vasc. Biol.* 17:1053–1059).

2.3. Reverse Transport of other Lipids

HDL is not only involved in the reverse transport of cholesterol, but also plays a role in the reverse transport of other lipids, i.e., the transport of lipids from cells, organs, and tissues to the liver for catabolism and excretion. Such lipids include sphingomyelin, oxidized lipids, and lysophophatidylcholine. For example, Robins and Fasulo (1997, *J Clin. Invest.* 99:380–384) have shown that HDL stimulates the transport of plant sterol by the liver into bile secretions.

2.4. Peroxisome Proliferator Activated Receptor Pathway

Peroxisome proliferators are a structurally diverse group of compounds that, when administered to rodents, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, 1985, *Ann. Rev. Cell Biol.* 1:489–530; Vamecq and Draye, 1989, *Essays Biochem.* 24:1115–225; and Nelali et al., 1988, *Cancer Res.* 48:5316–5324). Chemicals included in this group are the fibrate class of hypolipidermic drugs, herbicides, and phthalate plasticizers (Reddy and Lalwani, 1983, *Crit. Rev. Toxicol.* 12:1–58). Peroxisome proliferation can also be elicited by dietary or physiological factors, such as a high-fat diet and cold acclimatization.

Insight into the mechanism whereby peroxisome proliferators exert their pleiotropic effects was provided by the identification of a member of the nuclear hormone receptor superfamily activated by these chemicals (Isseman and Green, 1990, *Nature* 347:645–650). This receptor, termed peroxisome proliferator activated receptor α ($PPAR_\alpha$), was subsequently shown to be activated by a variety of medium and long-chain fatty acids. PPAR, activates transcription by binding to DNA sequence elements, termed peroxisome proliferator response elements (PPRE), in the form of a heterodimer with the retinoid X receptor (RXR). RXR is activated by 9-cis retinoic acid (see Kliewer et al., 1992, *Nature* 358:771–774; Gearing et al., 1993, *Proc. Natl. Acad. Sci. USA* 90:1440–1444, Keller et al, 1993, *Proc. Natl. Acad. Sci. USA* 90:2160–2164; Heyman et al., 1992, *Cell* 68:397–406, and Levin et al., 1992, *Nature* 355:359–361). Since the discovery of $PPAR_\alpha$, additional isoforms of PPAR have been identified, e.g., $PPAR_\beta$ (also known as $PPAR_\delta$) and $PPAR_\gamma$ and, which have similar functions and are similarly regulated.

PPREs have been identified in the enhancers of a number of gene-encoding proteins that regulate lipid metabolism. These proteins include the three enzymes required for peroxisomal β-oxidation of fatty acids; apolipoprotein A-I; medium-chain acyl-CoA dehydrogenase, a key enzyme in mitochondrial β-oxidation; and aP2, a lipid binding protein expressed exclusively in adipocytes (reviewed in Keller and Whali, 1993, *TEM,* 4:291–296; see also Staels and Auwerx, 1998, *Atherosclerosis* 137 Suppl:S19–23). The nature of the PPAR target genes coupled with the activation of PPARs by fatty acids and hypolipidemic drugs suggests a physiological role for the PPARs in lipid homeostasis.

It is clear that none of the commercially available cholesterol management drugs has a general utility in regulating lipid, lip oprotein, insulin and glucose levels in the blood. Thus, compounds that have one or more of these utilities are clearly needed. Further, there is a clear need to develop safer drugs that are efficacious at lowering serum cholesterol, increasing HDL serum levels, preventing coronary heart disease, and/or treating existing disease such as atherosclerosis, obesity, diabetes, and other diseases that are affected by lipid metabolism and/or lipid levels. There is also a clear need to develop drugs that may be used with other lipid-altering treatment regimens in a synergistic manner. There is still a further need to provide useful therapeutic agents whose solubility and Hydrophile/Lipophile Balance (HLB) can be readily varied.

Citation or identification of any reference in Section 2 of this application is not an admission that such reference is available as prior art to the present invention.

3. SUMMARY OF THE INVENTION

The present invention relates to ether compounds and pharmaceutically acceptable salts, hydrates, solvates, clathrates, stereoisomers, diastereomers, geometric isomers, or mixtures thereof; compositions comprising the ether compounds, and methods for treating or preventing disorders in mammals, particularly in humans.

As used herein, the phrase "compounds of the invention" means, collectively, the compounds of formulas I, Ia–Id, II, Ia, III, and IV and pharmaceutically acceptable salts, hydrates, solvates, clathrates, enantiomers, diastereomers, racemates, or mixtures of stereoisomers thereof.

The compounds of the invention are identified herein by their chemical structure and/or chemical name. Where a compound is referred to by both a chemical structure and a chemical name, and the chemical structure and chemical name conflict, the chemical structure is determinative of the compound's identity.

In one embodiment the invention provides compounds of formula I:

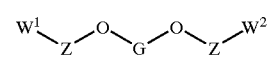

I or a pharmaceutically acceptable salt, hydrate, solvate, clathrate, stereoisomer, diastereomer, geometric isomer, or mixtures thereof, wherein:

(a) each occurrence of Z is independently $(CH_2)_m$, $(CH=CH)_t$, or phenyl, where each occurrence of m and t is an independent integer ranging from 1 to 9;

(b) G is $(CH_2)_x$, $CH_2CH=CHCH_2$, $CH=CH$, $CH_2$-phenyl-$CH_2$, or phenyl, where x is 2, 3, or 4;

(c) $W^1$ and $W^2$ are independently $C(R^1)(R^2)(CH_2)_n$—Y, V, $C(R^3)(R^4)$—$(CH_2)_c$—$C(R^5)(R^6)$—$(CH_2)_n$—Y, or $C(R^1)(R^2)$—$(CH_2)_c$—V where c is 1 or 2 and n is an integer ranging from 0 to 4;

(d) each occurrence of $R^1$ and $R^2$ is independently $(C_1–C_6)$ alkyl, $(C_2–C_6)$alkenyl, $(C_2–C_6)$alkynyl, phenyl, or benzyl;

(e) each occurrence of $R^3$ and $R^4$ is independently H, $(C_1–C_6)$alkyl, $(C_2–C_6)$alkenyl, $(C_2–C_6)$alkynyl, phenyl, or benzyl;

(f) $R^5$ is H, $(C_1–C_6)$alkyl, $(C_2–C_6)$alkenyl, $(C_2–C_6)$alkynyl, $(C_1–C_6)$alkoxy, phenyl, benzyl, Cl, Br, CN, $NO_2$, or $CF_3$;

(g) $R^6$ is OH, $(C_1–C_6)$alkyl, $(C_2–C_6)$alkenyl, $(C_2–C_6)$ alkynyl, $(C_1–C_6)$alkoxy, phenyl, benzyl, Cl, Br, CN, $NO_2$, or $CF_3$;

(h) V is

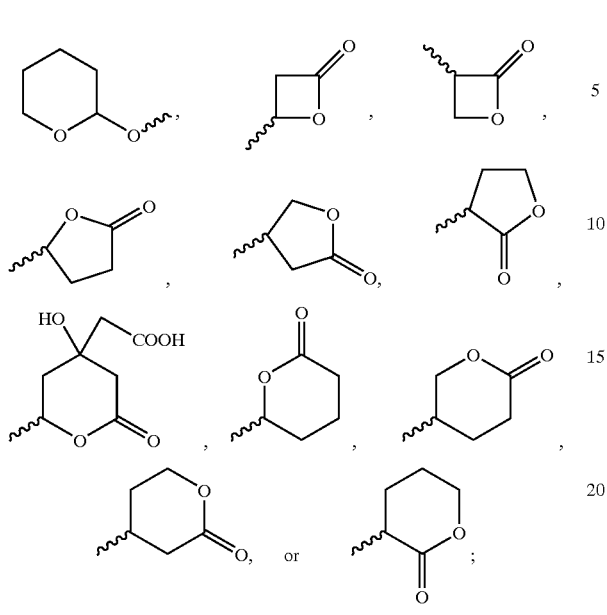

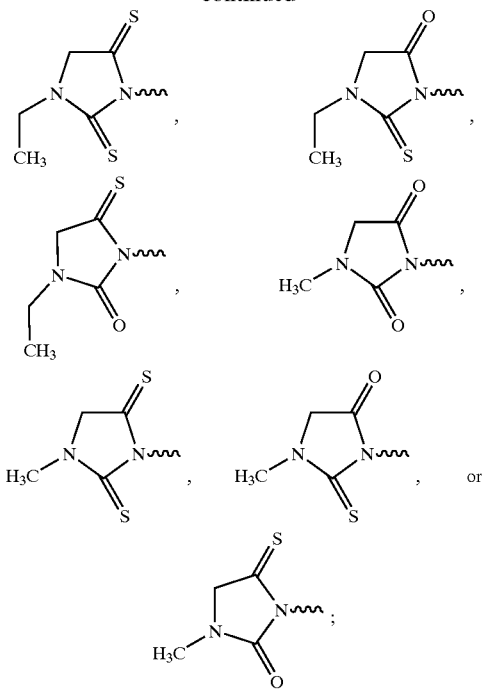

(i) each occurrence of Y is independently OH, COOH, CHO, COOR$^7$, SO$_3$H,

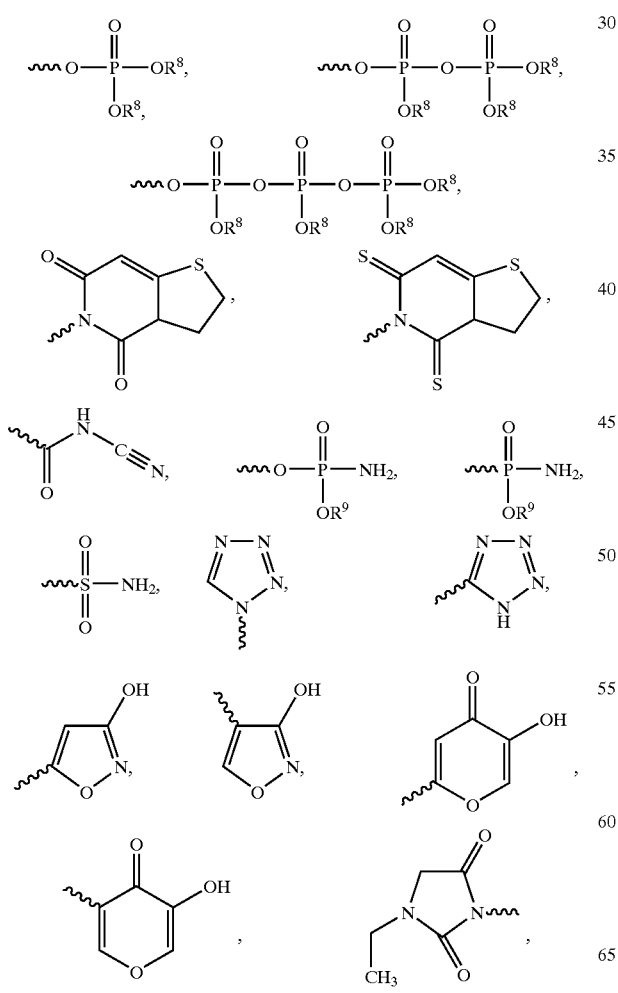

(j) R$^7$ is (C$_1$–C$_6$)alkyl, (C$_2$–C$_6$)alkenyl, (C$_2$–C$_6$)alkynyl, phenyl, or benzyl and is unsubstituted or substituted with one or more halo, OH, (C$_1$–C$_6$)alkoxy, or phenyl groups;

(k) each occurrence of R$^8$ is independently H, (C$_1$–C$_6$)alkyl, (C$_2$–C$_6$)alkenyl, or (C$_2$–C$_6$)alkynyl and is unsubstituted or substituted with one or two halo, OH, (C$_1$–C$_6$)alkoxy, or phenyl groups;

(l) each occurrence of R$^9$ is independently H, (C$_1$–C$_6$)alkyl, (C$_2$–C$_6$)alkenyl, or (C$_2$–C$_6$)alkynyl; and Preferably, in the compounds of formula I:
(i) when G is(CH$_2$)$_x$, then W$^1$ and W$^2$ cannot both be C(R$^1$)(R$^2$)—CHO or cannot both be

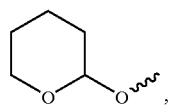

(ii) that when G is phenyl, then W$^1$ and W$^2$ cannot:
both be C(R$^1$)(R$^2$)—COOH,
both be C(R$^1$)(R$^2$)—CH$_2$OH,
both be C(R$^1$)(R$^2$)—COOR$^7$,
both be (CH$_2$)$_3$—C(H)(OH)—CH$_2$OH
both be (CH$_2$)$_2$—C(H)(OH)—CH$_2$OH,
both be C(R$^1$)(R$^2$)CHO, or
both be

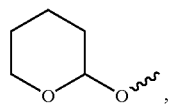

and
(iii) that when every occurrence of Z is phenyl, then W$^1$ and W$^2$ cannot both be C(R$^1$)(R$^2$)—OH.

Preferably, in the compounds of formula I, W$^1$ and W$^2$ are independently C(R$^1$)(R$^2$)(CH$_2$)$_n$—Y, V, C(R$^3$)(R$^4$)—(CH$_2$)$_c$—C(R$^5$)(R$^6$)—Y, or C(R$^1$)(R$^2$)—(CH$_2$)$_c$—V. More preferably, $W^1$ and $W^2$ are independent $C(R^1)(R^2)(CH_2)_n$—Y groups, where Y is independently OH, $COOR^7$, or COOH.

It is also preferably in the compound of formula I, that m is an integer ranging from 1 to 4 and t is 1.

In another embodiment, the invention provides compounds of a formula Ia:

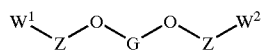

or a pharmaceutically acceptable salt, hydrate, solvate, clathrate, stereoisomer, diastereomer, geometric isomer, or mixtures thereof, wherein:

(a) each occurrence of Z is independently $(CH_2)_m$ or $(CH=CH)_t$, where each occurrence of m and t is an independent integer ranging from 1 to 9;
(b) G is $(CH_2)_x$, $CH_2CH=CHCH_2$, or CH=CH, where x is 2, 3, or 4;
(c) $W^1$ and $W^2$ are independently $C(R^1)(R^2)(CH_2)_n$—Y, V, or $C(R^1)(R^2)$—$(CH_2)_c$—V, where c is 1 or 2 and n is an integer ranging from 0 to 4;
(d) each occurrence of $R^1$ and $R^2$ is independently $(C_1-C_6)$ alkyl, $(C_2-C_6)$alkenyl, $(C_2-C_6)$alkynyl, phenyl, or benzyl;
(e) V is

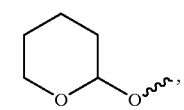 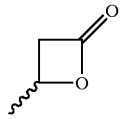 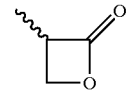

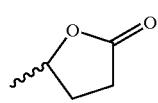 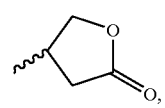 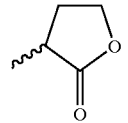

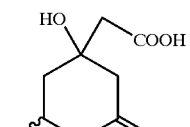 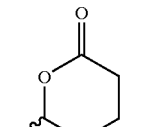 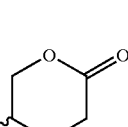

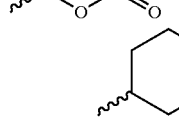 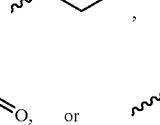 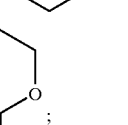

(f) each occurrence of Y is independently OH, COOH, CHO, $COOR^7$, $SO_3H$,

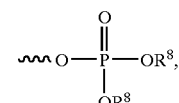 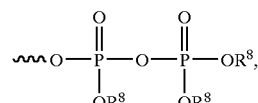

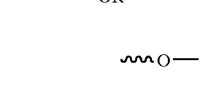 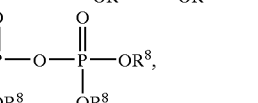

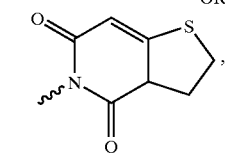 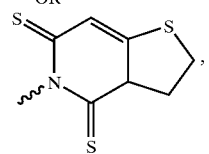

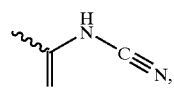 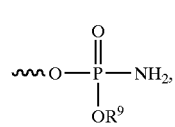 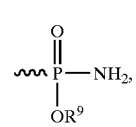

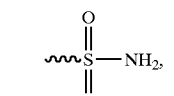  

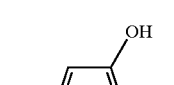 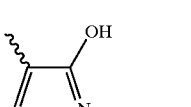 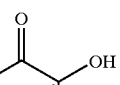

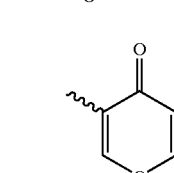 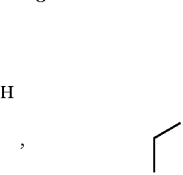 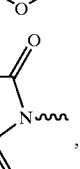

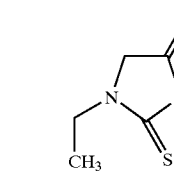 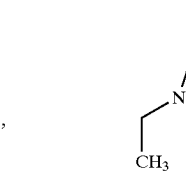 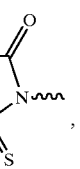

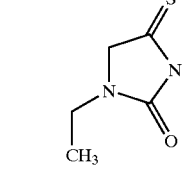 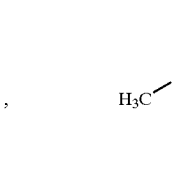 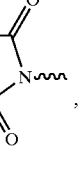

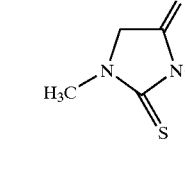 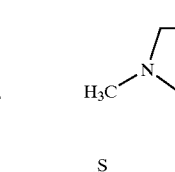  or

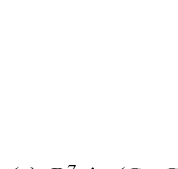 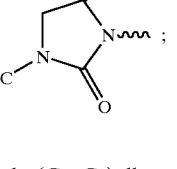 ;

(g) $R^7$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups;
(h) each occurrence of $R^1$ is independently H, $(C_1-C_6)$alkyl, $(C_2-C_6)$alkenyl, or $(C_2-C_6)$alkynyl and is unsubstituted or substituted with one or two halo, OH, $(C_1-C_6)$alkoxy, or phenyl groups; and
(i) each occurrence of $R^9$ is independently H, $(C_1-C_6)$alkyl, $(C_2-C_6)$alkenyl, or $(C_2-C_6)$alkynyl.

Preferably, in the compounds of formula Ia, when G is $(CH_2)_x$, then $W^1$ and $W^2$ cannot both be $C(R^1)(R^2)$—CHO or cannot both be

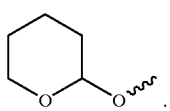

In still another embodiment, the invention relates to compounds of the formula Ib

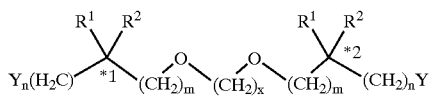

Ib or a pharmaceutically acceptable salt, hydrate, solvate, clathrate, stereoisomer, diastereomer, geometric isomer, or mixtures thereof, wherein:

(a) each occurrence of m is independently an integer ranging from 1 to 9;
(b) each occurrence of n is an independent integer ranging from 0 to 4;
(c) x is 2, 3, or 4;
(d) each occurrence of $R^1$ and $R^2$ is independently $(C_1-C_6)$ alkyl, $(C_2-C_6)$alkenyl, $(C_2-C_6)$alkynyl, phenyl, or benzyl;
(e) each occurrence of Y is independently OH, COOH, CHO, $COOR^7$, $SO_3H$,

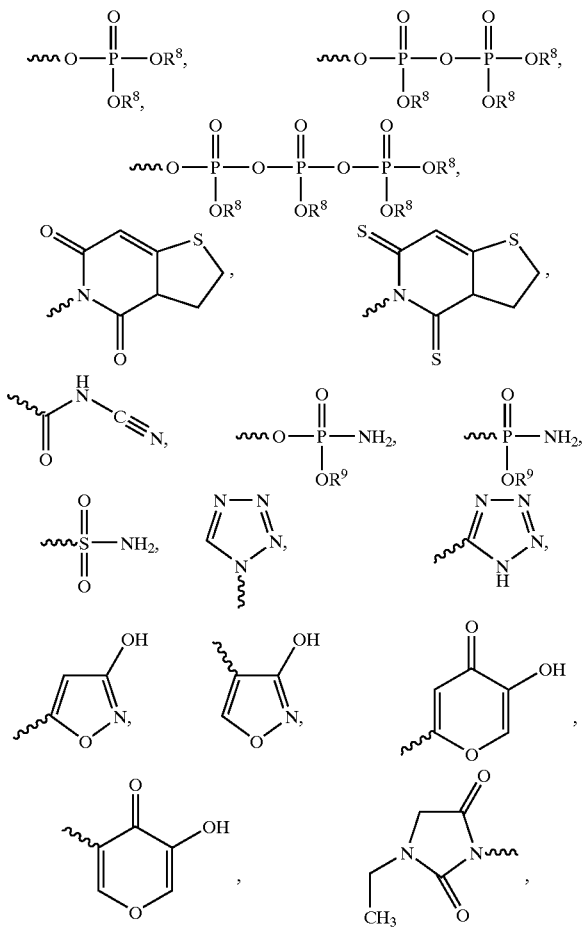

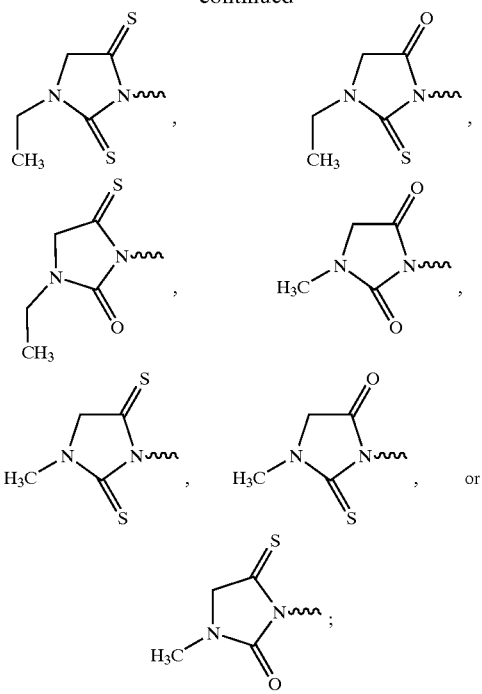

(f) $R^7$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups;
(g) each occurrence of $R^1$ is independently H, $(C_1-C_6)$alkyl, $(C_2-C_6)$alkenyl, or $(C_2-C_6)$alkynyl and is unsubstituted or substituted with one or two halo, OH, $(C_1-C_6)$alkoxy, or phenyl groups;
(h) each occurrence of $R^8$ is independently H, $(C_1-C_6)$alkyl, $(C_1-C_6)$alkenyl, or $(C_2-C_6)$alkynyl; and
(i) with the proviso that both occurrences of Y cannot both be CHO.

When $R^1$ and $R^2$ attached to the same carbon are different chemical groups, the symbols *¹ and *² represent independent chiral-carbon centers. Each chiral center is independent of the other and is racemic, substantially of configuration R, substantially of configuration S, or any mixture thereof. Thus in one embodiment, the compounds of formula Ib are optically active.

In a separate embodiment of compounds of formula Ib, the chiral center represented by *¹ is of the stereochemical configuration R or substantially R.

In another embodiment, the chiral center represented by *¹ is of the stereochemical configuration S or substantially S.

In still another embodiment, the chiral center represented by *² is of the stereochemical configuration R or substantially R.

In one more embodiment, the chiral center represented by *² is of the stereochemical configuration S or substantially S.

In yet another embodiment, the chiral centers represented by *¹*² both have the same stereochemical configuration.

In another embodiment, the chiral centers represented by *¹*² are of the stereochemical configuration $(S^1,S^2)$ or substantially $(S^1,S^2)$.

In yet another embodiment, the chiral centers represented by *¹*² are of the stereochemical configuration $(S^1,R^2)$ or substantially $(S^1,R^2)$.

In still another embodiment, the chiral centers represented by *¹*² are of the stereochemical configuration $(R^1,R^2)$ or substantially $(R^1,R^2)$.

In another embodiment, the chiral centers represented by *1*2 are of the stereochemical configuration ($R^1,S^2$) or substantially ($R^1,S^2$).

In another embodiment, the invention provides compounds of the formula Ic

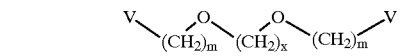

Ic or a pharmaceutically acceptable salt, hydrate, solvate, clathrate, stereoisomer, diastereomer, geometric isomer, or mixtures thereof, wherein:

(a) each occurrence of m is an independent integer ranging from 1 to 9;
(b) x is 2, 3, or 4;
(c) V is

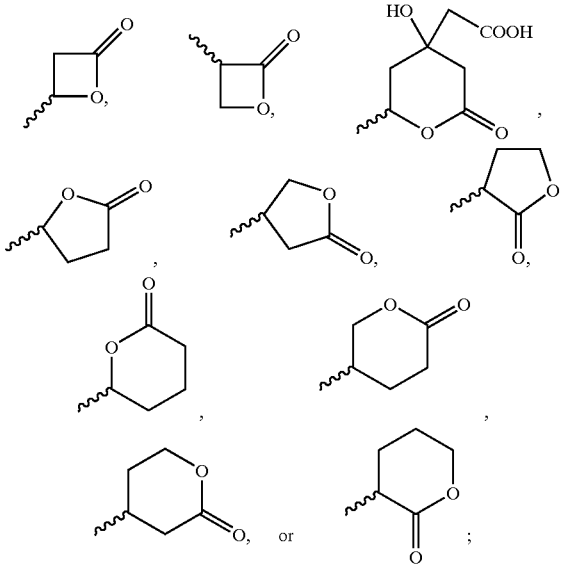

In yet another embodiment, the invention concerns compounds of the formula Id:

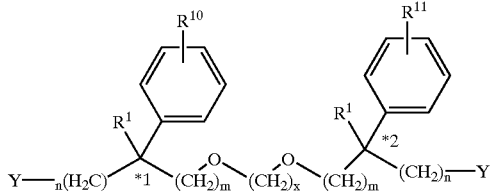

Id or a pharmaceutically acceptable salt, hydrate, solvate, clathrate, enantiomer, diastereomer, racemate, or mixture of stereoisomers thereof wherein (a) each occurrence of m is independently an integer ranging from 1 to 9;
(b) each occurrence of n is an independent integer ranging from 0 to 4;
(c) x is 2, 3, or 4;
(d) each occurrence of $R^1$ is independently ($C_1$–$C_6$)alkyl, ($C_2$–$C_6$)alkenyl, ($C_2$–$C_6$)alkynyl, phenyl, or benzyl;
(e) each occurrence of Y is OH, COOH, CHO, COOR$^7$, SO$_3$H,

(f) $R^7$ is H, ($C_1$–$C_4$) alkyl, phenyl, or benzyl, and is substituted or unsubstituted with one or more halo, OH, ($C_1$–$C_6$)alkoxy, or phenyl groups;

(g) each occurrence of $R^8$ is independently H, $(C_1-C_6)$alkyl, $(C_2-C_6)$alkenyl, or $(C_2-C_6)$alkynyl and is unsubstituted or substituted with one or two halo, OH, $(C_1-C_6)$alkoxy, or phenyl groups;

(h) each occurrence of $R^9$ is independently H, $(C_1-C_6)$alkyl, $(C_2-C_6)$alkenyl, or $(C_2-C_6)$alkynyl;

(i) $R^{10}$ and $R^{11}$ are independently H, halogen, $(C_1-C_4)$alkyl, $(C_1-C_4)$alkoxy, $(C_6)$aryl, $(C_6)$aryloxy, CN, or $NO_2$, $N(R^7)_2$.

In formula Id, the symbols *¹ and *² represent chiral-carbon centers. Each chiral center is independent of the other and is racemic, substantially of configuration R, substantially of configuration S, or any mixture thereof. Thus in one embodiment, the compounds of formula Id are optically active.

In a separate embodiment of compounds of formula Id, the chiral center represented by *¹ is of the stereochemical configuration R or substantially R.

In another embodiment, the chiral center represented by *¹ is of the stereochemical configuration S or substantially S.

In still another embodiment, the chiral center represented by *² is of the stereochemical configuration R or substantially R.

In one more embodiment, the chiral center represented by *² is of the stereochemical configuration S or substantially S.

In yet another embodiment, the chiral centers represented by *¹*² both have the same stereochemical configuration.

In another embodiment, the chiral centers represented by *¹*² are of the stereochemical configuration $(S^1, S^2)$ or substantially $(S^1, S^2)$.

In yet another embodiment, the chiral centers represented by *¹*² are of the stereochemical configuration $(S^1, R^2)$ or substantially $(S^1, R^2)$.

In still another embodiment, the chiral centers represented by *¹*² are of the stereochemical configuration $(R^1, R^2)$ or substantially $(R^1, R^2)$.

In another embodiment, the chiral centers represented by *¹*² are of the stereochemical configuration $(R^1, S^2)$ or substantially $(R^1, S^2)$.

In another embodiment, the invention relates to compound of the formula II:

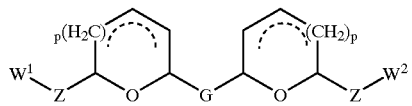

II or a pharmaceutically acceptable salt, hydrate, solvate, clathrate, stereoisomer, diastereomer, geometric isomer, or mixtures thereof, wherein:

(a) each occurrence of Z is independently $(CH_2)_m$, $(CH=CH)_t$, or phenyl, where each occurrence of m and t are independent integers ranging from 1 to 5;

(b) G is $(CH_2)_x$, $CH_2CH=CHCH_2$, $CH=CH$, $CH_2$-phenyl-$CH_2$, or phenyl, where x is an integer ranging from 1 to 4;

(c) $W^1$ and $W^2$ are independently $C(R^1)(R^2)(CH_2)_n$—Y, V, or $C(R^1)(R^2)$-$(CH_2)_c$—V where c is 1 or 2 and n is an integer ranging from 0 to 4;

(d) each occurrence of $R^1$ and $R^2$ is independently $(C_1-C_6)$alkyl, $(C_2-C_6)$alkenyl, $(C_2-C_6)$alkynyl, phenyl, or benzyl;

(e) V is

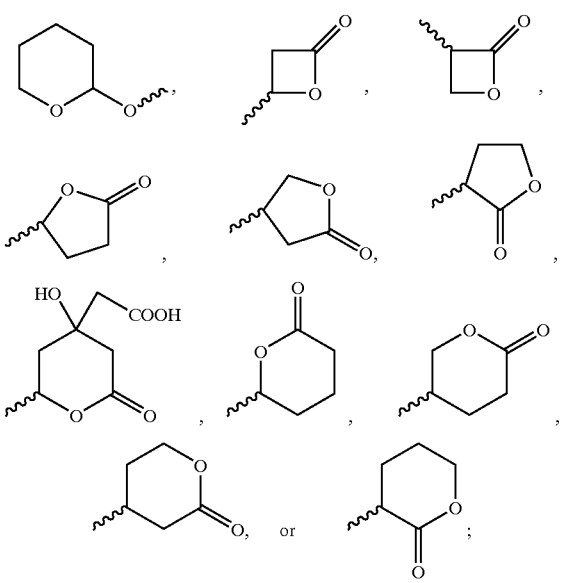

(f) each occurrence of Y is independently OH, COOH, CHO, $COOR^7$, $SO_3H$,

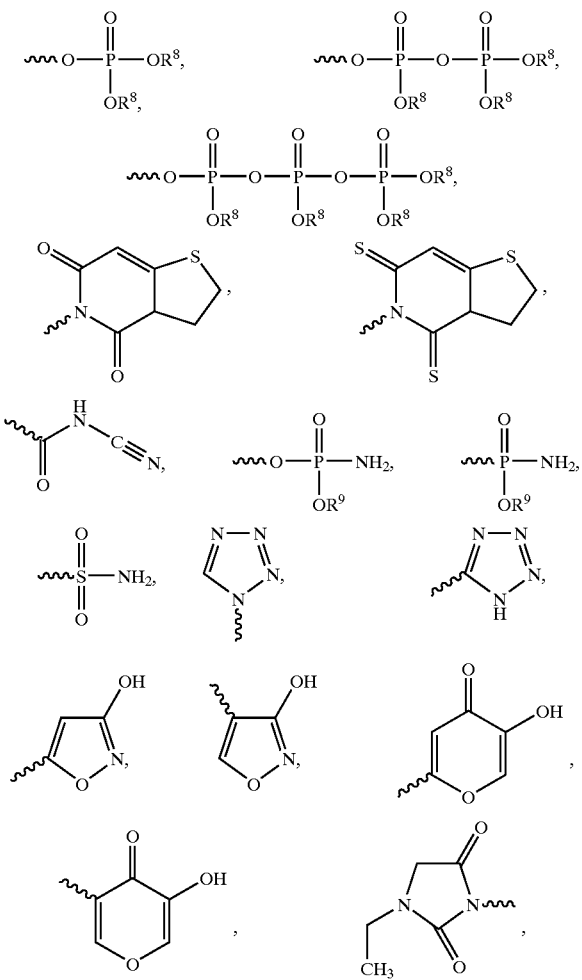

-continued

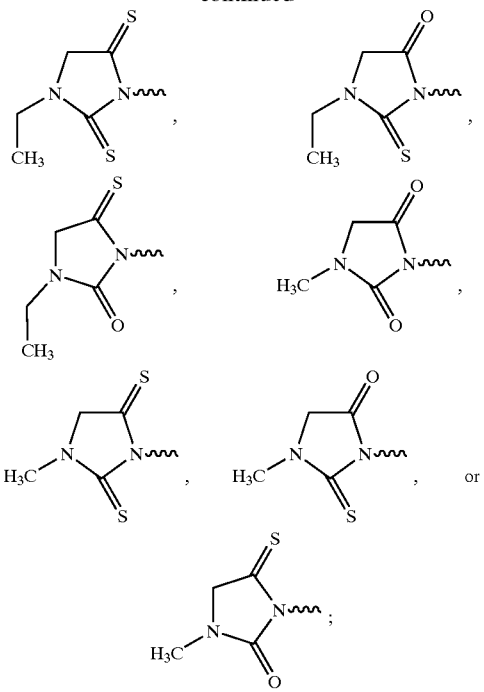

(e) V is

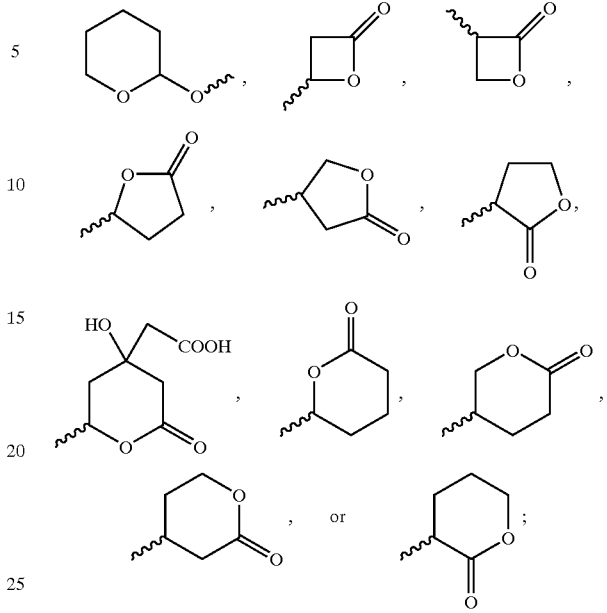

(g) $R^7$ ($C_1$–$C_6$)alkyl, ($C_2$–$C_6$)alkenyl, ($C_2$–$C_6$)alkynyl, phenyl, or benzyl and is unsubstituted or substituted with one or more halo, OH, ($C_1$–$C_6$)alkoxy, or phenyl groups;
(h) each occurrence of $R^8$ is independently H, ($C_1$–$C_6$)alkyl, ($C_2$–$C_6$)alkenyl, or ($C_2$–$C_6$)alkynyl and is unsubstituted or substituted with one or two halo, OH, ($C_1$–$C_6$)alkoxy, or phenyl groups;
(i) each occurrence of $R^9$ is independently H, ($C_1$–$C_6$)alkyl, ($C_2$–$C_6$)alkenyl, or ($C_2$–$C_6$)alkynyl; and
(j) each occurrence of p is independently 0 or 1 where the broken line represents an optional presence of 1 or 2 additional carbon—carbon bonds that when present complete 1 or 2 carbon—carbon double bonds.

Preferably, in compounds of formula II, $W^1$ and $W^2$ are independent $C(R^1)(R^2)(CH_2)_n$—Y groups and each occurrence of Y is independently OH, $COOR^7$, or OOH. In one embodiment of compounds of formula II that p is 0 in another p is 1. In still another embodiment of compounds of formula II, t is 1.

In a separate embodiment, the invention provides compounds of the formula Ia:

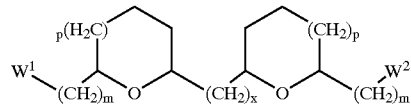

IIa or a pharmaceutically acceptable salt, hydrate, solvate, clathrate, stereoisomer, diastereomer, geometric isomer, or mixtures thereof, wherein:
(a) each occurrence of m is independently an integer ranging from 1 to 5;
(b) x is an integer ranging from 1 to 4;
(c) $W^1$ and $W^2$ are independently $C(R^1)(R^2)(CH_2)_n$—Y, V, or $C(R^1)(R^2)$—$(CH_2)_c$—V where c is 1 or 2 and n is an integer ranging from 0 to 4;
(d) each occurrence of $R^1$ and $R^2$ is independently ($C_1$–$C_6$) alkyl, ($C_2$–$C_6$)alkenyl, ($C_2$–$C_6$)alkynyl, phenyl, or benzyl;

(f) Y is OH, COOH, CHO, $COOR^7$, $SO_3H$,

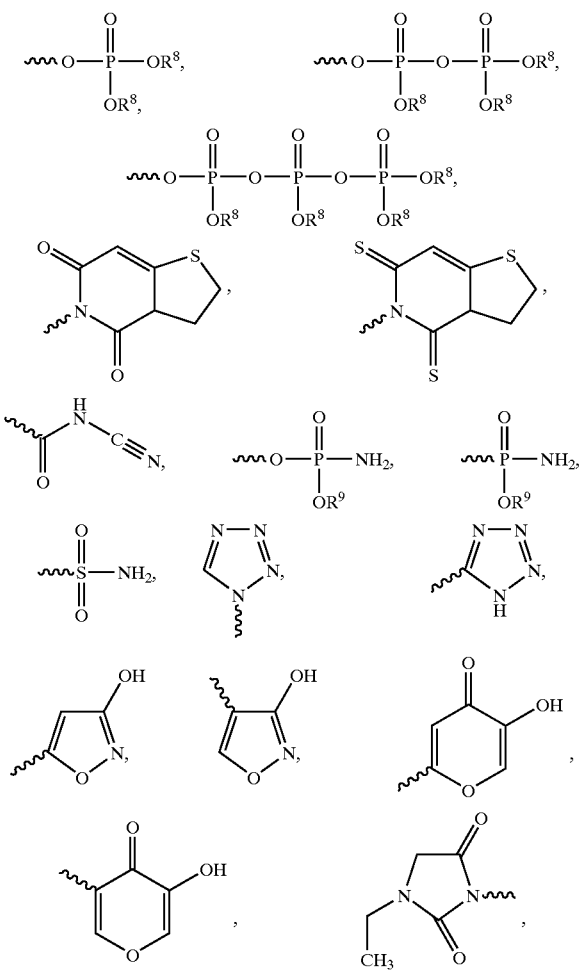

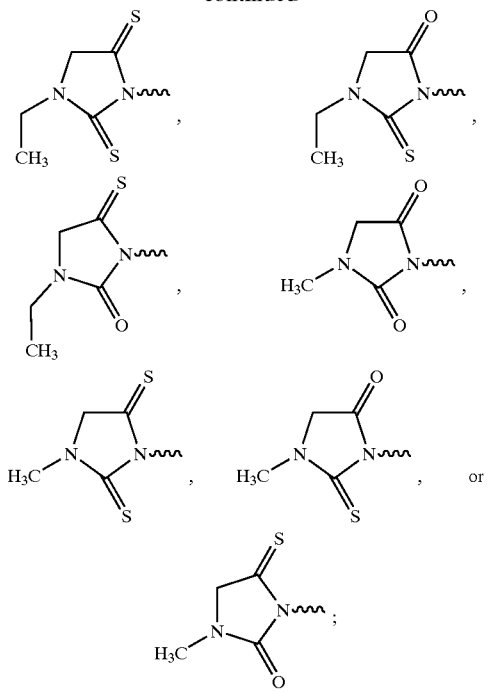

(g) $R^7$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups;

(h) each occurrence of $R^8$ is independently H, $(C_1-C_6)$alkyl, $(C_2-C_6)$alkenyl, or $(C_2-C_6)$alkynyl and is unsubstituted or substituted with one or two halo, OH, $(C_1-C_6)$alkoxy, or phenyl groups;

(i) each occurrence of $R^9$ is independently H, $(C_1-C_6)$alkyl, $(C_2-C_6)$alkenyl, or $(C_2-C_6)$alkynyl; and (f) each occurrence of p is independently 0 or 1.

In yet another embodiment, the invention relates to compounds of the formula III:

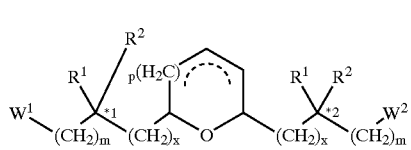

or a pharmaceutically acceptable salt, hydrate, solvate, clathrate, stereoisomer, diastereomer, geometric isomer, or mixtures thereof, wherein:

(a) each occurrence of $R^1$ and $R^2$ is independently $(C_1-C_6)$alkyl, $(C_2-C_6)$alkenyl, $(C_2-C_6)$alkynyl, phenyl, or benzyl; or $R^1$, $R^2$, and the carbon to which they are both attached are taken together to form a $(C_3-C_7)$cycloalkyl group;

(b) each occurrence of m is an independent integer ranging from 0 to 4;

(c) each occurrence of x is independently 2 or 3;

(d) $W^1$ and $W^2$ are independently OH, C(O)OH, CHO, OC(O)$R^7$, C(O)O$R^7$, SO$_3$H,

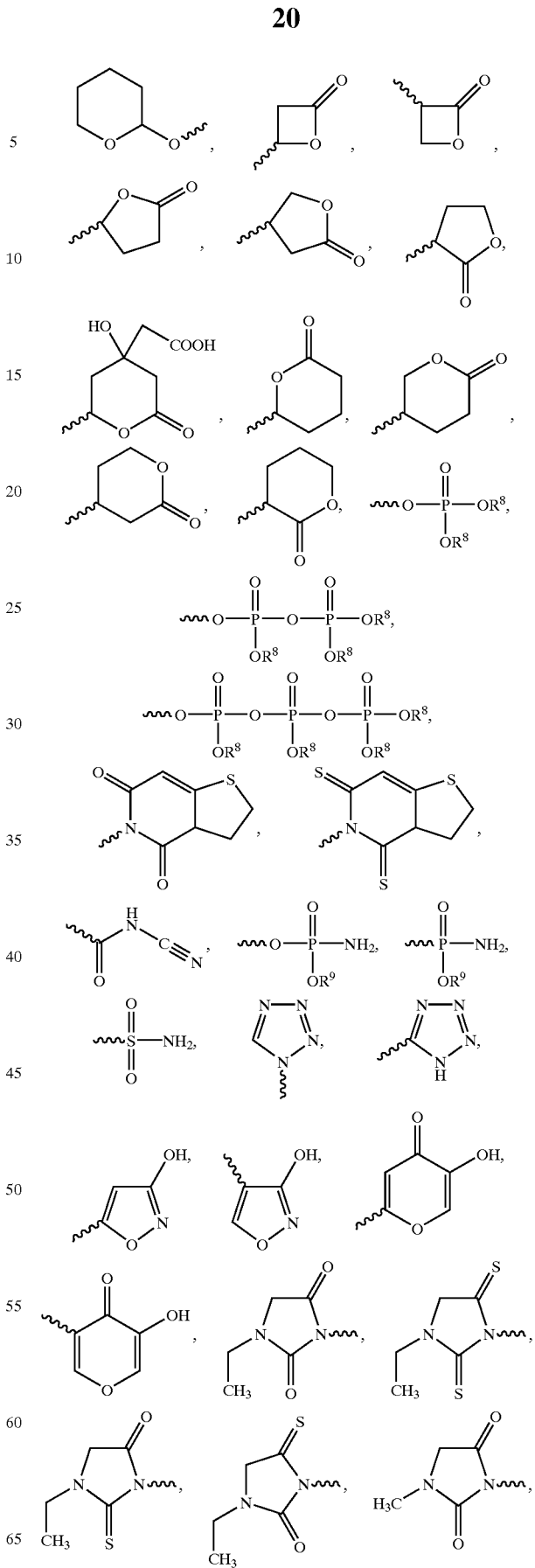

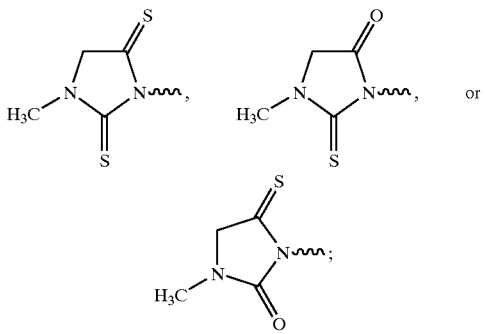

(e) $R^7$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups;
(f) each occurrence of $R^8$ is independently H, $(C_1-C_6)$alkyl, $(C_2-C_6)$alkenyl, or $(C_2-C_6)$alkynyl and is unsubstituted or substituted with one or two halo, OH, $(C_1-C_6)$alkoxy, or phenyl groups;
(g) each occurrence of $R^9$ is independently H, $(C_1-C_6)$alkyl, $(C_2-C_6)$alkenyl, or $(C_2-C_6)$alkynyl; and
(h) p is 0 or 1 where the broken line represents an optional presence of 1 or 2 additional carbon—carbon bonds that when present complete 1 or 2 carbon—carbon double bonds.

Preferably, in compound of formula III, $W^1$ and $W^2$ are independently OH, $COOR^7$, or COOH.

The ring in formula III can be saturated or contain one or two double bonds. For example, the ring in compounds of formula III can be:

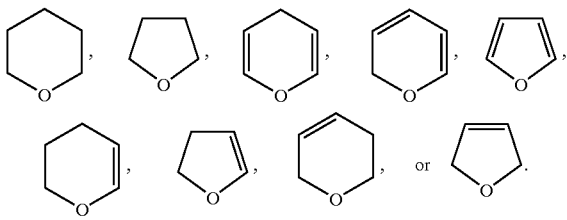

Preferably, in compound of formula III, $W^1$ and $W^2$ are independently OH, $COOR^7$, or COOH.

In one more embodiment of compound of formula III, p is 0; in another, p is 1.

In still another embodiment of compounds of formula III, the broken line is absent.

In yet another embodiment of compounds of formula III, each occurrence of $R^1$ and $R^2$ is independently $(C_1-C_6)$ alkyl, $(C_2-C_6)$alkenyl, $(C_2-C_6)$alkynyl, phenyl, or benzyl.

In compounds of formula III, when $R^1$ and $R^2$ attached to the same carbon are different chemical groups, the symbols $*^1$ and $*^2$ represent chiral-carbon centers. Each chiral center is independent of the other and is racemic, substantially of configuration R, substantially of configuration S, or any mixture thereof. Thus in one embodiment, the compounds of formula III are optically active.

In a separate embodiment of compounds of formula III, the chiral center represented by $*^1$ is of the stereochemical configuration R or substantially R.

In another embodiment, the chiral center represented by $*^1$ is of the stereochemical configuration S or substantially S.

In still another embodiment, the chiral center represented by $*^2$ is of the stereochemical configuration R or substantially R.

In one more embodiment, the chiral center represented by $*^2$ is of the stereochemical configuration S or substantially S.

In yet another embodiment, the chiral centers represented by $*^1*^2$ both have the same stereochemical configuration.

In another embodiment, the chiral centers represented by $*^1*^2$ are of the stereochemical configuration $(S^1,S^2)$ or substantially $(S^1,S^2)$.

In yet another embodiment, the chiral centers represented by $*^1*^2$ are of the stereochemical configuration $(S^1,R^2)$ or substantially $(S^1,R^2)$.

In still another embodiment, the chiral centers represented by $*^1*^2$ are of the stereochemical configuration $(R^1,R^2)$ or substantially $(R^1,R^2)$.

In another embodiment, the chiral centers represented by $*^1*^2$ are of the stereochemical configuration $(R^1,S^2)$ or substantially $(R^1,S^2)$.

In a separate embodiment, the invention provides compounds of the formula IV:

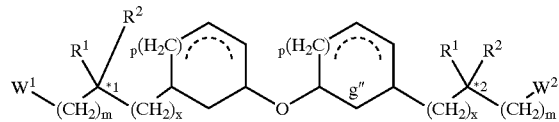

IV or a pharmaceutically acceptable salt, hydrate, solvate, clathrate, stereoisomer, diastereomer, geometric isomer, or mixtures thereof, wherein:

(a) each occurrence of $R^1$ and $R^2$ is independently $(C_1-C_6)$ alkyl, $(C_2-C_6)$alkenyl, $(C_2-C_6)$alkynyl, phenyl, or benzyl; or $R^1$, $R^2$, and the carbon to which they are both attached are taken together to form a $(C_3-C_7)$cycloalkyl group;
(b) each occurrence of m is independently an integer ranging from 0 to 4;
(c) each occurrence of x is independently 0 or 1;
(d) $W^1$ and $W^2$ are independently OH, C(O)OH, CHO, $OC(O)R^7$, $C(O)OR^7$, $SO_3H$,

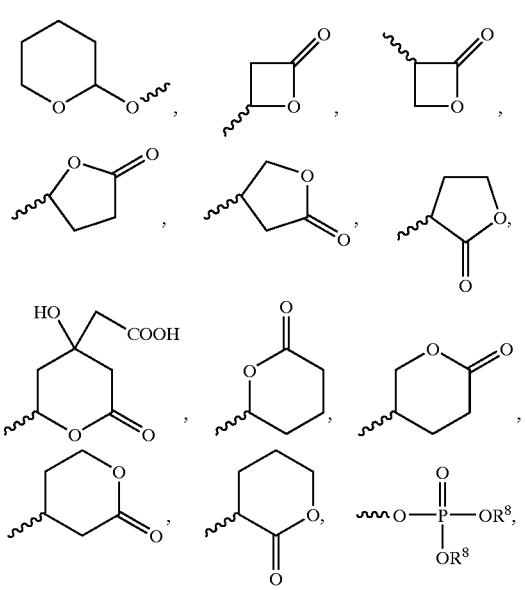

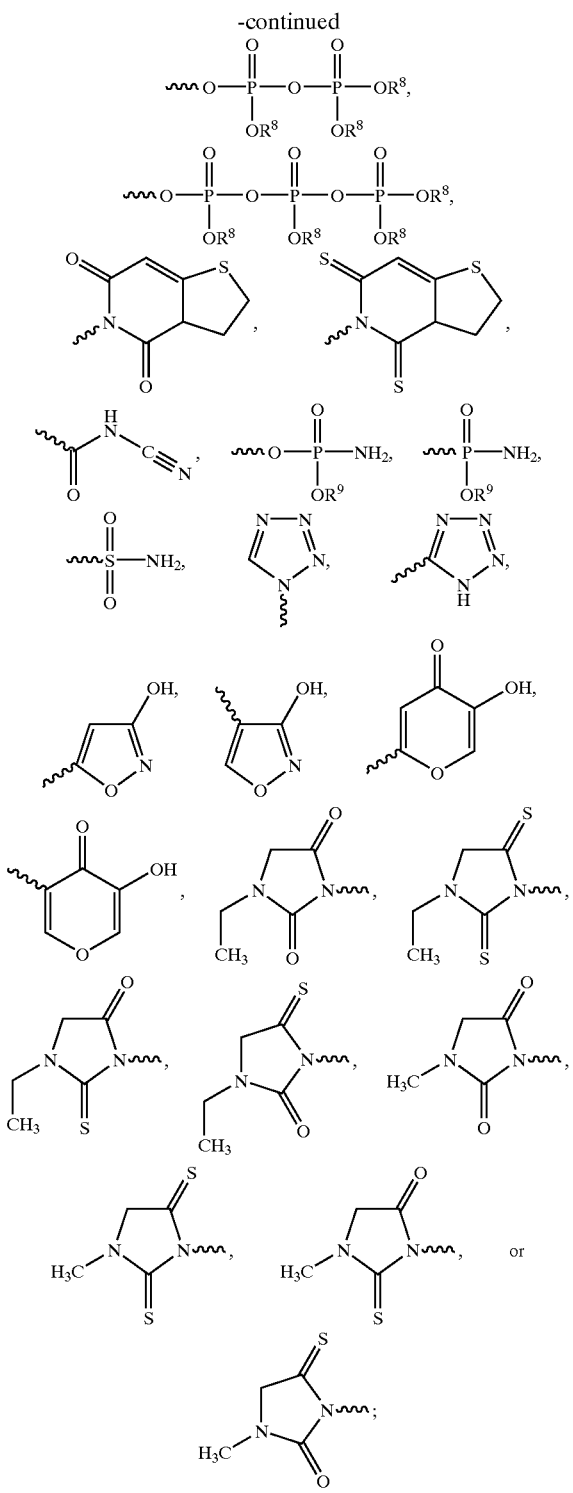

(e) $R^7$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups;
(f) each occurrence of $R^8$ is independently H, $(C_1-C_6)$alkyl, $(C_2-C_6)$alkenyl, or $(C_2-C_6)$alkynyl and is unsubstituted or substituted with one or two halo, OH, $(C_1-C_6)$alkoxy, or phenyl groups;
(g) each occurrence of $R^9$ is independently H, $(C_1-C_6)$alkyl, $(C_2-C_6)$alkenyl, or $(C_2-C_6)$alkynyl; and (h) each occurrence of p is independently 0 or 1 where the broken line represents an optional presence of 1, 2, or 3 additional carbon—carbon bonds that when present form a cycloalkenyl group, a cyclodienyl group, or a phenyl group.

In compounds of formula IV, when $R^1$ and $R^2$ attached to the same carbon are different chemical groups, the symbols *[1] and *[2] represent independent chiral-carbon centers. Each chiral center is independent of the other and is racemic, substantially of configuration R, substantially of configuration S, or any mixture thereof. Thus in one embodiment, the compounds of formula IV are optically active.

In a separate embodiment of compounds of formula IV, the chiral center represented by *[1] is of the stereochemical configuration R or substantially R.

In another embodiment, the chiral center represented by *[1] is of the stereochemical configuration S or substantially S.

In still another embodiment, the chiral center represented by *[2] is of the stereochemical configuration R or substantially R.

In one more embodiment, the chiral center represented by *[2] is of the stereochemical configuration S or substantially S.

In yet another embodiment, the chiral centers represented by *[1]*[2] both have the same stereochemical configuration.

In another embodiment, the chiral centers represented by *[1]*[2] are of the stereochemical configuration $(S^1,S^2)$ or substantially $(S^1,S^2)$.

In yet another embodiment, the chiral centers represented by *[1]*[2] are of the stereochemical configuration $(S^1,R^2)$ or substantially $(S^1,R^2)$.

In still another embodiment, the chiral centers represented by *[1]*[2] are of the stereochemical configuration $(R^1,R^2)$ or substantially $(R^1,R^2)$.

In another embodiment, the chiral centers represented by *[1]*[2] are of the stereochemical configuration $(R^1,S^2)$ or substantially $(R^1,S^2)$.

The rings in compounds IV can be saturated or contain 1, 2, or 3 double bonds. Of course with 3 double bonds, the ring is a phenyl group. For example, the ring groups in compounds of formula IV can independently be:

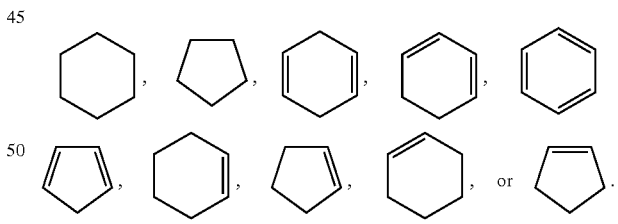

Preferably, the ring of compounds IV is a phenyl ring.

Preferably, in compounds of formula IV, $W^1$ and $W^2$ are independently OH, $COOR_7$, or COOH.

In another embodiment of compounds of formula IV, each occurrence of $R^1$ and $R^2$ is independently $(C_1-C_6)$alkyl, $(C_2-C_6)$alkenyl, $(C_2-C_6)$alkynyl, phenyl, or benzyl.

In still another embodiment of compounds of formula IV, p is 0, and in another, p is 1.

In one more embodiment of compounds of formula 4, the broken line is absent.

In another embodiment, compound of formula IV have the formula:

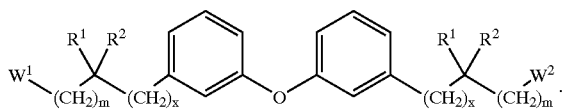

And in still another embodiment, compound of formula IV have the formula:

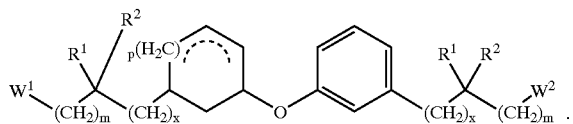

The compounds of the invention are useful for treating or preventing cardiovascular diseases, dyslipidemias, dyslipoproteinemias, disorders of glucose metabolism, Alzheimer's disease, Syndrome X, PPAR-associated disorders, septicemia, thrombotic disorders, obesity, pancreatitis, hypertension, renal diseases, cancer, inflammation, and impotence.

The invention further provides pharmaceutical compositions comprising one or more compounds of the invention or a pharmaceutically acceptable salt, hydrate, solvate, clathrate, enantiomer, diastereomer, racemate, or a mixture of stereoisomers thereof and a pharmaceutically acceptable vehicle, excipient, or diluent and a pharmaceutically acceptable vehicle, excipient, or diluent.

These pharmaceutical compositions are useful for treating or preventing a disease or disorder selected from the group consisting of a cardiovascular disease, dyslipidemia, dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, and impotence. These pharmaceutical composition are also useful for reducing the fat content of meat in livestock and reducing the cholesterol content of eggs.

The present invention provides a method for treating or preventing a cardiovascular disease, dyslipidemia, dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, and impotence, comprising administering to a patient in need of such treatment or prevention a therapeutically effective amount of a compound of the invention or a pharmaceutical composition comprising a compound of the invention and a pharmaceutically acceptable vehicle, excipient, or diluent.

The present invention provides a method for treating or preventing stroke, peripheral vascular disease, polymylagia rheumatica, polymyositis, fibrositis, gastrointestinal disease, irritable bowel syndrome, inflammatory bowel disease, asthma, vasculitis, ulcerative colitis, Crohn's disease, Kawasaki disease, Wegener's granulomatosis, systemic lupus erythematosus, multiple sclerosis, autoimmune chronic hepatitis, osteoporosis, rheumatoid arthritis, juvenile rheumatoid arthritis, osteoarthritis, tendonitis, bursitis, systemic lupus, erythematosus, scleroderma, ankylosing spondylitis, gout, pseudogout, non-insulin dependent diabetes mellitus, polycystic ovarian disease, hyperlipidemias, familial hypercholesterolemia, familial combined hyperlipidemia, lipoprotein lipase deficiencies, hypertriglyceridemia, hypoalphalipoproteinemia, hypercholesterolemia, lipoprotein abnormalities associated with diabetes, lipoprotein abnormalities associated with obesity, lipoprotein abnormalities associated with Alzheimer's Disease, high levels of blood triglycerides, high levels of low density lipopotein cholesterol, high levels of apolipoprotein B, high levels of lipoprotein Lp(a) cholesterol, high levels of very low density lipoprotein cholesterol, high levels of fibrinogen, high levels of insulin, high levels of glucose, low levels of high density lipoprotein cholesterol, or NIDDM in a patient comprising administering to a patient in need of such treatment or prevention a therapeutically effective amount of a compound of the invention or a pharmaceutical composition comprising a compound of the invention and a pharmaceutically acceptable vehicle, excipient, or diluent.

The present invention further provides a method for reducing the fat content of meat in livestock comprising administering to livestock in need of such fat-content reduction a therapeutically effective amount of a compound of the invention or a pharmaceutical composition comprising a compound of the invention and a pharmaceutically acceptable vehicle, excipient, or diluent.

The present invention provides a method for reducing the cholesterol content of a fowl egg comprising administering to a fowl species a therapeutically effective amount of a compound of the invention or a pharmaceutical composition comprising a compound of the invention and a pharmaceutically acceptable vehicle, excipient, or diluent.

The present invention may be understood by reference to the detailed description and examples, which are intended to exemplify non-limiting embodiments of the invention.

4. BRIEF DESCRIPTION OF THE FIGURE

FIG. 1. Shows the rate of lipid synthesis of saponified and non-saponified lipids in primary rat hepatocyte cells upon treatment with Compound A, Compound B, or lovastatin.

5. DETAILED DESCRIPTION OF THE INVENTION

The present invention provides novel compounds useful for treating or preventing a cardiovascular disease, dyslipidemia, dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, and impotence. In this regard, the compounds of the invention are particularly useful when incorporated in a pharmaceutical composition having a carrier, excipient, diluent, or a mixture thereof. A composition of the invention need not contain additional ingredients, such as an excipient, other than a compound of the invention. Accordingly, in one embodiment, the compositions of the invention can omit pharmaceutically acceptable excipients and diluents and can be delivered in a gel cap or drug delivery device. Accordingly, the present invention provides methods for treating or preventing cardiovascular diseases, dyslipidemias, dyslipoproteinemias, disorders of glucose metabolism, Alzheimer's Disease, Syndrome X, PPAR-associated disorders, septicemia, thrombotic disorders, obesity, pancreatitis, hypertension, renal diseases, cancer, inflammation, or impotence, comprising administering to a patient in need thereof a therapeutically effective amount of a compound or composition of the invention.

In certain embodiments of the invention, a compound of the invention is administered in combination with another therapeutic agent. The other therapeutic agent provides additive or synergistic value relative to the administration of a compound of the invention alone. The therapeutic agent can be a lovastatin; a thiazolidinedione or fibrate; a bile-acid-binding-resin; a niacin; an anti-obesity drug; a hormone; a tyrophostine; a sulfonylurea-based drug; a biguanide; an α-glucosidase inhibitor; an apolipoprotein A-I agonist; apolipoprotein E; a cardiovascular drug; an HDL-raising drug; an HDL enhancer; or a regulator of the apolipoprotein A-I, apolipoprotein A-IV and/or apolipoprotein genes.

A few non-limiting examples of compounds of the invention are shown in Table 1 below.

TABLE 1

COMPOUNDS OF THE INVENTION

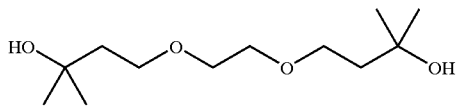

I-1:
4-[2-(3-Hydroxy-3-methyl-butoxy)-ethoxy]-2-methyl-butan-2-ol

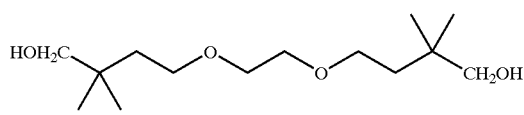

I-2:
4-[2-(4-Hydroxy-3,3-dimethyl-butoxy)-ethoxy]-2,2-dimethyl-butan-1-ol

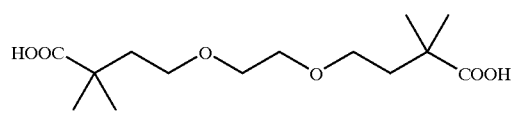

I-3:
4-[2-(3-Carboxy-3-methyl-butoxy)-ethoxy]-2,2-dimethyl-butyric acid

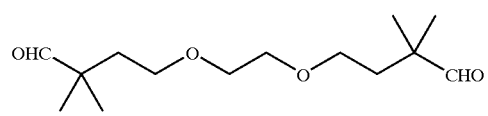

I-4:
4-[2-(3,3-Dimethyl-4-oxo-butoxy)-ethoxy]-2,2-dimethyl-butanal

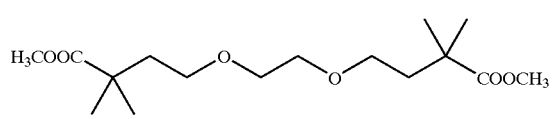

I-5:
4-[2-(3-Methoxycarbonyl-3-methyl-butoxy)-ethoxy]-2,2-dimethyl-butyric acid methyl ester

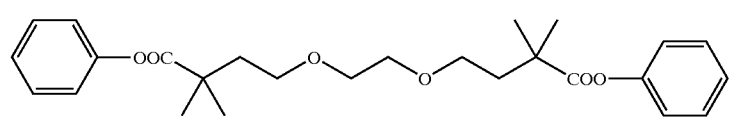

I-6:
2,2-Dimethyl-4-[2-(3-methyl-3-phenoxycarbonyl-butoxy)-ethoxy]-butyric acid phenyl ester

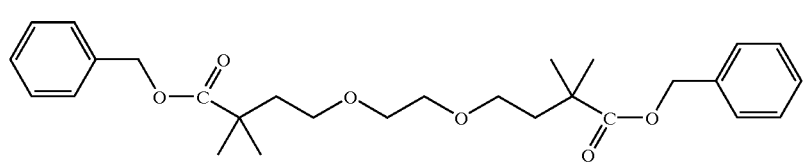

I-7:
Benzyl-2,2,2',2'-tetramethyl-4,4'-[ethylenebis(oxadiyl)]-dibutryrate

TABLE 1-continued

COMPOUNDS OF THE INVENTION

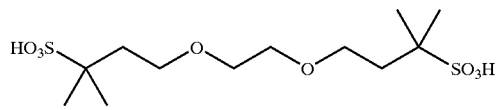

I-8:
2,2'-Dimethyl-4,4'-[ethylenebis(oxadiyl)]dibutane-2-sulfonic acid

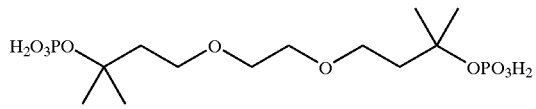

I-9:
Phosphoric acid mono-{3-[2-(3,3-dimethyl-butoxy)-ethoxy]-1,1-dimethyl-propyl} ester

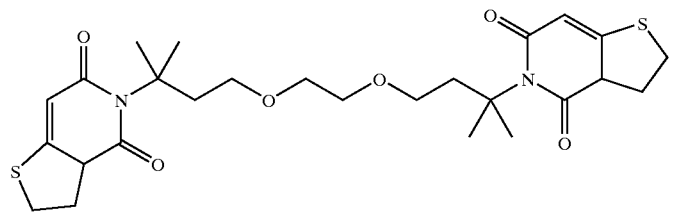

I-10:
1-Ethyl-3-(3-{2-[3-(4,6-dioxo-2,3,3a,6-tetrahydro-4H-thieno[3,2-c]pyridin-5-yl))-3-methyl-butoxy]-ethoxy}-1,1-dimethyl-propyl)-4,6-dioxo-2,3,3a,6-tetrahydro-4H-thieno[3,2-c]pyridin-5-yl-4,6-dione

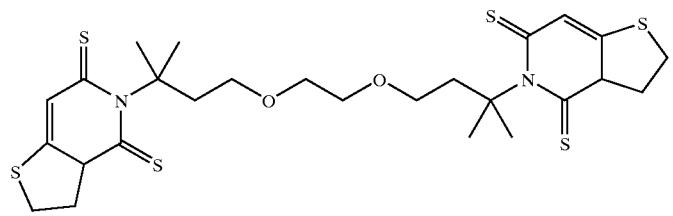

I-11:
1-Ethyl-3-(3-{2-[3-(4,6-dithioxo-2,3,3a,6-tetrahydro-4H-thieno[3,2-c]pyridin-5-yl))-3-methyl-butoxy]-ethoxy}-1,1-dimethyl-propyl)-4,6-dioxo-2,3,3a,6-tetrahydro-4H-thieno[3,2-c]pyridin-5-yl-4,6-dithione

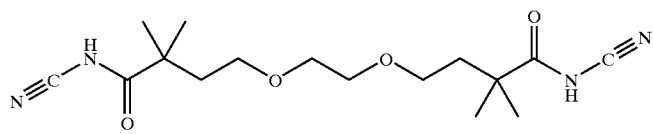

I-12:
2,2-Dimethyl-4-[2-(3-methyl-3-cyanocarbamoyl-butoxy)-ethoxy]-N-cyano-butyramide

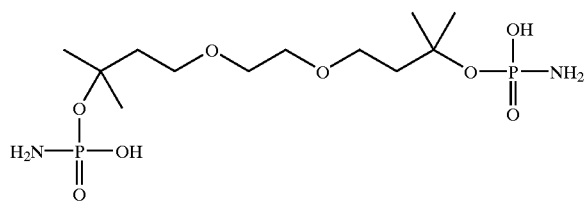

I-13:
Phosphoradimic acid mono-(3-{2-[3-(amino-hydroxy-phosphoryloxy)-3-methyl-butoxy]-ethoxy}-1,1-dimethyl-propyl) ester

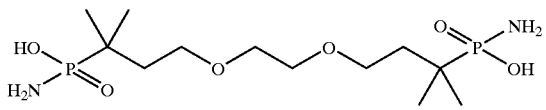

TABLE 1-continued

COMPOUNDS OF THE INVENTION

I-14:
{1,1-Dimethyl-3-[2-(3-methyl-3-phosphonamido-butoxy)-ethoxy]-propyl}-phosphonic acid amide

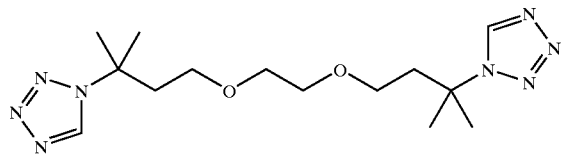

I-15:
1-{3-[2-(3-Methyl-3-{(1H)-tetrazol-1-yl}-butoxy)-ethoxy]-1,1-dimethyl-propyl}-1H-tetrazole

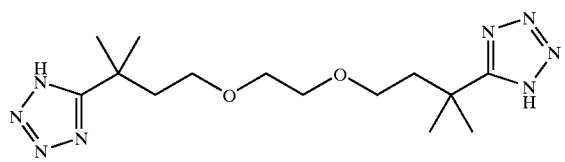

I-16:
5-{3-[2-(3-Methyl-3-{(1H)tetrazol-5-yl}-butoxy)-ethoxy]-1,1-dimethyl-propyl}-1H-tetrazole

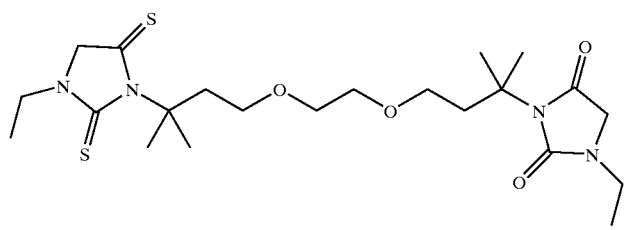

I-17:
1-Ethyl-3-(3-{2-[3-(3-ethyl-2,5-dithioxo-imidazolidin-1-yl)-3-methyl-butoxy]-ethoxy}-1,1-dimethyl-propyl)-imidazolidine-2,4-dione

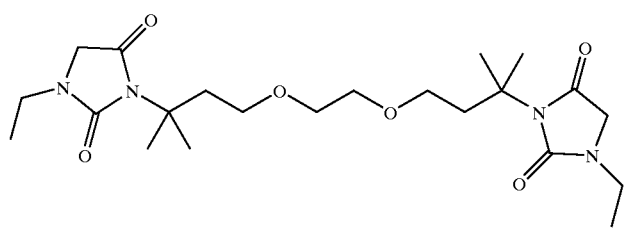

I-18:
1-Ethyl-3-(3-{2-[3-(3-ethyl-2,5-dioxo-imidazolidin-1-yl)-3-methyl-butoxy]-ethoxy}-1,1-dimethyl-propyl)-imidazolidine-2,4-dione

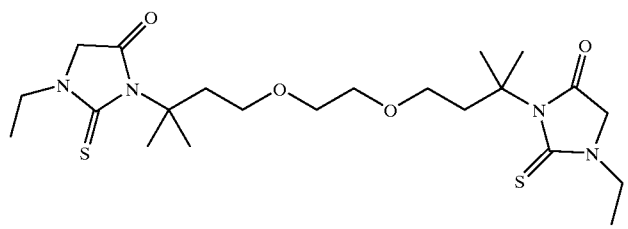

I:19:
1-Ethyl-3-(3-{2-[3-(3-ethyl-2-oxo-5-thioxo-imidazolidin-1-yl)-3-methyl-butoxy]-ethoxy}-1,1-dimethyl-propyl)-imidazolidine-2-thioxo-4-one TABLE 1-continued

COMPOUNDS OF THE INVENTION

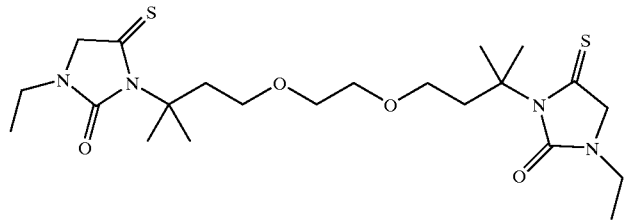

I-20:
1-Ethyl-3-(3-{2-[3-(3-ethyl-5-oxo-2-thioxo-imidazolidin-1-yl)-3-methyl-butoxy]-ethoxy}-1,1-dimethyl-propyl)-imidazolidine-4-thioxo-2-one

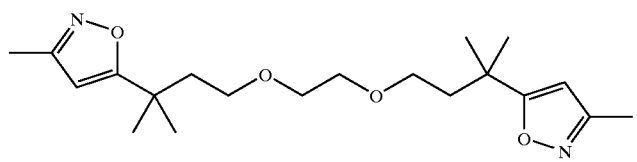

I-21:
1-{3-[2-(3-Methyl-3-(3-methyl-isoxazol-5-yl)-butoxy)-ethoxy]-1,1-dimethyl-propyl}-5-isoxazole

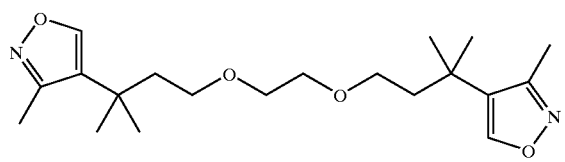

I-22:
1-{3-[2-(3-Methyl-3-(3-methyl-isoxazol-4-yl)-butoxy)-ethoxy]-1,1-dimethyl-propyl}-4-isoxazole

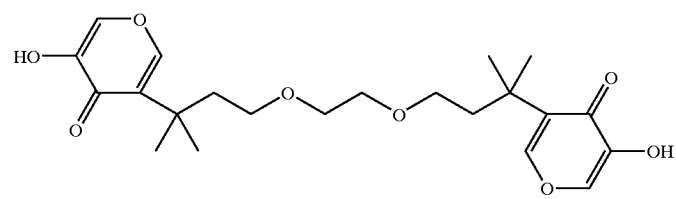

I-23:
3-{3-[2-(3-Methyl-3-(5-hydroxy-pyran-3-yl-4-one)-butoxy)-ethoxy]-1,1-dimethyl-propyl}-5-hydroxy-pyran-4-one

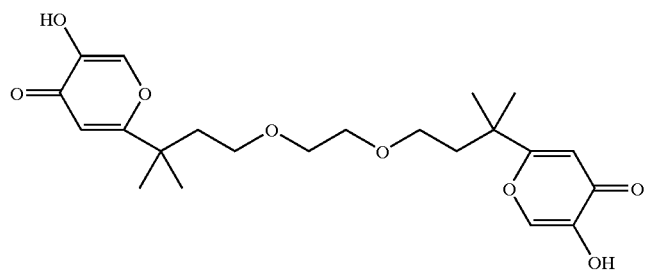

I-24:
2-{3-(2-[3-Methyl-3-(5-hydroxy-pyran-2-yl-4-one)-butoxy]-ethoxy)]-1,1-dimethyl-propyl}-5-hydroxy-pyran-4-one TABLE 1-continued

COMPOUNDS OF THE INVENTION

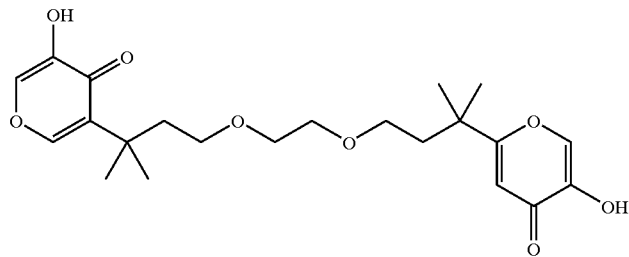

I-25:
2-{3-[2-(3-Methyl-3-(5-hydroxy-pyran-3-yl-4-one)-butoxy]-ethoxy}-1,1-dimethyl-propyl}-5-hydroxy-pyran-4-one

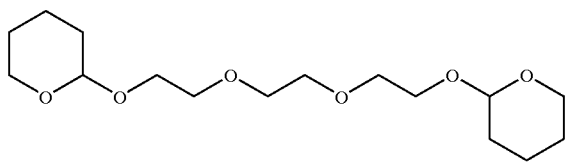

I-26:
1-(2-Tetrahydropyranyloxy)-2-{2-[2-(2-tetrahydropyranyloxy)-ethoxy]-ethoxy}ethane

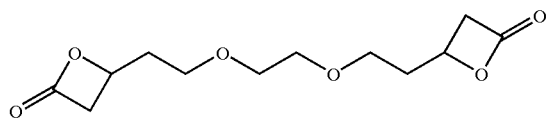

I-27:
4-{2-[2-(4-Oxetan-2-one)-propoxy-ethoxy]-ethyl}-oxetan-2-one

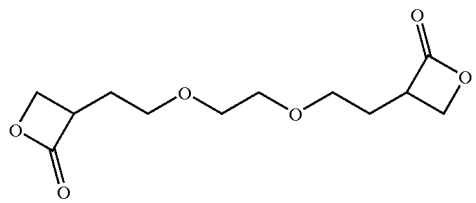

I-28:
3-{2-[2-(3-Oxetan-2-one)-propoxy-ethoxy]-ethyl}-oxetan-2-one

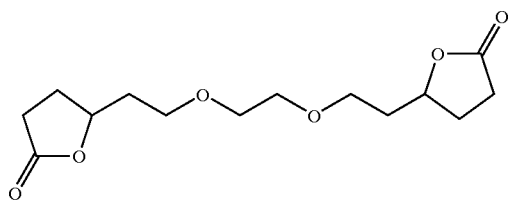

I-29:
5-{2-[2-(5-Dihydro-furan-2-one)-propoxy-ethoxy]-ethyl}-dihydro-furan-2-one

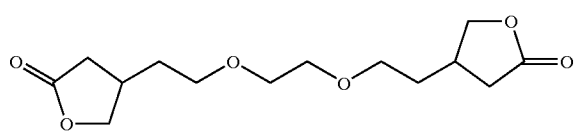

I-30:
4-{2-[2-(4-Dihydro-furan-2-one)-propoxy-ethoxy]-ethyl}-dihydro-furan-2-one TABLE 1-continued

COMPOUNDS OF THE INVENTION

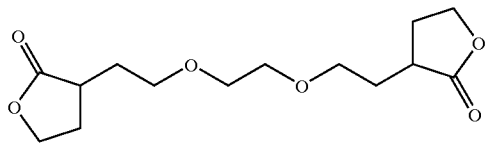

I-31:
3-{2-[2-(3-Dihydro-furan-2-one)-propoxy-ethoxy]-ethyl}-dihydro-furan-2-one

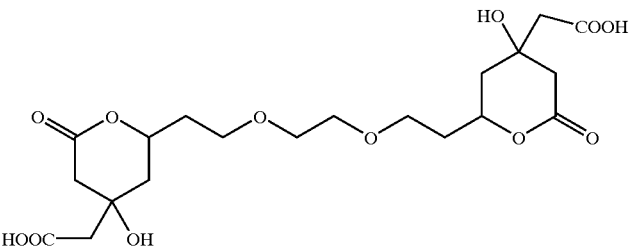

I-32:
2-{2-[2-(2-{2-[4-(Carboxy-methyl)-4-hydroxy-6-oxo-tetrahydro-pyran-2-yl]-ethoxy}-ethoxy)-ethyl]-4-hydroxy-6-oxo-tetrahydro-pyran-4-yl}-acetic acid

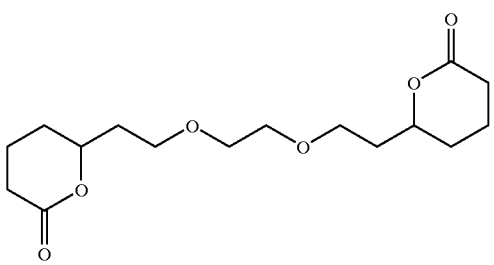

I-33:
2,2'-[Ethylenebis(oxadiyl)]diethane-6-δ-valerolactone

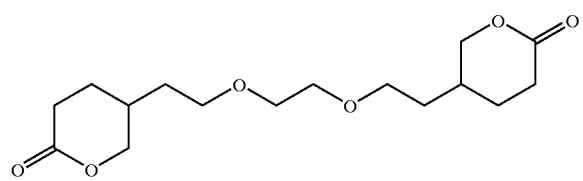

I-34:
2,2'-[Ethylenebis(oxadiyl)]diethane-5-δ-valerolactone

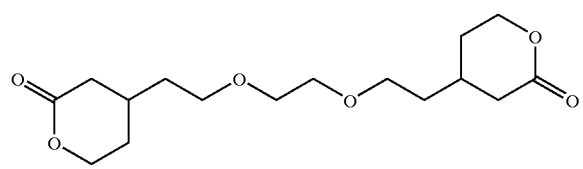

I-35:
2,2'-[Ethylenebis(oxadiyl)]diethane-4-δ-valerolactone

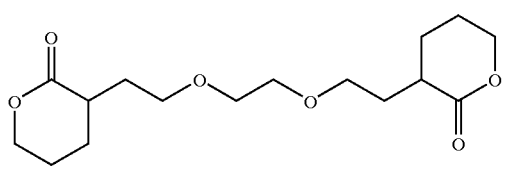

I-36:

TABLE 1-continued

COMPOUNDS OF THE INVENTION 2,2'-[Ethylenebis(oxadiyl)]diethane-3-δ-valerolactone

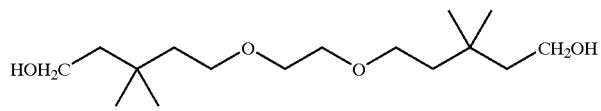

I-37:
3,3,3',3'-Tetramethyl-5,5'-[ethylenebis(oxadiyl)]dipentanol

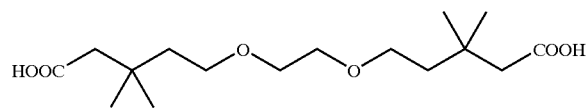

I-38:
3,3,3',3'-Tetramethyl-5,5'-[ethylenebis(oxadiyl)]dipentanoic acid

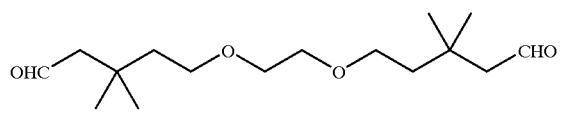

I-39:
3,3,3',3'-Tetramethyl-5,5'-[ethylenebis(oxadiyl)]dipentanal

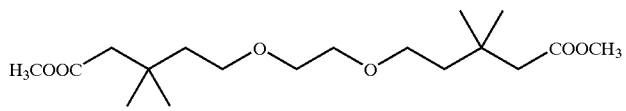

I-40:
Methyl-3,3,3',3'-tetramethyl-5,5'-[ethylenebis(oxadiyl)]dipentanoate

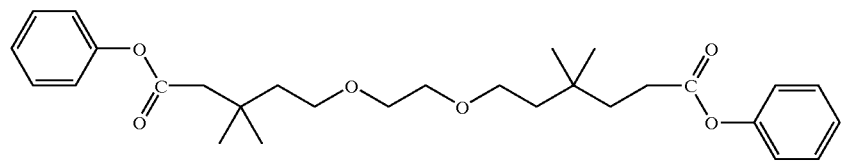

I-41:
Phenyl-3,3,3',3'-tetramethyl-5,5'-[ethylenebis(oxadiyl)]dipentanoate

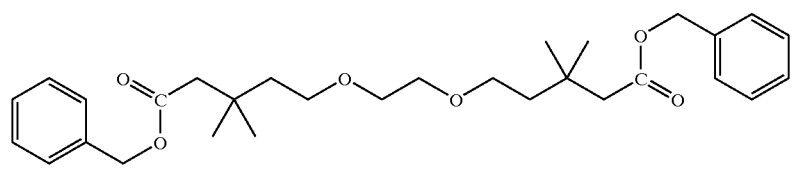

I-42:
Benzyl-3,3,3',3'-tetramethyl-5,5'-[ethylenebis(oxadiyl)]dipentanoate

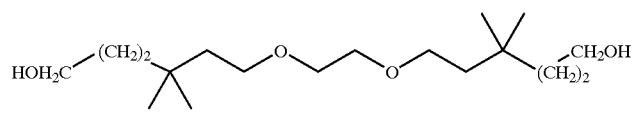

I-43:
4,4,4',4'-Tetramethyl-6,6'-[ethylenebis(oxadiyl)]dihexanol

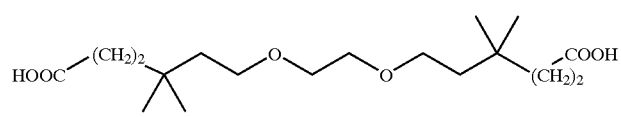

TABLE 1-continued

COMPOUNDS OF THE INVENTION

I-44:
4,4,4',4'-Tetramethyl-6,6'-[ethylenebis(oxadiyl)]dihexanoic acid

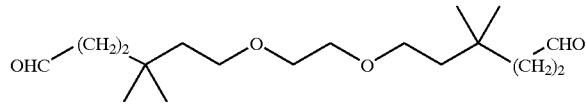

I-45:
4,4,4',4'-Tetramethyl-6,6'-[ethylenebis(oxadiyl)]dihexanal

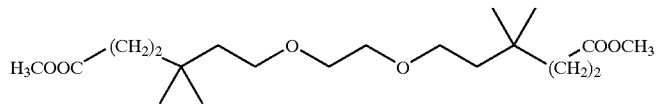

I-46:
Methyl-4,4,4',4'-tetramethyl-6,6'-[ethylene-(oxadiyl)]-dihexanoate

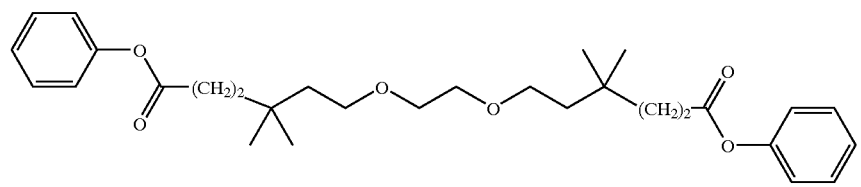

I-47:
Phenyl-4,4,4',4'-tetramethyl-6,6'-[ethylenebis(oxadiyl)]dihexanoate

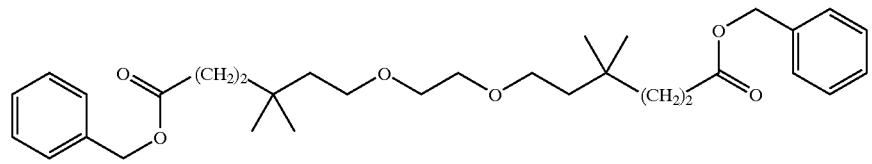

I-48:
Benzyl-4,4,4',4'-tetramethyl-6,6'-[ethylenebis(oxadiyl)]dihexanoate

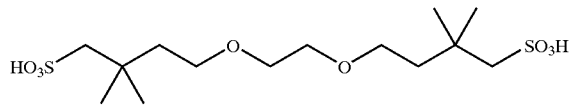

I-49:
2,2,2',2'-Tetramethyl-4,4'-[ethylenebis(oxadiyl)]dibutane sulfonic acid

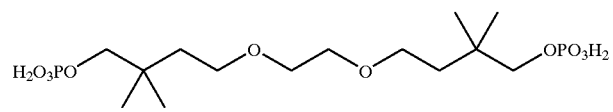

I-50:
Phosphoric acid mono-{4-[2-(3,3-dimethyl-4-phosphonooxy-butoxy)-ethoxy]-2,2-dimethyl-butyl}ester

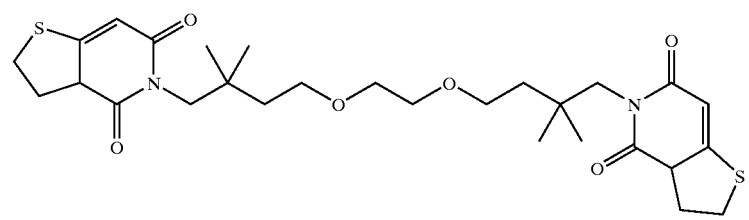

I-51:
5-{4-[2-(3,3-Dimethyl-4-(5-(3,3a-dihydro-2H-thieno-[3,2-c]pyridine-4,6-dioxo)pentyloxy)-ethoxy]-2,2-di- TABLE 1-continued

COMPOUNDS OF THE INVENTION methyl-butyl}-3,3a-dihydro 3,3a-dihydro-2H-thieno-[3,2-c]pyridine-4,6-dione

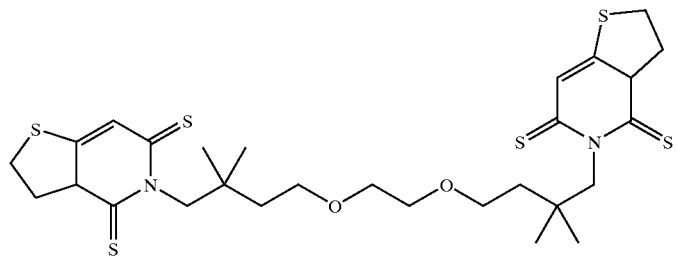

I-52:
5-{4-[2-(3,3-Dimethyl-4-(5-(3,3a-dihydro-2H-thieno-[3,2-c]pyridine-4,6-dithioxo)pentyloxy)-ethoxy]-2,2-di-
methyl-butyl}-3,3a-dihydro 3,3a-dihydro-2H-thieno-[3,2-c]pyridine-4,6-dithione

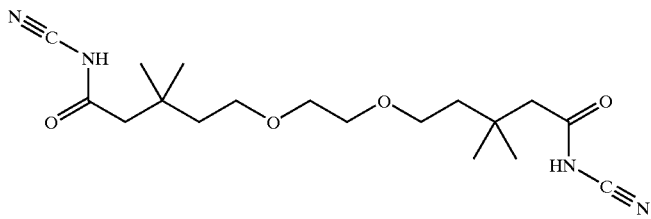

I-53:
5-[2-(3,3-Dimethyl-4-cyanocarbamoyl-butoxy)-ethoxy]-3,3-dimethyl-N-cyano-pentanoic acid-amide

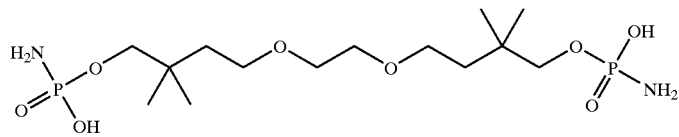

I-54:
Phosphoramidic acid mono-(4-{2-[4-(amino-hydroxy-phosphoryloxy)-3,3-dimethyl-butoxy]-ethoxy}-2,2-dimethyl-butyl) ester

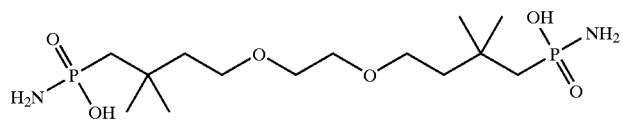

I-55:
{4-[2-(3,3-Dimethyl-4-phosphonamido-butoxy)-ethoxy]-2,2-dimethyl-butyl}-phosphonamide

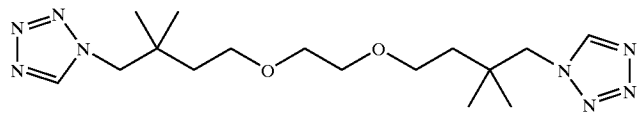

I-56:
1-{4-[2-(3,3-Dimethyl-5-{1H-tetrazol-1-yl}-butoxy)-ethoxy]-2,2-dimethyl-butyl}-1H-tetrazole

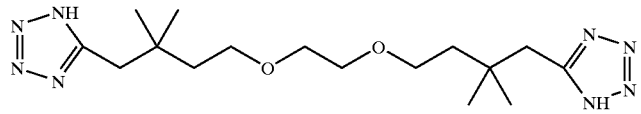

I-57:
5-{4-[2-(3,3-Dimethyl-5-{1H-tetrazol-5-yl}-butoxy)-ethoxy]-2,2-dimethyl-butyl}-1H-tetrazole

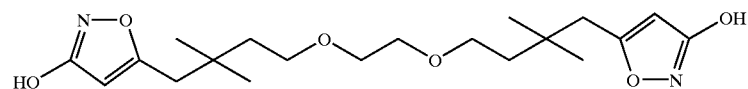

TABLE 1-continued

COMPOUNDS OF THE INVENTION

I-58:
5-{4-[2-(3,3-Dimethyl-5-{3-hydroxy-isoxazol-5-yl}-butoxy)-ethoxy]-2,2-dimethyl-butyl}-3-hydroxy-isoxazole

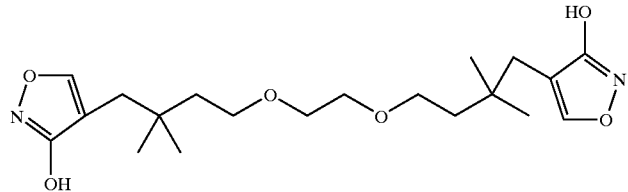

I-59:
4-{4-[2-(3,3-Dimethyl-5-{3-hydroxy-isoxazol-4-yl}-butoxy)-ethoxy]-2,2-dimethyl-butyl}-3-hydroxy-isoxazole

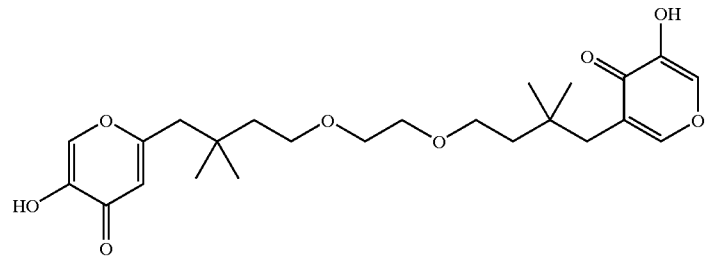

I-60:
2-{4-[2-(3,3-Dimethyl-5-{5-hydroxy-pyran-4-oxo-3-yl}-butyloxy)-ethoxy]-2,2-dimethyl-butyl}-5-hydroxy-pyran-4-one

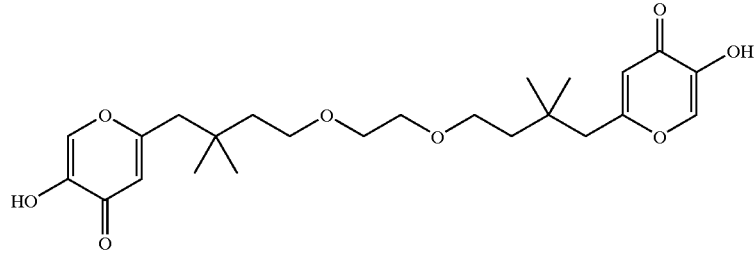

I-61:
2-{4-[2-(3,3-Dimethyl-5-{5-hydroxy-pyran-4-oxo-2-yl}-butyloxy)-ethoxy]-2,2-dimethyl-butyl}-5-hydroxy-pyran-4-one

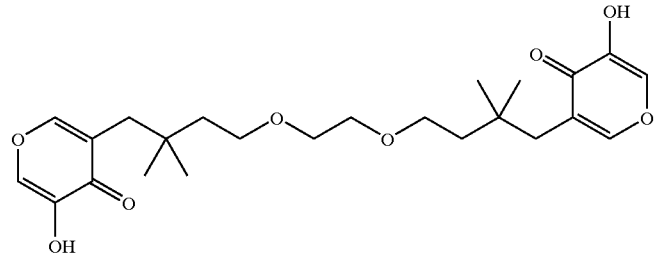

I-62:
3-{4-[2-(3,3-Dimethyl-5-{5-hydroxy-pyran-4-oxo-3-yl}-butyloxy)-ethoxy]-2,2-dimethyl-butyl}-5-hydroxy-pyran-4-one

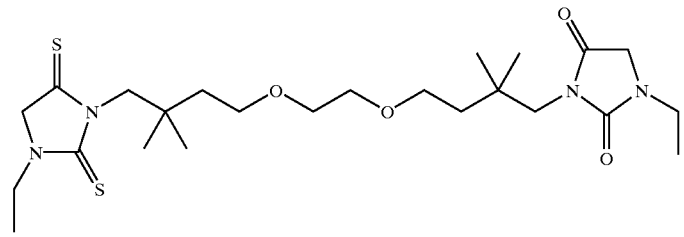

TABLE 1-continued

COMPOUNDS OF THE INVENTION

I-63:
1-Ethyl-3-(4-{2-[4-(3-ethyl-2,5-dithioxo-imidazolidin-1-yl)-3,3-dimethyl-butoxy]-ethoxy}-2,2-dimethyl-butyl)-imidazolidine-2,4-dione

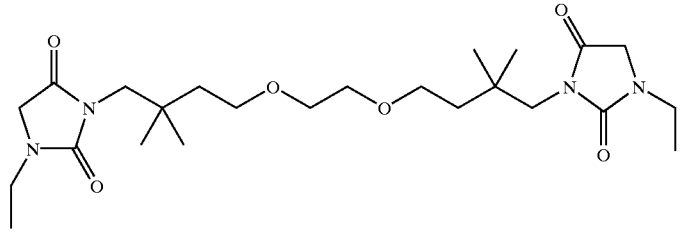

I-64:
1-Ethyl-3-(4-{2-[4-(3-ethyl-2,5-dioxo-imidazolidin-1-yl)-3,3-dimethyl-butoxy]-ethoxy}-2,2-dimethyl-butyl)-imidazolidine-2,4-dione

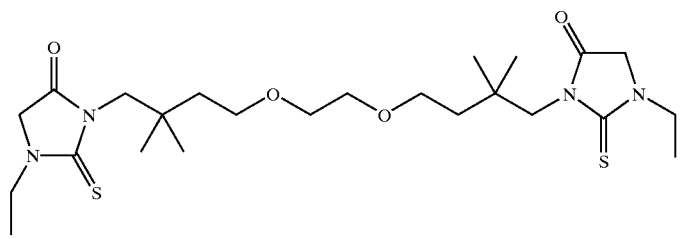

I-65:
1-Ethyl-3-(4-{2-[4-(3-ethyl-2-thioxo-4-oxo-imidazolidin-1-yl)-3,3-dimethyl-butoxy]-ethoxy}-2,2-dimethyl-butyl)-imidazolidine-2-thioxo-4-one

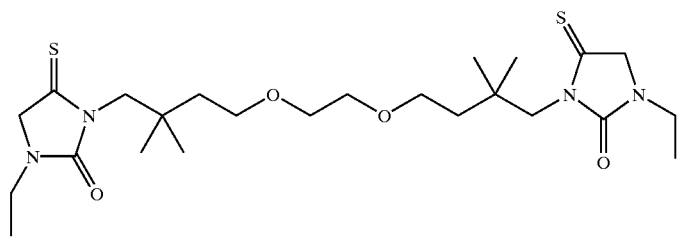

I-66;
1-Ethyl-3-(4-{2-[4-(3-ethyl-2-oxo-4-thioxo-imidazolidin-1-yl)-3,3-dimethyl-butoxy]-ethoxy}-2,2-dimethyl-butyl)-imidazolidine-2-oxo-4-thione

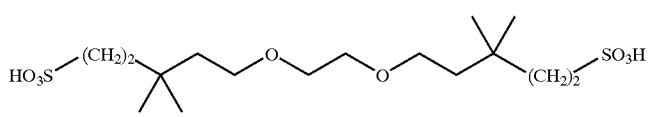

I-67:
3,3,3',3'-tetramethyl-5,5'-[ethylenebis(oxadiyl)]dipentane sulfonic acid

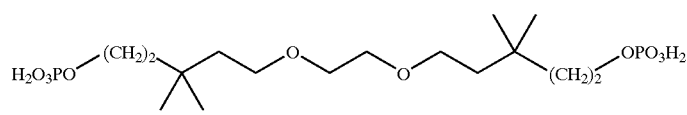

I-68:
Phosphoric acid mono-{1,1-dimethyl-3-[2-(3-methyl-3-phosphonooxy-butoxy)-ethoxy]-propyl}ester

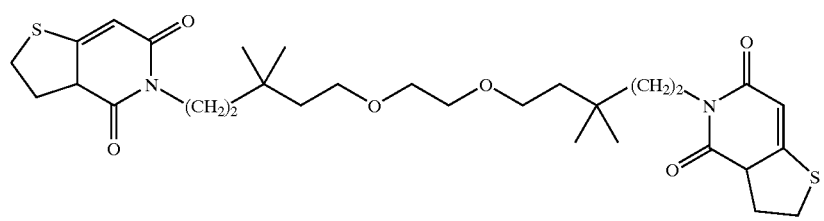

TABLE 1-continued

COMPOUNDS OF THE INVENTION

I-69:
5-(5-{2-[3,3-Dimethyl-5-(4,6-dioxo-2,3,3a,6-tetrahydro-4H-thieno[3,2-c]pyridin-5-yl)-pentyloxy]-ethoxy}-3,3-dimethyl-pentyl)-3,3a-dihydro-2H-thieno[3,2-c]pyridine-4,6-dione

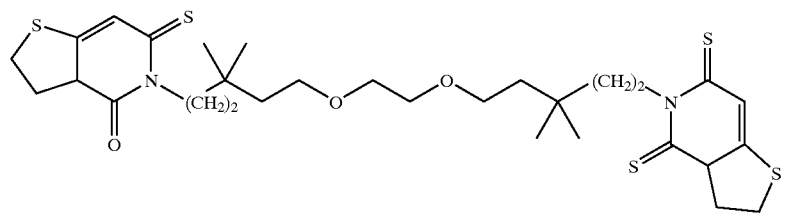

I-70:
5-(5-{2-[3,3-Dimethyl-5-(4,6-dithioxo-2,3,3a,6-tetrahydro-4H-thieno[3,2-c]pyridin-5-yl)-pentyloxy]-ethoxy}-3,3-dimethyl-pentyl)-3,3a-dihydro-2H-thieno[3,2-c]pyridine-4,6-dione

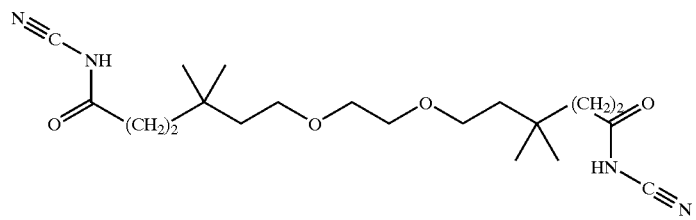

I-71:
6-[2-(3,3-Dimethyl-5-cyano-carbamoyl-butoxy)-ethoxy]-4,4-dimethyl-N-cyano-hexanoic acid-amide

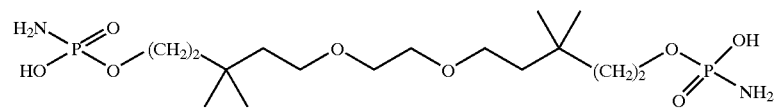

I-72:
Phosphoramidic acid mono-(5-{2-[5-(amino-hydroxy-phosphoryloxy)-3,3-dimethyl-pentyloxy]-ethoxy}-3,3-dimethyl-pentyl) ester

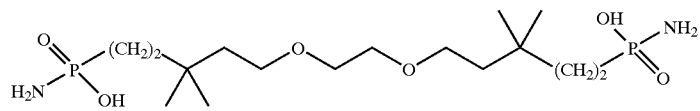

I-73:
{5-[2-(3,3-Dimethyl-5-phosphonamido-pentyloxy)-ethoxy]-3,3-dimethyl-pentyl}-phosphonamide

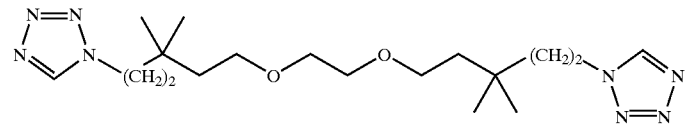

I-74:
1-{[2-(3,3-Dimethyl-5-tetrazol-1-yl-pentyloxy)-ethoxy]-3,3-dimethyl-pentyl}-1H-tetrazole

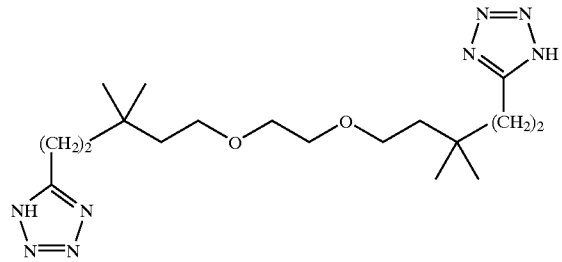

I-75:
5-{5-[2-(3,3-Dimethyl-5-tetrazol-1-yl-pentyloxy)-ethoxy]-3,3-dimethyl-pentyl}-1H-tetrazole TABLE 1-continued

COMPOUNDS OF THE INVENTION

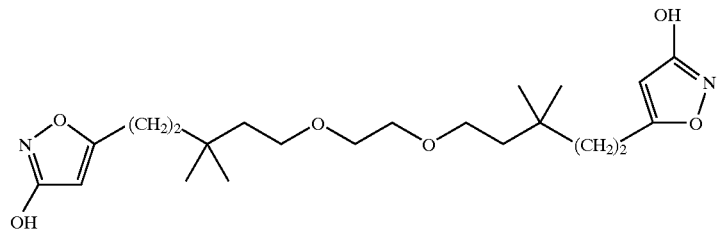

I-76:
5-{5-[2-(3,3-Dimethyl-5-{3-hydroxy-isoxazol-5-yl}-pentyloxy)-ethoxy]-3,3-dimethyl-pentyl}-isoxazol-3-ol

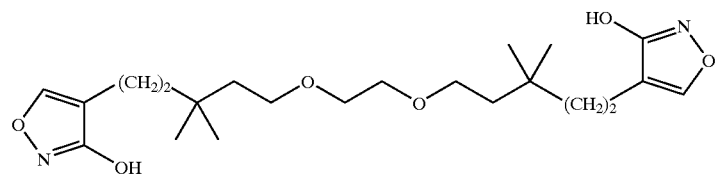

I-77:
4-{5-[2-(3,3-Dimethyl-5-{3-hydroxy-isoxazol-4-yl}-pentyloxy)-ethoxy]-3,3-dimethyl-pentyl}-isoxazol-3-ol

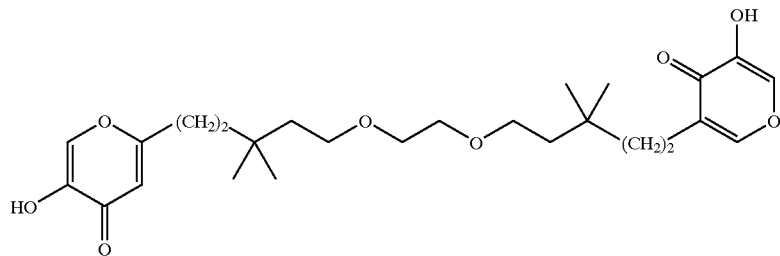

I-78:
3-{5-[2-(5-{5-Hydroxy-4-oxo-4H-pyran-2-yl}-3,3-dimethyl-pentyloxy)-3,3-dimethyl-pentyl]-5-hydroxy-pyran-4-one

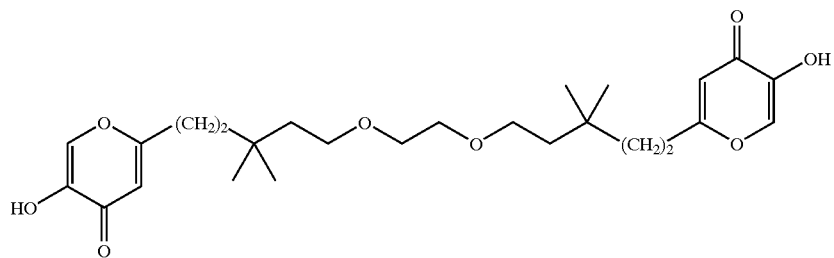

I-79:
2-{5-[2-(5-{5-Hydroxy-4-oxo-4H-pyran-2-yl}-3,3-dimethyl-pentyloxy)-3,3-dimethyl-pentyl]-5-hydroxy-pyran-4-one

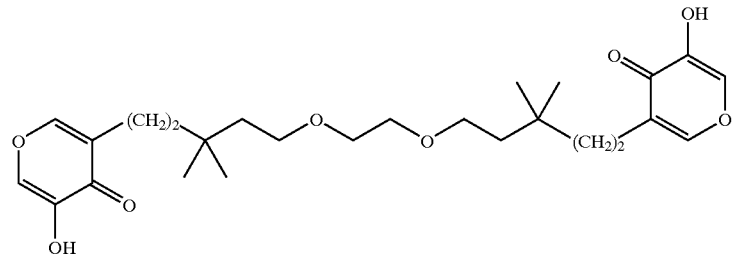

I-80:
3-{5-[2-(5-{5-Hydroxy-4-oxo-4H-pyran-3-yl}-3,3-dimethyl-pentyloxy)-3,3-dimethyl-pentyl]-5-hydroxy-pyran-4-one TABLE 1-continued

COMPOUNDS OF THE INVENTION

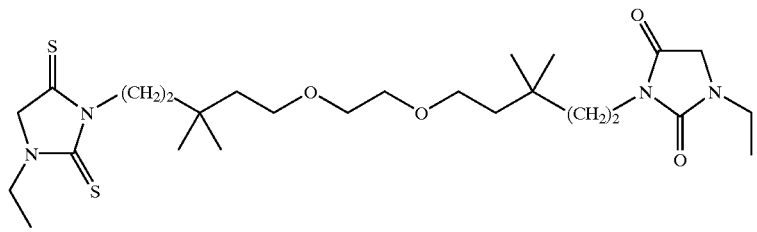

I-81:
1-Ethyl-3-(5-{2-[5-(3-ethyl-2,5-dithioxo-imidazolidin-1-yl)-3,3-dimethyl-pentyloxy]-ethoxy}-3,3-dimethyl-pentyl)-imidazolidine-2,4-dione

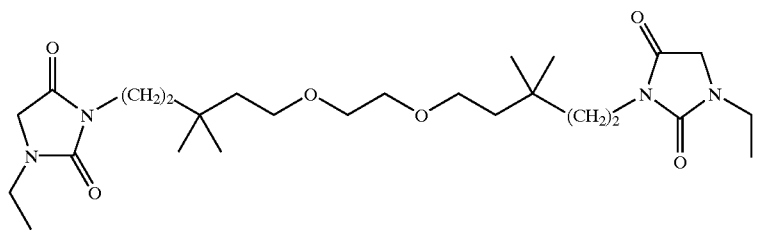

I-82:
1-Ethyl-3-(5-{2-[5-(3-ethyl-2,5-dioxo-imidazolidin-1-yl)-3,3-dimethyl-pentyloxy]-ethoxy}-3,3-dimethyl-pentyl)-imidazolidine-2,4-dione

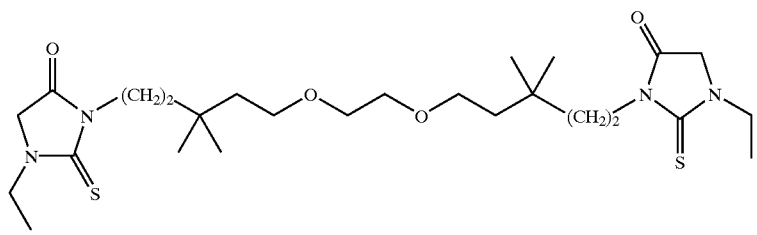

I-83:
1-Ethyl-3-(5-{2-[5-(1-ethyl-2-thioxo-5-oxo-imidazolidin-3-yl)-3,3-dimethyl-pentyloxy]-ethoxy}-3,3-dimethyl-pentyl)-imidazolidine-2-thioxo-4-one

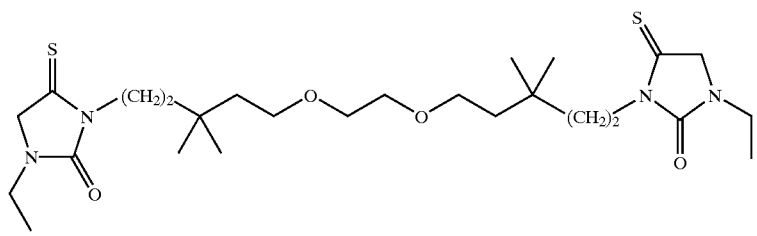

I-84:
1-Ethyl-3-(5-{2-[5-(1-ethyl-2-oxo-5-thioxo-imidazolidin-3-yl)-3,3-dimethyl-pentyloxy]-ethoxy}-3,3-dimethyl-pentyl)-imidazolidine-2-oxo-4-thione

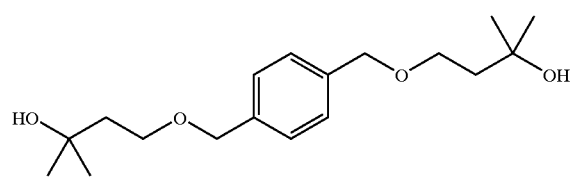

I-85:
4-[4-(3-Hydroxy-3-methyl-butoxymethyl)-benzyloxy]-2-methyl-butan-2-ol

TABLE 1-continued

COMPOUNDS OF THE INVENTION

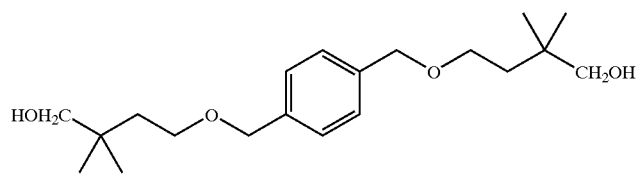

I-86:
4-[4-(4-Hydroxy-3,3-dimethyl-butoxymethyl)-benzyloxy]-2,2-dimethyl-butan-1-ol

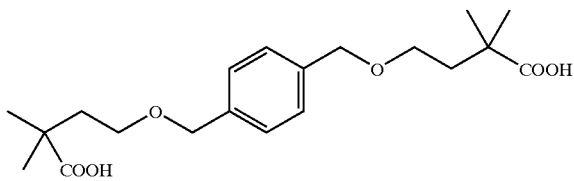

I-87:
4-[4-(3-Carboxyl-3,3-dimethyl-butoxymethyl)-benzyloxy]-2,2-dimethyl-butyric acid

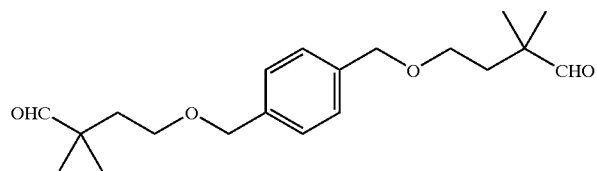

I-88:
4-[4-(4-Hydroxy-3,3-dimethyl-butoxymethyl-benxyloxy]-2,2-dimethyl-butanal

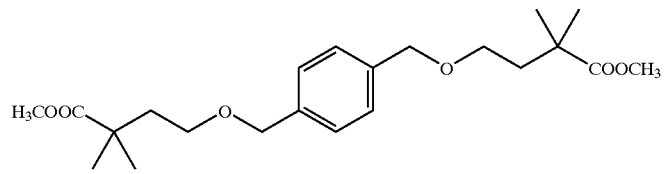

I-89:
4-[4-(3,3-Dimethyl-3-carboxymethyl-butoxymethyl)-benzyloxy]-2,2-dimethyl-butyric acid methyl ester

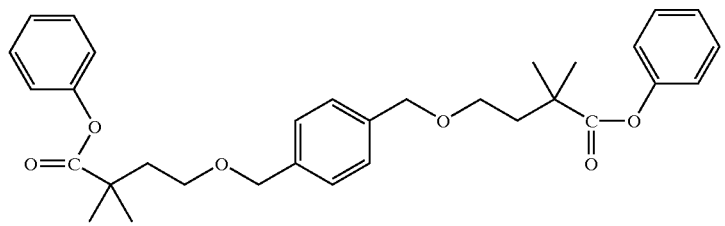

I-90:
2,2-Dimethyl-4-[4-(3-methyl-3-phenoxycarbonyl-butoxymethyl)-benzyloxy]-butyric acid phenyl ester

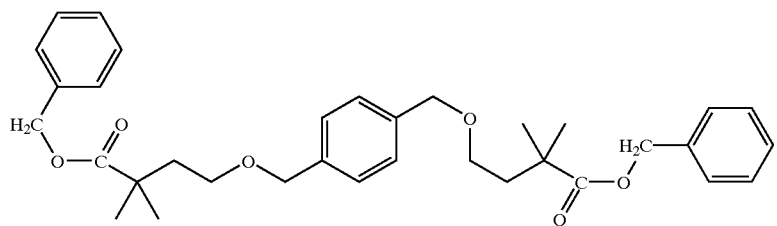

I-91:
4-[4-(3-Benzyloxycarbonyl-3-methyl-butoxymethyl)-benzyloxy]-2,2-dimethyl-butyric acid benzyl ester TABLE 1-continued

COMPOUNDS OF THE INVENTION

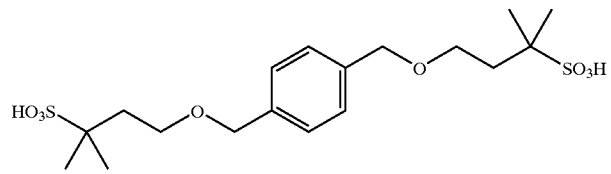

I-92:
2,2'-Dimethyl-4,4'-[vinylbis(oxadiyl)]dibutane-2-sulfonic acid

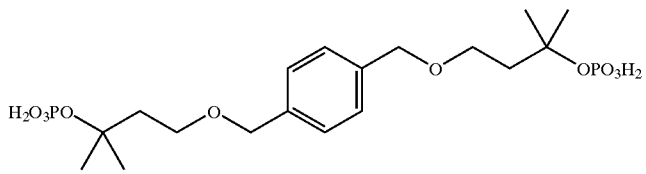

I-93:
Phosphoric acid mono-{1,1-dimethyl-3-[4-(3-methyl-3-phosphonooxy-butoxymethyl)-benzyloxy]-propyl}ester

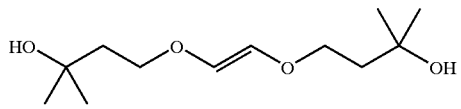

I-94:
2,2'-Dimethyl-4,4'-[vinylbis(oxadiyl)]dibutanol

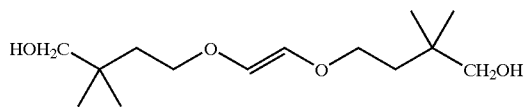

I-95:
4-[2-(4-Hydroxy-3,3-dimethyl-butoxy)-vinyloxy]-2,2-dimethyl-butan-1-ol

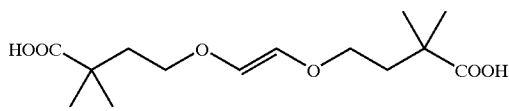

I-96:
4-[2-(3-Carboxyl-3,3-dimethyl-butoxy)-vinyloxy]-2,2-dimethyl-butyric acid

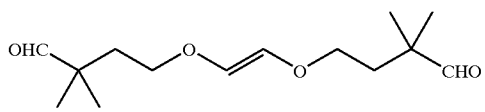

I-97:
4-[2-(4-Hydroxy-3,3-dimethyl-butoxy)-vinyloxy]-2,2-dimethyl-butanal

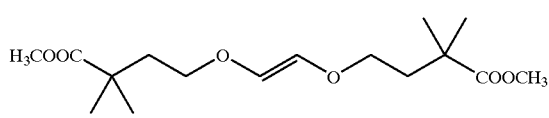

I-98:
4-[2-(3,3-Dimethyl-3-carboxymethyl-3-butoxy)-vinyloxy]-2,2-dimethyl-butyric acid methyl ester

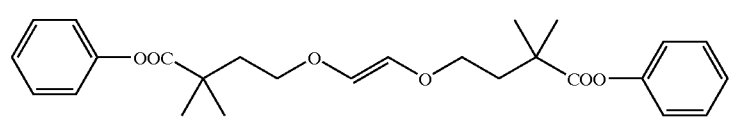

TABLE 1-continued

COMPOUNDS OF THE INVENTION

I-99:
2,2-Dimethyl-4-[2-(3-methyl-3-phenoxycarbonyl-butoxy)-vinyloxy]-butyric acid phenyl ester

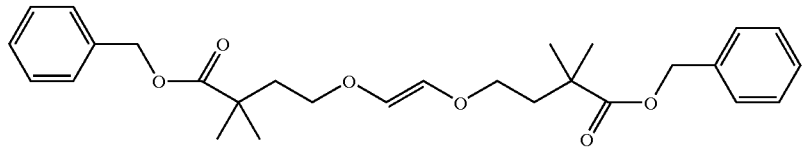

I-100:
2,2-Dimethyl-4-[2-(3-methyl-3-benzyloxycarbonyl-butoxy)-vinyloxy]-butyric acid benzyl ester

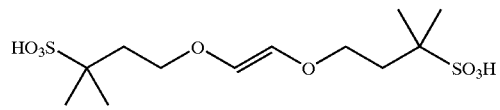

I-101:
4-[2-(3,3-Dimethyl-3-sulfono-butoxy)-vinyloxy]-2-methyl-butane-2-sulfonic acid

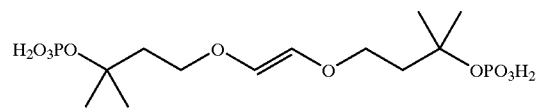

I-102:
Phosphoric acid mono-{3-[2-(3,3-dimethyl-butoxy)-vinyloxy]-1,1-dimethyl-propyl}ester

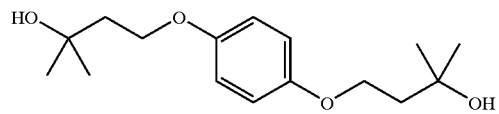

I-103:
4-[4-(3-Hydroxy-3-methyl-butoxy)-phenoxy]-2-methyl-butan-2-ol

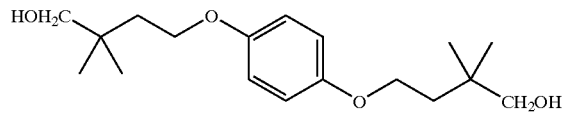

I-104:
4-[4-(4-Hydroxy-3,3-dimethyl-butoxy)-phenoxy]-2,2-dimethyl-butan-1-ol

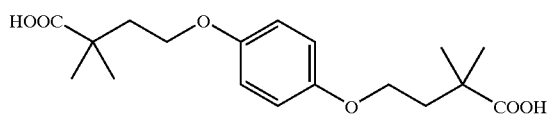

I-105:
4-[4-(3-Carboxyl-3,3-dimethyl-butoxy)-phenoxy]-2,2-dimethyl-butyric acid

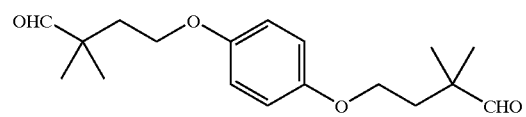

I-106:
4-[4-(4-Hydroxy-3,3-dimethyl-butoxy)-phenoxy]-2,2-dimethyl-butanal

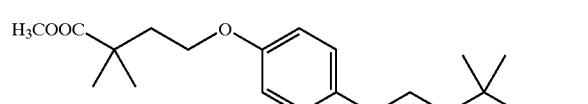

I-107:
4-[4-(3,3-Dimethyl-3-carboxymethyl-butoxy)-phenoxy]-2,2-dimethyl-butyric acid methyl ester TABLE 1-continued

COMPOUNDS OF THE INVENTION

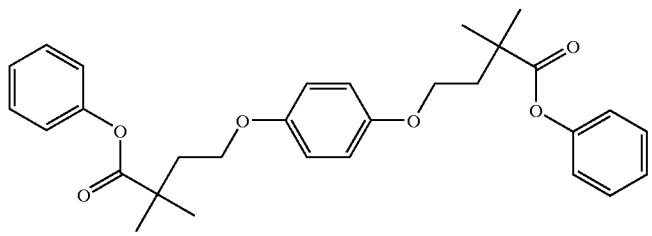

I-108:
2,2-Dimethyl-4-[4-(3-methyl-3-phenoxycarbonyl-butoxy)-phenoxy]-butyric acid phenyl ester

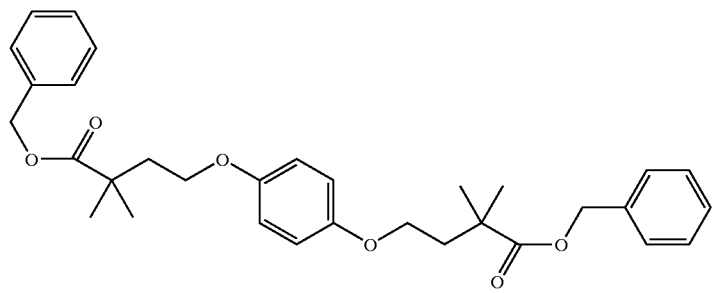

I-109:
4-[4-(3-Benzyloxycarbonyl-3-methyl-butoxy)-phenoxy]-2,2-dimethyl-butyric acid benzyl ester

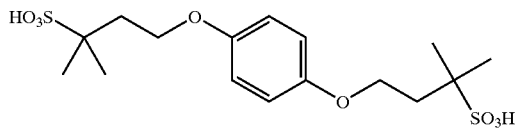

I-110:
4-[4-(3,3-Dimethyl-3-sulfono-butoxy)-phenoxy]-2-methyl-butane-2-sulfonic acid

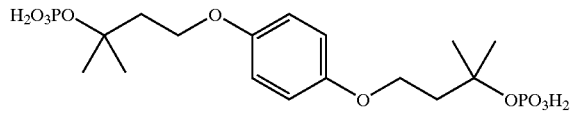

I-111:
4-[4-(3,3-Dimethyl-3-oxyphosphono-butoxy)-phenoxy]-2-methyl-butane-2-oxyphosphoric acid

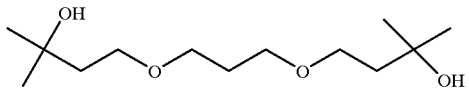

I-112:
4-[3-(3-Hydroxy-3-methyl-butoxy)-propoxy]-2-methyl-butan-2-ol

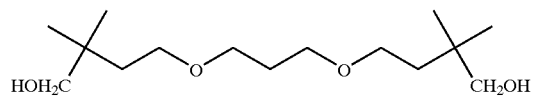

I-113:
4-[3-(4-Hydroxy-3,3-dimethyl-butoxy)-propoxy]-2,2-dimethyl-butan-1-ol

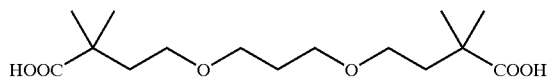

I-114:
4-[3-(3-Carboxy-3-methyl-butoxy)-propoxy]-2,2-dimethyl-butyric acid

TABLE 1-continued

COMPOUNDS OF THE INVENTION

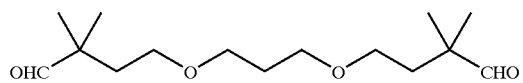

I-115:
4-[3-(3,3-Dimethyl-4-oxo-butoxy)-propoxy]-2,2-dimethyl-butanal

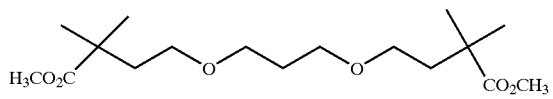

I:116:
4-[3-(3-Methoxycarbonyl-3-methyl-butoxy)-propoxy]-2,2-dimethyl-butyric acid methyl ester

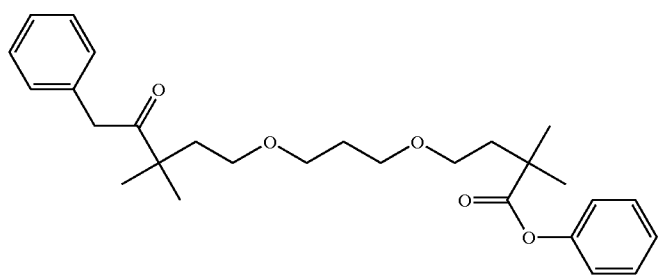

I-117:
4-[3-(3,3-Dimethyl-4-oxo-5-phenyl-pentyloxy)-propoxy]-2,2-dimethyl-butyric acid phenyl ester

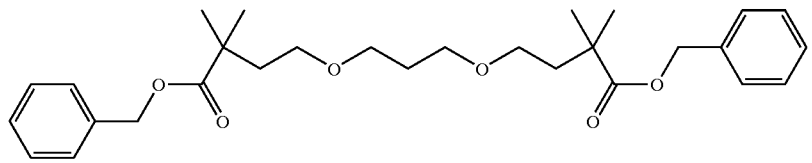

I-118:
4-[3-(3-Benzyloxycarbonyl-3-methyl-butoxy)-propoxy]-2,2-dimethyl-butyric acid benzyl ester

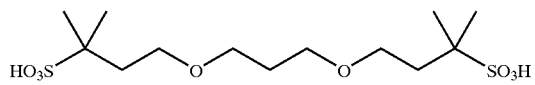

I-119:
2-Methyl-4-[3-(3-methyl-3-sulfo-butoxy)-propoxy]-butane-2-sulfonic acid

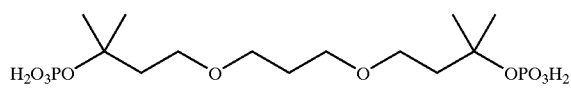

I-120:
Phosphoric acid mono-{1,1-dimethyl-3-[3-(3-methyl-3-phosphonooxy-butoxy)-propoxy]-propyl} ester

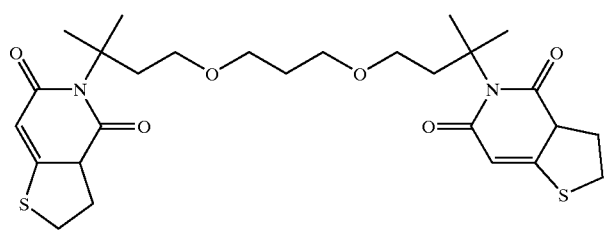

I-121:
1-Ethyl-3-(3-{3-[3-(4,6-dioxo-2,3,3a,6-tetrahydro-4H-thieno[3,2-c]pyridin-5-yl))-3-methyl-butoxy]-propoxy}-1,1-di-
methyl-propyl)-4,6-dioxo-2,3,3a,6-tetrahydro-4H-thieno[3,2-c]pyridin-5-yl-4,6-dione

TABLE 1-continued

COMPOUNDS OF THE INVENTION

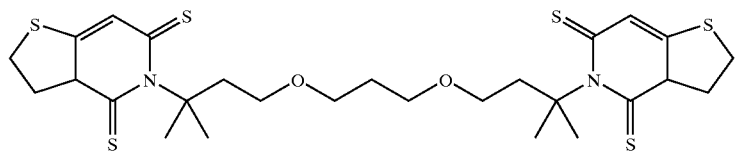

I-122:
1-Ethyl-3-(3-{3-[3-(4,6-dithioxo-2,3,3a,6-tetrahydro-4H-thieno[3,2-c]pyridin-5-yl))-3-methyl-butoxy]-propoxy}-1,1-dimethyl-propyl)-4,6-dioxo-2,3,3a,6-tetrahydro-4H-thieno[3,2-c]pyridin-5-yl-4,6-dithione

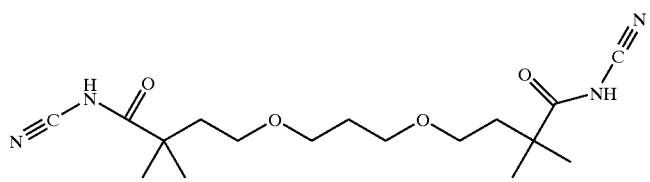

I-123:
2,2-Dimethyl-4-[3-(3-methyl-3-cyano-carbamoyl-butoxy)-propoxy]-N-cyano-butyric acid-amide

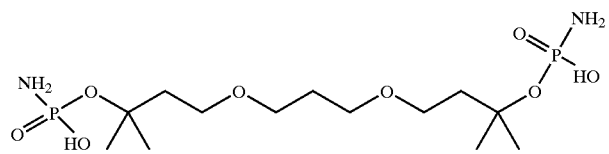

I-124:
Phosphoramidic acid mono-(3-{3-[3-(amino-hydroxy-phosphoryloxy)-3-methyl-butoxy]-propoxy}-1,1-dimethyl-propyl} ester

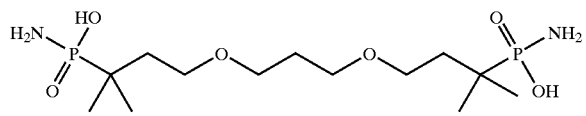

I-125:
{1,1-Dimethyl-3-[3-(3-(methyl-3-phosponamido-butoxy)-propoxy]-propyl}-phosphonamide

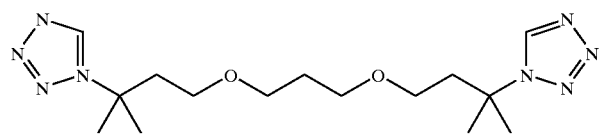

I-126:
1-{3-[3-(3-Methyl-3-tetrazol-1-yl-butoxy)-propoxy]-1,1-dimethyl-propyl}-1H-tetrazole

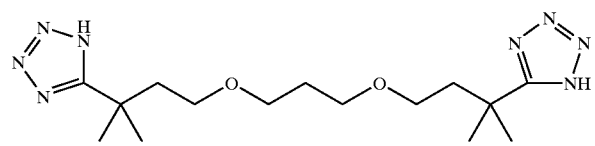

I-127:
5-{3-[3-(3-Methyl-3-tetrazol-5-yl-butoxy)-propoxy]-1,1-dimethyl-propyl}-(1H)-tetrazole

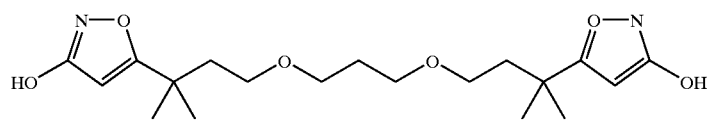

I-128:
5-{3-[3-(3-Methyl-3-(3-methyl-isoxazol-5-yl)-butoxy)-propoxy]-1,1-dimethyl-propyl}-3-methyl-isoxazole TABLE 1-continued

COMPOUNDS OF THE INVENTION

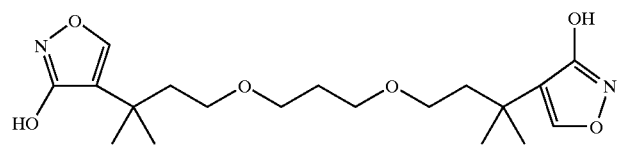

I-129:
4-{3-[3-(3-Methyl-3-(3-methyl-isoxazol-4-yl)-butoxy)-propoxy]-1,1-dimethyl-propyl}-3-methyl-isoxazole

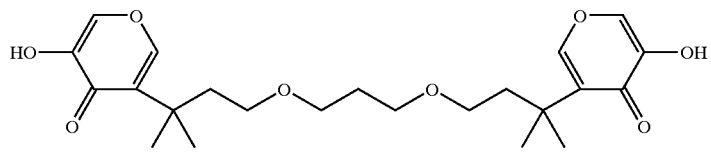

I-130:
3-{3-[3-(3-Methyl-3-(5-hydroxy-pyran-3-yl-4-one)-butoxy)-propoxy]-1,1-dimethyl-propyl}-5-hydroxy-pyran-4-one

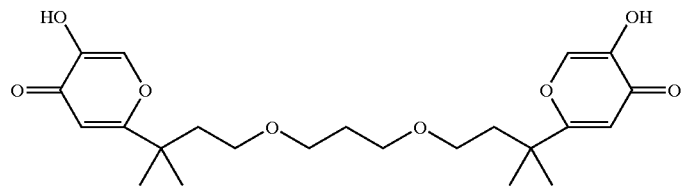

I-131:
2-{3-[3-(3-Methyl-3-(5-hydroxy-pyran-2-yl-4-one)-butoxy)-propoxy]-1,1-dimethyl-propyl}-5-hydroxy-pyran-4-one

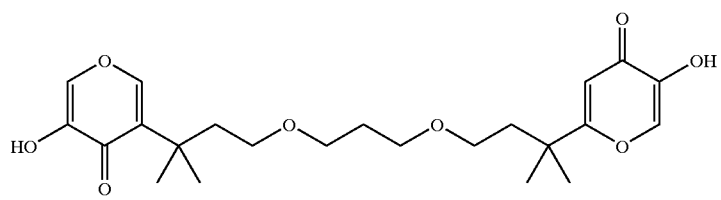

I-132:
3-{3-[3-(3-Methyl-3-(5-hydroxy-pyran-2-yl-4-one)-butoxy)-propoxy]-1,1-dimethyl-propyl}-5-hydroxy-pyran-4-one

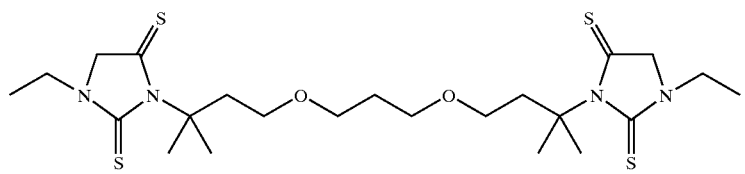

I-133:
1-Ethyl-3-(3-{3-[3-(3-ethyl-2,5-dithioxo-imidazolidin-1-yl)-3-methyl-butoxy]-propoxy}-1,1-dimethyl-propyl)-imidazolidine-2,4-dithione

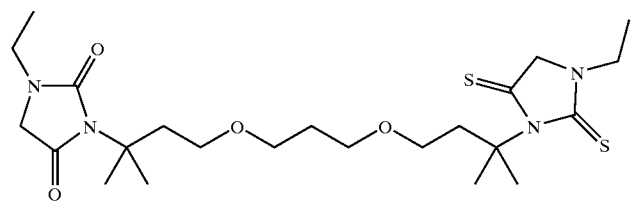

I-134:
1-Ethyl-3-(3-{3-[3-(3-ethyl-2,5-dioxo-imidazolidin-1-yl)-3-methyl-butoxy]-propoxy}-1,1-dimethyl-propyl)-imidazolidine-2,4-dithione TABLE 1-continued

COMPOUNDS OF THE INVENTION

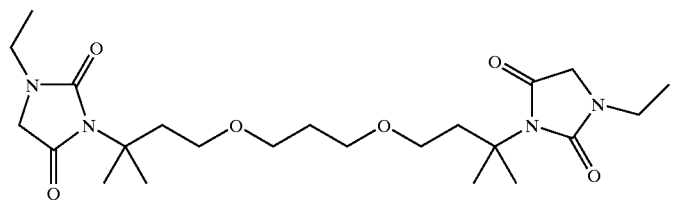

I-135:
1-Ethyl-3-(3-{3-[3-(3-ethyl-2,5-dioxo-imidazolidin-1-yl)-3-methyl-butoxy]-propoxy}-1,1-dimethyl-propyl)-imidazolidine-2,4-dione

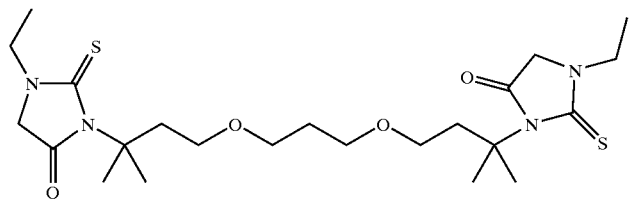

I-136:
1-Ethyl-3-(3-{3-[3-(3-ethyl-2-thioxo-5-oxo-imidazolidin-1-yl)-3-methyl-butoxy]-propoxy}-1,1-dimethyl-propyl)-imidazolidine-2-thioxo-4-one

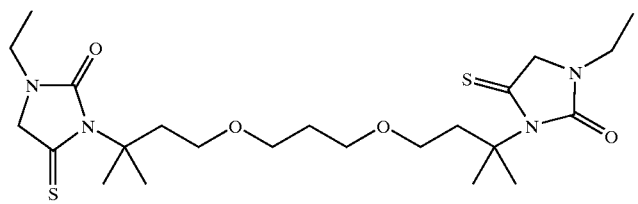

I-137:
1-Ethyl-3-(3-{3-[3-(3-ethyl-2-oxo-5-thioxo-imidazolidin-1-yl)-3-methyl-butoxy]-propoxy}-1,1-dimethyl-propyl)-imidazolidine-2-oxo-4-thione

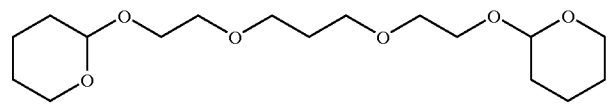

I-138:
1-(2-Tetrahydropyranyloxy)-2-{2-[2-(2-tetrahydropyranyloxy)-ethoxy]-propoxy}ethane

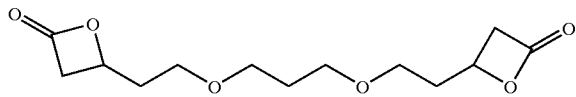

I-139:
4-{2-[3-(Oxetan-4-yl-2-one)-propoxy-propoxy]-ethyl}-oxetan-2-one

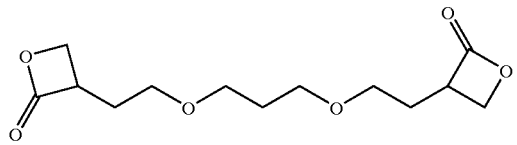

I-140:
3-{2-[3-(Oxetan-3-yl-2-one)-propoxy-propoxy]-ethyl}-oxetan-2-one

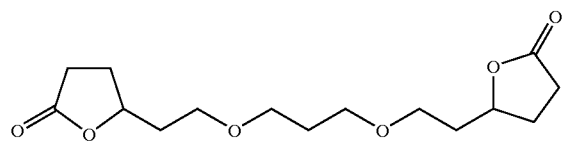

I-141:

TABLE 1-continued

COMPOUNDS OF THE INVENTION

5-{2-[3-(Dihydro-furan-5-yl-2-one)-propoxy-propoxy]-ethyl}-dihydro-furan-2-one

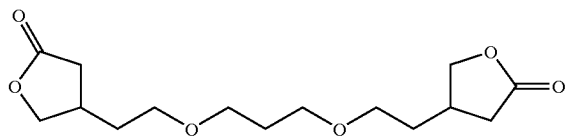

I-142:
4-{2-[3-(Dihydro-furan-4-yl-2-one)-propoxy-propoxy]-ethyl}-dihydro-furan-2-one

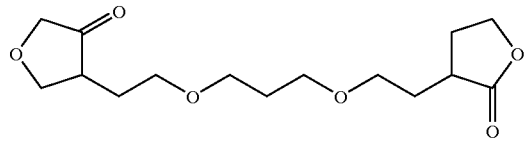

I-143:
3-{2-[3-(Dihydro-furan-3-yl-2-one)-propoxy-propoxy]-ethyl}-dihydro-furan-2-one

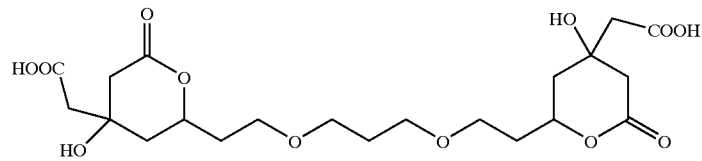

I-144:
[2-(2-{3-[2-(4-Carboxymethyl-4-hydroxy-6-oxo-tetrahydro-pyran-2-yl)-ethoxy]-propoxy}-ethyl)-4-hydroxy-6-oxo-tetrahydro-pyran-4-yl]-acetic acid

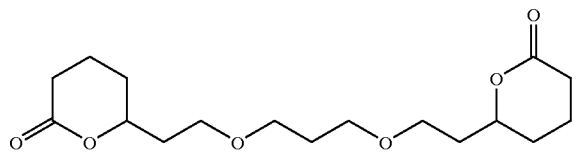

I-145:
2,2'-[Propylenebis(oxadiyl)]diethane-6-δ-valerolactone

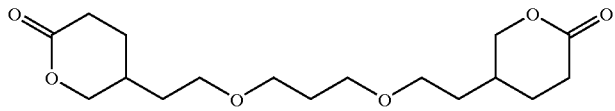

I-146:
2,2'-[Propylenebis(oxadiyl)]diethane-5-δ-valerolactone

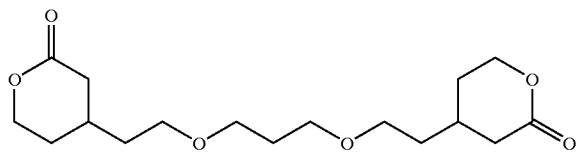

I-147:
2,2'-[Propylenebis(oxadiyl)]diethane-4-δ-valerolactone

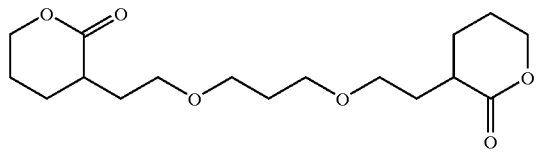

I-148:
2,2'-[Propylenebis(oxadiyl)]diethane-3-δ-valerolactone

TABLE 1-continued

COMPOUNDS OF THE INVENTION

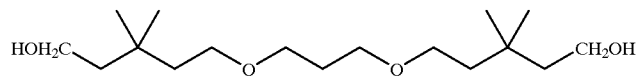

I-149:
5-[3-(5-Hydroxy-3,3-dimethyl-pentyloxy)-propoxy]-3,3-dimethyl-pentan-1-ol

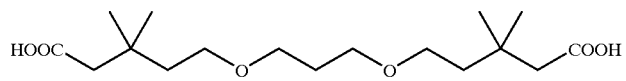

I-150:
5-[3-(4-Carboxy-3,3-dimethyl-butoxy)-propoxy]-3,3-dimethyl-pentanoic acid

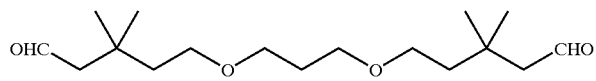

I-151:
5-[3-(3,3-Dimethyl-5-oxo-pentyloxy)-propoxy]-3,3-dimethyl-pentanal

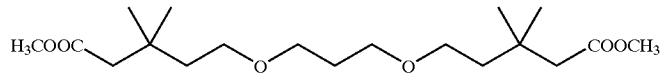

I-152:
5-[3-(4-Methoxycarbonyl-3,3-dimethyl-butoxy)-propoxy]-3,3-dimethyl-pentanoic acid methyl ester

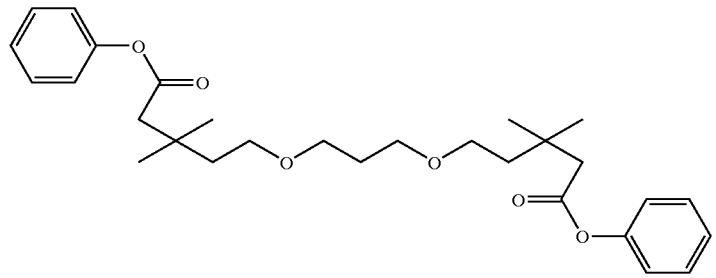

I-153:
5-[3-(3,3-Dimethyl-4-phenoxycarbonyl-butoxy)-propoxy]-3,3-dimethyl-pentanoic acid phenyl ester

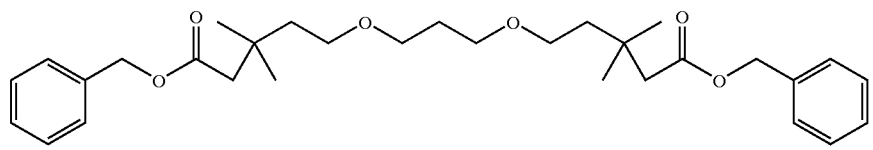

I-154:
5-[3-(4-Benzyloxycarbonyl-3,3-dimethyl-butoxy)-propoxy]-3,3-dimethyl-pentanoic acid benzyl ester

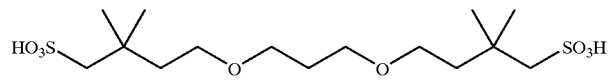

I-155:
4-[3-(3,3-Dimethyl-pentyloxy)-propoxy]-2,2-dimethyl-butane-1-sulfonic acid

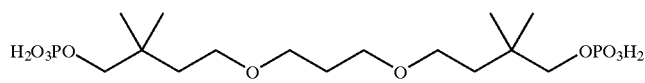

I-156:
Phosphoric acid mono-{4-[3-(3,3-dimethyl-4-phosphonooxy-butoxy)-propoxy]-2,2-dimethyl-butyl}ester TABLE 1-continued

COMPOUNDS OF THE INVENTION

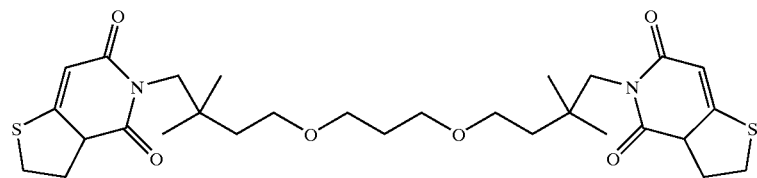

I-157:
5-{4-[3-(3,3-Dimethyl-4-(5-(3,3a-dihydro-2H-thieno-[3,2-c]pyridine-4,6-dioxo)pentyloxy)-propoxy]-2,2-di-
methyl-butyl}-3,3a-dihydro 3,3a-dihydro-2H-thieno-[3,2-c]pyridine-4,6-dione

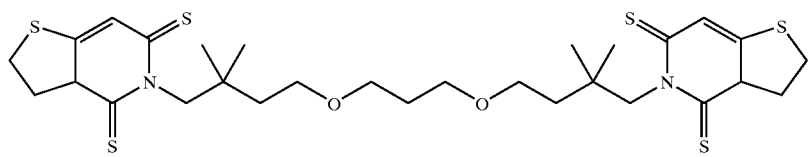

I-158:
5-{4-[3-(3,3-Dimethyl-4-(5-(3,3a-dihydro-2H-thieno-[3,2-c]pyridine-4,6-dithioxo)pentyloxy)-propoxy]-2,2-dimethyl-butyl}- 3,3a-di-
hydro 3,3a-dihydro-2H-thieno-[3,2-c]pyridine-4,6-dithione

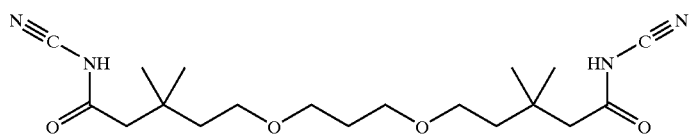

I-159:
5-[3-(3,3-Dimethyl-4-cyano-carbamoyl-butoxy)-propoxy]-3,3-dimethyl-N-cyano-pentanoic acid-amide

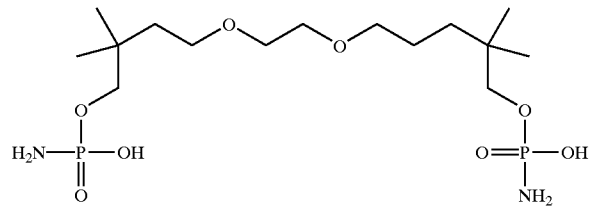

I-160:
Phosphoramidic acid mono-(5-{2-[4-(amino-hydroxy-phosphoryloxy)-3,3-dimethyl-butoxy]-ethoxy}-2,2-dimethyl-pentyl) ester

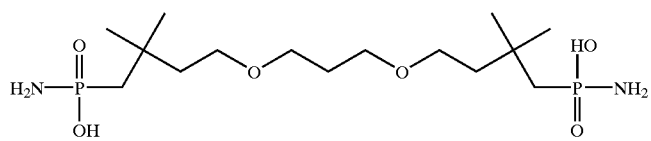

I-161:
{4-[3-(3,3-Dimethyl-4-phosponamido-butoxy)-propoxy]-2,2-dimethyl-butyl}-phosphonamide

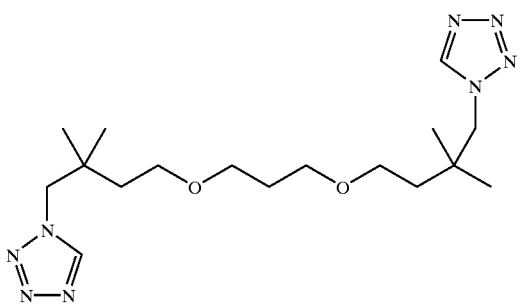

I-162:
1-{4-[3-(3,3-Dimethyl-5-(1H-tetrazol-1-yl)-butoxy)-propoxy]-2,2-dimethyl-butyl}-1H-tetrazole TABLE 1-continued
COMPOUNDS OF THE INVENTION
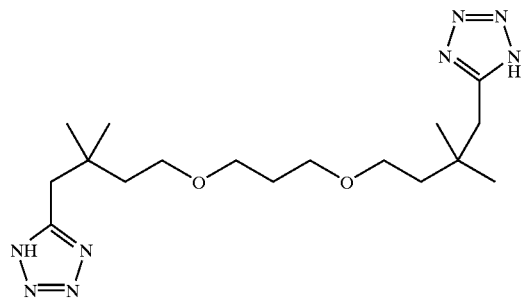
I-163:
5-{4-[3-(3,3-Dimethyl-5-(1H-tetrazol-5-yl)-butoxy)-propoxy]-2,2-dimethyl-butyl}-1H-tetrazole
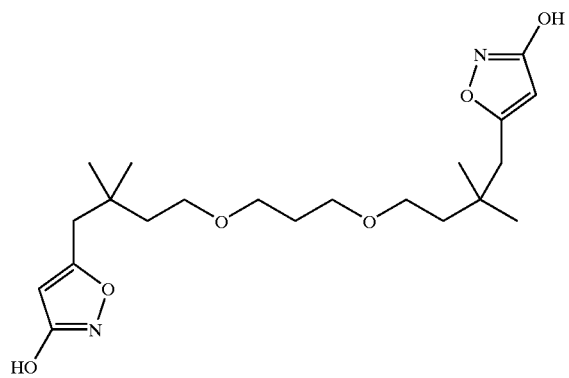
I-164:
5-{4-[3-(3,3-Dimethyl-5-(3-hydroxy-isoxazol-5-yl)-butoxy)-propoxy]-2,2-dimethyl-butyl}-3-hydroxy-isoxazole
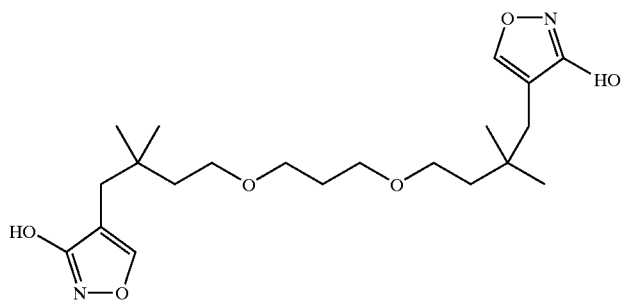
I-165:
4-{4-[3-(3,3-Dimethyl-5-(3-hydroxy-isoxazol-4-yl)-butoxy)-propoxy]-2,2-dimethyl-butyl}-3-hydroxy-isoxazole
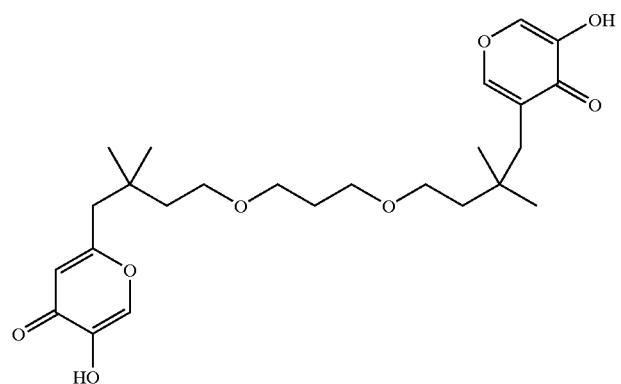

TABLE 1-continued

COMPOUNDS OF THE INVENTION

I-166:
2-{4-[3-(3,3-Dimethyl-4-{5-hydroxy-pyran-4-oxo-3-yl}-butyloxy)-propoxy]-2,2-dimethyl-butyl}-5-hydroxy-pyran-4-one

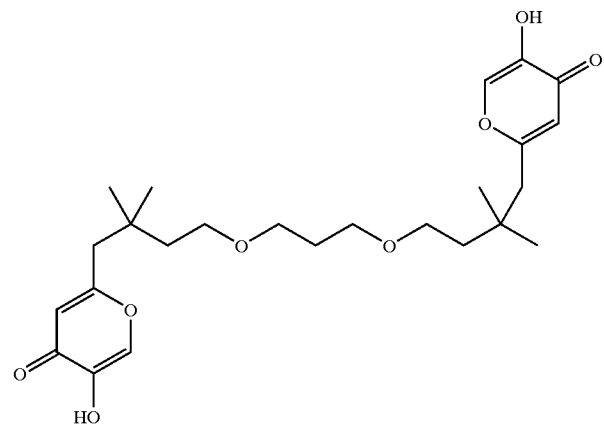

I-167:
2-{4-[3-(3,3-Dimethyl-4-{5-hydroxy-pyran-4-oxo-2-yl}-butyloxy)-propoxy]-2,2-dimethyl-butyl}-5-hydroxy-pyran-4-one

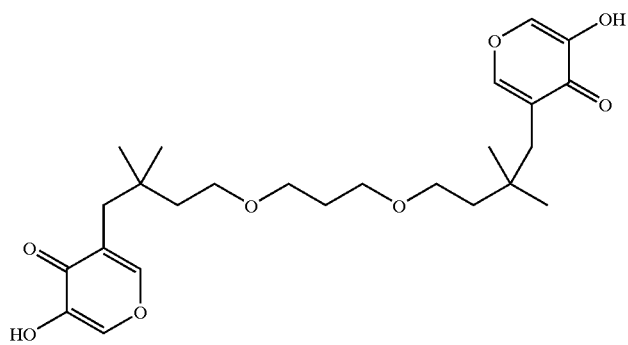

I-168:
3-{4-[3-(3,3-Dimethyl-4-{5-hydroxy-pyran-4-oxo-3-yl}-butyloxy)-propoxy]-2,2-dimethyl-butyl}-5-hydroxy-pyran-4-one

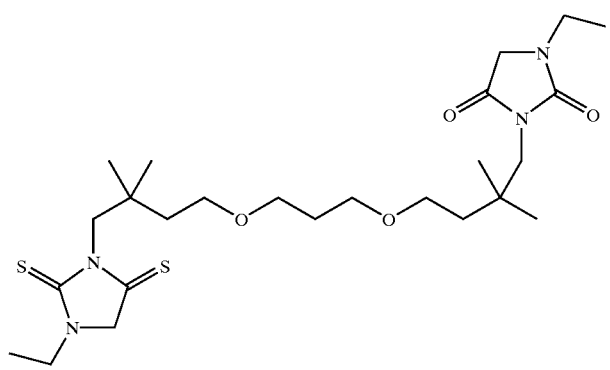

I-169:
1-Ethyl-3-(4-{3-[4-(3-ethyl-2,5-dithioxo-imidazolidin-1-yl)-3,3-dimethyl-butoxy]-propoxy}-2,2-dimethyl-butyl)-imidazolidine-2,4-dione TABLE 1-continued

COMPOUNDS OF THE INVENTION

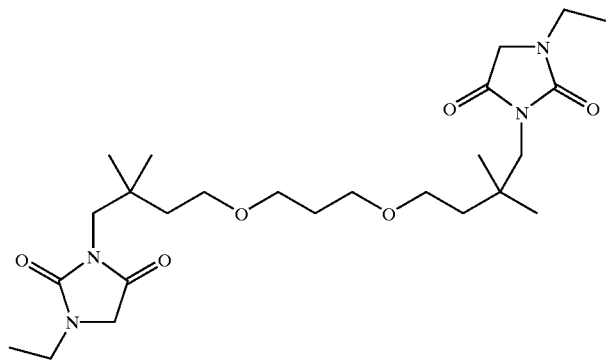

I-170:
1-Ethyl-3-(4-{3-[4-(3-ethyl-2,5-oxo-imidazolidin-1-yl)-3,3-dimethyl-butoxy]-propoxy}-2,2-dimethyl-butyl)-imidazolidine-2,4-dio

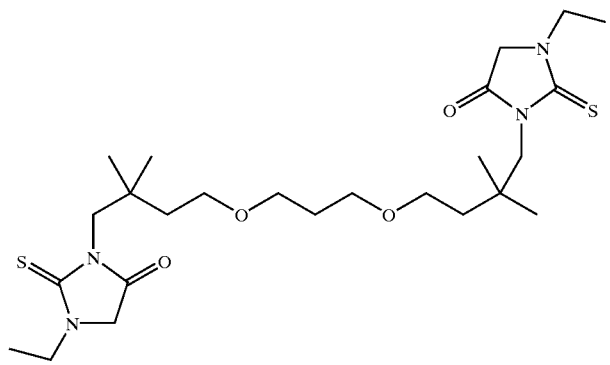

I-171:
1-Ethyl-3-(4-{3-[4-(3-ethyl-2-thioxo-5-oxo-imidazolidin-1-yl)-3,3-dimethyl-butoxy]-propoxy}-2,2-dimethyl-butyl)-imidazolidine-2-thioxo-4-one

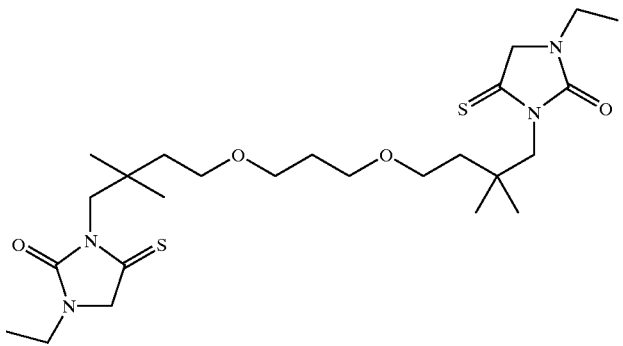

I-172:
1-Ethyl-3-(4-{3-[4-(3-ethyl-2-oxo-5-thioxo-imidazolidin-1-yl)-3,3-dimethyl-butoxy]-propoxy}-2,2-dimethyl-butyl)-imidazolidine-2-oxo-4-thione

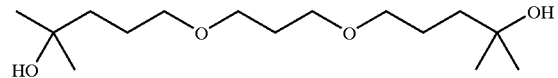

I-173:
5-[3-(4-Hydroxy-4-methyl-pentyloxy)-propoxy]-2-methyl-pentan-2-ol

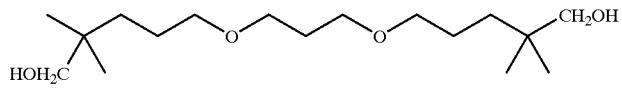

I-174:
5-[3-(5-Hydroxy-4,4-dimethyl-pentyloxy)-propoxy]-2,2-dimethyl-pentan-1-ol TABLE 1-continued

COMPOUNDS OF THE INVENTION

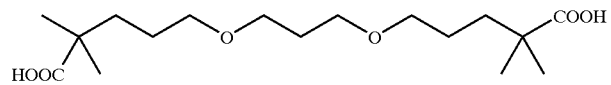

I-175:
5-[3-(4-Carboxy-4-methyl-pentyloxy)-propoxy]-2,2-dimethyl-pentanoic acid

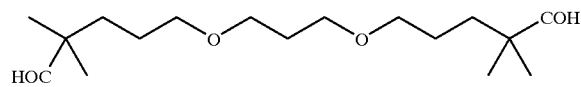

I-176:
5-[3-(4,4-Dimethyl-5-oxo-pentyloxy)-propoxy]-2,2-dimethyl-pentanal

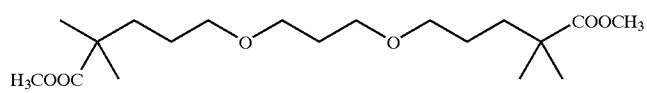

I-177:
5-[3-(4-Methoxycarbonyl-4-methyl-pentyloxy)-propoxy]-2,2-dimethyl-pentanoic acid methyl ester

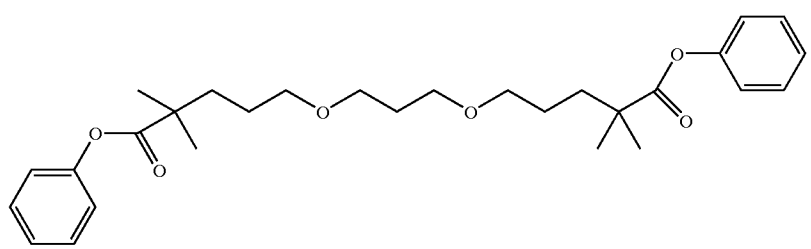

I-178:
5-[3-(4,4-Dimethyl-5-oxo-6-phenyl-hexyloxy)-propoxy]-2,2-dimethyl-pentanoic acid phenyl ester

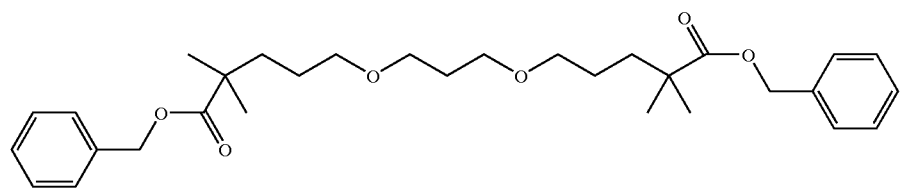

I-179:
4-{3-[1-(2-Benzyloxycarbonyl-2-methyl-propyl)-vinyloxy]-propoxy}-2,2-dimethyl-pent-4-enoic acid benzyl ester

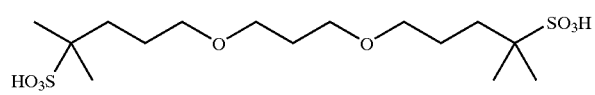

I-180:
2-Methyl-5-[3-(4-methyl-4-sulfo-pentyloxy)-propoxy]-pentane-2-sulfonic acid

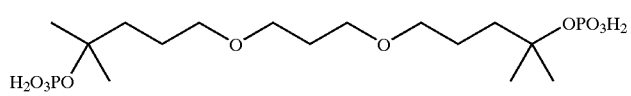

I-181:
Phosphoric acid mono-{1,1-dimethyl-4-[3-(4-methyl-4-phosphonooxy-pentyloxy)-propoxy]-butyl}ester TABLE 1-continued

COMPOUNDS OF THE INVENTION

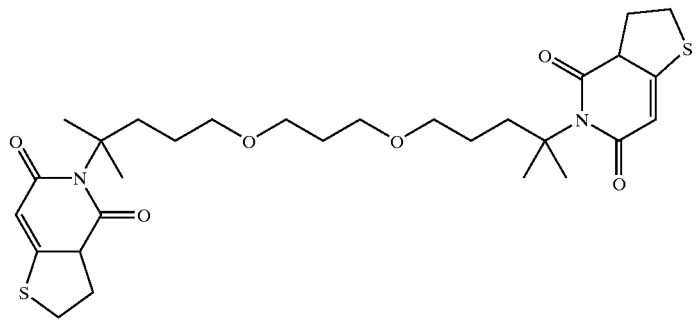

I-182:
5-(5-{3-[3,3-Dimethyl-5-(4,6-dioxo-2,3,3a,6-tetrahydro-4H-thieno[3,2-c]pyridin-5-yl)-pentyloxy]-propoxy}-3,3-di-methyl-pentyl)-3,3a-dihydro-2H-thieno[3,2-c]pyridine-4,6-dione

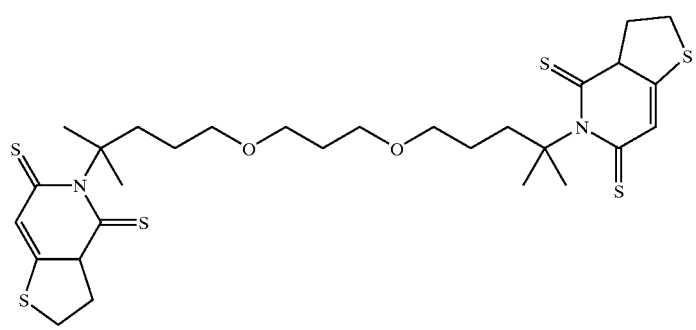

I-183:
5-(5-{3-[3,3-Dimethyl-5-(4,6-dithioxo-2,3,3a,6-tetrahydro-4H-thieno[3,2-c]pyridin-5-yl)-pentyloxy]-propoxy}-3,3-di-methyl-pentyl)-3,3a-dihydro-2H-thieno[3,2-c]pyridine-4,6-dithione

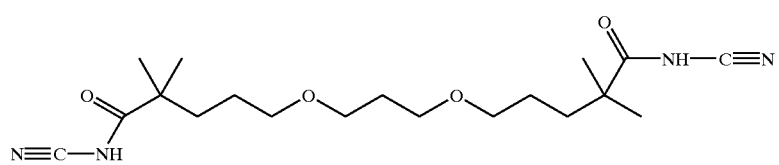

I-184:
5-{3-[4-N-Cyano-carbamoyl-4-methyl-pentyloxy)-propoxy]-2,2-dimethyl-N-cyano-pentanoic acid-amide

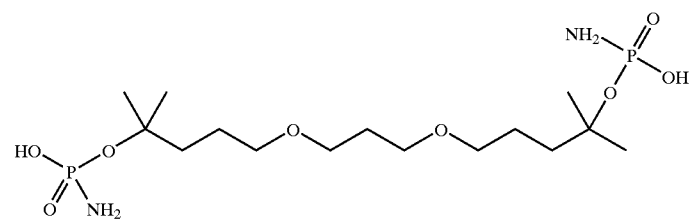

I-185:
Phosphoramidic acid mono-[3-(3-{1-[2-(amino-hydroxy-phosphoryloxy)-2-methyl-propyl]-vinyloxy}-propoxy)-1,1-dimethyl-but-3-enyl] ester

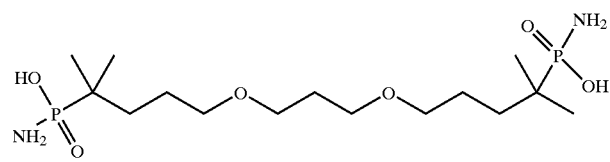

I-186:
{1,1-Dimethyl-4-[3-(4-methyl-4-phosphonamido-pentyloxy)-propoxy]-butyl}-phosphonamide TABLE 1-continued

COMPOUNDS OF THE INVENTION

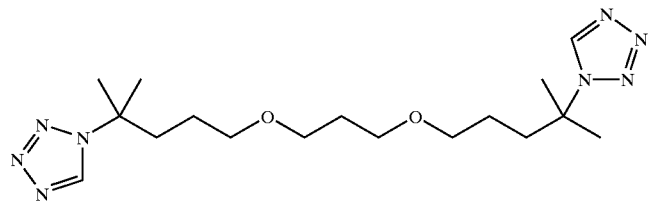

I-187:
1-{4-[3-(4-{1H-tetrazol-1-yl}-4-methyl-pentyloxy)-propoxy]-1,1-dimethyl-butyl}-1H-tetrazol

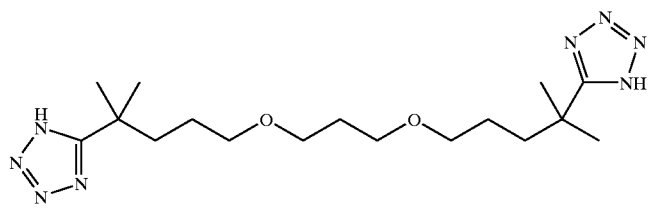

I-188:
5-{4-[3-(4-{1H-Tetrazol-5-yl}-4-methyl-pentyloxy)-propoxy]-1,1-dimethyl-butyl}-1H-tetrazole

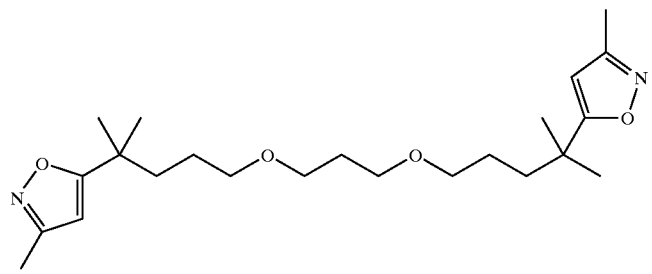

I-189:
5-{4-[3-(4-{3-Methyl-isoxazol-5-yl}-4-methyl-pentyloxy)-propoxy]-1,1-dimethyl-butyl}-3-methyl-isoxazole

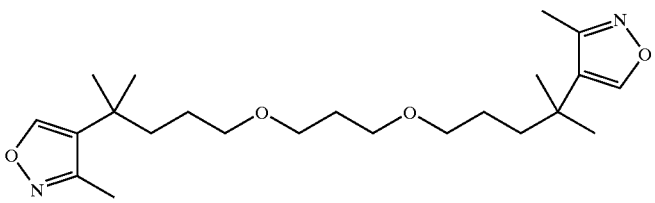

I-190:
4-{4-[3-(4-{3-Methyl-isoxazol-4-yl}-4-methyl-pentyloxy)-propoxy]-1,1-dimethyl-butyl}-3-methyl-isoxazole

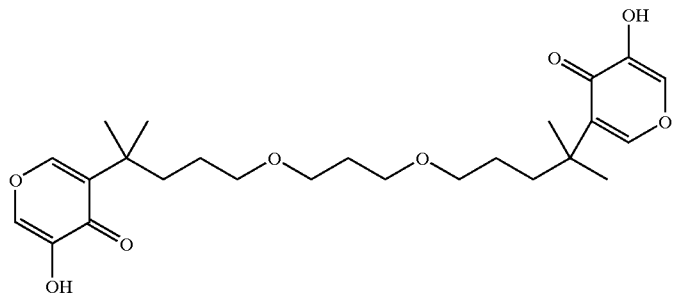

I-191:
3-{4-[3-(4-{5-Hydroxy-4-oxo-pyran-3-yl}-4-methyl-pentyloxy)-propoxy]-1,1-dimethyl-butyl}-5-hydroxy-pyran-4-one TABLE 1-continued

COMPOUNDS OF THE INVENTION

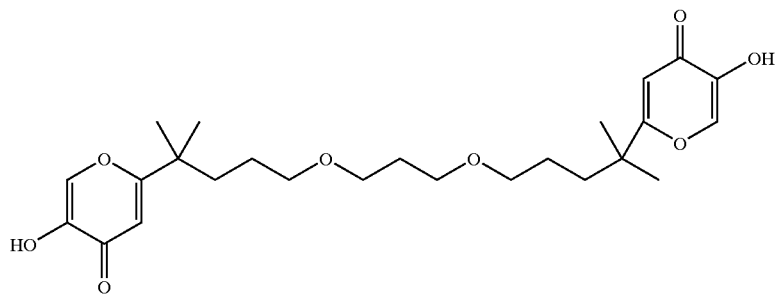

I-192:
2-{4-[3-(4-{5-Hydroxy-4-oxo-pyran-2-yl}-4-methyl-pentyloxy)-propoxy]-1,1-dimethyl-butyl}-5-hydroxy-pyran-4-one

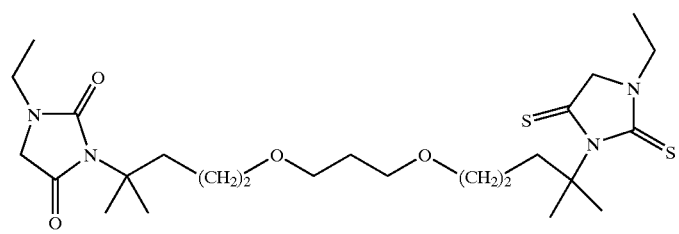

I-193:
1-Ethyl-3-(4-{3-[4-(3-ethyl-2,5-dithioxo-imidazolidin-1-yl)-4-methyl-pentyloxy]-propoxy}-1,1-dimethyl-butyl)-imidazolidine-2,4-dione

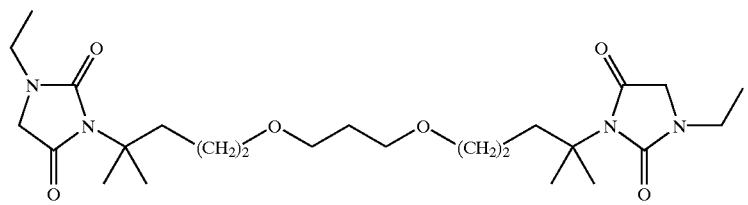

I-194:
1-Ethyl-3-(4-{3-[4-(3-ethyl-2,5-dioxo-imidazolidin-1-yl)-4-methyl-pentyloxy]-propoxy}-1,1-dimethyl-butyl)-imidazolidine-2,4-dione

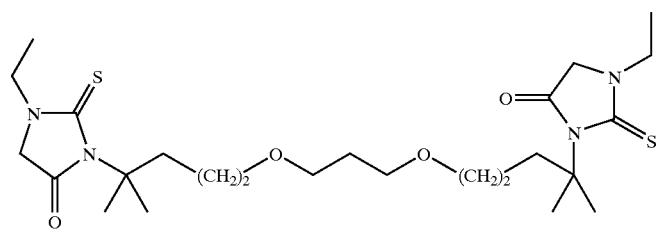

I-195:
1-Ethyl-3-(4-{3-[4-(3-ethyl-5-oxo-2-thioxo-imidazolidin-1-yl)-4-methyl-pentyloxy]-propoxy}-1,1-dimethyl-butyl)-imidazolidine-4-oxo-2-thione

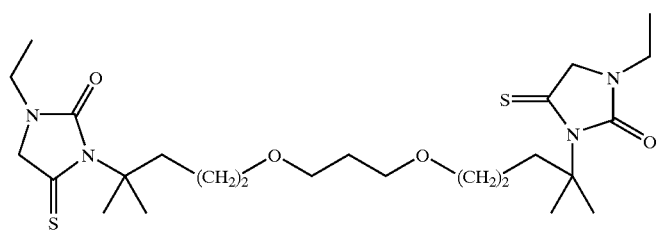

I-196:
1-Ethyl-3-(4-{3-[4-(3-ethyl-2-oxo-5-thioxo-imidazolidin-1-yl)-4-methyl-pentyl-oxy]-propoxy}-1,1-dimethyl-butyl)-imidazolidine-2-oxo-4-thione TABLE 1-continued

COMPOUNDS OF THE INVENTION

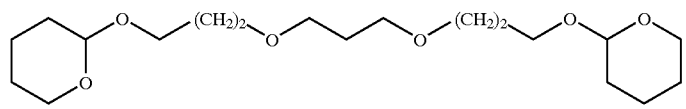

I-197:
2-{3-[3-(3-{Tetrahydro-pyran-2-yl}-propoxy)-propoxy]-propoxy}-tetrahydro-pyran

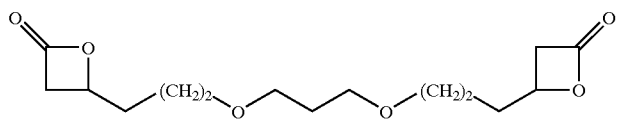

I-198:
4-{3-[3-(3-{Oxetan-2-one-4-yl}propoxy)-propoxy]-propyl}-oxetan-2-one

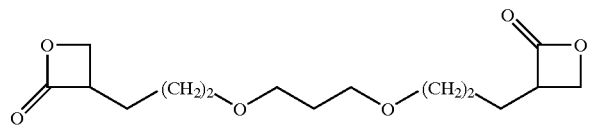

I-199:
3-{3-[3-(3-{Oxetan-2-one-3-yl}propoxy)-propoxy]-propyl}-oxetan-2-one

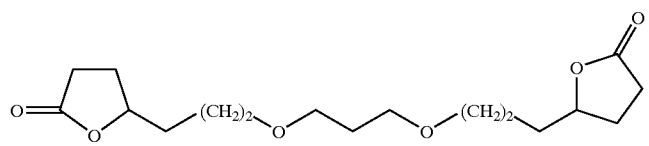

I-200:
5-{3-[3-(3-{Dihydro-furan-2-one-5-yl}-propoxy)-propoxy]-propyl}-dihydro-furan-2-one

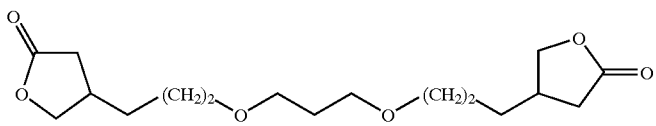

I-201:
4-{3-[3-(3-{Dihydro-furan-2-one-4-yl}-propoxy)-propoxy]-propyl}-dihydro-furan-2-one

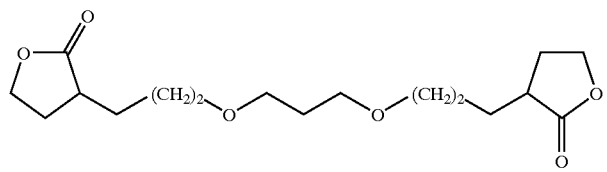

I-202:
3-{3-[3-(3-{Dihydro-furan-2-one-3-yl}-propoxy)-propoxy]-propyl}-dihydro-furan-2-one

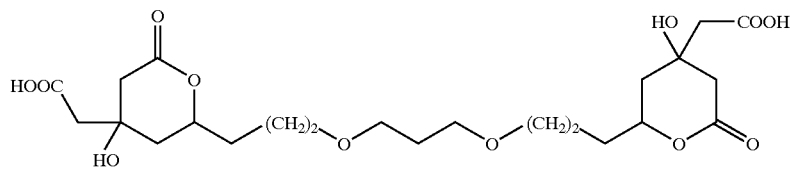

I-203:
{2-[3-(3-{3-[4-Carboxymethyl-4-hydroxy-6-oxo-tetrahydro-pyran-2-yl}-propoxy}-propoxy)-propyl]-4-hydroxy-6-oxo-tetrahydro-pyran-4-yl}-acetic acid TABLE 1-continued

COMPOUNDS OF THE INVENTION

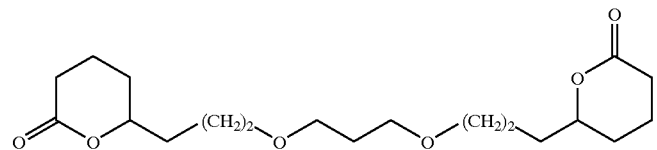

I-204:
6-{3-[3-(3-{Dihydro-pyran-2-one-6-yl}-propoxy)-propoxy]-propyl}-dihydro-pyran-2-one

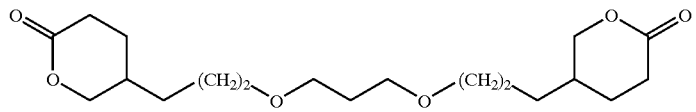

I-205:
5-{3-[3-(3-{Dihydro-pyran-2-one-5-yl}-propoxy)-propoxy]-propyl}-dihydro-pyran-2-one

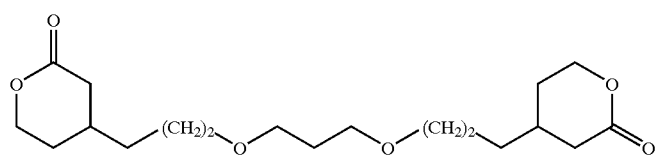

I-206:
4-{3-[3-(3-{Dihydro-pyran-2-one-4-yl}-propoxy)-propoxy]-propyl}-dihydro-pyran-2-one

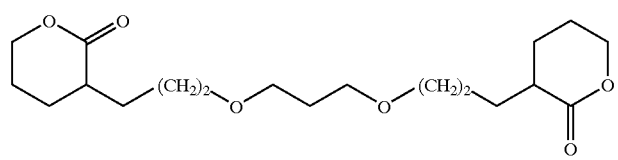

I-207:
3-{3-[3-(3-{Dihydro-pyran-2-one-3-yl}-propoxy)-propoxy]-propyl}-dihydro-pyran-2-one

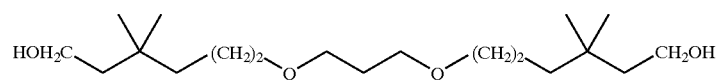

I-208:
6-[3-(6-Hydroxy-4,4-dimethyl-hexyloxy)-propoxy]-3,3-dimethyl-hexan-1-ol

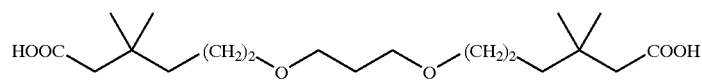

I-209:
6-[3-(5-Carboxy-4,4-dimethyl-pentyloxy)-propoxy]-3,3-dimethyl-hexanoic acid

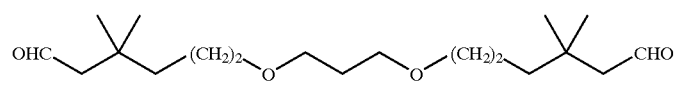

I-210:
6-[3-(4,4-Dimethyl-6-oxo-hexyloxy)-propoxy]-3,3-dimethyl-hexanal

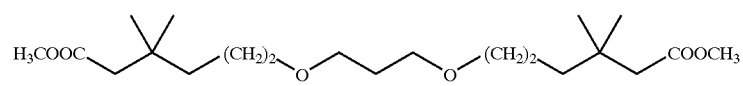

I-211:
6-[3-(5-Methoxycarbonyl-4,4-dimethyl-pentyloxy)-propoxy]-3,3-dimethyl-hexanoic acid methyl ester TABLE 1-continued

COMPOUNDS OF THE INVENTION

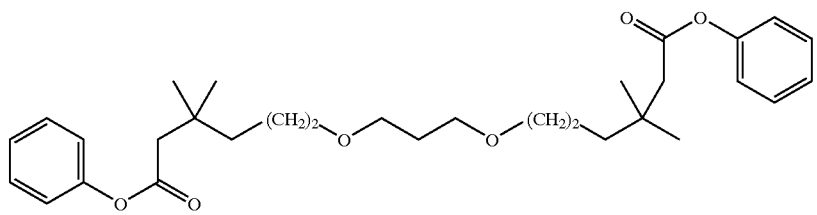

I-212:
6-[3-(4,4-Dimethyl-5-phenoxycarbonyl-pentyloxy)-propoxy]-3,3-dimethyl-hexanoic acid cyclohexyl ester

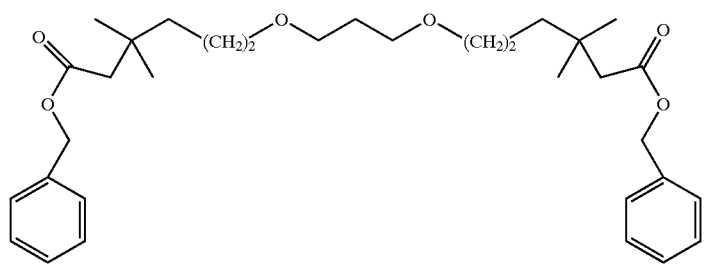

I-213:
6-[3-(5-Benzyloxycarbonyl-4,4-dimethyl-pentyloxy)-propoxy]-3,3-dimethyl-hexanoic acid benzyl ester

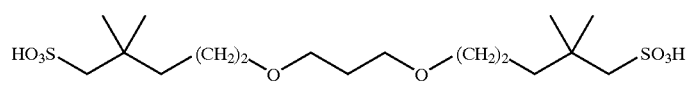

I-214:
5-[3-(4,4-Dimethyl-5-sulfo-pentyloxy)-propoxy]-2,2-dimethyl-pentane-1-sulfonic acid

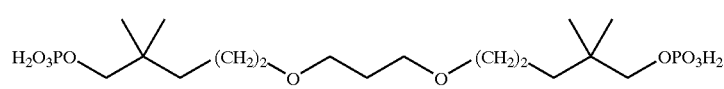

I-215:
5-[3-(4,4-Dimethyl-5-phospho-pentyloxy)-propoxy]-2,2-dimethyl-pentane-1-phosphonic acid

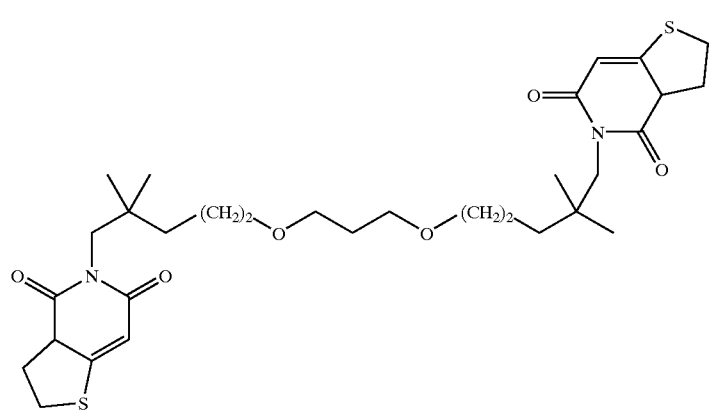

I-216:
5-{5-[3-(5-{3,3a-Dihydro-2H-thieno[3,2-c]pyridine-4,6-dione-5-yl}-4,4-dimethyl-pentyl-oxy)-propoxy]-2,2-dimethyl-3-pentyl}-3,3a-dihydro-2H-thieno[3,2-c]pyridine-4,6-dione TABLE 1-continued

COMPOUNDS OF THE INVENTION

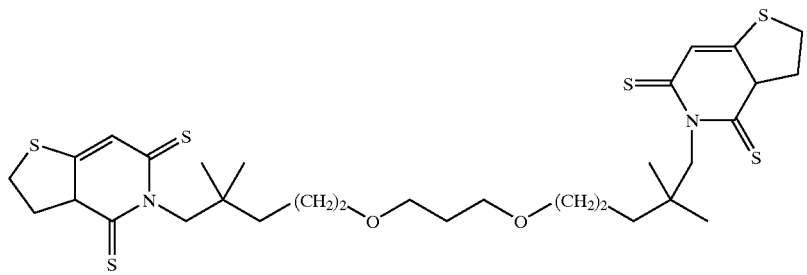

I-217:
5-{5-[3-(5-{3,3a-Dihydro-2H-thieno[3,2-c]pyridine-4,6-dithione-5-yl}-4,4-dimethyl-pentyl-
oxy)-propoxy]-2,2-dimethyl-3-pentyl}-3,3a-dihydro-2H-thieno[3,2-c]pyridine-4,6-dithione

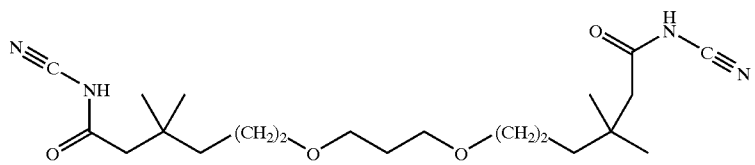

I-218:
6-[3-(5-Cyano-carbamoyl-4,4-dimethyl-pentyloxy)-propoxy]-3,3-dimethyl-N-cyano-hexanoic acid-amide

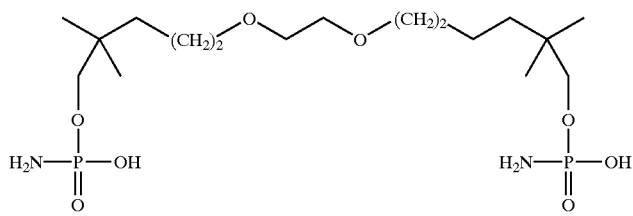

I-219:
Phosphoramidic acid mono-(6-{2-[5-(amino-hydroxy-phosphoryloxy)-4,4-dimethyl-pentyl-
oxy]-ethoxy}-2,2-dimethyl-hexyl) ester

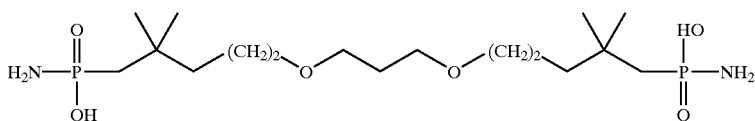

I-220:
{5-[3-(4,4-Dimethyl-5-phosphonamido-pentyloxy)-propoxy]-2,2-dimethyl-pentyl}-phosphonamide

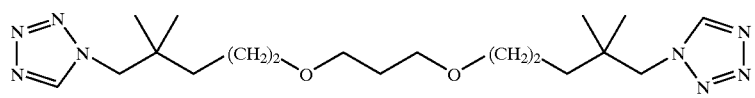

I-221:
1-{5-[3-(5-{1H-Tetrazol-1-yl}-4,4-dimethyl-pentyloxy)-propoxy]-2,2-dimethyl-pentyl}-1H-tetrazole

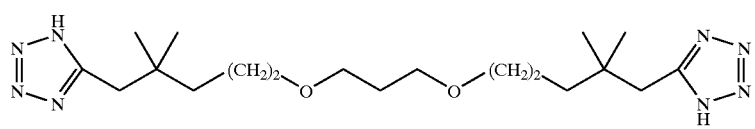

I-222:
5-{5-[3-(5-{1H-Tetrazol-5-yl}-4,4-dimethyl-pentyloxy)-propoxy]-2,2-dimethyl-pentyl}-1H-tetrazole TABLE 1-continued

COMPOUNDS OF THE INVENTION

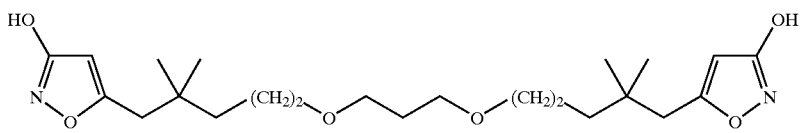

I-223:
5-{5-[3-(5-{3-Hydroxy-isoxazol-5-yl}-4,4-dimethyl-pentyloxy)-propoxy]-2,2-dimethyl-pentyl}-3-hydroxy-isoxazole

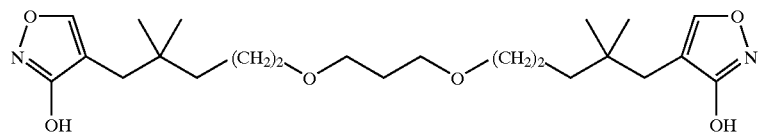

I-224:
4-{5-[3-(5-{3-Hydroxy-isoxazol-4-yl}-4,4-dimethyl-pentyloxy)-propoxy]-2,2-dimethyl-pentyl}-3-hydroxy-isoxazole

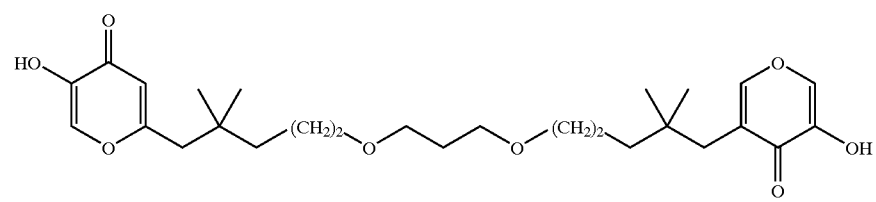

I-225:
2-{5-[3-(5-{5-Hydroxy-4-oxo-pyran-3-yl}-4,4-dimethyl-pentyloxy)-propoxy]-2,2-dimethyl-pentyl}-5-hydroxy-pyran-4-one

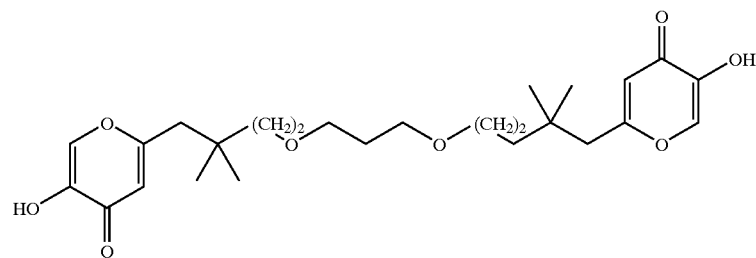

I-226:
2-{5-[3-(5-{5-Hydroxy-4-oxo-pyran-2-yl}-4,4-dimethyl-pentyloxy)-propoxy]-2,2-dimethyl-pentyl}-5-hydroxy-pyran-4-one

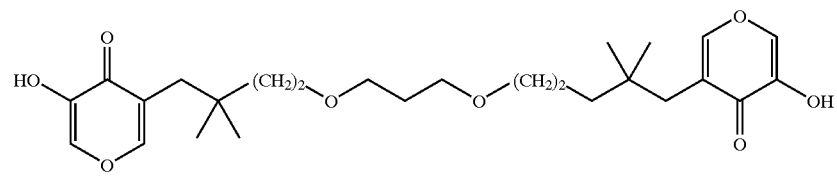

I-227:
3-{5-[3-(5-{5-Hydroxy-4-oxo-pyran-3-yl}-4,4-dimethyl-pentyloxy)-propoxy]-2,2-dimethyl-pentyl}-5-hydroxy-pyran-4-one

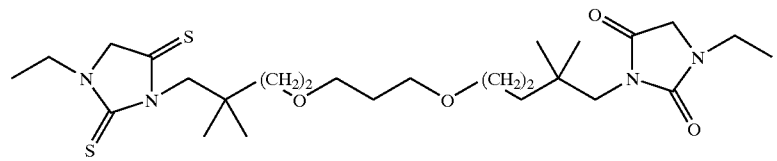

I-228:
3-{4-[3-(5-{3-Ethyl-2,5-dithioxo-imidazolidin-1-yl}-4,4-dimethyl-pentyloxy)-propoxy]-2,2-dimethyl-butyl}-1-ethyl-imidazolidine-2,4-dithione TABLE 1-continued

COMPOUNDS OF THE INVENTION

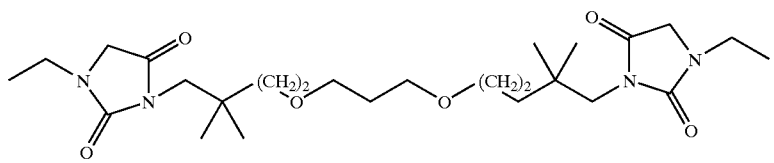

I-229:
3-{4-[3-(5-{3-Ethyl-2,5-dioxo-imidazolidin-1-yl}-4,4-dimethyl-pentyloxy)-propoxy]-2,2-di-
methyl-butyl}-1-ethyl-imidazolidine-2,4-dione

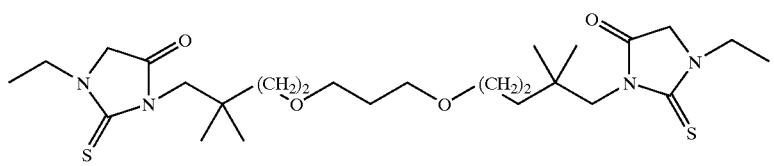

I-230:
3-{4-[3-(5-{3-Ethyl-5-oxo-2-thioxo-imidazolidin-1-yl}-4,4-dimethyl-pentyloxy)-propoxy]-2,2-dimethyl-butyl}-1-ethyl-imidazolidine-4-oxo-2-thione

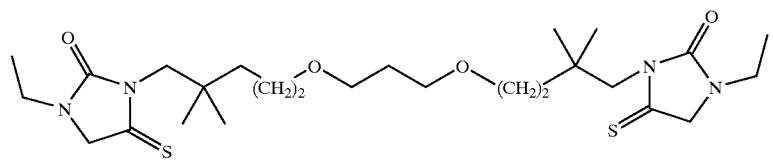

I-231:
3-{4-[3-(5-{3-Ethyl-5-oxo-2-thioxo-imidazolidin-1-yl}-4,4-dimethyl-pentyloxy)-propoxy]-2,2-di-
methyl-butyl}-1-ethyl-imidazolidine-2-oxo-4-thione

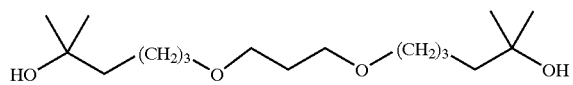

I-232:
6-[3-(5-Hydroxy-5-methyl-hexyloxy)-propoxy]-2-methyl-hexan-2-ol

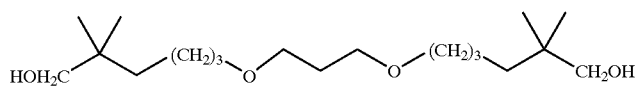

I-233:
6-[3-(6-Hydroxy-5,5-dimethyl-hexyloxy)-propoxy]-2,2-dimethyl-hexan-1-ol

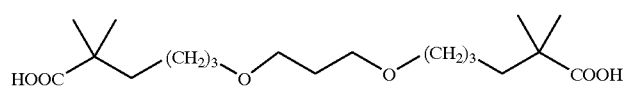

I-234:
6-[3-(5-Carboxy-5-methyl-hexyloxy)-propoxy]-2,2-dimethyl-hexanoic acid

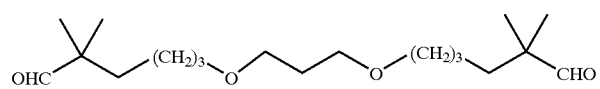

I-235:
6-[3-(5,5-Dimethyl-6-oxo-hexyloxy)-propoxy]-2,2-dimethyl-hexanal

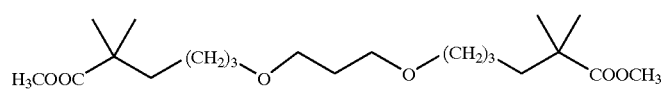

I-236:
6-[3-(5-Methoxycarbonyl-5-methyl-hexyloxy)-propoxy]-2,2-dimethyl-hexanoic acid methyl ester TABLE 1-continued

COMPOUNDS OF THE INVENTION

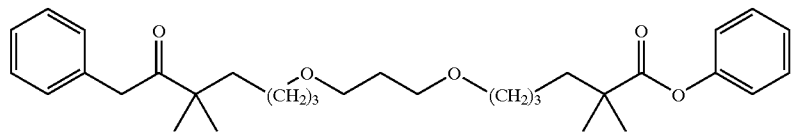

I-237:
6-[3-(5,5-Dimethyl-6-oxo-7-phenyl-heptyloxy)-propoxy]-2,2-dimethyl-hexanoic acid phenyl ester

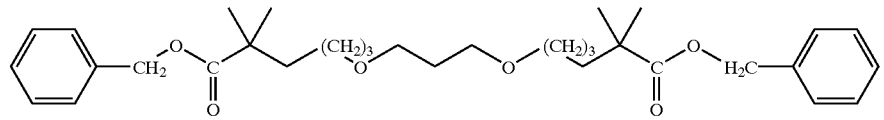

I-238:
6-[3-(5-Benzyloxycarbonyl-5-methyl-hexyloxy)-propoxy]-2,2-dimethyl-hexanoic acid benzyl ester

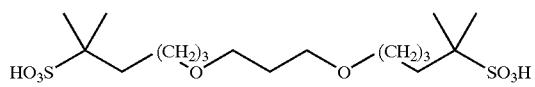

I-239:
2-Methyl-6-[3-(5-methyl-5-sulfo-hexyloxy)-propoxy]-hexane-2-sulfonic acid

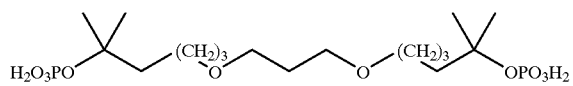

I-240:
Phosphoric acid mono-{1,1-dimethyl-5-[3-(5-methyl-5-phosphonooxy-hexyloxy)-propoxy]-pentyl} ester

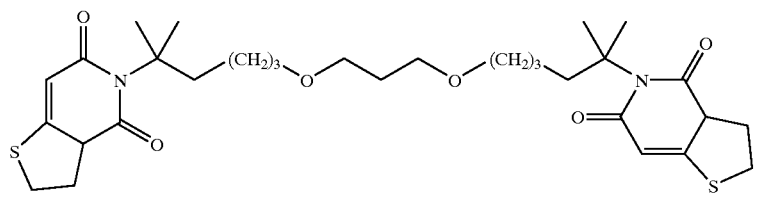

I-241:
5-(5-{3-[4-(4,6-Dioxo-hexahydro-thieno[3,2-c]pyridin-5-yl)-4-methyl-pentyloxy]-pro-
poxy}-1,1-dimethyl-pentyl)-3,3a-dihydro-2H-thieno[3,2-c]pyridine-4,6-dione

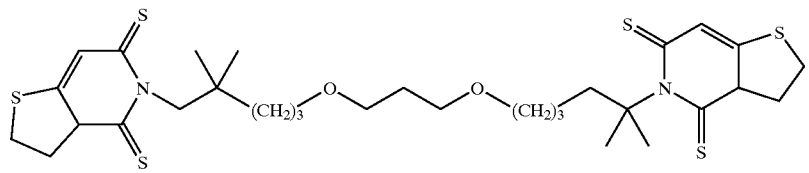

I-242:
5-(5-{3-[4-(4,6-Dithioxo-hexahydro-thieno[3,2-c]pyridin-5-yl)-4-methyl-pentyloxy]-pro-
poxy}-1,1-dimethyl-pentyl)-3,3a-dihydro-2H-thieno[3,2-c]pyridine-4,6-dithione

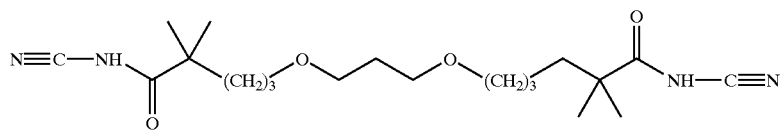

I-243:
6-[3-(4-N-Cyano-carbamoyl-4-methyl-pentyloxy)-propoxy]-2,2-dimethyl-N-cyano-hexanoic acid-amide TABLE 1-continued

COMPOUNDS OF THE INVENTION

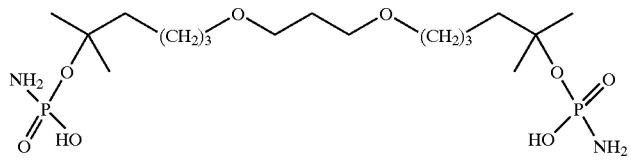

I-244:
Phosphoramidic acid mono(5-{3-[5-(amino-hydroxy-phosphoryloxy)-5-methyl-hexyloxy]-propoxy}-1,1-dimethyl-pentyl) ester

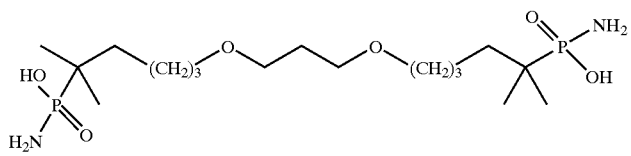

I-245:
{1,1-Dimethyl-5-[3-(5-methyl-5-phosphonamido-hexyloxy)-propoxy]-pentyl}-phosphonamide

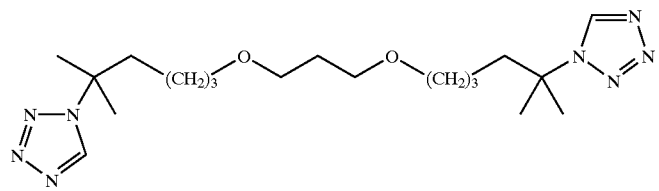

I-246:
1-{5-[3-(5-{1H-Tetrazol-1-yl}-5-methyl-hexyloxy)-propoxy]-1,1-dimethyl-pentyl}-1H-tetrazole

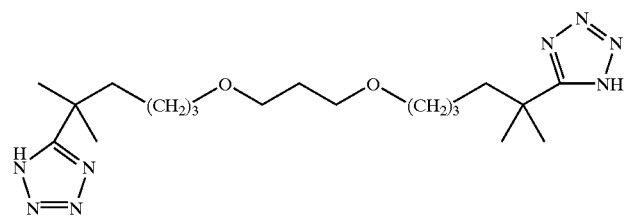

I-247:
5-{5-[3-(5-{1H-Tetrazol-5-yl}-5-methyl-hexyloxy)-propoxy]-1,1-dimethyl-pentyl}-1H-tetrazole

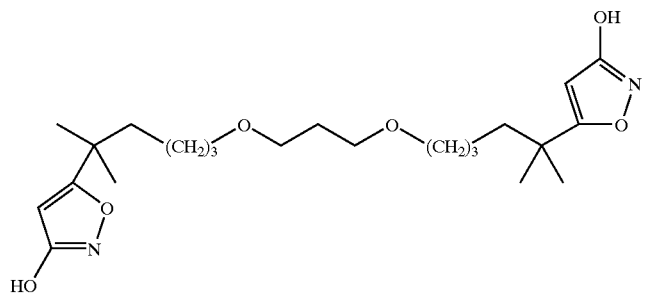

I-248:
5-{5-[3-(5-{3-Hydroxy-isoxazol-5-yl}-5-methyl-hexyloxy)-propoxy]-1,1-dimethyl-pentyl}-3-hydroxy-isoxazole TABLE 1-continued

COMPOUNDS OF THE INVENTION

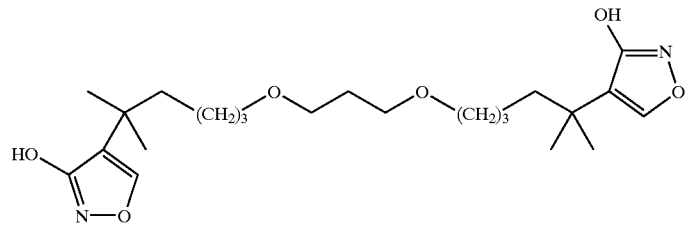

I-249:
4-{5-[3-(5-{3-Hydroxy-isoxazol-4yl}-5-methyl-hexyloxy)-propoxy]-1,1-dimethyl-pentyl}-3-hydroxy-isoxazole

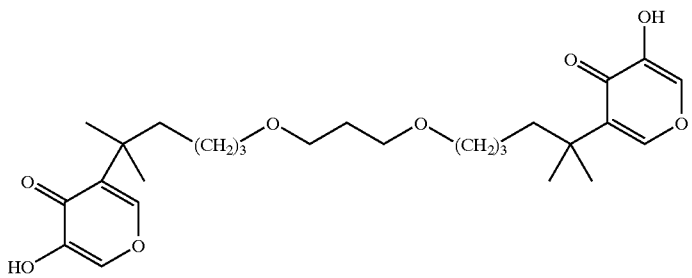

I-250:
3-{5-[3-(5-{5-Hydroxy-4-oxo-pyran-3-yl}-5-methyl-hexyloxy)-propoxy]-1,1-dimethyl-pentyl}-5-hydroxy-pyran-4-one

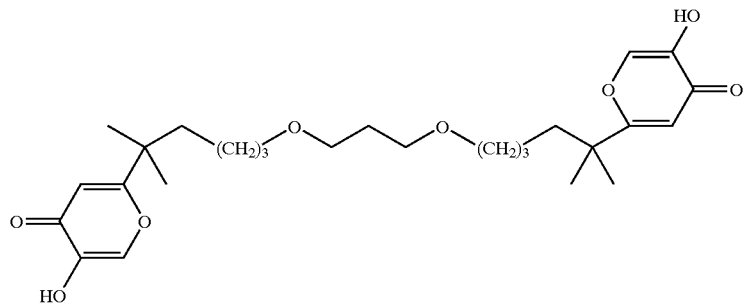

I-251:
2-{5-[3-(5-{5-Hydroxy-4-oxo-pyran-2-yl}-5-methyl-hexyloxy)-propoxy]-1,1-dimethyl-pentyl}-5-hydroxy-pyran-4-one

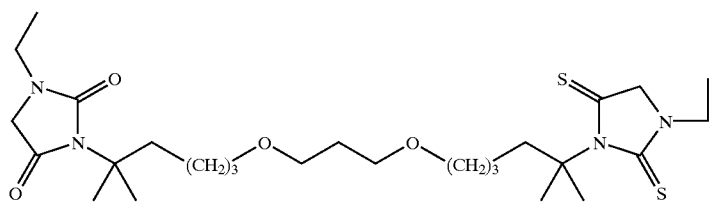

I-252:
1-Ethyl-3-(5-{3-[5-(3-ethyl-2,5-dithioxo-imidazolidin-1-yl)-5-methyl-hexyloxy]-pro-
poxy}-2,2-dimethyl-hexyl)-imidazolidine-2,4-dione

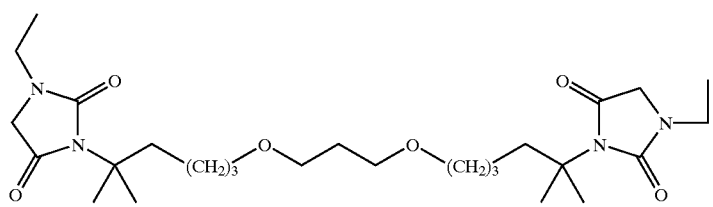

I-253:
1-Ethyl-3-(5-{3-[5-(3-ethyl-2,5-dioxo-imidazolidin-1-yl)-5-methyl-hexyloxy]-pro- TABLE 1-continued

COMPOUNDS OF THE INVENTION poxy}-2,2-dimethyl-hexyl)-imidazolidine-2,4-dione

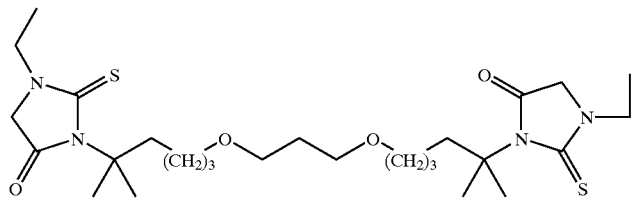

I-254:
1-Ethyl-3-(5-{3-[5-(3-ethyl-2-thioxo-5-oxo-imidazolidin-1-yl)-5-methyl-hexyloxy]-pro-
poxy}-2,2-dimethyl-hexyl)-imidazolidine-4-oxo-2-thione

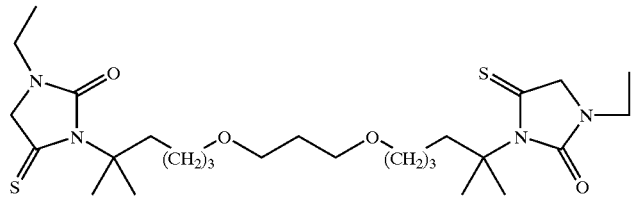

I-255:
1-Ethyl-3-(5-{3-[5-(3-ethyl-5-thioxo-2-oxo-imidazolidin-1-yl)-5-methyl-hexyloxy]-pro-
poxy}-2,2-dimethyl-hexyl)-imidazolidine-2-oxo-4-thione

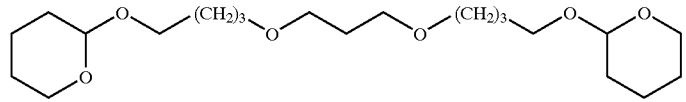

I-256:
2-{4-[3-(4-{Tetrahydro-pyran-2-yl}-butoxy)-propoxy]-butoxy}-tetrahydro-pyran

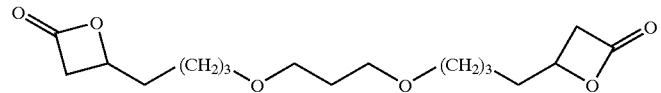

I-257:
4-{4-[3-(4-{Oxetan-2-one-4-yl}-butoxy)-propoxy]-butyl}-oxetan-2-one

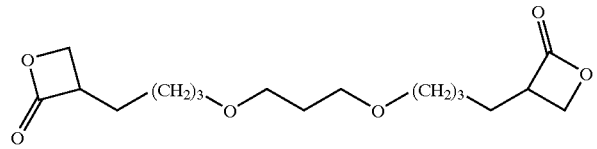

I-258:
3-{4-[3-(4-{Oxetan-2-one-3-yl}-butoxy)-propoxy]-butyl}-oxetan-2-one

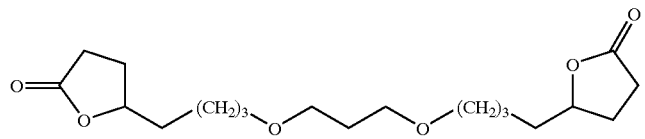

I-259:
5-{4-[3-(4-{Tetrahydro-furan-2-one-5-yl}-butoxy)-propoxy]-butyl}-tetrahydro-furan-2-one

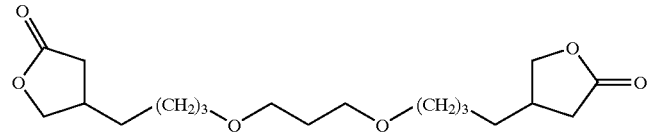

TABLE 1-continued

COMPOUNDS OF THE INVENTION

I-260:
4-{4-[3-(4-{Tetrahydro-furan-2-one-4-yl}-butoxy)-propoxy]-butyl}-tetrahydro-furan-2-one

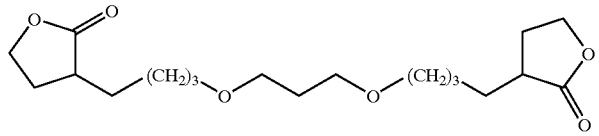

I-261:
3-{4-[3-(4-{Tetrahydro-furan-2-one-3-yl}-butoxy)-propoxy]-butyl}-tetrahydro-furan-2-one

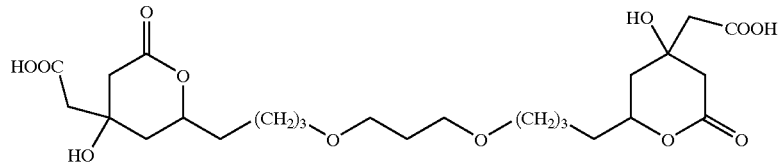

I-262:
[2-(4-{3-[4-(4-Carboxymethyl-4-hydroxy-6-oxo-tetrahydro-pyran-2-yl)-butoxy]-propoxy}-butyl)-4-hydroxy-6-oxo-tetrahydro-pyran-4-yl)-acetic acid

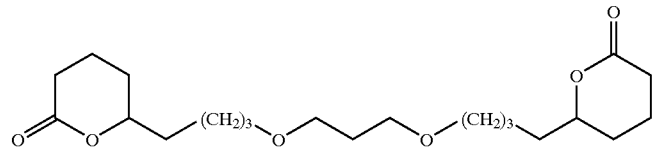

I-263:
6-{4-[3-(4-{Tetrahydro-pyran-2-one-6-yl}-butoxy)-propoxy]-butyl}-tetrahydro-pyran-2-one

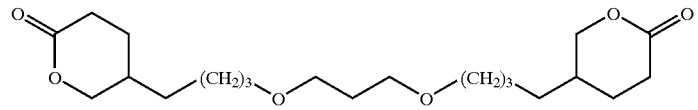

I-264:
5-{4-[3-(4-{Tetrahydro-pyran-2-one-5-yl}-butoxy)-propoxy]-butyl}-tetrahydro-pyran-2-one

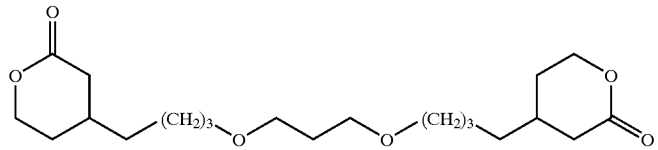

I-265:
4-{4-[3-(4-{Tetrahydro-pyran-2-one-4-yl}-butoxy)-propoxy]-butyl}-tetrahydro-pyran-2-one

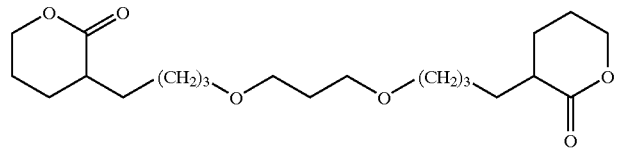

I-266:
3-{4-[3-(4-{Tetrahydro-pyran-2-one-3-yl}-butoxy)-propoxy]-butyl}-tetrahydro-pyran-2-one

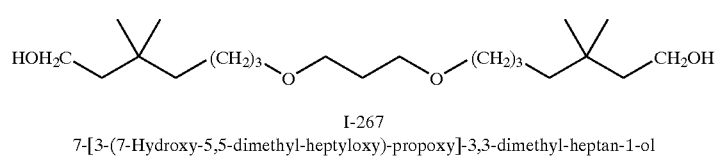

I-267
7-[3-(7-Hydroxy-5,5-dimethyl-heptyloxy)-propoxy]-3,3-dimethyl-heptan-1-ol

TABLE 1-continued

COMPOUNDS OF THE INVENTION

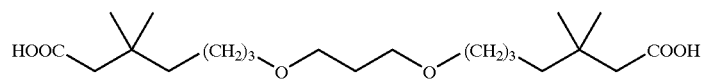

I-268:
7-[3-(6-Carboxy-5,5-dimethyl-hexyloxy)-propoxy]-3,3-dimethyl-heptanoic acid

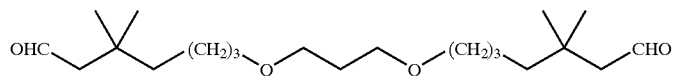

I-269:
7-[3-(5,5-dimethyl-6-oxo-hexyloxy)-propoxy]-3,3-dimethyl-heptanal

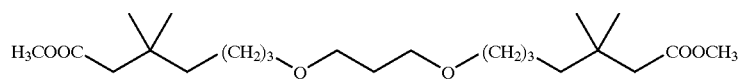

I-270:
7-[3-(6-Methoxycarbonyl-5,5-dimethyl-hexyloxy)-propoxy]-3,3-dimethy-heptanoic acid methyl ester

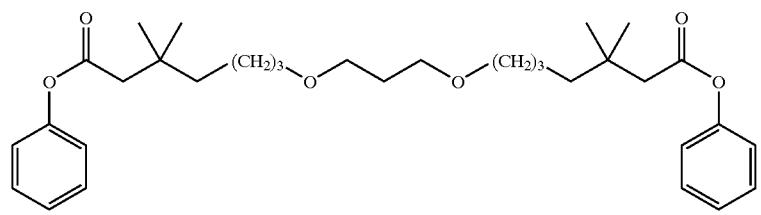

I-271:
7-[3-(5,5-Dimethyl-6-phenoxycarbonyl-hexyloxy)-propoxy]-3,3-dimethyl-heptanoic acid phenyl ester

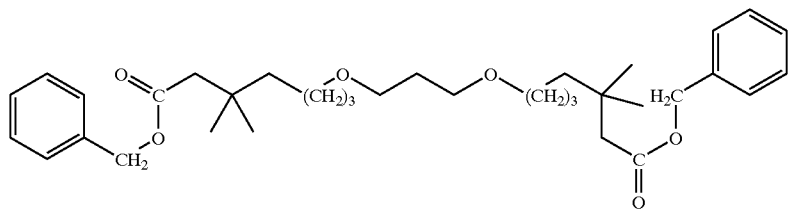

I-272:
7-[3-(6-Benzyloxycarbonyl-5,5-dimethyl-hexyloxy)-propoxy]-3,3-dimethyl-heptanoic acid benzyl ester

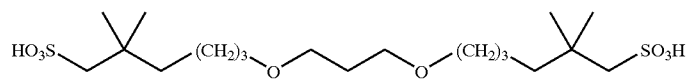

I-273:
6-[3-(5,5-Dimethyl-6-sulfo-hexyloxy)-propoxy]-2,2-dimethyl-hexane-1-sulfonic acid

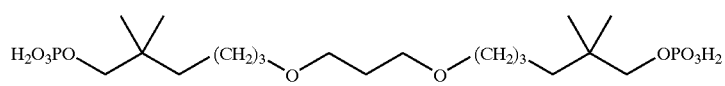

I-274:
Phosphoric acid mono-{6-[3-(5,5-dimethyl-6-phosphonooxy-hexyloxy)-propoxy]-2,2-dimethyl-hexyl}-ester

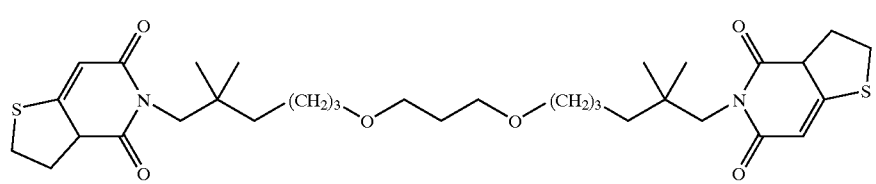

I-275:

TABLE 1-continued

COMPOUNDS OF THE INVENTION 5-(6-{3-[6-(4,6-Dioxo-hexahydro-thieno[3,2-c]pyridin-5-yl)-5,5-dimethyl-hexyloxy]-propoxy}-2,2-di-
methyl-hexyl)-3,3a-dihydro-2H-thieno[3,2-c]pyridine-4,6-dione

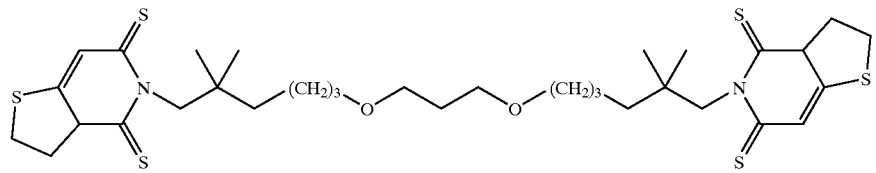

I-276:
5-(5-{3-[4-(4,6-Dithioxo-hexahydro-thieno[3,2-c]pyridin-5-yl)-4-methyl-pentyloxy]-pro-
poxy}-1,1-dimethyl-pentyl)-3,3a-dihydro-2H-thieno[3,2-c]pyridine-4,6-dithione

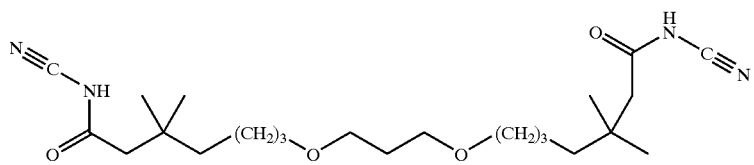

I-277:
7-[3-(6-N-Cyano-carbamoyl-5,5-dimethyl-hexyloxy)-propoxy]-3,3-dimethyl-N-cyano-hepta-
noic acid-amide

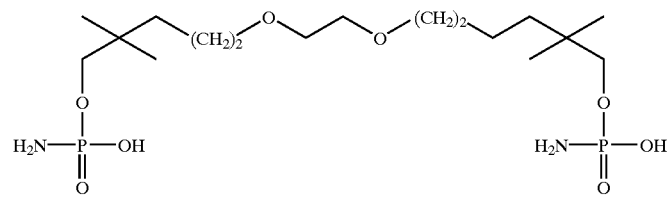

I-278:
Phosphoramidic acid mono-{7-[2-(6-{amino-hydroxy-phosphoryloxy}-5,5-dimethyl-hexyl-
oxy)-ethoxy]-2,2-dimethyl-heptyl}ester

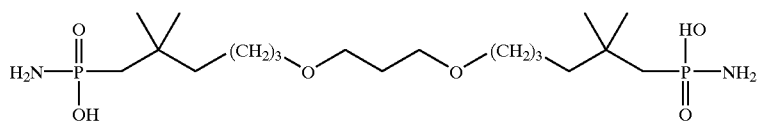

I-279:
{6-[3-(5,5-Dimethyl-6-phosphonamido-hexyloxy)-propoxy]-2,2,-dimethyl-hexyl}-phosphonamide

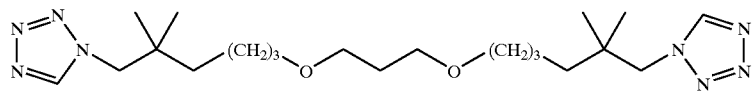

I-280:
1-{6-[3-(6-{1H-Tetrazol-1-yl}-5,5-dimethyl-hexyloxy)-propoxy]-2,2-dimethyl-hexyl}-1H-tetrazole

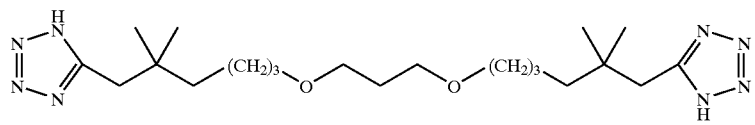

I-281:
5-{6-[3-(6-{1H-Tetrazol-5-yl}-5,5-dimethyl-hexyloxy)-propoxy]-2,2-dimethyl-hexyl}-1H-tetrazole

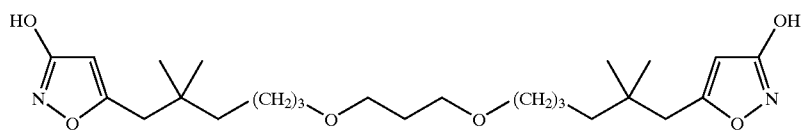

TABLE 1-continued

COMPOUNDS OF THE INVENTION

I-282:
5-{6-[3-(6-{3-Hydroxy-isoxazol-5-yl}-5,5-dimethyl-hexyloxy)-propoxy]-2,2-dimethyl-hexyl}-3-hydroxy-isoxazole

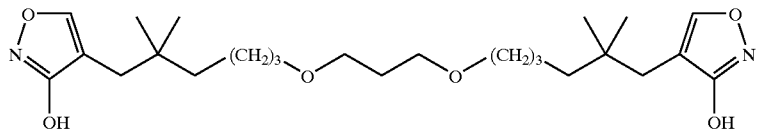

I-283:
4-{6-[3-(6-{3-Hydroxy-isoxazol-4-yl}-5,5-dimethyl-hexyloxy)-propoxy]-2,2-dimethyl-hexyl}-3-hydroxy-isoxazole

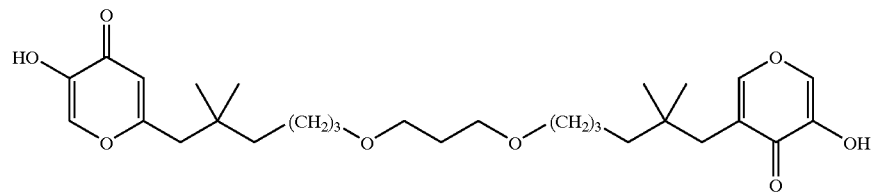

I-284:
2-{6-[3-(6-{5-Hydroxy-4-oxo-pyran-3-yl}-5,5-dimethyl-hexyloxy)-propoxy]-2,2-di-
methyl-hexyl}-5-hydroxy-pyran-4-one

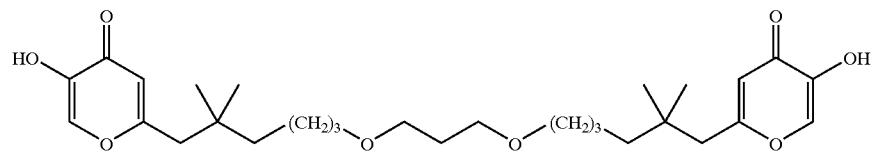

I-285:
2-{6-[3-(6-{5-Hydroxy-4-oxo-pyran-2-yl}-5,5-dimethyl-hexyloxy)-propoxy]-2,2-di-
methyl-hexyl}-5-hydroxy-pyran-4-one

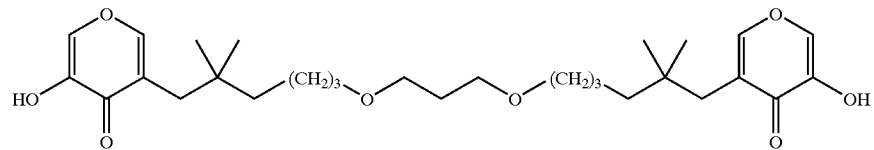

I-286:
3-{6-[3-(6-{5-Hydroxy-4-oxo-pyran-3-yl}-5,5-dimethyl-hexyloxy)-propoxy]-2,2-di-
methyl-hexyl}-5-hydroxy-pyran-4-one

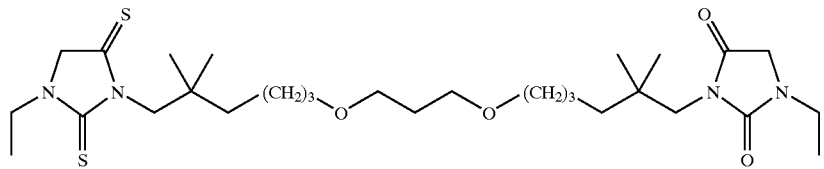

I-287:
1-Ethyl-3-(6-{3-[6-(3-ethyl-2,5-dithioxo-imidazolidin-1-yl)-5,5-dimethyl-hexyloxy]-pro-
poxy}-2,2-dimethyl-hexyl)-imidazolidine-2,4-dione

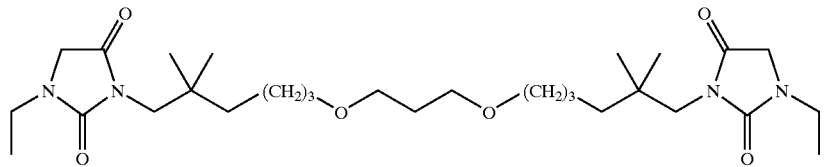

I-288:
1-Ethyl-3-(6-{3-[6-(3-ethyl-2,5-dioxo-imidazolidin-1-yl)-5,5-dimethyl-hexyloxy]-pro-
poxy}-2,2-dimethyl-hexyl)-imidazolidine-2,4-dione TABLE 1-continued

COMPOUNDS OF THE INVENTION

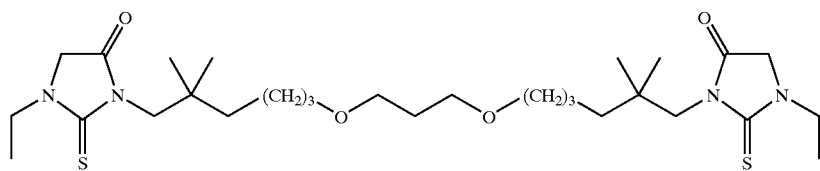

I-289:
1-Ethyl-3-(6-{3-[6-(3-ethyl-5-oxo-2-thioxo-imidazolidin-1-yl)-5,5-dimethyl-hexyl-oxy]-propoxy}-2,2-dimethyl-hexyl)-imidazolidine-4-oxo-2-thione

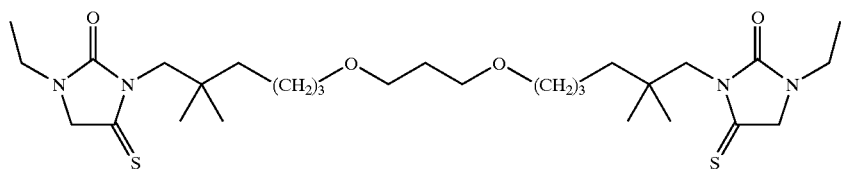

I-290:
1-Ethyl-3-(6-{3-[6-(3-ethyl-2-oxo-5-thioxo-imidazolidin-1-yl)-5,5-dimethyl-hexyl-oxy]-propoxy}-2,2-dimethyl-hexyl)-imidazolidine-2-oxo-4-thione

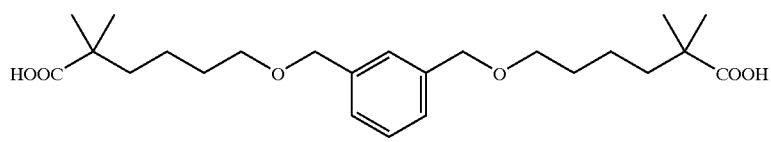

I-291:
6-[3-(5-Carboxy-5-methyl-hexyloxymethyl)-benzyloxy]-2,2-dimethyl-hexanoic acid

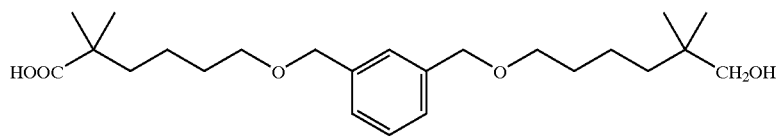

I-292:
6-[3-(5-Carboxy-5-methyl-hexyloxymethyl)-benzyloxy]-2,2-dimethyl-hexan-1-ol

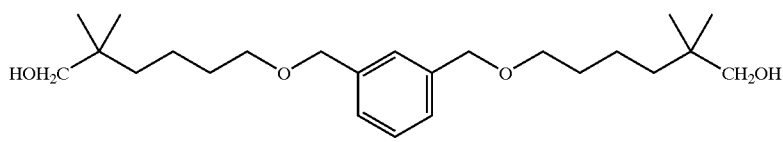

I-293:
6-[3-(6-Hydroxy-5,5-dimethyl-hexyloxymethyl)-benzyloxy]-2,2-dimethyl-hexan-1-ol

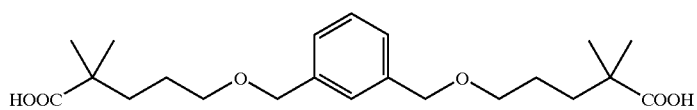

I-294:
5-[3-(4-Carboxy-4-methyl-pentyloxymethyl)-benzyloxy]-2,2-dimethyl-pentanoic acid

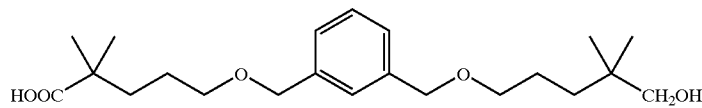

I-295:
5-[3-(4-Carboxy-4-methyl-pentyloxymethyl)-benzyloxy]-2,2-dimethyl-hexan-1-ol TABLE 1-continued

COMPOUNDS OF THE INVENTION

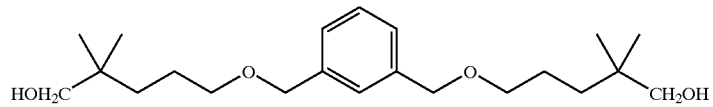

I-296:
5-[3-(5-Hydroxy-4,4-dimethyl-pentyloxymethyl)-benzyloxy]-2,2-dimethyl-pentan-1-ol

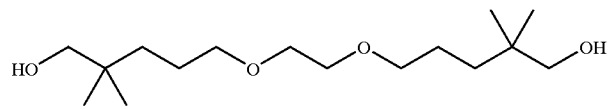

I-297
5-[2-(5-hydroxy-4,4-dimethyl-pentyloxy)-ethoxy]-2,2-dimethyl-pentan-1-ol

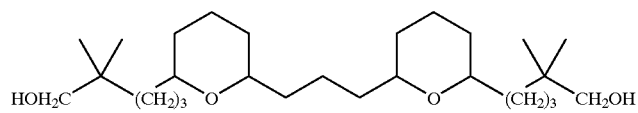

II-1:
5-(6-{3-[6-(5-Hydroxy-4,4-dimethyl-pentyl)-tetrahydro-pyran-2-yl]-propyl}-tetra-
hydro-pyran-2-yl)-2,2-dimethyl-pentan-1-ol

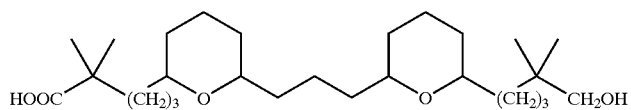

II-2:
5-(6-{3-[6-(5-Hydroxy-4,4-dimethyl-pentyl)-tetrahydro-pyran-2-yl]-propyl}-tetrahydro-py-
ran-2-yl)-2,2-dimethyl-pentanoic acid

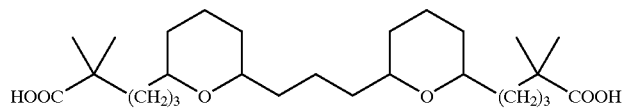

II-3:
5-(6-{3-[6-(4-Carboxyl-4,4-dimethyl-pentyl)-tetrahydro-pyran-2-yl]-propyl}-tetrahydro-py-
ran-2-yl)-2,2-dimethyl-pentanoic acid

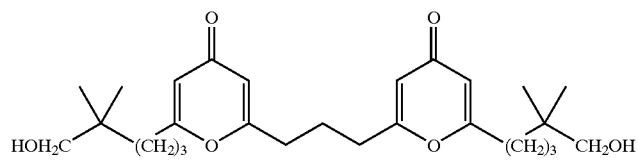

II-4:
5-(6-{3-[6-(5-Hydroxy-4,4-dimethyl-pentyl)-4-oxo-pyran-2-yl]-propyl}-4-oxo-py-
ran-2-yl)-2,2-dimethyl-pentan-1-ol

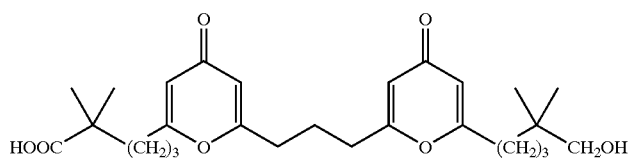

II-5:
5-(6-{3-[6-(5-Hydroxy-4,4-dimethyl-pentyl)-4-oxo-pyran-2-yl]-propyl}-4-oxo-pyran-2-yl)-2,2-dimethyl-pentanoic acid TABLE 1-continued

COMPOUNDS OF THE INVENTION

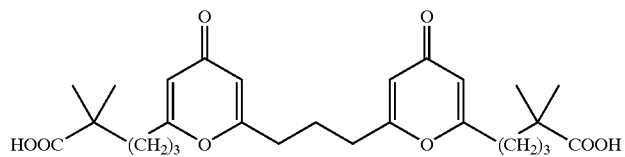

II-6:
5-(6-{3-[6-(4-Carboxyl-4,4-dimethyl-pentyl)-4-oxo-pyran-2-yl]-propyl}-4-oxo-pyran-2-yl)-2,2-dimethyl-pentanoic acid

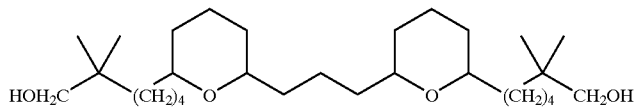

II-7:
6-(6-{3-[6-(6-Hydroxy-5,5-dimethyl-hexyl)-tetrahydro-pyran-2-yl]-propyl}-tetra-
hydro-pyran-2-yl)-2,2-dimethyl-hexan-1-ol

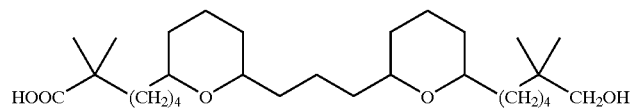

II-8:
6-(6-{3-[6-(6-Hydroxy-5,5-dimethyl-hexyl)-tetrahydro-pyran-2-yl]-propyl}-tetrahydro-py-
ran-2-yl)-2,2-dimethyl-hexanoic acid

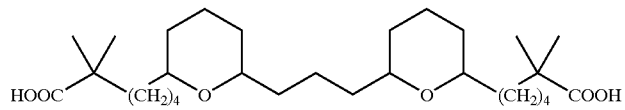

II-9:
6-(6-{3-[6-(5-Carboxyl-5,5-dimethyl-hexyl)-tetrahydro-pyran-2-yl]-propyl}-tetra-
hydro-pyran-2-yl)-2,2-dimethyl-hexanoic acid

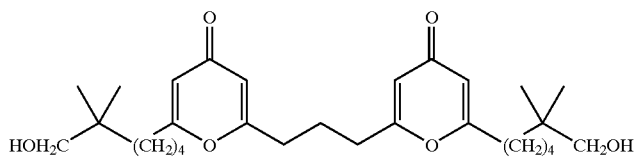

II-10:
6-(6-{3-[6-(6-Hydroxy-5,5-dimethyl-hexyl)-4-oxo-pyran-2-yl]-propyl}-4-oxo-py-
ran-2-yl)-2,2-dimethyl-hexan-1-ol

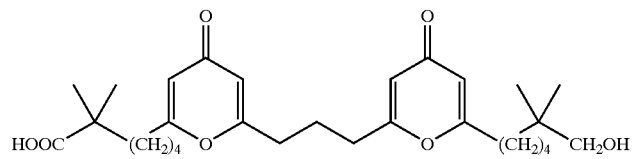

II-11:
6-(6-{3-[6-(6-Hydroxy-5,5-dimethyl-hexyl)-4-oxo-pyran-2-yl]-propyl}-4-oxo-py-
ran-2-yl)-2,2-dimethyl-hexanoic acid

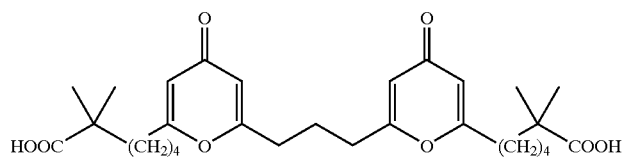

II-12:
6-(6-{3-[6-(5-Carboxyl-5,5-dimethyl-hexyl)-4-oxo-pyran-2-yl]-propyl}-4-oxo-py-
ran-2-yl)-2,2-dimethyl-hexanoic acid TABLE 1-continued

COMPOUNDS OF THE INVENTION

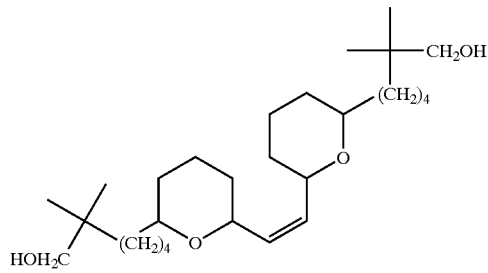

II-13:
6-(6-{2-[6-(6-Hydroxy-5,5-dimethyl-hexyl)-tetrahydro-pyran-2-yl]-vinyl}-tetrahydro-pyran-2-yl)-2,2-dimethyl-hexan-1-ol

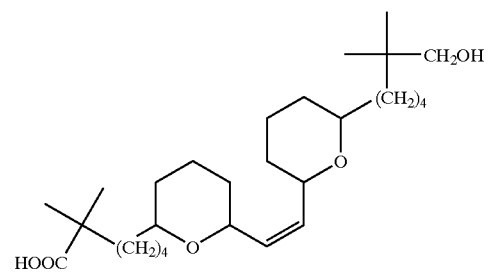

II-14:
6-(6-{2-[6-(6-Hydroxy-5,5-dimethyl-hexyl)-tetrahydro-pyran-2-yl]-vinyl}-tetrahydro-pyran-2-yl)-2,2-dimethyl-hexanoic acid

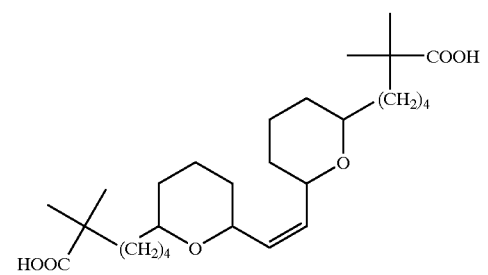

II-15:
6-(6-{2-[6-(5-Carboxyl-5,5-dimethyl-hexyl)-tetrahydro-pyran-2-yl]-vinyl}-tetrahydro-pyran-2-yl)-2,2-dimethyl-hexanoic acid

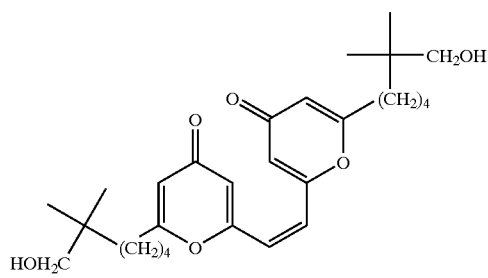

II-16:
6-(6-{2-[6-(6-Hydroxy-5,5-dimethyl-hexyl)-4-oxo-pyran-2-yl]-vinyl}-4-oxo-pyran-2-yl)-2,2-dimethyl-hexan-1-ol TABLE 1-continued

COMPOUNDS OF THE INVENTION

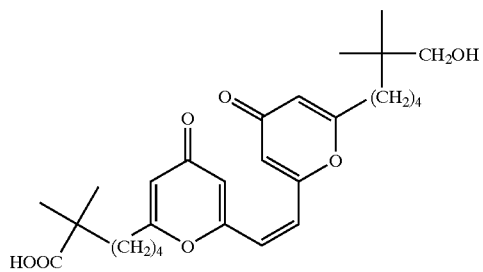

II-17:
6-(6-{2-[6-(6-Hydroxy-5,5-dimethyl-hexyl)-4-oxo-pyran-2-yl]-vinyl}-4-oxo-pyran-2-yl)-2,2-dimethyl-hexanoic acid

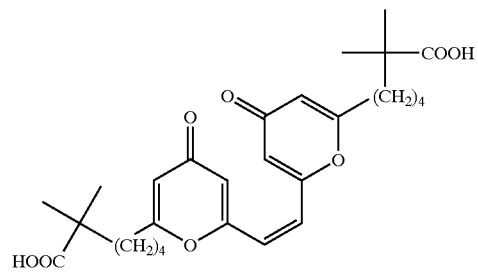

II-18:
6-(6-{2-[6-(5-Carboxyl-5,5-dimethyl-hexyl)-4-oxo-pyran-2-yl]-vinyl}-4-oxo-pyran-2-yl)-2,2-dimethyl-hexanoic acid

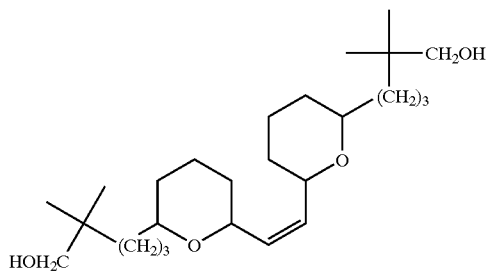

II-19:
5-(6-{2-[6-(5-Hydroxy-4,4-dimethyl-pentyl)-tetrahydro-pyran-2-yl]-vinyl}-tetrahydro-pyran-2-yl)-2,2-dimethyl-pentan-1-ol

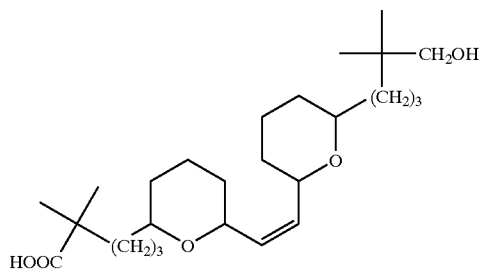

II-20:
5-(6-{2-[6-(5-Hydroxy-4,4-dimethyl-pentyl)-tetrahydro-pyran-2-yl]-vinyl}-tetrahydro-pyran-2-yl)-2,2-dimethyl-pentanoic acid TABLE 1-continued

COMPOUNDS OF THE INVENTION

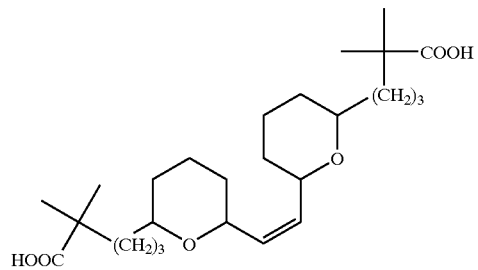

II-21:
5-(6-{2-[6-(4-Carboxyl-4,4-dimethyl-pentyl)-tetrahydro-pyran-2-yl]-vinyl}-tetra-
hydro-pyran-2-yl)-2,2-dimethyl-pentanoic acid

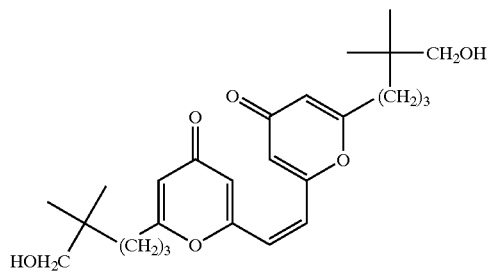

II-22:
5-(6-{2-[6-(5-Hydroxy-4,4-dimethyl-pentyl)-4-oxo--pyran-2-yl]-vinyl}-4-oxo-py-
ran-2-yl)-2,2-dimethyl-pentan-1-ol

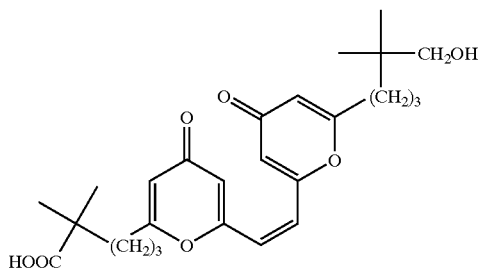

II-23:
5-(6-{2-[6-(5-Hydroxy-4,4-dimethyl-pentyl)-4-oxo-pyran-2-yl]-vinyl}-4-oxo-py-
ran-2-yl)-2,2-dimethyl-pentanoic acid

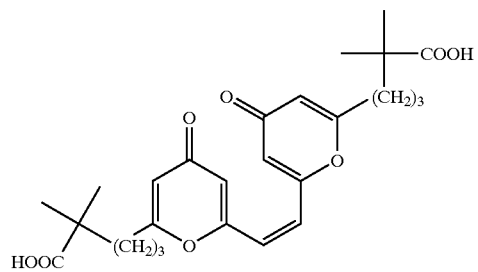

II-24:
5-(6-{2-[6-(4-Carboxyl-4,4-dimethyl-pentyl)-4-oxo-pyran-2-yl]-vinyl}-4-oxo-py-
ran-2-yl)-2,2-dimethyl-pentanoic acid TABLE 1-continued

COMPOUNDS OF THE INVENTION

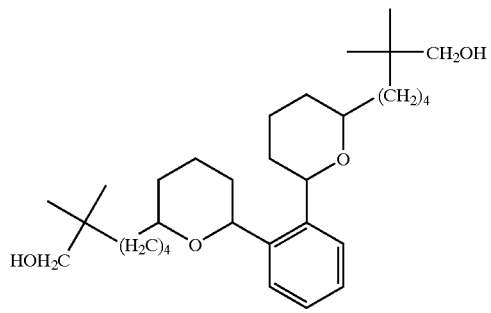

II-25:
6-(6-{2-[6-(6-Hydroxy-5,5-dimethyl-hexyl)-tetrahydro-pyran-2-yl]-phenyl}-tetrahydro-py-
ran-2-yl)-2,2-dimethyl-hexan-1-ol

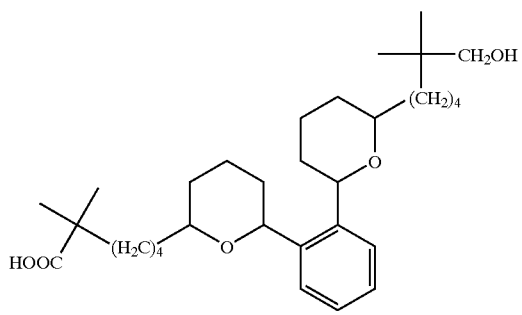

II-26:
6-(6-{2-[6-(6-Hydroxy-5,5-dimethyl-hexyl)-tetrahydro-pyran-2-yl]-phenyl}-tetrahydro-py-
ran-2-yl)-2,2-dimethyl-hexanoic acid

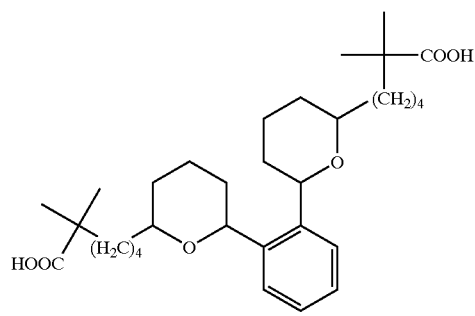

II-27:
6-(6-{2-[6-(5-Carboxyl-5,5-dimethyl-hexyl)-tetrahydro-pyran-2-yl]-phenyl}-tetrahydro-py-
ran-2-yl)-2,2-dimethyl-hexanoic acid

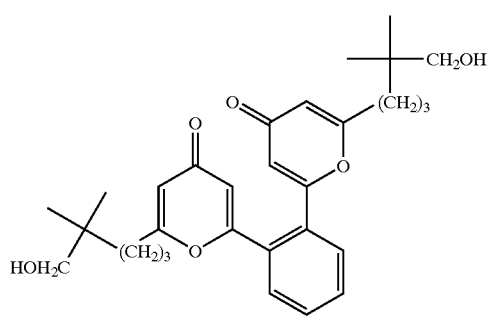

II-28:
5-(6-{2-[6-(5-Hydroxy-4,4-dimethyl-pentyl)-4-oxo-pyran-2-yl]-phenyl}-4-oxo-pyran-2-yl)-2,2-dimethyl-pentan-1-ol TABLE 1-continued
COMPOUNDS OF THE INVENTION
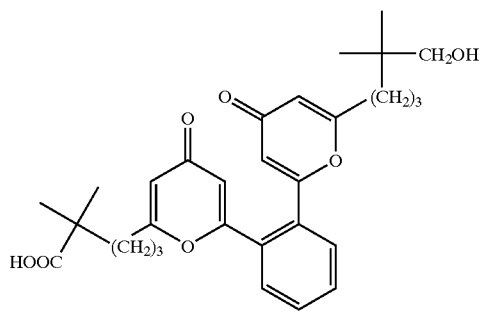
II-29:
5-(6-{2-[6-(5-Hydroxy-4,4-dimethyl-pentyl)-4-oxo-pyran-2-yl]-phenyl}-4-oxo-pyran-2-yl)-2,2-dimethyl-pentanoic acid
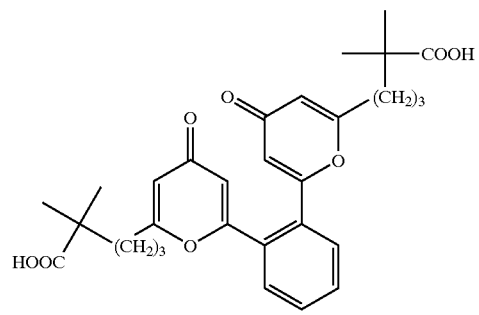
II-30:
5-(6-{2-[6-(4-Carboxyl-4,4-dimethyl-pentyl)-4-oxo-pyran-2-yl]-phenyl}-4-oxo-pyran-2-yl)-2,2-dimethyl-pentan-1-ol
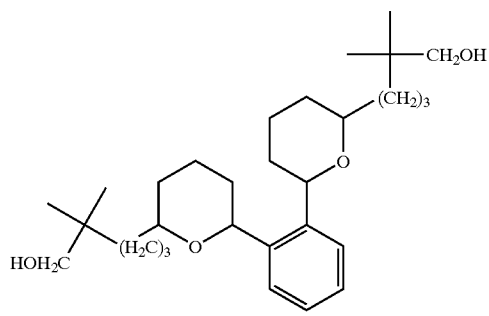
II-31:
5-(6-{2-[6-(5-Hydroxy-4,4-dimethyl-pentyl)-tetrahydro-pyran-2-yl]-phenyl}-tetrahydro-pyran-2-yl)-2,2-dimethyl-pentan-1-ol
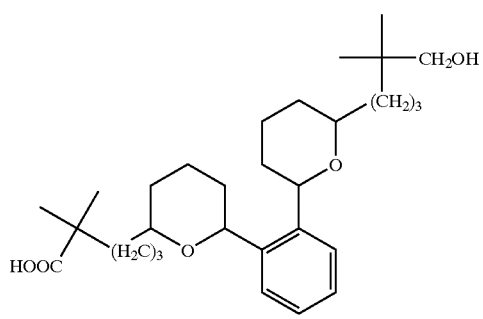
II-32:

TABLE 1-continued

COMPOUNDS OF THE INVENTION 5-(6-{2-[6-(5-Hydroxy-4,4-dimethyl-pentyl)-4-oxo-pyran-2-yl]-phenyl}-4-oxo-pyran-2-yl)-2,2-dimethyl-pentanoic acid

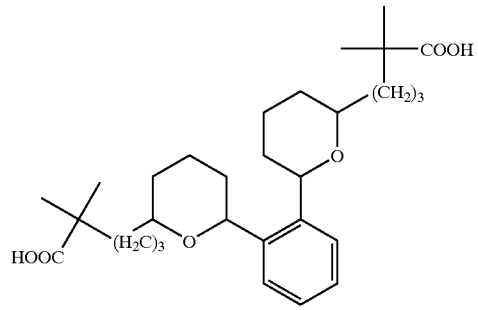

II-33:
5-(6-{2-[6-(4-Carboxyl-4,4-dimethyl-pentyl)-4-oxo-pyran-2-yl]-phenyl}-4-oxo-pyran-2-yl)-2,2-dimethyl-pentanoic acid

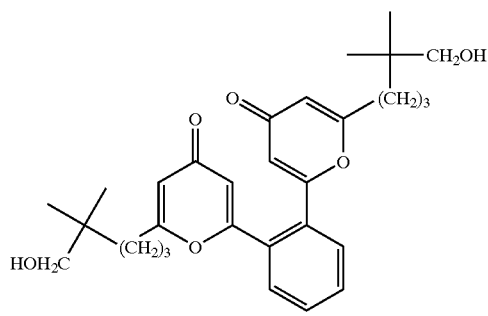

II-34:
6-(6-{2-[6-(6-Hydroxy-5,5-dimethyl-hexyl)-4-oxo-pyran-2-yl]-phenyl}-4-oxo-pyran-2-yl)-2,2-dimethyl-hexan-1-ol

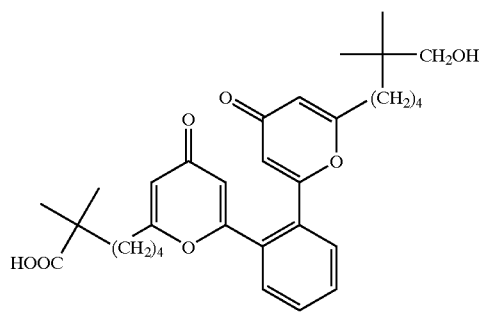

II-35:
6-(6-{2-[6-(6-Hydroxy-5,5-dimethyl-hexyl)-4-oxo-pyran-2-yl]-phenyl}-4-oxo-pyran-2-yl)-2,2-dimethyl-hexanoic acid

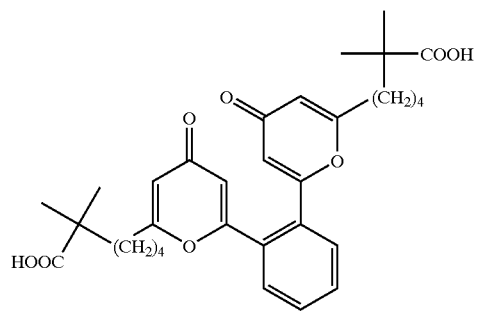

TABLE 1-continued

COMPOUNDS OF THE INVENTION

II-36:
6-(6-{2-[6-(5-Carboxyl-5,5-dimethyl-hexyl)-4-oxo-pyran-2-yl]-phenyl}-4-oxo-pyran-2-yl)-2,2-dimethyl-hexanoic acid

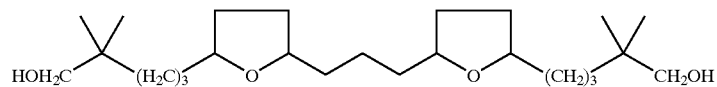

II-37:
5-(5-{3-[5-(5-Hydroxy-4,4-dimethyl-pentyl)-tetrahydro-furan-2-yl]-propyl}-tetrahydro-furan-2-yl)-2,2-dimethyl-pentan-1-ol

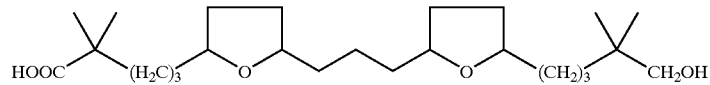

II-38:
5-(5-{3-[5-(5-Hydroxy-4,4-dimethyl-pentyl)-tetrahydro-furan-2-yl]-propyl}-tetrahydro-furan-2-yl)-2,2-dimethyl-pentanoic acid

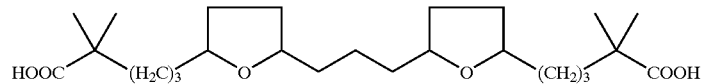

II-39:
5-(5-{3-[5-(4-Carboxyl-4,4-dimethyl-pentyl)-tetrahydro-furan-2-yl]-propyl}-tetrahydro-furan-2-yl)-2,2-dimethyl-pentanoic acid

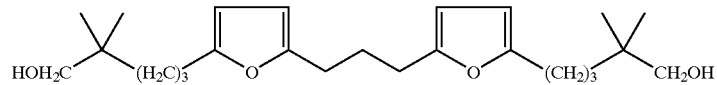

II-40:
5-(5-{3-[5-(5-Hydroxy-4,4-dimethyl-pentyl)-furan-2-yl]-propyl}-furan-2-yl)-2,2-dimethyl-pentan-1-ol

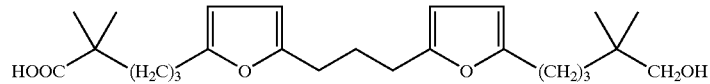

II-41:
5-(5-{3-[5-(5-Hydroxy-4,4-dimethyl-pentyl)-furan-2-yl]-propyl}-furan-2-yl)-2,2-dimethyl-pentanoic acid

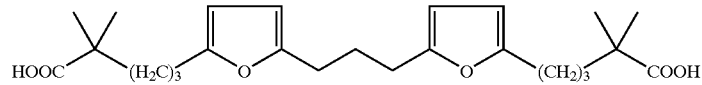

II-42:
5-(5-{3-[5-(4-Carboxyl-4,4-dimethyl-pentyl-furan-2-yl]-propyl}-furan-2-yl)-2,2-dimethyl-pentanoic acid

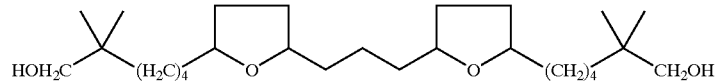

II-43:
6-(5-{3-[5-(6-Hydroxy-5,5-dimethyl-hexyl)-tetrahydro-furan-2-yl]-propyl}-tetrahydro-furan-2-yl)-2,2-dimethyl-hexan-1-ol

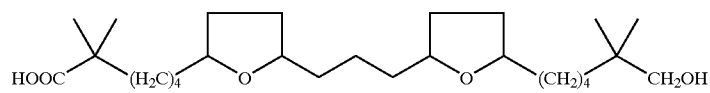

II-44:
6-(5-{3-[5-(6-Hydroxy-5,5-dimethyl-hexyl)-tetrahydro-furan-2-yl]-propyl}-tetrahydro-furan-2-yl)-2,2-dimethyl-hexanoic acid TABLE 1-continued

COMPOUNDS OF THE INVENTION

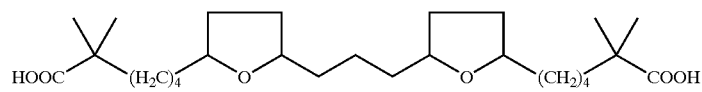

II-45:
6-(5-{3-[5-(5-Carboxyl-5,5-dimethyl-hexyl)-tetrahydro-furan-2-yl]-propyl}-tetra-
hydro-furan-2-yl)-2,2-dimethyl-hexanoic acid

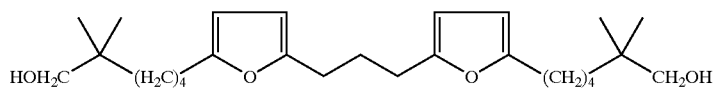

II-46:
6-(5-{3-[5-(6-Hydroxy-5,5-dimethyl-hexyl)-furan-2-yl]-propyl}-furan-2-yl)-2,2-dimethyl-hexan-1-ol

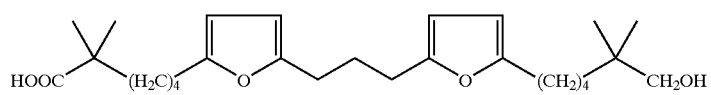

II-47:
6-(5-{3-[5-(6-Hydroxy-5,5-dimethyl-hexyl)-furan-2-yl]-propyl}-furan-2-yl)-2,2-dimethyl-hexanoic acid

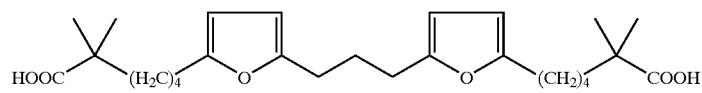

II-48:
6-(5-{3-[5-(5-Carboxyl-5,5-dimethyl-hexyl)-furan-2-yl]-propyl}-furan-2-yl)-2,2-di-
methyl-hexanoic acid

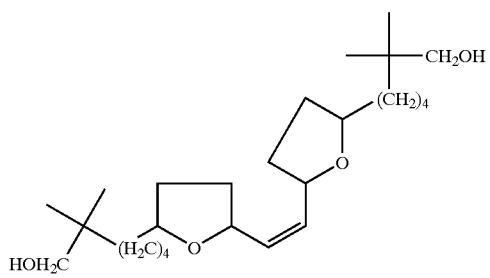

II-49:
6-(5-{2-[5-(6-Hydroxy-5,5-dimethyl-hexyl)-tetrahydro-furan-2-yl]-vinyl}-tetra-
hydro-furan-2-yl)-2,2-dimethyl-hexan-1-ol

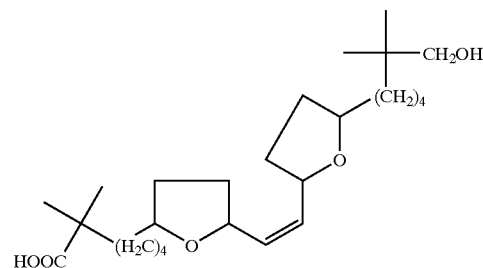

II-50:
6-(5-{2-[5-(6-Hydroxy-5,5-dimethyl-hexyl)-tetrahydro-furan-2-yl]-vinyl}-tetra-
hydro-furan-2-yl)-2,2-dimethyl-hexanoic acid TABLE 1-continued
COMPOUNDS OF THE INVENTION
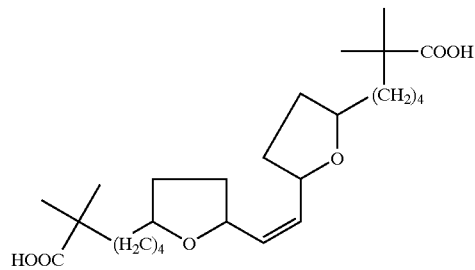
II-51:
6-(5-{2-[5-(5-Carboxyl-5,5-dimethyl-hexyl)-tetrahydro-furan-2-yl]-vinyl}-tetra-
hydro-furan-2-yl)-2,2-dimethyl-hexanoic acid
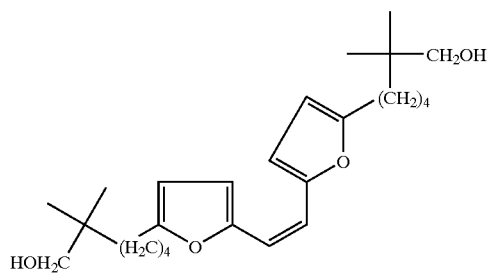
II-52:
6-(5-{2-[5-(6-Hydroxy-5,5-dimethyl-hexyl)-furan-2-yl]-vinyl}-furan-2-yl)-2,2-dimethyl-hexan-1-ol
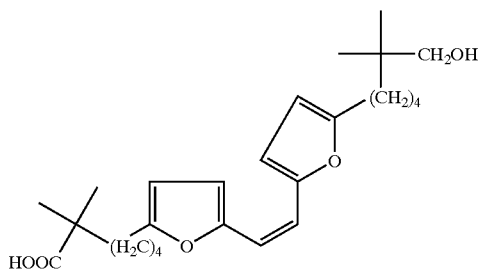
II-53:
6-(5-{2-[5-(6-Hydroxy-5,5-dimethyl-hexyl)-furan-2-yl]-vinyl}-furan-2-yl)-2,2-dimethyl-hexanoic acid
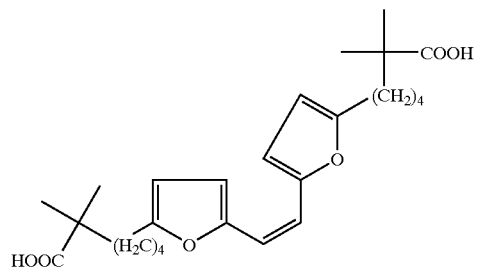
II-54:
6-(5-{2-[5-(5-Carboxyl-5,5-dimethyl-hexyl)-furan-2-yl]-vinyl}-furan-2-yl)-2,2-dimethyl-hexanoic acid TABLE 1-continued

COMPOUNDS OF THE INVENTION

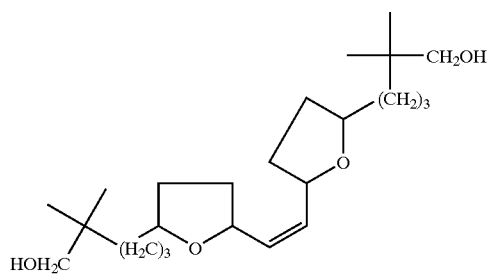

II-55:
5-(5-{2-[5-(5-Hydroxy-4,4-dimethyl-pentyl)-tetrahydro-furan-2-yl]-vinyl}-tetra-hydro-furan-2-yl)-2,2-dimethyl-pentan-1-ol

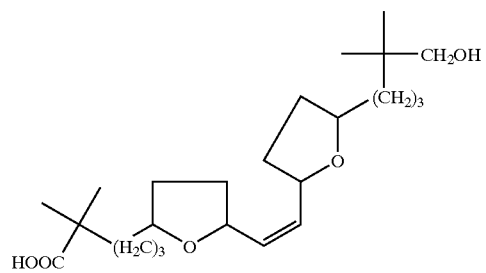

II-56:
5-(5-{2-[5-(5-Hydroxy-4,4-dimethyl-pentyl)-tetrahydro-furan-2-yl]-vinyl}-tetrahydro-furan-2-yl)-2,2-dimethyl-pentanoic acid

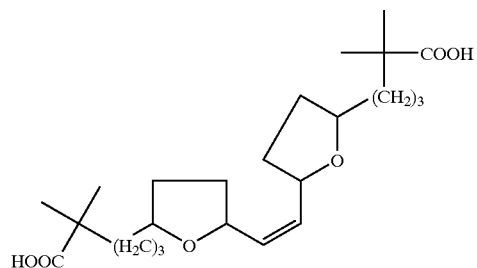

II-57:
5-(5-{2-[5-(4-Carboxyl-4,4-dimethyl-pentyl)-tetrahydro-furan-2-yl]-vinyl}-tetrahydro-furan-2-yl)-2,2-dimethyl-pentanoic acid

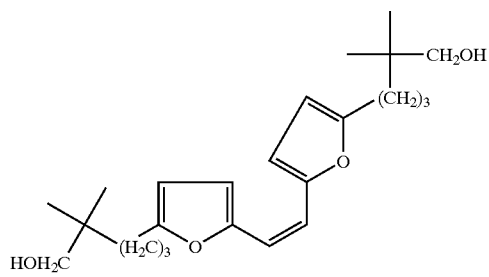

II-58:
5-(5-{2-[5-(5-Hydroxy-4,4-dimethyl-pentyl)-furan-2-yl]-vinyl}-furan-2-yl)-2,2-dimethyl-pentan-1-ol TABLE 1-continued

COMPOUNDS OF THE INVENTION

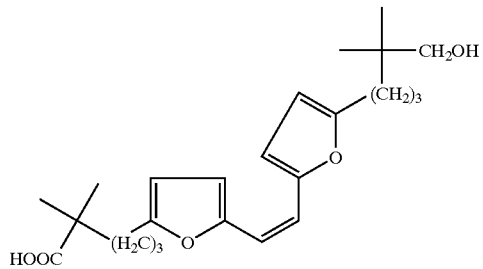

II-59:
5-(5-{2-[5-(5-Hydroxy-4,4-dimethyl-pentyl)-furan-2-yl]-vinyl}-furan-2-yl)-2,2-dimethyl-pentanoic acid

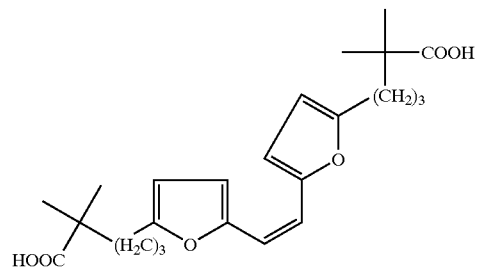

II-60:
5-(5-{2-[5-(4-Carboxyl-4,4-dimethyl-pentyl)-furan-2-yl]-vinyl}-furan-2-yl)-2,2-dimethyl pentanoic acid

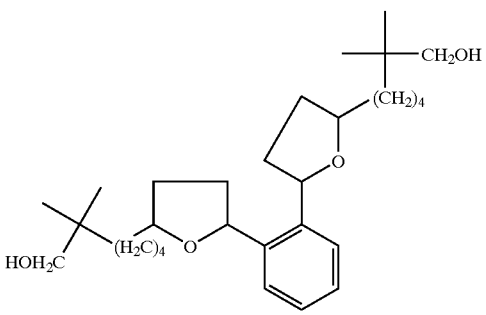

II-61:
6-(5-{2-[5-(6-Hydroxy-5,5-dimethyl-hexyl)-tetrahydro-furan-2-yl]-phenyl}-tetrahydro-furan-2-yl)-2,2-di-methyl-hexan-1-ol

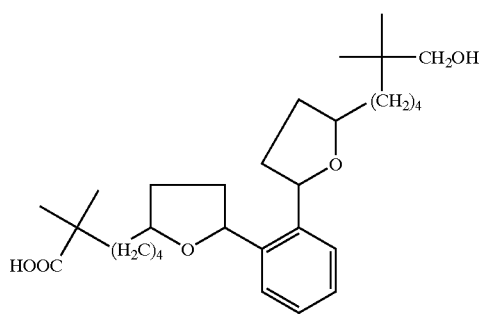

II-62:
6-(5-{2-[5-(6-Hydroxy-5,5-dimethyl-hexyl)-tetrahydro-furan-2-yl]-phenyl}-tetra-hydro-furan-2-yl)-2,2-dimethyl-hexanoic acid TABLE 1-continued

COMPOUNDS OF THE INVENTION

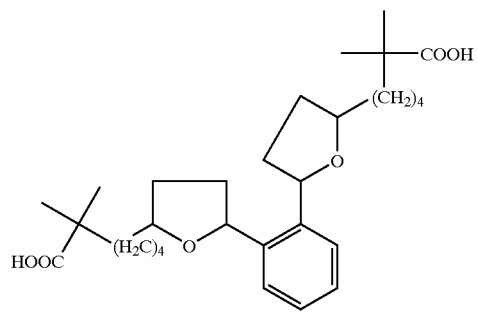

II-63:
6-(5-{2-[5-(5-Carboxyl-5,5-dimethyl-hexyl)-tetrahydro-furan-2-yl]-phenyl}-tetrahydro-furan-2-yl)-2,2-di-
methyl-hexanoic acid

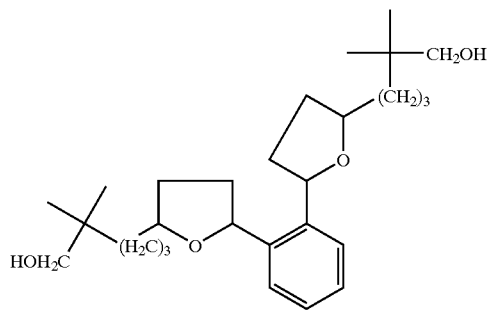

II-64:
5-(5-{2-[5-(5-Hydroxy-4,4-dimethyl-pentyl)-tetrahydro-furan-2-yl]-phenyl}-tetrahydro-furan-2-yl)-2,2-di-
methyl-pentan-1-ol

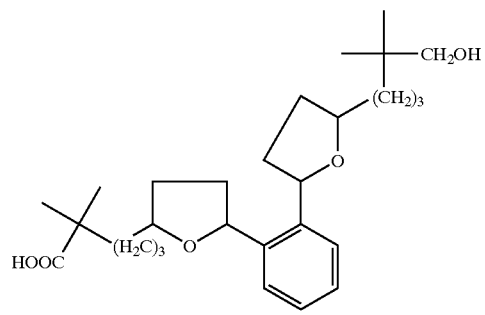

II-65:
5-(5-{2-[5-(5-Hydroxy-4,4-dimethyl-pentyl)-tetrahydro-furan-2-yl]-phenyl}-tetra-
hydro-furan-2-yl)-2,2-dimethyl-pentanoic acid

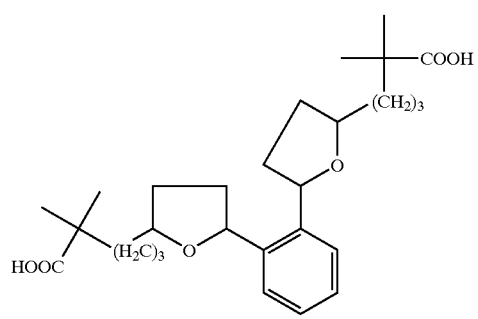

II-66:
5-(5-{2-[5-(4-Carboxyl-4,4-dimethyl-pentyl)-tetrahydro-furan-2-yl]-phenyl}-tetra- TABLE 1-continued
COMPOUNDS OF THE INVENTION
hydro-furan-2-yl)-2,2-dimethyl-pentanoic acid
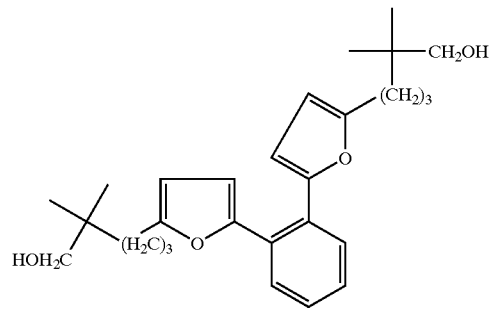
II-67:
5-(5-{2-[5-(5-Hydroxy-4,4-dimethyl-pentyl)-furan-2-yl]phenyl}-furan-2-yl)-2,2-dimethyl-pentan-1-ol
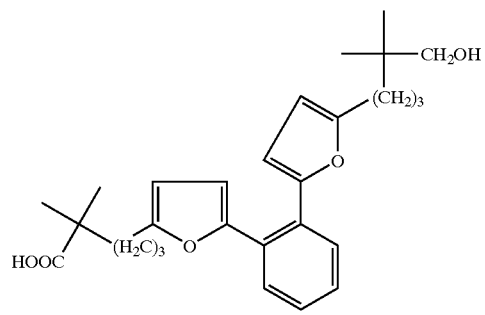
II-68:
5-(5-{2-[5-(5-Hydroxy-4,4-dimethyl-pentyl)-furan-2-yl]-phenyl}-furan-2-yl)-2,2-dimethyl-pentanoic acid
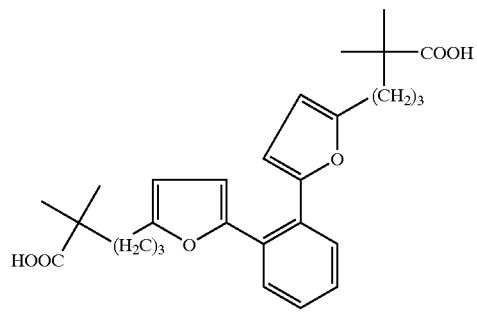
II-69:
5-(5-{2-[5-(4-Carboxyl-4,4-dimethyl-pentyl)-furan-2-yl]-phenyl}-furan-2-yl)-2,2-dimethyl-pentanoic acid
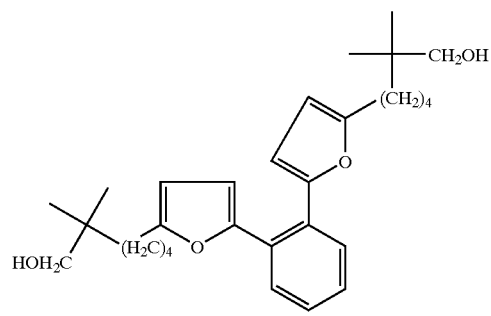

TABLE 1-continued

COMPOUNDS OF THE INVENTION

II-70:
6-(5-{2-[5-(6-Hydroxy-5,5-dimethyl-hexyl)-furan-2-yl]-phenyl}-furan-2-yl)-2,2-di-
methyl-hexan-1-ol

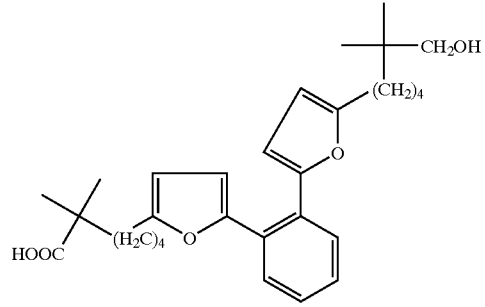

II-71:
6-(5-{2-[5-(6-Hydroxy-5,5-dimethyl-hexyl)-furan-2-yl]-phenyl}-furan-2-yl)-2,2-di-
methyl-hexanoic acid

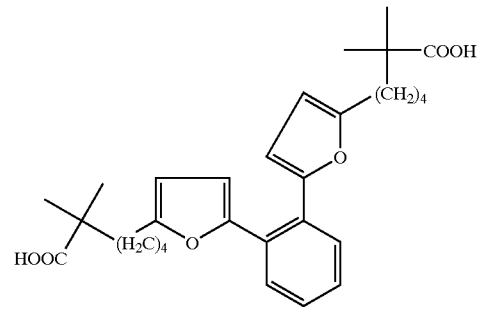

II-72:
6-(5-{2-[5-(5-Carboxyl-5,5-dimethyl-hexyl)-furan-2-yl]-phenyl}-furan-2-yl)-2,2-dimethyl-hexanoic acid

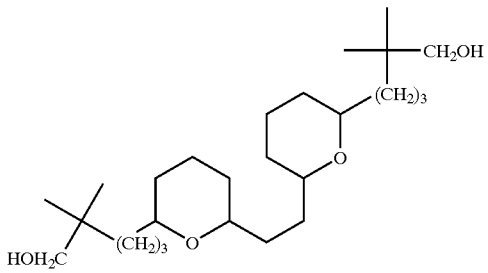

II-73:
5-(6-{2-[6-(5-Hydroxy-4,4-dimethyl-pentyl)-tetrahydro-pyran-2-yl]-ethyl}-tetrahydro-pyran-2-yl)-2,2-di-
methyl-pentan-1-ol

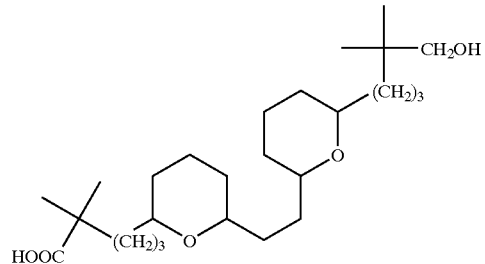

II-74:
5-(6-{2-[6-(5-Hydroxy-4,4-dimethyl-pentyl)-tetrahydro-pyran-2-yl]-ethyl}-tetra-
hydro-pyran-2-yl)-2,2-dimethyl-pentanoic acid TABLE 1-continued

COMPOUNDS OF THE INVENTION

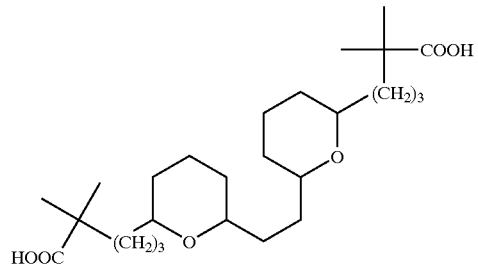

II-75:
5-(6-{2-[6-(4-Carboxyl-4,4-dimethyl-pentyl)-tetrahydro-pyran-2-yl]-ethyl}-tetra-hydro-pyran-2-yl)-2,2-dimethyl-pentanoic acid

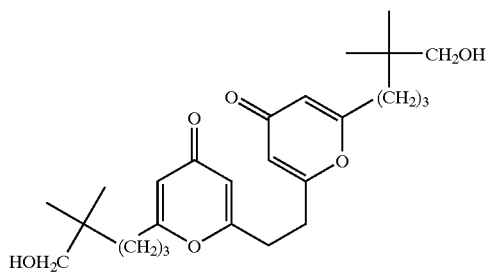

II-76:
5-(6-{2-[6-(5-Hydroxy-4,4-dimethyl-pentyl)-4-oxo-pyran-2-yl]-ethyl}-4-oxo-pyran-2-yl)-2,2-dimethyl-pentan-1-ol

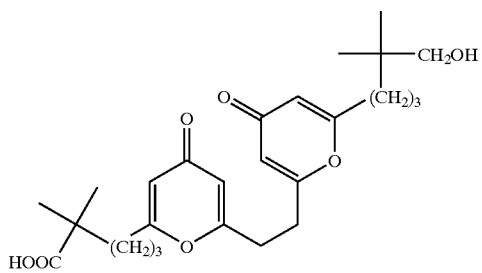

II-77:
5-(6-{2-[6-(5-Hydroxy-4,4-dimethyl-pentyl)-4-oxo-pyran-2-yl]-ethyl}-4-oxo-pyran-2-yl)-2,2-dimethyl-pentanoic acid

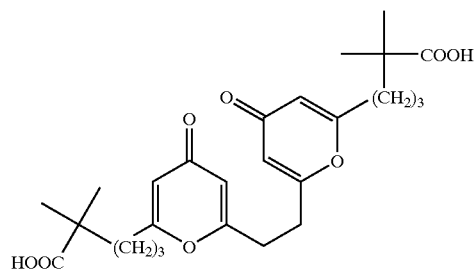

II-78:
5-(6-{2-[6-(4-Carboxyl-4,4-dimethyl-pentyl)-4-oxo-pyran-2-yl]-ethyl}-4-oxo-pyran-2-yl)-2,2-dimethyl-pentanoic acid TABLE 1-continued

COMPOUNDS OF THE INVENTION

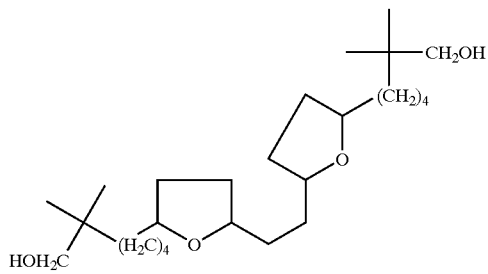

II-79:
6-(5-{2-[5-(6-Hydroxy-5,5-dimethyl-hexyl)-tetrahydro-furan-2-yl]-ethyl}-tetrahydro-furan-2-yl)-2,2-dimethyl-hexan-1-ol

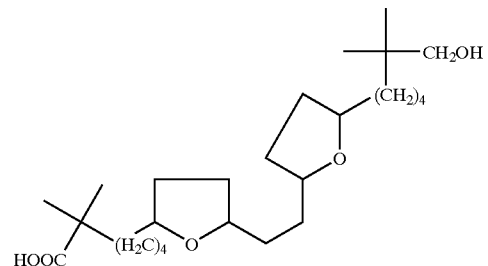

II-80:
6-(5-{2-[5-(6-Hydroxy-5,5-dimethyl-hexyl)-tetrahydro-furan-2-yl]-ethyl}-tetrahydro-furan-2-yl)-2,2-dimethyl-hexanoic acid

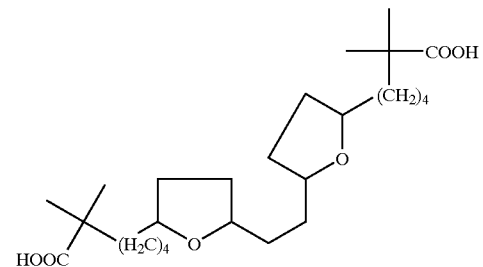

II-81:
6-(5-{2-[5-(5-Carboxyl-5,5-dimethyl-hexyl)-tetrahydro-furan-2-yl]-ethyl}-tetrahydro-furan-2-yl)-2,2-dimethyl-hexanoic acid

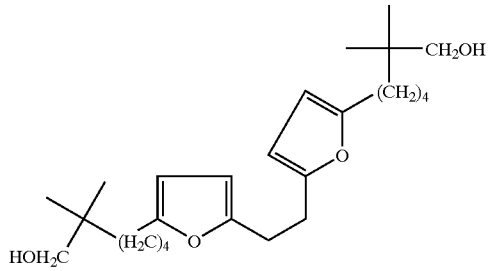

II-82:
6-(5-{2-[5-(6-Hydroxy-5,5-dimethyl-hexyl)-furan-2-yl]-ethyl}-furan-2-yl)-2,2-dimethyl-hexan-1-ol TABLE 1-continued
COMPOUNDS OF THE INVENTION
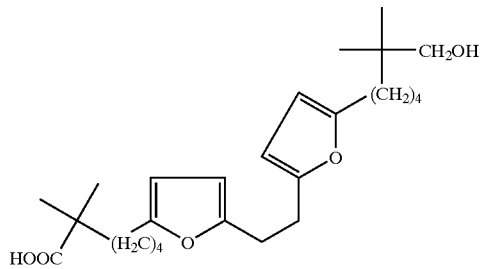
II-83:
6-(5-{2-[5-(6-Hydroxy-5,5-dimethyl-hexyl)-furan-2-yl]-ethyl}-furan-2-yl)-2,2-dimethyl hexanoic acid
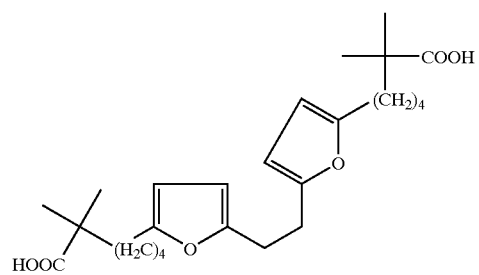
II-84:
6-(5-{2-[5-(5-Carboxyl-5,5-dimethyl-hexyl)-furan-2-yl]-ethyl}-furan-2-yl)-2,2-dimethyl-hexanoic acid
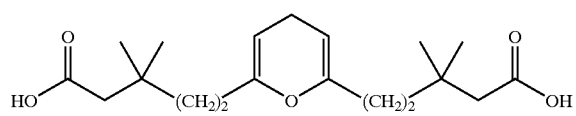
III-1
5-[6-(4-Carboxy-3,3-dimethyl-butyl)-4H-pyran-2-yl]-3,3-dimethyl-pentanoic acid
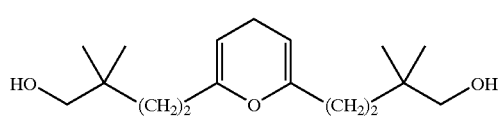
III-2
4-[6-(4-Hydroxy-3,3-dimethyl-butyl)-4H-pyran-2-yl]-2,2-dimethyl-butan-1-ol
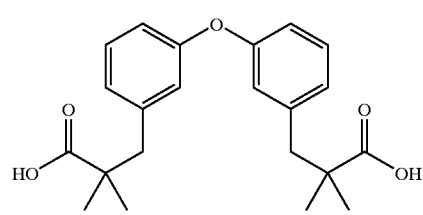

TABLE 1-continued

COMPOUNDS OF THE INVENTION

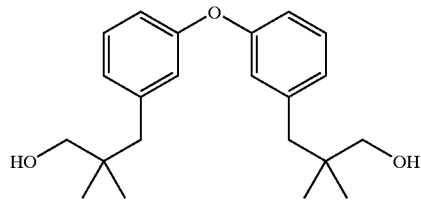

(IV-1)
3-{3-[3-(2-Carboxy-2-methyl-propyl)-phenoxy]-phenyl}-2,2-dimethyl-propionic acid IV-2
1-{3-[3-(2-Hydroxy-2-methyl-propyl)-phenoxy]-phenyl}-2-methyl-propan-2-ol A few examples of preferred compounds of the invention are listed in Table 2 below.

TABLE 2

Preferred Compounds of the Invention

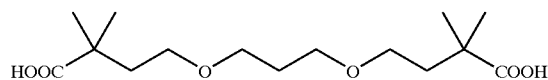

Compound A (I-114)
4-[3-(3-Carboxy-3-methyl-butoxy)-propoxy]-2,2-dimethyl-butyric acid

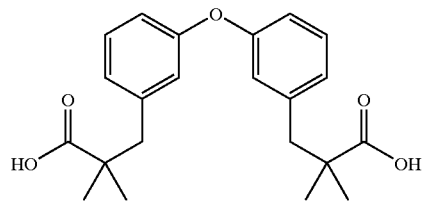

Compound B (IV-1)
3-{3-[3-(2-Carboxy-2-methyl-propyl)-phenoxy]-phenyl}-2,2-dimethyl-propionic acid

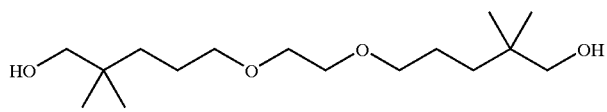

I-297
5-[2-(5-hydroxy-4,4-dimethyl-pentyloxy)-ethoxy]-2,2-dimethyl-pentan-1-ol

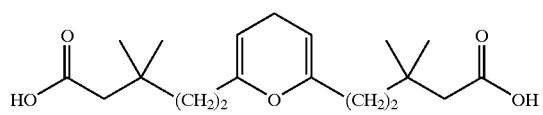

III-1
5-[6-(4-Carboxy-3,3-dimethyl-butyl)-4H-pyran-2-yl]-3,3-dimethyl-pentanoic acid

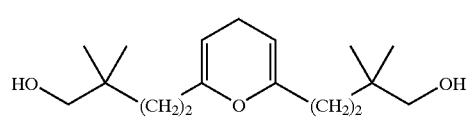

III-2
4-[6-(4-Hydroxy-3,3-dimethyl-butyl)-4H-pyran-2-yl]-2,2-dimethyl-butan-ol

TABLE 2-continued

Preferred Compounds of the Invention

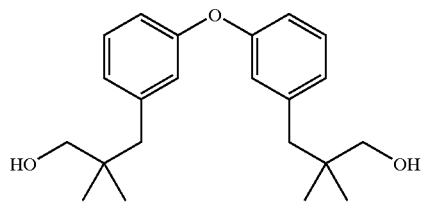

IV-2
1-{3-[3-(2-Hydroxy-2-methyl-propyl)-phenoxy]-phenyl}-2-methyl-propan-2-ol

5.1. Definitions and Abbreviations

Apo(a): apolipoprotein(a)
Apo A-I: apolipoprotein A-I
Apo B: apolipoprotein B
Apo E: apolipoprotein E
FH: Familial hypercholesterolemia
FCH: Familial combined hyperlipidemia
GDM: Gestational diabetes mellitus
HDL: High density lipoprotein
IDL: Intermediate density lipoprotein
IDDM: Insulin dependent diabetes mellitus
LDH: Lactate dehdyrogenase
LDL: Low density lipoprotein
Lp(a): Lipoprotein (a)
MODY: Maturity onset diabetes of the young
NIDDM: Non-insulin dependent diabetes mellitus
PPAR: Peroxisome proliferator activated receptor
RXR: Retinoid X receptor
VLDL: Very low density lipoprotein The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass the racemic form of compounds of the invention as well as all enantiomers and stereoisomers, that is, both the stereomerically pure form (e.g., geometrically pure, enantiomerically pure, or diastereomerically pure) and enantiomeric and stereoisomeric mixtures.

A compound of the invention is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A compound of the invention is considered to be in enantiomerically enriched form when the compound has an enantiomeric excess of greater than about 80% ee, preferably greater than about. As used herein, a racemic mixture means about 50% of one enantiomer and about 50% of is corresponding enantiomer relative to all chiral centers in the molecule. Thus, the invention encompasses all enantiomerically pure, enantiomerically enriched, and racemic mixtures of compounds of formulas I, Ia–Id, II, IIa, III, and IV.

Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

When administered to a patient, e.g., to an animal for veterinary use or for improvement of livestock, or to a human for clinical use, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single ether compound of the invention by weight of the isolate.

The term "therapeutically effective amount" means the amount of a compound of the invention that will elicit the biological or medical response in a mammal that is being that is being treated by the veterinarian, medical doctor, or other clinician.

The term "prophylactically effective" or "preventive" means the amount of a compound of the invention that will prevent or inhibit affliction or mitigate affliction of a mammal with a medical condition that a veterinarian, medical doctor, or other clinician is trying to prevent, inhibit, or mitigate.

The phrase "pharmaceutically acceptable salt(s)," as used herein includes but are not limited to salts of acidic or basic groups that may be present in the compounds of the invention. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds of the invention that include an amino moiety also can form pharmaceutically acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, the term "solvate" means a compound of the invention or a salt thereof, that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a compound of the invention or a salt thereof, that further includes a stoichiometric or non-stoichiometric amount of water bound by non-covalent intermolecular forces.

The term "clathrate" means a compound of the invention or a salt thereof in the form of a crystal lattice that contains spaces (e.g., channels) that have a guest molecule (e.g., a solvent or water) trapped within.

"Altering lipid metabolism" indicates an observable (measurable) change in at least one aspect of lipid metabolism, including but not limited to total blood lipid content, blood HDL cholesterol, blood LDL cholesterol, blood VLDL cholesterol, blood triglyceride, blood Lp(a), blood apo A-I, blood apo E and blood non-esterified fatty acids.

"Altering glucose metabolism" indicates an observable (measurable) change in at least one aspect of glucose metabolism, including but not limited to total blood glucose content, blood insulin, the blood insulin to blood glucose ratio, insulin sensitivity, and oxygen consumption.

As used herein, the term "alkyl group" means a saturated, monovalent, unbranched or branched hydrocarbon chain. Examples of alkyl groups include, but are not limited to, $(C_1-C_6)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

An "alkenyl group" means a monovalent, unbranched or branched hydrocarbon chain having one or more double bonds therein. The double bond of an alkenyl group can be unconjugated or conjugated to another unsaturated group. Suitable alkenyl groups include, but are not limited to $(C_2-C_6)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

An "alkynyl group" means monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_6)$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl.

An alkynyl group can be unsubstituted or substituted with one or two suitable substituents.

An "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "$(C_6)$aryl".

A "heteroaryl group" means a monocyclic- or polycyclic aromatic ring comprising carbon atoms, hydrogen atoms, and one or more heteroatoms, preferably 1 to 3 heteroatoms, independently selected from nitrogen, oxygen, and sulfur. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, furyl, phienyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "$(C_2-C_5)$heteroaryl".

A "cycloalkyl group" means a monocyclic or polycyclic saturated ring comprising carbon and hydrogen atoms and having no carbon—carbon multiple bonds. Examples of cycloalkyl groups include, but are not limited to, $(C_3-C_7)$ cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. Preferably, the cycloalkyl group is a monocyclic ring or bicyclic ring.

A "heterocycloalkyl group" means a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as $(C_1-C_6)$heterocycloalkyl.

As used herein a "heterocyclic radical" or "heterocyclic ring" means a heterocycloalkyl group or a heteroaryl group.

The term "alkoxy group" means an -O-alkyl group, wherein alkyl is as defined above. An alkoxy group can be unsubstituted or substituted with one or two suitable substituents. Preferably, the alkyl chain of an alkyloxy group is from 1 to 6 carbon atoms in length, referred to herein as "$(C_1-C_6)$alkoxy".

The term "aryloxy group" means an -O-aryl group, wherein aryl is as defined above. An aryloxy group can be unsubstituted or substituted with one or two suitable substituents. Preferably, the aryl ring of an aryloxy group is a monocyclic ring, wherein the ring comprises 6 carbon atoms, referred to herein as "$(C_6)$aryloxy".

The term "benzyl" means —$CH_2$-phenyl.

The term "phenyl" means —$C_6H_5$. A phenyl group can be unsubstituted or substituted with one or two suitable substituents.

The term "phenylene" means a divalent —$C_6H_5$— group. A phenylene group can be unsubstituted or substituted with one or two suitable substituents.

A "hydrocarbyl" group means a monovalent group selected from ($C_1$-$C_8$)alkyl, ($C_2$-$C_8$)alkenyl, and ($C_2$-$C_8$) alkynyl, optionally substituted with one or two suitable substituents. Preferably, the hydrocarbon chain of a hydrocarbyl group is from 1 to 6 carbon atoms in length, referred to herein as "($C_1$-$C_6$)hydrocarbyl".

A "carbonyl" group is a divalent group of the formula —C(O)—.

An "alkoxycarbonyl" group means a monovalent group of the formula —C(O)-alkoxy. Preferably, the hydrocarbon chain of an alkoxycarbonyl group is from 1 to 8 carbon atoms in length, referred to herein as a "lower alkoxycarbonyl" group.

A "carbamoyl" group means the radical —C(O)N(R')$_2$, wherein R' is chosen from the group consisting of hydrogen, alkyl, and aryl.

As used herein, "halogen" means fluorine, chlorine, bromine, or iodine. Correspondingly, the meaning of the terms "halo" and "Hal" encompass fluoro, chloro, bromo, and iodo.

As used herein, a "suitable substituent" means a group that does not nullify the synthetic or pharmaceutical utility of the compounds of the invention or the intermediates useful for preparing them. Examples of suitable substituents include, but are not limited to: ($C_1$-$C_8$)alkyl; ($C_1$-$C_8$) alkenyl; ($C_1$-$C_8$)alkynyl; aryl; ($C_2$-$C_5$)heteroaryl; ($C_1$-$C_6$) heterocycloalkyl; ($C_3$-$C_7$)cycloalkyl; O-($C_1$-$C_8$)alkyl; O-($C_1$-$C_8$)alkenyl; O-($C_1$-$C_8$)alkynyl; O-aryl; CN; OH; oxo; halo; C(O)OH; COhalo; O(CO)halo; $CF_3$; $N_3$; $NO_2$; $NH_2$; NH(($C_1$-$C_8$)alkyl); N(($C_1$-$C_8$)alkyl)$_2$; NH(aryl); N(aryl)$_2$; (CO)$NH_2$; (CO)NH(($C_1$-$C_8$)alkyl); (CO)N (($C_1$-$C_8$)alkyl)$_2$; (CO)NH(aryl); (CO)N(aryl)$_2$;O(CO)$NH_2$; NHOH; NOH(($C_1$-$C_8$)alkyl); NOH(aryl); O(CO)NH (($C_1$-$C_8$)alkyl); O(CO)N(($C_1$-$C_8$)alkyl)$_2$; O(CO)NH(aryl); O(CO)N(aryl)$_2$; CHO; CO(($C_1$-$C_8$)alkyl); CO(aryl); C(O) O(($C_1$-$C_8$)alkyl); C(O)O(aryl); O(CO)(($C_1$-$C_8$)alkyl); O(CO)(aryl); O(CO)O(($C_1$-$C_8$)alkyl); O(CO)O(aryl); S-($C_1$-$C_8$)alkyl; S-($C_1$-$C_8$)alkenyl; S-($C_1$-$C_8$)alkynyl; and S-aryl. One of skill in art can readily choose a suitable substituent based on the stability and pharmacological and synthetic activity of the compound of the invention.

5.2. Synthesis

The compounds of the invention can be obtained via standard, synthetic methodology. Some convenient methods are illustrated in Schemes 1–9. Starting materials useful for preparing the compounds of the invention and intermediates therefor, are commercially available or can be prepared from commercially available materials using known synthetic methods and reagents.

SCHEME 1:
Synthesis of Compounds of Formula X

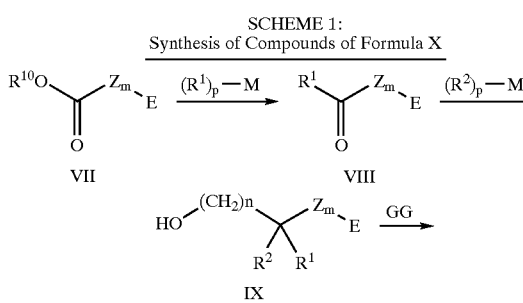

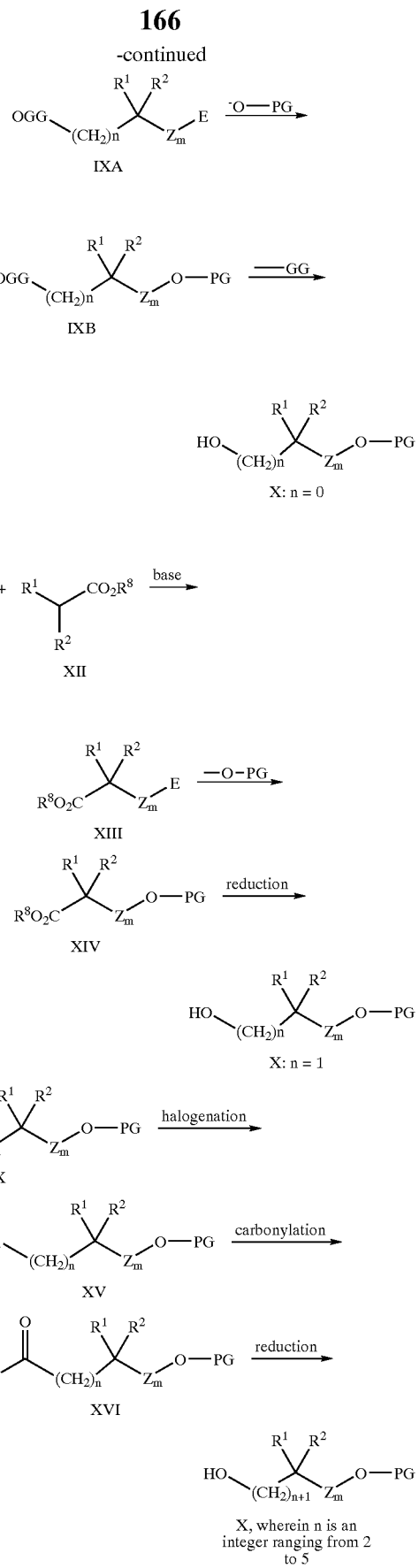

SCHEME 2:
Synthesis of Compounds of Formula XVIIIa, which correspond to Compounds $W^{(1)(2)}—Z_{\overline{m}}—OH$, Wherein $W^{(1)(2)}$ is $C(R^1)(R^2)(CH_2)_{\overline{n}}—Y$
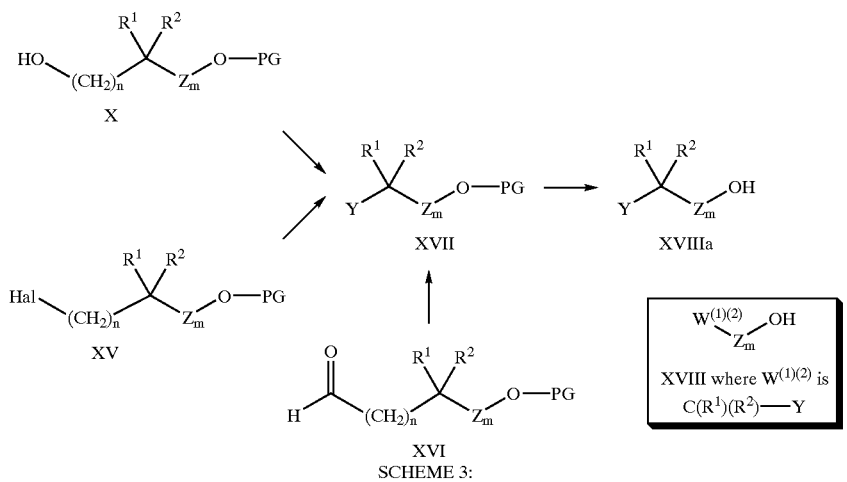
SCHEME 3:
Synthesis of Compounds of Formula XVIIIb, which correspond to $W^{(1)(2)}—Z_{\overline{m}}—OH$, Wherein $W^{(1)(2)}$ is a Lactone Group
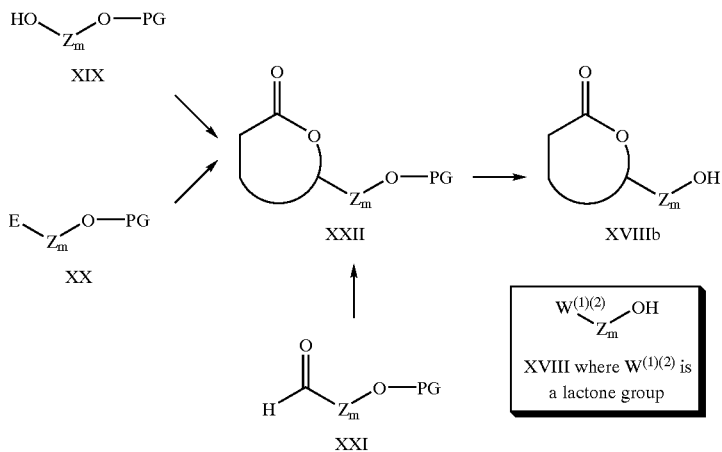
SCHEME 4:
Synthesis of Compounds of Formula XXVIII
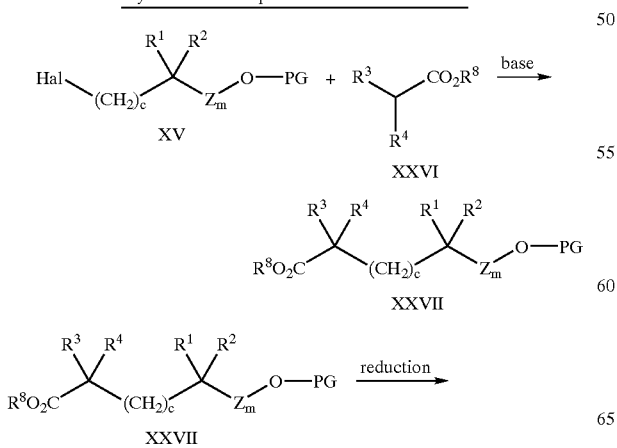
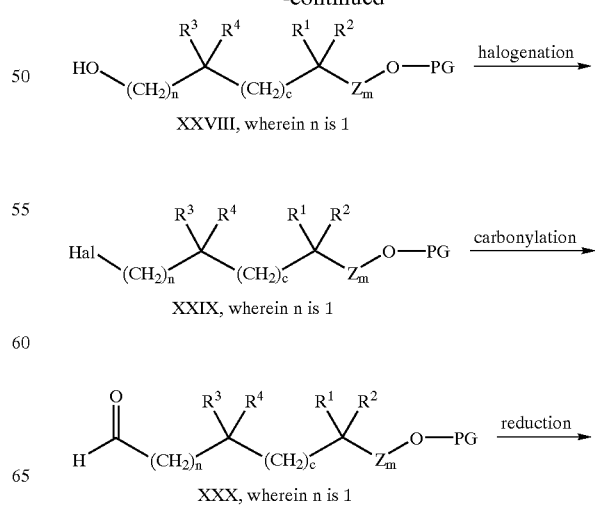

-continued

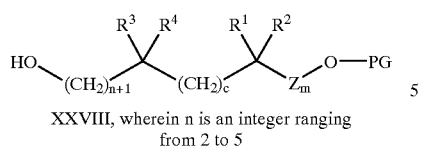

XXVIII, wherein n is an integer ranging from 2 to 5

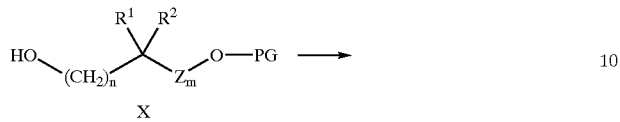

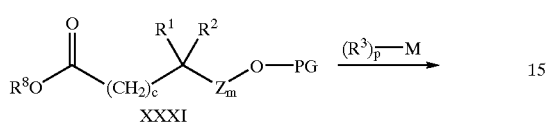

-continued

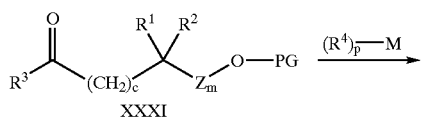

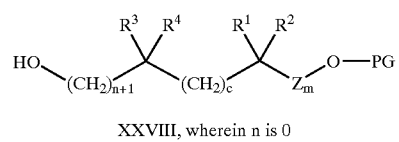

XXVIII, wherein n is 0

SCHEME 5:
Synthesis of Compounds of Formula XVIIIc, which correspond to compounds $W^{(1)(2)}$—$Z_{\overline{m}}$—OH, Where $W^{(1)(2)}$ is $C(R^1)(R^2)$—$(CH_2)_c C(R^5)(R^6)$—Y

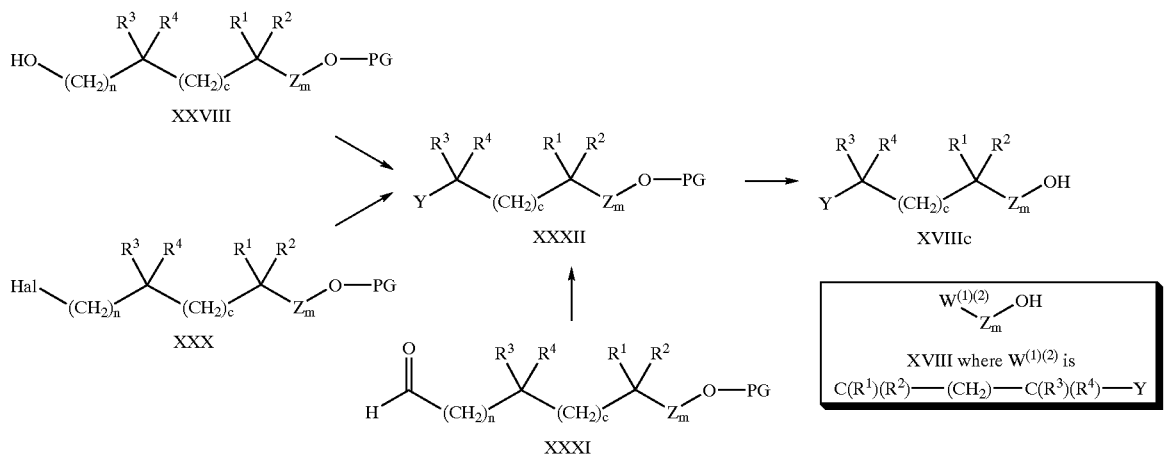

SCHEME 6:
Synthesis of Compounds of Formula XVIIId, which correspond to compounds $W^{(1)(2)}$—$Z_{\overline{m}}$—OH, Wherein $W^{(1)(2)}$ is $C(R^1)(R^2)(CH_2)_{\overline{c}}$—V where V is a Lactone Group

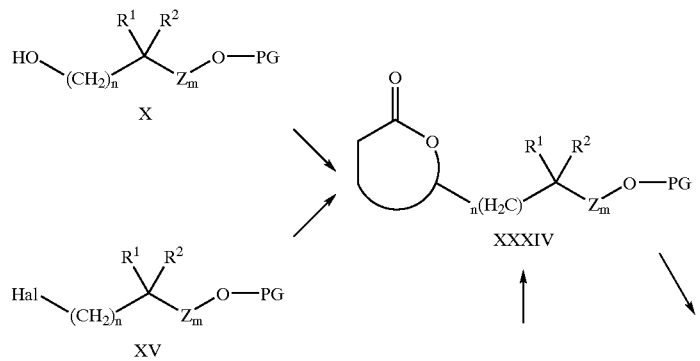

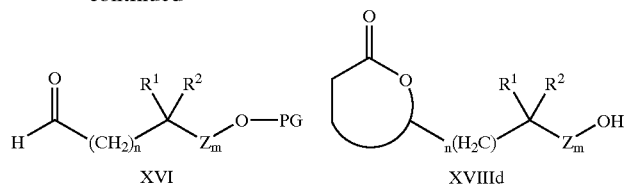

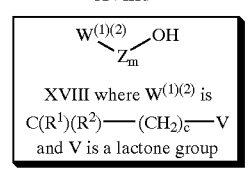

SCHEME 7:
Synthesis of Compounds of Formula I

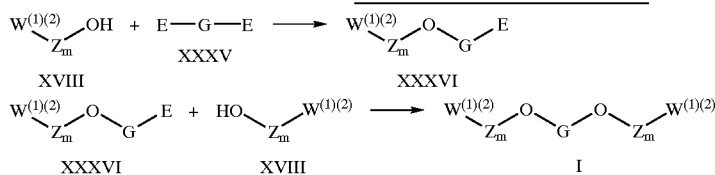

Scheme 1 illustrates the synthesis of mono-protected diols of the formula X, wherein n is an integer ranging from 0 to 4 and $R^1$ and $R^2$ are as defined above. Scheme 1 first outlines the synthesis of mono-protected diols X, wherein n is 0, where esters VII are successively reacted with a first (($R^1$)$_p$-M) then a second (($R^2$)$_p$-M) organometallic reagent providing ketones VIII and alcohols IX, respectively. M is a metal group and p is the metal's valency value (e.g., the valency of Li is 1 and that of Zn is 2). Suitable metals include, but are not limited to, Zn, Na, Li, and —Mg—Hal, wherein Hal is a halide selected from iodo, bromo, or chloro. Preferably, M is —Mg—Hal, in which case the organometallic reagents, ($R^1$)$_p$—Mg—Hal and ($R^2$)$_p$—Mg—Hal, are known in the art as Grignard reagents. Esters VII are available commercially (e.g., Aldrich Chemical Co., Milwaukee, Wis.) or can be prepared by well-known synthetic methods, for example, via esterification of the appropriate 5-halovaleric acid (commercially available, e.g., Aldrich Chemical Co., Milwaukee, Wis.). Both ($R^1$)$_p$-M and ($R^2$)$_p$-M are available commercially (e.g., Aldrich Chemical Co., Milwaukee, Wis.) or can be prepared by well-known methods (see e.g., Kharasch et al., *Grignard Reactions of Non-Metallic Substances*; Prentice-Hall, Englewood Cliffs, N.J., pp. 138–528 (1954) and Hartley; Patai, *The Chemistry of the Metal-Carbon Bond*, Vol.4, Wiley: N.Y., pp. 159–306 and pp. 162–175 (1989), both citations are incorporated by reference herein). The reaction of a first (($R^1$)$_p$-M) then a second (($R^2$)$_p$-M) organometallic reagent with esters VII can be performed using the general procedures referenced in March, J. *Advanced Organic Chemistry; Reactions Mechanisms, and Structure*, 4th ed., 1992, pp. 920–929 and Eicher, Patai, *The Chemistry of the Carbonyl Group*, pt. 1, pp. 621–693; Wiley: New York, (1966), incorporated by reference herein. For example, the synthetic procedure described in Comins et al., 1981,*Tetrahedron Lett.* 22:1085, incorporated by reference herein, can be used. As one example, the reaction can be performed by adding an organic solution of ($R^1$)$_p$-M (about 0.5 to about 1 equivalents) to a stirred, cooled (about 0° C. to about −80° C.) solution comprising esters VII, under an inert atmosphere (e.g., nitrogen) to give a reaction mixture comprising ketones VIII. Preferably, ($R^1$)$_p$-M is added at a rate such that the reaction-mixture temperature remains within about one to two degrees of the initial reaction-mixture temperature. The progress of the reaction can be followed by using an appropriate analytical method, such as thin-layer chromatography or high-performance-liquid chromatography. Next, an organic solution of ($R^2$)$_p$-M (about 0.5 to about 1 equivalent) is added to the reaction mixture comprising ketones VIII in the same manner used to add ($R^1$)$_p$-M. After the reaction providing alcohols IX is substantially complete, the reaction mixture can be quenched and the product can be isolated by workup. Suitable solvents for obtaining alcohols IX include, but are not limited to, dichloromethane, diethyl ether, tetrahydrofuran, benzene, toluene, xylene, hydrocarbon solvents (e.g., pentane, hexane, and heptane), and mixtures thereof. Preferably, the organic solvent is diethyl ether or tetrahydrofuran. Next, alcohols IX are converted to mono-protected diols X, wherein n is 0, using the well-known Williamson ether synthesis. This involves reacting alcohols IX with ⁻O-PG, wherein -PG is a hydroxy-protecting group. For a general discussion of the Williamson ether synthesis, see March, J. *Advanced Organic Chemistry; Reactions Mechanisms, and Structure*, 4th ed., 1992, pp. 386–387, and for a list of procedures and reagents useful in the Williamson ether synthesis see Larock *Comprehensive Organic Transformations*; VCH: New York, 1989, pp. 446–448, both of which references are incorporated herein by reference. As used herein, a "hydroxy-protecting group" means a group that is reversibly attached to a hydroxy moiety that renders the hydroxy moiety unreactive during a subsequent reaction(s) and that can be selectively cleaved to regenerate the hydroxy moiety once its protecting purpose has been served. Examples of hydroxy-protecting groups are found in Greene et al., *Protective Groups in Organic Synthesis*, 3rd ed., John Wiley & Sons, Inc., pp. 17–237 (1999), incorporated herein by reference. Preferably, the hydroxy-protecting group is stable in a basic reaction medium, but can be cleaved by acid. Examples of suitable base-stable acid-labile hydroxy-protecting groups suitable for use with the invention include, but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahyrofuranyl, tetrahydrothiofuranyl, 1-ethoxyethyl, 1-methyl-1-methoxyethyl, t-butyl, allyl, benzyl, o-nitrobenzyl, triphenylmethyl, a-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, and triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably -PG is methoxymethyl ($CH_3OCH_2$—). Reaction of alcohols IX with $^-$O-PG under the conditions of the Williamson ether synthesis require the protection of the hydroxy group. Alcohols IX are protected with a base-labile protecting group, but stable in the presence of nucleophiles of NaH, Na or other metals used in the next step. Protecting groups recommended for this step are: pivaloate, 2,4,6-trimethylbenzoate (mesitoate), alkylmethyl carbonate, or other similar reagents described in Greene et al., *Protective Groups in Organic Synthesis*, 3rd ed., John Wiley & Sons, Inc., pp.170–187 (1999). In a typical experiment, the alcohol IX is protected with a hydroxy-protecting group GG, by treating IX with an acid chloride or an anhydride in the presence of a suitable base preferably pyridine or dimethylamino-pyridine in a temperature range of –20 to 100° C., preferably at 0° C., for various periods of time, from a few hours to a few days. The reaction may occur with or without the presence of a solvent, with the base catalyst acting as one, or if a solvent is required dichloromethane, tetrachloroethylene, and toluene are preferred. The protected alcohols IXA are then subjected to the Williamson ether synthesis, which involves adding a base to a stirred organic solution comprising HO-PG (e.g., methoxymethanol), maintained at a constant temperature within the range of about 0° C. to about 80° C., preferably at about room temperature. Preferably, the base is added at a rate such that the reaction-mixture temperature remains within about one to two degrees of the initial reaction-mixture temperature. The base can be added as an organic solution or in undiluted form. Preferably, the base will have a base strength sufficient to deprotonate a proton, wherein the proton has a $pK_a$ of greater than about 15, preferably greater than about 20. As is well known in the art, the $pK_a$ is a measure of the acidity of an acid H-A, according to the equation $pK_a = -\log K_a$, wherein $K_a$ is the equilibrium constant for the proton transfer. The acidity of an acid H-A is proportional to the stability of its conjugate base $^-$A. For tables listing $pK_a$ values for various organic acids and a discussion on $pK_a$ measurement, see March, J. *Advanced Organic Chemistry; Reactions Mechanisms, and Structure*, 4th ed., 1992, pp. 248–272, incorporated herein by reference. Suitable bases include, but are not limited to, alkyl-metal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. The preferred base is sodium hydride. Solvents suitable for reacting alcohols IXA with -OPG include, but are not limited, to dimethyl sulfoxide, dichloromethane, ethers, and mixtures thereof, preferably tetrahydrofuran. After addition of the base, the reaction mixture can be adjusted to within a temperature range of about 0° C. to about room temperature and alcohols IXA can be added, preferably at a rate such that the reaction-mixture temperature remains within about one to two degrees of the initial reaction-mixture temperature. Alcohols IXA can be diluted in an organic solvent or added in their undiluted form. The resulting reaction mixture is stirred until the reaction is substantially complete as determined by using an appropriate analytical method, preferably by gas chromatography, then the bis-protected diols IXB can be isolated by workup and purification. Bis-protected diols IXB are further treated with a suitable base or nucleophile to remove the GG protection. The preferred reagent for this purpose is lithium aluminum hydride, using as solvent THF, diethyl ether, diisopropyl either, t-butyl-methyl ether or mixtures of solvents, at temperatures ranging from –20 to 50° C. and reaction times from 1 hr to 24 hr. Such procedures are extensively describes in Greene et al., *Protective Groups in Organic Synthesis*, 3rd ed., John Wiley & Sons, Inc., pp.170–187 (1999). The workup of the resulting reaction mixture is performed when the deprotection is complete, which is determined by using the appropriate analytical method, such as thin-layer chromatography or HPLC. Alcohols IX are isolated from the reaction mixture by methods well-known in the art.

Next, Scheme 1 outlines a method useful for synthesizing mono-protected diols X, wherein n is 1. First, compounds XI, wherein E is a suitable leaving group, are reacted with compounds XII, wherein $R^1$ and $R^2$ are as defined above and $R^8$ is H, ($C_1$–$C_6$)alkyl or ($C_6$)aryl, providing compounds XIII. Suitable leaving groups are well known in the art, for example, but not limited to halides, such as chloride, bromide, and iodide; aryl- or alkyl-sulfonyloxy, substituted arylsulfonyloxy (e.g., tosyloxy or mesyloxy); substituted alkyl-sulfonyloxy (e.g., haloalkylsulfonyloxy); phenoxy or subsituted phenoxy; and acyloxy groups. Compounds XI are available commercially (e.g., Aldrich Chemical Co., Milwaukee, Wis.) or can be prepared by well-known methods such as halogenation or sulfonation of butanediol. Compounds XII are also available commercially (e.g., Aldrich Chemical Co., Milwaukee, Wis.) or can be prepared by well-known methods, such as those listed in Larock *Comprehensive Organic Transformations*; Wiley-VCH: New York, 1999, pp. 1754–1755 and 1765. A review on alkylation of esters of type XII is given in J. Mulzer in Comprehensive Organic Functional Transformations, Pergamon, Oxford 1995, pp. 148–151 and exemplary synthetic procedures for reacting compounds XI with compounds XII are described in U.S. Pat. No. 5,648,387, column 6 and Ackerly, et al., 1995, *J Med. Chem.* 1608, all of which citations are incorporated by reference herein. The reaction requires the presence of a suitable base. Preferably, a suitable base will have a $pK_a$ of greater than about 25, more preferably greater than about 30. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; hydride bases such as sodium hydride and potassium hydride. Metal amide bases, such as lithium diisopropylamide are preferred. Preferably, to react compounds XI with compounds XII, a solution of about 1 to about 1.2 equivalents of a suitable base is added to a stirred solution comprising esters XII and a suitable organic solvent, under an inert atmosphere, the solution maintained at a constant temperature within the range of about –95° C. to about room temperature, preferably at about −78° C. to about −20° C. Preferably, the base is diluted in a suitable organic solvent before addition. Preferably, the base is added at a rate of about 1.5 moles per hour. Organic solvents suitable for the reaction of compounds XI with the compounds XII include, but are not limited to, diethyl ether, tetrahydrofuran, benzene, toluene, xylene, hydrocarbon solvents (e.g., pentane, hexane, and heptane), and mixtures thereof. After addition of the base, the reaction mixture is allowed to stir for about 1 to about 4 hours, and a compound XI, preferably dissolved in a suitable organic solvent, is added, preferably at a rate such that the reaction-mixture temperature remains within about one to two degrees of the initial reaction-mixture temperature. After addition of compounds XI, the reaction-mixture temperature can be adjusted to within a temperature range of about −20° C. to about room temperature, preferably to about room temperature, and the reaction mixture is allowed to stir until the reaction is substantially complete as determined by using an appropriated analytical method, preferably thin-layer chromatography or high-performance liquid chromatography. Then the reaction mixture is quenched and compounds XIII, wherein n is 1 can be isolated by workup. Compounds XIV are then synthesized by reacting compounds XIII with ⁻O-PG according to the protocol described above for reacting alcohols IX with ⁻-PG. Next, compounds XIV can be converted to mono-protected diols X, wherein n is 1, by reduction of the ester group of compounds XIV to an alcohol group with a suitable reducing agent. A wide variety of reagents are available for reduction of such esters to alcohols, e.g., see M. Hudlicky, *Reductions in Organic Chemistry*, 2nd ed., 1996 pp. 212–217, incorporated by reference herein. Preferably, the reduction is effected with a hydride type reducing agent, for example, lithium aluminum hydride, lithium borohydride, lithium triethyl borohydride, diisobutylaluminum hydride, lithium trimethoxyaluminum hydride, or sodium bis(2-methoxy)aluminum hydride. For exemplary procedures for reducing esters to alcohols, see Nystrom et al., 1947, *J Am. Chem. Soc.* 69:1197; and Moffet et al., 1963, *Org. Synth., Collect.* 834(4), lithium aluminum hydride; Brown et al, 1965, *J. Am. Chem. Soc.* 87:5614, lithium trimethoxyaluminum hydride; Cerny et al., 1969, *Collect. Czech. Chem. Commun.* 34:1025, sodium bis(2-methoxy)aluminum hydride; Nystrom et al, 1949, *J. Am. Chem.* 71:245, lithium borohydride; and Brown et al, 1980, *J. Org. Chem.* 45: 1, lithium triethyl borohydride, all of which citations are incorporated herein by reference. Preferably, the reduction is conducted by adding an organic solution of compounds XIV to a stirred mixture comprising a reducing agent, preferably lithium aluminum hydride, and an organic solvent. During the addition, the reaction mixture is maintained at a constant temperature within the range of about −20° C. to about 80° C., preferably at about room temperature. Organic solvents suitable for reacting XIII with -OPG include, but are not limited to, dichloromethane, diethyl ether, tetrahydrofuran or mixtures thereof, preferably tetrahydrofuran. After the addition, the reaction mixture is stirred at a constant temperature within the range of about room temperature to about 60° C., until the reaction is substantially complete as determined by using an appropriate analytical method, preferably thin-layer chromatography or high-performance-liquid chromatography. Then the reaction mixture can be quenched and mono-protected diols X, wherein n is 1, can be isolated by workup and purification.

Scheme 1 next illustrates a three step synthetic sequence for homologating mono-protected diols X comprising: (a) halogenation (converting —CH$_2$OH to —CH$_2$—Hal); (b) carbonylation (replacing —Hal with —CHO); and (c) reduction (converting —CHO to —CH$_2$OH), wherein a reaction sequence of (a), (b), and (c) increases the value of n by 1. In step (a) protected halo-alcohols XV, wherein Hal is a halide selected from the group of chloro, bromo, or iodo, preferably iodo, can be prepared by halogenating mono-protected diols X, by using well-known methods (for a discussion of various methods for conversion of alcohols to halides see March, J. *Advanced Organic Chemistry; Reactions Mechanisms, and Structure*, 4th ed., 1992, pp. 431–433, incorporated herein by reference). For example, protected iodo-alcohols XV can be synthesized starting from mono-protected diols X by treatment with Ph$_3$/I$_2$/imidazole (Garegg et al., 1980, *J. C.S Perkin I* 2866); 1,2-dipheneylene phosphorochloridite/I$_2$ (Corey et al, 1967, *J. Org. Chem.* 82:4160); or preferably with Me$_3$SiCl/NaI (Olah et al., 1979, *J. Org. Chem.* 44:8, 1247), all of which citations are incorporated by reference herein. Step (b); carbonylation of alkyl halides, such as protected halo-alcohols XV, is reviewed in Olah et al., 1987, *Chem Rev.* 87:4, 671; and March, J., *Advanced Organic Chemistry; Reactions Mechanisms, and Structure*, 4th ed., 1992, pp. 483–484, both of which are incorporated by reference herein). Protected halo-alcohols XV can be carbonylated with Li(BF$_3$.Et$_2$O)/HCONMe$_2$ using the procedure described in Maddaford et al., 1993, *J. Org. Chem.* 58:4132; Becker et al., 1982, *J. Org. Chem.* 3297; or Myers et al., 1992, *J Am. Chem. Soc.* 114:9369 or, alternatively, with an organometallic/N-formylmorpholine using the procedure described in Olah et al., 1984, *J. Org. Chem.* 49:3856 or Vogtle et al., 1987, *J. Org. Chem.* 52:5560, all of which citations are incorporated by reference herein. The method described in Olah et al., 1984, *J. Org. Chem.* 49:3856 is preferred. Reduction step (c) useful for synthesizing mono-protected diols X from aldehydes XVI, can be accomplished by well-known methods in the art for reduction of aldehydes to the corresponding alcohols (for a discussion see M. Hudlicky, *Reductions in Organic Chemistry*, 2nd ed., 1996 pp 137–139), for example, by catalytic hydrogenation (see e.g., Carothers, 1949, *J. Am. Chem Soc.* 46:1675) or, preferably by reacting aldehydes XVI with a hydride reducing agent, such as lithium aluminum hydride, lithium borohydride, sodium borohydride (see e.g., the procedures described in Chaikin et al., 1949, *J. Am. Chem. Soc.* 71:3245; Nystrom et al., 1947, *J. Am. Chem. Soc.* 69:1197; and Nystrom et al., 1949, *J. Am. Chem.* 71:3245, all of which are incorporated by reference herein). Reduction with lithium aluminum hydride is preferred.

Scheme 2 outlines methodology for the synthesis of protected alcohols XVIIIa wherein Y, R$^1$, R$^2$, Z, and m are defined as above. Protected alcohols XVIIIa correspond to compounds of the formula W$^{(1)(2)}$-Zm-OPG, wherein W$^{(1)(2)}$ is C(R$^1$)(R$^2$)(CH$_2$)$_n$—Y.

O-Protected alcohols XVII, wherein Y comprises a —C(O)OH group, can be synthesized by oxidizing mono-protected diols X with an agent suitable for oxidizing a primary alcohol to a carboxylic acid (for a discussion see M. Hudlicky, *Oxidations in Organic Chemistry*, ACS Monograph 186, 1990, pp. 127–130, incorporated by reference herein). Suitable oxidizing agents include, but are not limited to, pyridinium dichromate (Corey et al., 1979, *Tetrahedron Lett.* 399); manganese dioxide (Ahrens et al., 1967, *J. HeterocycL. Chem.* 4:625); sodium permanganate monohydrate (Menger et al., 1981,*Tetrahedron Lett.* 22:1655); and potassium pernanganate (Sam et al., 1972, *J Am. Chem. Soc.* 94:4024), all of which citations are incorporated by reference herein. The preferred oxidizing reagent is pyridinium dichromate. In an alternative synthetic procedure, protected alcohols XVII, wherein Y comprises a —C(O)OH group, can be synthesized by treatment of O-protected halo-alcohols XV, wherein X is iodo, with CO or $CO_2$, as described in Bailey et al., 1990, *J. Org. Chem.* 55:5404 and Yanagisawa et al, 1994, *J. Am. Chem. Soc.* 116:6130, the two of which citations are incorporated by reference herein. Protected alcohols XVII, wherein Y comprises —C(O)OR$^7$, wherein R$^7$ is as defined above, can be synthesized by oxidation of mono-protected diols X in the presence of R$^7$OH (see generally, March, J. *Advanced Organic Chemistry; Reactions Mechanisms, and Structure*, 4th ed., 1992, p. 1196). An exemplary procedure for such an oxidation is described in Stevens et al., 1982, *Tetrahedron Lett.* 23:4647 (HOCl); Sundarararnan et al., 1978, *Tetrahedron Lett.* 1627 ($O_3$/KOH); Wilson et al., 1982, *J. Org. Chem.* 47:1360 (t-BuOOH/Et$_3$N); and Williams et al., 1988, *Tetrahedron Lett.* 29:5087 (Br$_2$), the four of which citations are incorporated by reference herein. Preferably, O-protected alcohols XVII, wherein Y comprises a —C(O)OR$^7$ group are synthesized from the corresponding carboxylic acid (i.e., XVII, wherein Y comprises —C(O)OH) by esterification with R$^7$OH (e.g., see March, J., *Advanced Organic Chemistry; Reactions Mechanisms, and Structure*, 4th ed., 1992, p. 393–394, incorporated by reference herein). In another alternative synthesis, protected alcohols XVII, wherein Y comprises —C(O)OR$^7$, can be prepared from protected halo-alcohols XV by carbonylation with transition metal complexes (see e.g., March, J. *Advanced Organic Chemistry; Reactions Mechanisms, and Structure*, 4th ed., 1992, p. 484–486; Urata et al., 1991, *Tetrahedron Lett.* 32:36, 4733); and Ogata et al., 1969, *J. Org. Chem.* 3985, the three of which citations are incorporated by reference herein).

O-Protected alcohols XVII, wherein Y comprises —OC(O)R$^7$, wherein R$^7$ is as defined above, can be prepared by acylation of mono-protected diols X with a carboxylate equivalent such as an acyl halide (i.e., R$^7$C(O)—Hal, wherein Hal is iodo, bromo, or chloro, see e.g., March, *J. Advanced Organic Chemistry; Reactions Mechanisms, and Structure*, 4th ed., 1992, p. 392 and *Org. Synth. Coll.* Vol. III, Wiley, N.Y., pp. 142, 144, 167, and 187 (1955)) or an anhydride (i.e., R$^7$C(O)—O—(O)CR$^7$, see e.g., March, *J. Advanced Organic Chemistry; Reactions Mechanisms, and Structure*, 4th ed., 1992, p. 392–393 and *Org. Synth. Coll.* Vol. III, Wiley, N.Y., pp. 11, 127, 141, 169, 237, 281, 428, 432, 690, and 833 (1955), all of which citations are incorporated herein by reference). Preferably, the reaction is conducted by adding a base to a solution comprising mono-protected diols X, a carboxylate equivalent, and an organic solvent, which solution is preferably maintained at a constant temperature within the range of 0° C. to about room temperature. Solvents suitable for reacting mono-protected diols X with a carboxylate equivalent include, but are not limited to, dichloromethane, toluene, and ether, preferably dichloromethane. Suitable bases include, but are not limited to, hydroxide sources, such as sodium hydroxide, potassium hydroxide, sodium carbonate, or potassium carbonate; or an amine such as triethylamine, pyridine, or dimethylaminopyridine. The progress of the reaction can be followed by using an appropriate analytical technique, such as thin layer chromatography or high performance liquid chromatography and when substantially complete, the product can be isolated by workup and purified if desired.

Protected alcohols XVII, wherein Y comprises one of the following phosphate ester groups

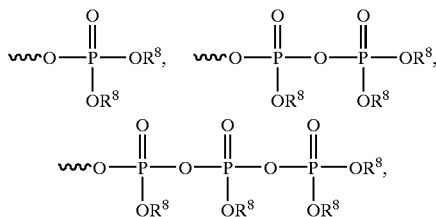

wherein R$^8$ is defined as above, can be prepared by phosphorylation of mono-protected diols X according to well-known methods (for a general reviews, see Corbridge *Phosphorus: An Outline of its Chemistry, Biochemistry, and Uses*, Studies in Inorganic Chemistry, 3rd ed., pp. 357–395 (1985); Ramirez et al.,1978, *Acc. Chem. Res.* 11:239; and Kalckare *Biological Phosphorylations*, Prentice-Hall, New York (1969); J. B. Sweeny in *Comprehensive Organic Functional Group Transformations*, A. R. Katritzky, O. Meth-Cohn and C. W. Rees, Eds. Pergamon: Oxford, 1995, vol 2, pp. 104–109, the four of which are incorporated herein by reference). Protected alcohols XVII wherein Y comprises a monophosphate group of the formula:

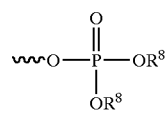

wherein R$^8$ is defined as above, can be prepared by treatment of mono-protected diol X with phosphorous oxychloride in a suitable solvent, such as xylene or toluene, at a constant temperature within the range of about 100° C. to about 150° C. for about 2 hours to about 24 hours. After the reaction is deemed substantially complete, by using an appropriate analytical method, the reaction mixture is hydrolyzed with R$^8$—OH. Suitable procedures are referenced in Houben-Weyl, Methoden der Organische Chemie, Georg Thieme Verlag Stuttgart 1964, vol. XII/2, pp. 143–210 and 872–879, incorporated by reference herein. Alternatively, when both R$^8$ are hydrogen, can be synthesized by reacting mono-protected diols X with silyl polyphosphate (Okamoto et al., 1985, *Bull Chem. Soc. Jpn.* 58:3393, incorporated herein by reference) or by hydrogenolysis of their benzyl or phenyl esters (Chen et al., 1998, *J. Org. Chem.* 63:6511, incorporated herein by reference). In another alternative procedure, when R$^8$ is $(C_1-C_6)$alkyl, $(C_2-C_6)$alkenyl, or $(C_2-C_6)$ alkynyl, the monophosphate esters can be prepared by reacting mono-protected diols X with appropriately substituted phophoramidites followed by oxidation of the intermediate with m-chloroperbenzoic acid (Yu et al., 1988, *Tetrahedron Lett.* 29:979, incorporated herein by reference) or by reacting mono-protected diols X with dialkyl or diaryl substituted phosphorochloridates (Pop et al, 1997, *Org. Prep. and Proc. Int.* 29:341, incorporated herein by reference). The phosphoramidites are commercially available (e.g., Aldrich Chemical Co., Milwaukee, Wis.) or readily prepared according to literature procedures (see e.g., Uhlmann et al. 1986, *Tetrahedron Lett.* 27:1023 and Tanaka et al., 1988, *Tetrahedron Lett.* 29:199, both of which are incorporated herein by reference). The phosphorochloridates are also commercially available (e.g., Aldrich Chemical Co., Milwaukee, Wis.) or prepared according to literature methods (e.g., Gajda et al, 1995, *Synthesis* 25:4099. In still another alternative synthesis, protected alcohols XVII, wherein Y comprises a monophosphate group and $R^8$ is alkyl or aryl, can be prepared by reacting $IP^+ (OR^8)_3$ with mono-protected diols X according to the procedure described in Stowell et al., 1995, *Tetrahedron Lett.* 36:11, 1825 or by alkylation of protected halo alcohols XV with the appropriate dialkyl or diaryl phosphates (see e.g., Okamoto, 1985, *Bull Chem. Soc. Jpn.* 58:3393, incorporated herein by reference).

Protected alcohols XVII wherein Y comprises a diphosphate group of the formula

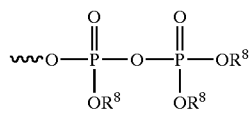

wherein $R^8$ is defined as above, can be synthesized by reacting the above-discussed monophosphates of the formula:

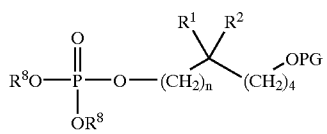

with a phosphate of the formula

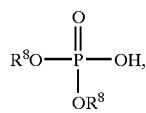

(commercially available, e.g., Aldrich Chemical Co., Milwaukee, Wis.), in the presence of carbodiimide such as dicyclohexylcarbodiimide, as described in Houben-Weyl, *Methoden der Organische Chemie*, Georg Thieme Verlag Stuttgart 1964, vol. XII/2, pp. 881–885. In the same fashion, protected alcohols XVII, wherein Y comprises a triphosphate group of the formula:

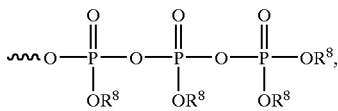

can be synthesized by reacting the above-discussed diphosphate protected alcohols, of the formula:

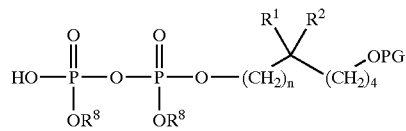

with a phosphate of the formula:

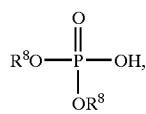

as described above. Alternatively, when $R^8$ is H, protected alcohols XVII wherein Y comprises the triphosphate group, can be prepared by reacting mono-protected diols X with salicyl phosphorochloridite and then pyrophosphate and subsequent cleavage of the adduct thus obtained with iodine in pyridine as described in Ludwig et al., 1989, *J. Org. Chem.* 54:631, incorporated herein by reference.

Protected alcohols XVII, wherein Y is $-SO_3H$ or a heterocyclic group selected from the group consisting of:

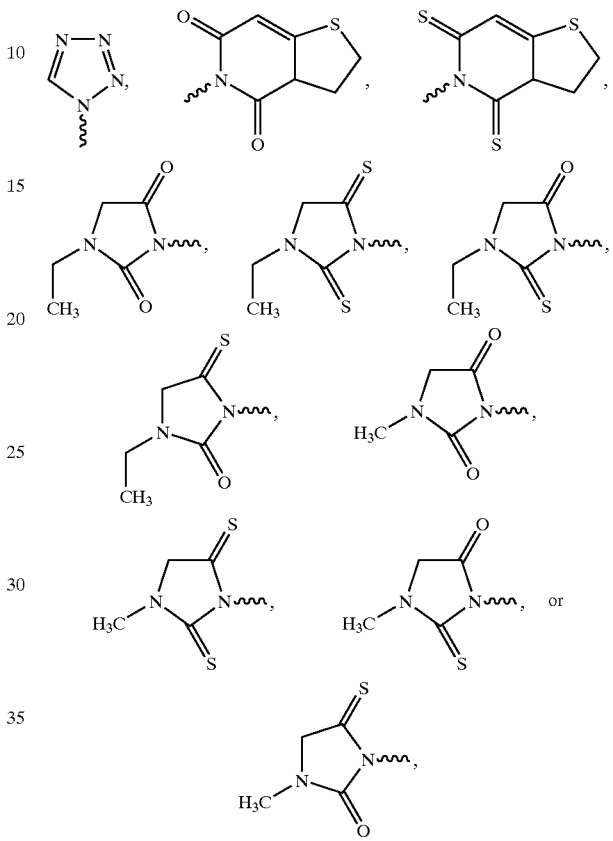

can be prepared by halide displacement from protected halo-alcohols XV. Thus, when Y is $-SO_3H$, protected alcohols XVII can by synthesized by reacting protected halo-alcohols XV with sodium sulfite as described in Gilbert Sulfonation and Related Reactions; Wiley: N.Y., 1965, pp. 136–148 and pp. 161–163; *Org. Synth. Coll. Vol.* 11, Wiley, N.Y., 558, 564 (1943); and *Org. Synth. Coll.* Vol. IV, Wiley, N.Y., 529 (1963), all three of which are incorporated herein by reference. When Y is one of the above-mentioned heterocycles, protected alcohols XVII can be prepared by reacting protected halo-alcohols XV with the corresponding heterocycle in the presence of a base. The heterocycles are available commercially (e.g., Aldrich Chemical Co., Milwaukee, Wis.) or prepared by well-known synthetic methods (see the procedures described in Ware, 1950, *Chem. Rev.* 46:403–470, incorporated herein by reference). Preferably, the reaction is conducted by stirring a mixture comprising XV, the heterocycle, and a solvent at a constant temperature within the range of about room temperature to about 100° C., preferably within the range of about 50° C. to about 70° C. for about 10 to about 48 hours. Suitable bases include hydroxide bases such as sodium hydroxide, potassium hydroxide, sodium carbonate, or potassium carbonate. Preferably, the solvent used in forming protected alcohols XVII is selected from dimethylformamide; formamide; dimethyl sulfoxide; alcohols, such as methanol or ethanol; and mixtures thereof. The progress of the reaction can be followed by using an appropriate analytical technique, such as thin layer chromatography or high performance liquid chromatography and when substantially complete, the product can be isolated by workup and purified if desired.

Protected alcohols XVII, wherein Y is a heteroaryl ring selected from

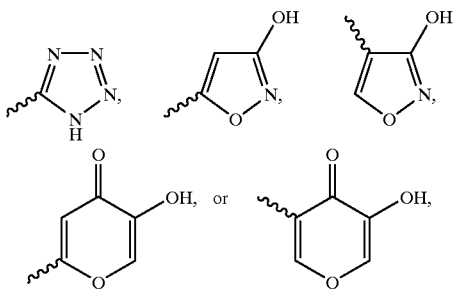

can be prepared by metallating the suitable heteroaryl ring then reacting the resulting metallated heteroaryl ring with protected halo-alcohols XV (for a review, see Katritzky *Handbook of Heterocyclic Chemistry*, Pergamon Press: Oxford 1985). The heteroaryl rings are available commercially or prepared by well-known synthetic methods (see e.g., Joule et al., *Heterocyclic Chemistry*, 3rd ed., 1995; De Sarlo et al., 1971, *J. Chem. Soc.* (C) 86; Oster et al., 1983, *J. Org. Chem.* 48:4307; Iwai et al., 1966, *Chem. Pharm. Bull.* 14:1277; and U.S. Pat. No. 3,152,148, all of which citations are incorporated herein by reference). As used herein, the term "metallating" means the forming of a carbon-metal bond, which bond may be substantially ionic in character. Metallation can be accomplished by adding about 2 equivalents of strong organometallic base, preferably with a $pK_a$ of about 25 or more, more preferably with a $pK_a$ of greater than about 35, to a mixture comprising a suitable organic solvent and the heterocycle. Two equivalents of base are required: one equivalent of the base deprotonates the —OH group or the —NH group, and the second equivalent metallates the heteroaryl ring. Alternatively, the hydroxy group of the heteroaryl ring can be protected with a base-stable, acid-labile protecting group as described in Greene, T. W., *Protective Groups in Organic Synthesis*, 3rd edition 17–237 (1999), incorporated herein by reference. Where the hydroxy group is protected, only one equivalent of base is required. Examples of suitable base-stable, acid-labile hydroxyl-protecting groups, include but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahyrofuranyl, tetrahydrothiofuranyl, 1-ethoxyethyl, 1-methyl-1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo) anthranyl, trimethylsilyl, isopropyldimethylsilyl, t-butyldimethylsilyl, t-butyldiphenylsilyl, tribenzylsilyl, triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably, the $pK_a$ of the base is higher than the $pK_a$ of the proton of the heterocycle to be deprotonated. For a listing of $pK_a$s for various heteroaryl rings, see Fraser et al., 1985, *Can. J. Chem.* 63:3505, incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. If desired, the organometallic base can be activated with a complexing agent, such as N,N,N',N'-tetramethylethylenediamine or hexamethylphosphoramide (1970, *J. Am. Chem. Soc.* 92:4664, incorporated by reference herein). Solvents suitable for synthesizing protected alcohols XVII, wherein Y is a heteroaryl ring include, but are not limited to, diethyl ether; tetrahydrofuran; and hydrocarbons, such as pentane. Generally, metallation occurs alpha to the heteroatom due to the inductive effect of the heteroatom, however, modification of conditions, such as the identity of the base and solvents, order of reagent addition, reagent addition times, and reaction and addition temperatures can be modified by one of skill in the art to achieve the desired metallation position (see e.g., Joule et al., *Heterocyclic Chemistry*, 3rd ed., 1995, pp. 30–42, incorporated by reference herein) Alternatively, the position of metallation can be controlled by use of a halogenated heteroaryl group, wherein the halogen is located on the position of the heteroaryl ring where metallation is desired (see e.g., Joule et al., *Heterocyclic Chemistry*, 3rd ed., 1995, p. 33 and Saulnier et al., 1982, *J. Org. Chem.* 47:757, the two of which citations are incorporated by reference herein). Halogenated heteroaryl groups are available commercially (e.g., Aldrich Chemical Co., Milwaukee, Wis.) or can be prepared by well-known synthetic methods (see e.g., Joule et al., *Heterocyclic Chemistry*, 3rd ed., 1995, pp. 78, 85, 122, 193, 234, 261, 280, 308, incorporated by reference herein). After metallation, the reaction mixture comprising the metallated heteroaryl ring is adjusted to within a temperature range of about 0° C. to about room temperature and protected halo-alcohols XV (diluted with a solvent or in undiluted form) are added, preferably at a rate such that the reaction-mixture temperature remains within about one to two degrees of the initial reaction-mixture temperature. After addition of protected halo-alcohols XV, the reaction mixture is stirred at a constant temperature within the range of about room temperature and about the solvent's boiling temperature and the reaction's progress can be monitored by the appropriate analytical technique, preferably thin-layer chromatography or high-performance liquid chromatography. After the reaction is substantially complete, protected alcohols XVII can be isolated by workup and purification. It is to be understood that conditions, such as the identity of protected halo-alcohol XV, the base, solvents, orders of reagent addition, times, and temperatures, can be modified by one of skill in the art to optimize the yield and selectivity. Exemplary procedures that can be used in such a transformation are described in Shirley et al., 1995, *J. Org. Chem.* 20:225; Chadwick et al., 1979, *J. Chem. Soc., Perkin Trans.* 1 2845; Rewcastle, 1993, *Adv. Het. Chem.* 56:208; Katritzky et al., 1993, *Adv. Het. Chem.* 56:155; and Kessar et al., 1997, *Chem. Rev.* 97:721.

When Y is

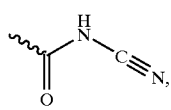

protected alcohols XVII can be prepared from their corresponding carboxylic acid derivatives (XVII, wherein Y is —CO$_2$H) as described in Belletire et al, 1988, *Synthetic Commun.* 18:2063 or from the corresponding acylchlorides (XVII, wherein Y is —CO-halo) as described in Skinner et al., 1995, *J. Am. Chem. Soc.* 77:5440, both citations are incorporated herein by reference. The acylhalides can be prepared from the carboxylic acids by well known procedures such as those described in March, J., *Advanced Organic Chemistry; Reactions Mechanisms, and Structure*, 4th ed., 1992, pp.437–438, incorporated by reference herein. When Y is

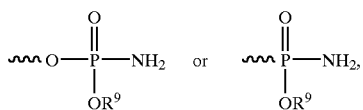

wherein R$^9$ is as defined above, protected alcohols XVII can be prepared by first reacting protected halo-alcohols XV with a trialkyl phosphite according to the procedure described in Kosolapoff, 1951, *Org. React.* 6:273 followed by reacting the derived phosphonic diester with ammonia according to the procedure described in Smith et al., 1957, *J. Org. Chem.* 22:265, incorporated herein by reference. When Y is

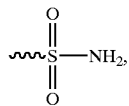

protected alcohols XVII can be prepared by reacting their sulphonic acid derivatives (i.e., XVII, wherein Y is —SO$_3$H) with ammonia as described in Sianesi et al., 1971, Chem. Ber. 104:1880 and Campagna et al, 1994, *Farmaco, Ed. Sci.* 49:653, both of which citations are incorporated herein by reference).

As further illustrated in Scheme 2, protected alcohols XVII can be deprotected providing alcohols XVIIIa. The deprotection method depends on the identity of the alcohol-protecting group, see e.g., the procedures listed in Greene, T. W., *Protective Groups in Organic Synthesis*, 3rd edition 17–237 (1999), particularly see pages 48–49, incorporated herein by reference. One of skill in the art will readily be able to choose the appropriate deprotection procedure. When the alcohol is protected as an ether function (e.g., methoxymethyl ether), the alcohol is preferably deprotected with aqueous or alcoholic acid. Suitable deprotection reagents include, but are not limited to, aqueous hydrochloric acid, p-toluenesulfonic acid in methanol, pyridinium-p-toluenesulfonate in ethanol, Amberlyst H-15 in methanol, boric acid in ethylene-glycol-monoethylether, acetic acid in a water-tetrahydrofuran mixture, aqueous hydrochloric acid is preferred. Examples of such procedures are described, respectively, in Bemady et al., 1979, *J. Org. Chem.* 44:1438; Miyashita et al., 1977, *J. Org. Chem.* 42:3772; Johnston et al., 1988, *Synthesis* 393; Bongini et al, 1979, *Synthesis* 618; and Hoyer et al., 1986, *Synthesis* 655; Gigg et al., 1967, *J. Chem. Soc. C*, 431; and Corey et al, 1978, *J. Am. Chem. Soc.* 100:1942, all of which are incorporated herein by reference.

Scheme 3 depicts the synthesis of protected lactone alcohols XXII and lactone alcohols XVIIIb. Compounds XXII and XVIIIb correspond to compounds of the formula W$^{(1)(2)}$-Zm-OPG and W$^{(1)(2)}$-Zm-OH respectively, wherein W$^{(1)(2)}$ is a lactone group selected from:

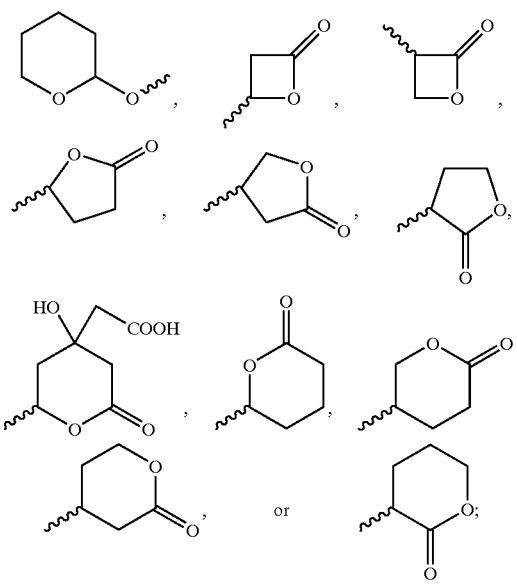

Protected lactone alcohols XXII can be prepared from compounds of the formula XIX, XX, or XXI by using well-known condensation reactions and variations of the Michael reaction. Methods for the synthesis of lactones are disclosed in Multzer in *Comprehensive Organic Functional Group Transformations*, A. R. Katritzky, O. Meth-Cohn and C. W. Rees, Eds. Pergamon: Oxford, 1995, vol 5, pp. 161–173, incorporated herein by reference. Mono-protected diols XIX, electrophilic protected alcohols XX, and aldehydes XXI are readily available ether commercially (e.g., Aldrich Chemical Co., Milwaukee, Wis.) or by well known synthetic procedures.

When W$^{(1)(2)}$ is a beta-lactone group of the formula:

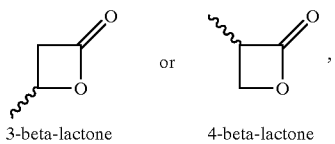

3-beta-lactone      4-beta-lactone protected lactone alcohols XXII can be prepared from aldehydes XXI and electrophilic protected alcohols XX, respectively, by a one-pot-addition-lactonization according to the procedure of Masamune et al.,1976, *J. Am. Chem. Soc.* 98:7874 and Danheiser et al., 1991, *J. Org. Chem.* 56:1176, both of which are incorporated herein by reference. This one-pot-addition-lactonization methodology has been reviewed by Multzer in *Comprehensive Organic Functional Group Transformations*, A. R. Katritzky, O. Meth-Cohn and C. W. Rees, Eds. Pergamon: Oxford, 1995, vol 5, pp. 161, incorporated herein by reference When W$^{(1)(2)}$ is a gamma- or delta-lactone group of the formula:

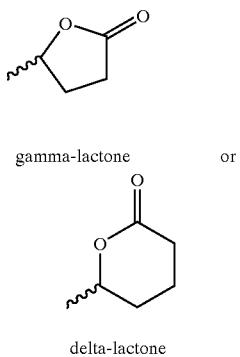

gamma-lactone or delta-lactone protected lactone alcohols XXII can be prepared from aldehydes XXI according to well known synthetic methodology. For example, the methodology described in Masuyama et al., 2000, *J. Org. Chem.* 65:494; Eisch et al., 1978, *J. Organometall. Chem.* C8 160; Eaton et al., 1947, *J. Org. Chem.* 37:1947; Yunker et al., 1978, *Tetrahedron Lett.* 4651; Bhanot et al., 1977, *J. Org. Chem.* 42:1623; Ehlinger et al., 1980, *J. Am. Chem. Soc.* 102:5004; and Raunio et al., 1957, *J. Org. Chem.* 22:570, all of which citations are incorporated herein by reference. For instance, as described in Masuyama et al., 2000, *J. Org. Chem.* 65:494, aldehydes XXI can be treated with about 1 equivalent of a strong organometallic base, preferably with a $pK_a$ of about 25 or more, more preferably with a $pK_a$ of greater than about 35, in a suitable organic solvent to give a reaction mixture. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran.

The reaction-mixture temperature is adjusted to within the range of about 0° C. to about 100° C., preferably about room temperature to about 50° C., and a halide of the formula:

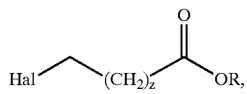

wherein z is 1 or 2 (diluted with a solvent or in undiluted form) is added. The reaction mixture is stirred for a period of about 2 hours to about 48 hours, preferably about 5 to about 10 hours, during which time the reaction's progress can be followed by using an appropriate analytical technique, such as thin layer chromatography or high performance liquid chromatography. When the reaction is deemed substantially complete, protected lactone alcohols XXII can be isolated by workup and purified if desired. When $W^{(1)(2)}$ is a gamma- or delta-lactone group of the formula:

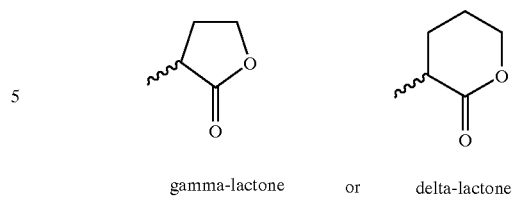

gamma-lactone or delta-lactone protected lactone alcohols XXII can be synthesized by deprotonating the corresponding lactone with a strong base providing the lactone enolate and reacting the enolate with electrophilic protected alcohols XX (for a detailed discussion of enolate formation of active methylene compounds such as lactones, see House *Modern Synthetic Reactions*; W. A. Benjamin, Inc. Philippines 1972 pp. 492–570, and for a discussion of reaction of lactone enolates with electrophiles such as carbonyl compounds, see March, J. *Advanced Organic Chemistry; Reactions Mechanisms, and Structure*, 4th ed., 1992, pp. 944–945, both of which are incorporated herein by reference). Lactone-enolate formation can be accomplished by adding about 1 equivalent of a strong organometallic base, preferably with a $pK_a$ of about 25 or more, more preferably with a $pK_a$ of greater than about 35, to a mixture comprising a suitable organic solvent and the lactone. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Solvents suitable for lactone-enolate formation include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols XX (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, protected lactone alcohols XXII can be isolated by workup and purified if desired. When $W^{(1)(2)}$ is a lactone group of the formula:

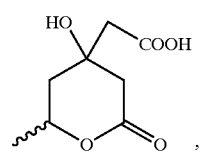

protected lactone alcohols XXII can be prepared from aldehydes XXI according to the procedure described in U.S. Pat. No. 4,622,338, incorporated by reference herein.

When $W^{(1)(2)}$ is a gamma- or delta-lactone group of the formula:

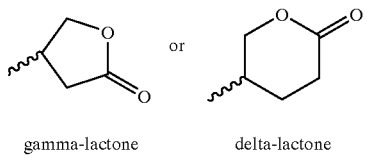

gamma-lactone     delta-lactone protected lactone alcohols XXII can be prepared according to a three step sequence. The first step comprises base-mediated reaction of electrophilic protected alcohols XX with succinic acid esters (i.e., $R^9O_2CCH_2CH_2CO_2R^9$, wherein $R^9$ is alkyl) or glutaric acid esters (i.e., $R^9O_2CCH_2CH_2CH_2CO_2R^9$, wherein $R^9$ is alkyl) providing a diester intermediate of the formula XXIV:

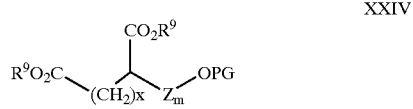

XXIV wherein x is 1 or 2 depending on whether the gamma or delta lactone group is desired. The reaction can be performed by adding about 1 equivalent of a strong organometallic base, preferably with a $pK_a$ of about 25 or more, more preferably with a $pK_a$ of greater than about 35, to a mixture comprising a suitable organic solvent and the succinic or glutaric acid ester. Suitable bases include, but are not limited to, alkyl-metal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols XX (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, the diester intermediate be isolated by workup and purified if desired. In the second step, the intermediate diester can be reduced, with a hydride reducing agent, to yield a diol of the formula XXV:

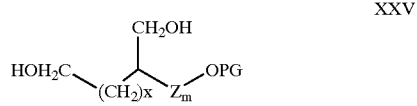

XXV

The reduction can be performed according to the procedures referenced in March, J. *Advanced Organic Chemistry; Reactions Mechanisms, and Structure,* 4th ed., 1992, p. 1214, incorporated herein by reference). Suitable reducing agents include, but are not limited to, lithium aluminum hydride, diisobutylaluminum hydride, sodium borohydride, and lithium borohydride). In the third step, the diol can be oxidatively cyclized with $RuH_2(PPh_3)_4$ to the product protected lactone alcohols XXII according to the procedure of Yoshikawa et al., 1986, *J. Org. Chem.* 51:2034 and Yoshikawa et al., 1983, *Tetrahedron Lett.* 26:2677, both of which citations are incorporated herein by reference. When $W^{(1)(2)}$ is a lactone group of the formula:

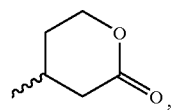

protected lactone alcohols XXII can be synthesized by reacting the Grignard salts of electrophilic protected alcohols XX, where E is a halide, with 5,6-dihydro-2H-pyran-2-one, commercially available (e.g., Aldrich Chemical Co., Milwaukee, Wis.), in the presence of catalytic amounts of a 1-dimethylaminoacetyl)pyrolidine-2yl)methyl-diarylphosphine-copper (I) iodide complex as described in Tomioka et al., 1995, *Tetrahedron Lett.* 36:4275, incorporated herein by reference.

Scheme 4 outlines methodology for the synthesis of protected alcohols XXVIII. Compounds XXVIII, wherein n is an integer ranging from 1 to 4 can be prepared from compounds XV using general synthetic strategy depicted and adapting the synthetic protocols from those discussed for Scheme 1.

Next, Scheme 4 depicts the general strategy for the synthesis of compounds XXVIII wherein n is 0. First, Esters XXXI, wherein $R^8$ is as defined above, are synthesized by oxidation of mono-protected diols X in the presence of $R^8OH$ (see generally, March, J. *Advanced Organic Chemistry; Reactions Mechanisms, and Structure,* 4th ed., 1992, p. 1196). An exemplary procedure for such an oxidation is described in Stevens et al., 1982, *Tetrahedron Lett.* 23:4647 (HOCl); Sundararaman et al., 1978, *Tetrahedron Lett.* 1627 ($O_3$/KOH); Wilson et al., 1982, *J. Org. Chem.* 47:1360 (t-BuOOH/$Et_3N$); and Williams et al., 1988, *Tetrahedron Lett.* 29:5087 ($Br_2$), the four of which citations are incorporated by reference herein. Compounds XXXI are converted to compounds XXVIII wherein n is 0 by adapting the synthetic procedures depicted in Scheme 1.

Scheme 5 outlines methodology for the synthesis of protected alcohols XXXII and alcohols XVIIIc, which correspond to $W^{(1)(2)}$-$Z_m$-OPG and $W^{(1)(2)}$-$Z_m$-OH, respectively, wherein $W^{(1)(2)}$ is $C(R^1)(R^2)$—$(CH_2)_c C(R^5)(R^6)$—Y. The synthesis of starting materials XXVIII, XXX and XXXI are depicted in Scheme 4 and the synthetic methods and procedures can be adapted from those described for Scheme 2.

Scheme 6 depicts the synthesis of protected lactone alcohols XXXIV and lactone alcohols XVIIId. Compounds XXXIV and XVIIId correspond to compounds of the formula, which correspond to compounds $W^{(1)(2)}$-$Z_m$OH, Wherein $W^{(1)(2)}$ is $C(R^1)(R^2)(CH2)_c$—V and V is a Group selected from:

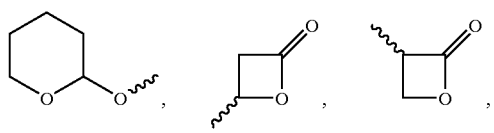

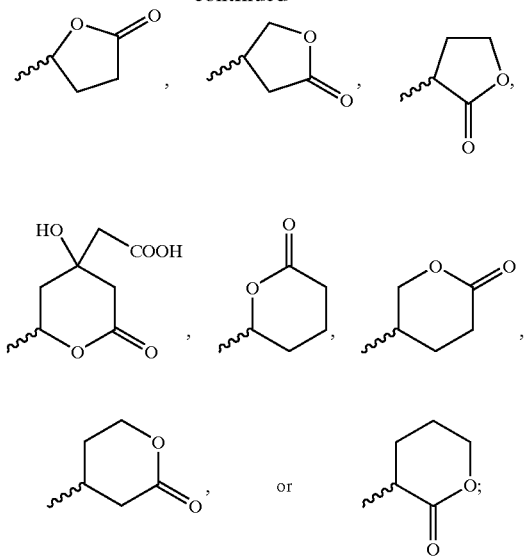

As shown in Scheme 6, protected lactone alcohols XXXIV and lactone alcohols XVIIId can be synthesized from compounds of the formula X, XV, or XVI by adaptation of the methods and procedures discussed above for Scheme 3.

Scheme 7 outlines the synthesis of compounds I. In the first step, compounds XXXVI are synthesized by reacting compounds XVIII (compounds XVIII a,b,c, and d are encompassed by XVIII) with compounds XXXV under the conditions of the Williamson ether synthesis. The conditions and methods discussed in Scheme 1 above for the synthesis of mono-protected diols X from alcohols IX can be adapted for the synthesis of compounds XXXVI. Compounds XXXV, wherein E is a suitable leaving group as defined above, preferably chloride or bromide, are readily obtained commercially (e.g., Aldrich Chemical Co. Milwaukee Wis.) or by well known synthetic methods. Compounds I are obtained by reacting compounds XXXVI with compounds XVII under the conditions of the Williamson ether synthesis. In a preferred Williamson procedure, first, a base is added to a stirred organic solution comprising alcohols XVIII, maintained at a constant temperature within the range of about 0° C. to about 80° C., preferably at about room temperature. Preferably, the base is added at a rate such that the reaction-mixture temperature remains within about one to two degrees of the initial reaction-mixture temperature. The base can be added as an organic solution or in undiluted form. Preferably, the base has a $pK_a$ of about 15 or greater. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. The preferred base is sodium hydride. Suitable solvents include, but are not limited, to dimethyl sulfoxide, dichloromethane, ethers, and mixtures thereof, preferably tetrahydrofuran. After addition of the base, the reaction mixture is adjusted to within a temperature range of about 0° C. to about room temperature and compounds XXXV are added, preferably at a rate such that the reaction-mixture temperature remains within about one to two degrees of the initial reaction-mixture temperature. Compounds XXXV can be diluted in an organic solvent or added in undiluted form. The resulting reaction mixture is heated at a constant temperature within the range of about room temperature to about the solvent's boiling temperature until the reaction is substantially complete as determined by using an appropriate analytical method, preferably by gas chromatography. The product I can be isolated by workup and purification.

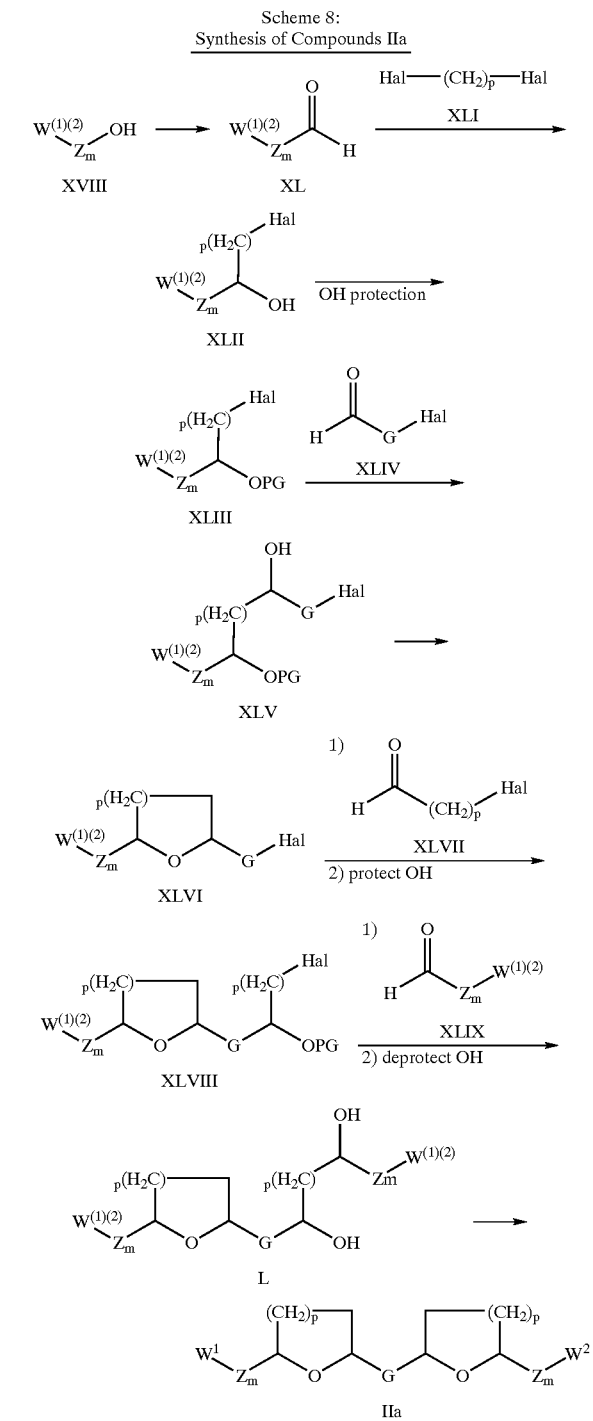

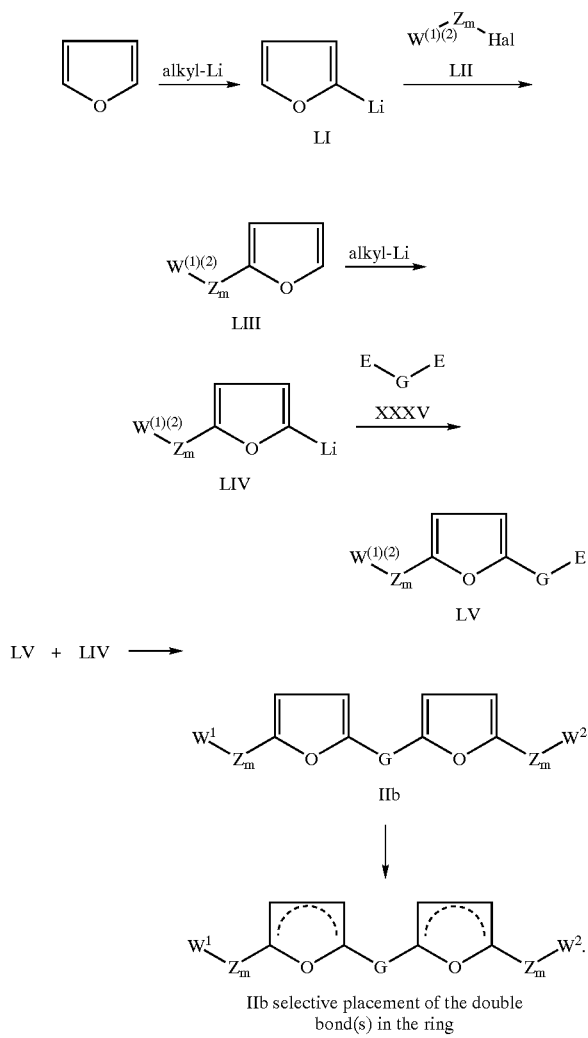

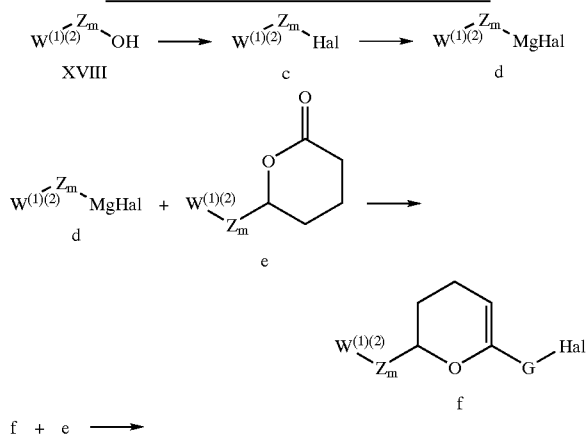

Scheme 8 depicts the synthesis of compounds IIa, that is, compounds of formula II here a double bond is not present in the ring. In the first step, compounds XVIII, prepared as discussed in Schemes 1 to 6 above, can be converted to compounds XL by standard oxidation of the primary alcohol to an aldehyde group. Such oxidations are described in M. Hudlicky, *Oxidations in Organic Chemistry*, ACS Monograph 186, 1990, pp. 114–127, incorporated by reference herein. In the next step Grignard reaction of XL with XLI followed by standard OH protection gives XLIII. Compounds XLI are commercially available (e.g., from Aldrich Chemical Co. Milwakee, Wis.) or readily prepared by standard synthetic methodology. For exemplary procedures for Grignard reaction see March, *J. Advanced Organic Chemistry; Reactions Mechanisms, and Structure,* 4th ed., 1992, pp. 920–929, incorporated herein by reference. Similarly, in the next step, the Grignard salt of XLIII is condensed with XLIV to provide XLV. Next XLV is cyclized to XLVI. When p is one, exemplary cyclization procedures are found in Friedrichsen, W. in *Comprehensive Heterocyclic Chemistry II*; Katritzky, A. R.; Rees, W. C.; Scriven, E. F. V. Eds.; Pergamon Press: Oxford, 1996; Vol.2, p 351, and *Comprehensive Heterocyclic Chemistry*; Katritzky, A. R.; Rees, W. C. Eds.; Pergamon Press: Oxford, 1986; Vol.3. When p is 0, cyclization procedures are found in Hepworth, J. D. in *Comprehensive Heterocyclic Chemistry II*; Katritzky, A. R.; Rees, W. C.; Scriven, E. F. V. Eds.; Pergamon Press: Oxford, 1996; Vol.5, p 351 and *Comprehensive Heterocyclic Chemistry*; Katritzky, A. R.; Rees, W. C. Eds.; Pergamon Press: Oxford, 1986; Vol.3, all of which citations are incorporated by reference herein.

Intermediates XLV and L can be cyclized as diols, or the newly introduced alcohol moiety is first oxidized to a ketone, then the hydroxy-protected ketone is subjected to cyclization, as described in the above Hepworth, J. D. in *Comprehensive Heterocyclic Chemistry II*; Katritzky, A. R.; Rees, W. C.; Scriven, E. F. V. Eds.; Pergamon Press: Oxford, 1996; Vol.5, p 386. For compounds II where $W^{(1)(2)}$ is $HO(CH_2)_n\text{-}R^1R^2$, the hydroxy group is first protected as described in Greene, T. W., *Protective Groups in Organic Synthesis,* 3rd edition(1999). For other structures, where Y is a group such as an acid, aldehydes, etc., protection is needed (acids as esters, preferably pivaloyl, aldehydes as silyl derivatives such as TIPS, stable in both basic and acidic conditions). When $W^{(1)(2)}$ is a lactone it can be introduced as discussed in Scheme 3 above.

Scheme 9a depicts the synthesis of compounds IIb, that is, compounds II where a double bond is present in the five membered ring. In the first step, the appropriate heterocycle is lithiated with an alkyl lithium base (alkyl-Li, e.g., butyl lithium or mixtures of alkyl lithiums with potassium t-butoxide, Wakefield, B. J., *Organolithium Methods*, Academic Press:London, 1998) by well known synthetic methods (for a review, see Katritzky *Handbook of Heterocyclic Chemistry*, Pergamon Press: Oxford 1985). Furan-type heterocycles are exclusively lithiated in the 2-position to provide compounds LI, which in turn are then reacted with electrophiles LII to produce derivatives LIII (Benkeser, R. A. et al., *J. Amer. Chem. Soc.* 1948, 70, 1780; Ramanathan, V. et al., *J. Amer. Chem. Soc.* 1962, 27, 1216;Chadwick, D. J. et al., *J. Chem. Soc. Perkin* 1 1977, 887; Feringa, B. L. et al., *Synthesis* 1988, 316, all of which citations are incorporated herein by reference). Lithiation is performed according to the literature methods, by reacting the heterocycles with alkyl-lithium derivatives such as methyl-lithium, n-,s-, or t-butyl-lithium in solvents such as ether, glyme or tetrahydrofuran, preferably ether. Preferably, ligands, such as TMEDA, DMPU or HMPA or another strong base, such as potassium t-butoxide are included in the reaction medium. Preferably, the reaction temperature is between −40° C. to +60° C., and the reaction time is about 1 to 5 hr. The heterocycles are available commercially or prepared by well-known synthetic methods. Next, in a similar fashion, LV is condensed with LIV to give IIb, wherein each ring has two double bonds. The reactions are performed under similar conditions for substituted heterocycles (for a review on lithiation of 2-substituted furans and thiophenes see *Comprehensive Heterocyclic Chemistry*; Katritzky, A. R.; Rees, W. C. Eds.; Pergamon Press: Oxford, 1986; Vol.3, p 771). After the formation of the metallated heterocylces, they are in situ reacted with electrophiles (e.g., LV) at temperatures between −40° C. to +60° C., for a reaction time of 1 hr to 5 days. The ring double bonds can be selectively reduced or otherwise manipulated by well known synthetic methods to give compounds IIb having only one selectively-placed double bond (i.e., the double bond can be positioned in the desired location within the ring), for example, the methods disclosed in March, J. *Advanced Organic Chemistry; Reactions Mechanisms, and Structure*, 4th ed., 1992, pp. 771–780, incorporated herein by reference.

Scheme 9b depicts the synthesis of compounds IIb, that is, compounds II where a double bond is present in the six membered ring. In the first step, compounds XVIII are converted to compounds c according to the halogenation procedure discussed for Scheme 1. Compound e, readily available by adaptation of the synthetic methods presented in Scheme 1 is reacted with the Grignard salt d to give f. For exemplary procedures for Grignard reactions see March, J. *Advanced Organic Chemistry; Reactions Mechanisms, and Structure*, 4th ed., 1992, pp. 920–929. In a similar fashion, Grignard reaction of f and e gives compounds g. The ring double bonds of g can be selectively reduced or otherwise manipulated by well known synthetic methods to give compounds IIb having only one selectively-placed double bond in the six-membered ring (i.e., the double bond can be positioned in the desired location within the ring), for example, the methods disclosed in March, J. *Advanced Organic Chemistry; Reactions Mechanisms, and Structure*, 4th ed., 1992, pp. 771–780, incorporated herein by reference.

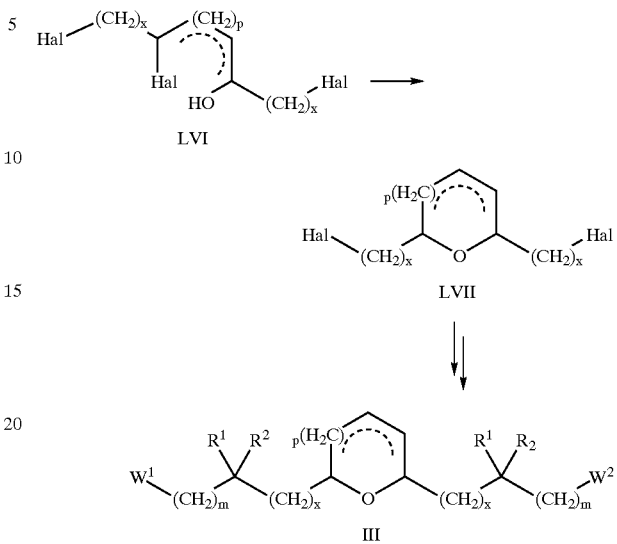

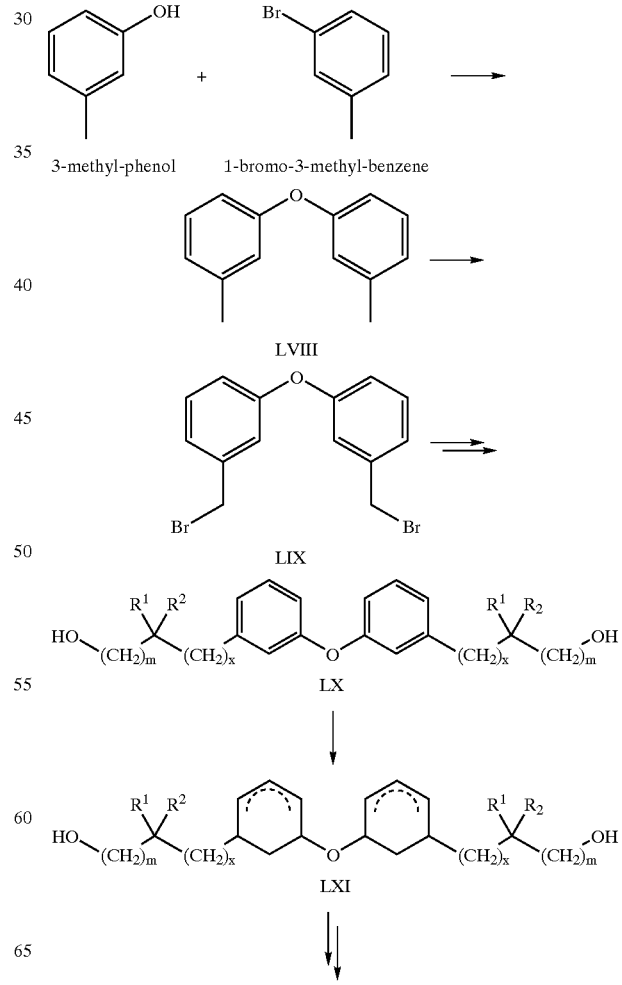

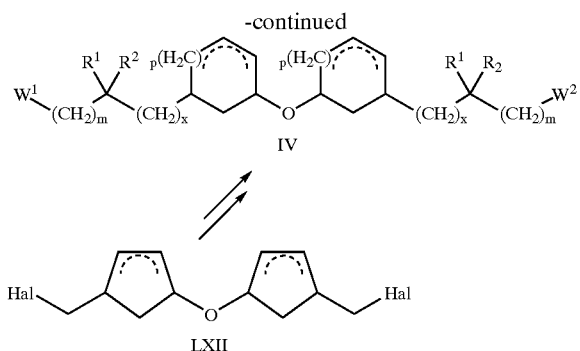

Scheme 10 depicts the general synthesis of compounds III. Compounds LVI where p is 1 or 2 are readily available either commercially (e.g. Aldrich Chemical Co. Milwaukee, Wis.) or by well known synthetic methods from readily available starting materials. Compounds LVI are cyclized to compounds LVII by well known cyclization methods. For example Hamonet, 1918, *Ann. Chim. (Paris)* 10:19, incorporated herein by reference. This cyclization can also be performed under the conditions of the Williamson ether synthesis discussed in detail for Scheme 7 and relying on the kinetic drive for 5 and 6- membered ring closure. Once general synthon LVII is obtained, it is a routine matter to convert it to the compounds III by adapting the chemistry discussed for Schemes 1 and 2.

Scheme 11 depicts the general synthesis of compounds IV. When p of compounds IV is 1, the first step involves Ullmann type coupling between 3-methyl-phenol and 1-bromo-3-methyl-benzene to give LVIII. The Ullmann reaction is well known, for example, see the procedures in March, J. *Advanced Organic Chemistry; Reactions Mechanisms, and Structure*, 4th ed., 1992, pp. 665, incorporated herein by reference. Next LVIII is oxidatively brominated in the benzylic position using well known methods, e.g., N-bromosuccinimide and benzoyl peroxide. Compounds LIX can then be converted to LX by adapting the methods discussed for Scheme 1. If desired, compounds LX can be selectively reduced or partially reduced to provide compounds LXI having mono and dienyl rings, according to well known procedures, see e.g., M. Hudlicky, *Reductions in Organic Chemistry*, ACS Monograph 188, 2nd ed., 1996, pp. 61–68 and 308–309, incorporated herein by reference. Compounds LX and LXI can be converted to compounds IV according to the methods discussed for Schemes 1 and 2. In a similar fashion, compounds LXII, available by well known synthetic methods, can be converted to compounds IV where p is 0.

5.3. Therapeutic Uses

In accordance with the invention, a compound of the invention or a composition of the invention, comprising a compound of the invention and a pharmaceutically acceptable vehicle, excipient, or diluent, is administered to a patient, preferably a human, with or at risk of cardiovascular disease, a dyslipidemia, a dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, or impotence. In one embodiment, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both.

In certain embodiments, the compounds of the invention or the compositions of the invention are administered to a patient, preferably a human, as a preventative measure against such diseases. As used herein, "prevention" or "preventing" refers to a reduction of the risk of acquiring a given disease or disorder. In a preferred mode of the embodiment, the compounds and compositions of the present invention are administered as a preventative measure to a patient, preferably a human having a genetic predisposition to a cardiovascular disease, a dyslipidemia, a dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, or impotence. Examples of such genetic predispositions include but are not limited to the ε4 allele of apolipoprotein E, which increases the likelihood of Alzheimer's Disease; a loss of function or null mutation in the lipoprotein lipase gene coding region or promoter (e.g., mutations in the coding regions resulting in the substitutions D9N and N291 S; for a review of genetic mutations in the lipoprotein lipase gene that increase the risk of cardiovascular diseases, dyslipidemias and dyslipoproteinemias, see Hayden and Ma, 1992, *Mol. Cell Biochem.* 113:171–176); and familial combined hyperlipidemia and familial hypercholesterolemia.

In another preferred mode of the embodiment, the compounds of the invention or compositions of the invention are administered as a preventative measure to a patient having a non-genetic predisposition to a cardiovascular disease, a dyslipidemia, a dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, or impotence. Examples of such non-genetic predispositions include but are not limited to cardiac bypass surgery and percutaneous transluminal coronary angioplasty, which often lead to restenosis, an accelerated form of atherosclerosis; diabetes in women, which often leads to polycystic ovarian disease; and cardiovascular disease, which often leads to impotence. Accordingly, the compounds and compositions of the invention may be used for the prevention of one disease or disorder and concurrently treating another (e.g., prevention of polycystic ovarian disease while treating diabetes; prevention of impotence while treating a cardiovascular disease).

5.3.1. Cardiovascular Diseases

The present invention provides methods for the treatment or prevention of a cardiovascular disease, comprising administering to a patient a therapeutically effective amount of a compound or a composition comprising a compound of the invention and a pharmaceutically acceptable vehicle, excipient, or diluent. As used herein, the term "cardiovascular diseases" refers to diseases of the heart and circulatory system. These diseases are often associated with dyslipoproteinemias and/or dyslipidemias. Cardiovascular diseases which the compounds and compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarcation; cerebral infarction and restenosis.

5.3.2. Dyslipidemias

The present invention provides methods for the treatment or prevention of a dyslipidemia comprising administering to a patient a therapeutically effective amount of a compound or a composition comprising a compound of the invention and a pharmaceutically acceptable vehicle, excipient, or diluent.

As used herein, the term "dyslipidemias" refers to disorders that lead to or are manifested by aberrant levels of circulating lipids. To the extent that levels of lipids in the blood are too high, the compounds and compositions of the invention are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (http://www.americanheart.org and http://rover.nhlbi.nih.gov/chd/, respectively). At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL.

Dyslipidemias which the compounds and compositions of the present invention are useful for preventing or treating include but are not limited to hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of ketone bodies (e.g. β-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, e.g., reducing LDL in the blood of a patient, reducing free triglycerides in the blood of a patient, increasing the ratio of HDL to LDL in the blood of a patient, and inhibiting saponified and/or non-saponified fatty acid synthesis, said methods comprising administering to the patient a compound or a composition comprising a compound of the invention in an amount effective alter lipid metabolism.

5.3.3. Dyslipoproteinemias

The present invention provides methods for the treatment or prevention of a dyslipoproteinemia comprising administering to a patient a therapeutically effective amount of a compound or a composition comprising a compound of the invention and a pharmaceutically acceptable vehicle, excipient, or diluent.

As used herein, the term "dyslipoproteinemias" refers to disorders that lead to or are manifested by aberrant levels of circulating lipoproteins. To the extent that levels of lipoproteins in the blood are too high, the compounds and compositions of the invention are administered to a patient to restore normal levels. Conversely, to the extent that levels of lipoproteins in the blood are too low, the compounds and compositions of the invention are administered to a patient to restore normal levels. Normal levels of lipoproteins are reported in medical treatises known to those of skill in the art.

Dyslipoproteinemias which the compounds and compositions of the present invention are useful for preventing or treating include but are not limited to high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with obesity; lipoprotein abnormalities associated with Alzheimer's Disease; and familial combined hyperlipidemia.

The present invention further provides methods for reducing apo C-II levels in the blood of a patient; reducing apo C-III levels in the blood of a patient; elevating the levels of HDL associated proteins, including but not limited to apo A-I, apo A-II, apo A-IV and apo E in the blood of a patient; elevating the levels of apo E in the blood of a patient, and promoting clearance of triglycerides from the blood of a patient, said methods comprising administering to the patient a compound or a composition comprising a compound of the invention in an amount effective to bring about said reduction, elevation or promotion, respectively.

5.3.4. Glucose Metabolism Disorders

The present invention provides methods for the treatment or prevention of a glucose metabolism disorder, comprising administering to a patient a therapeutically effective amount of a compound or a composition comprising a compound of the invention and a pharmaceutically acceptable vehicle, excipient, or diluent. As used herein, the term "glucose metabolism disorders" refers to disorders that lead to or are manifested by aberrant glucose storage and/or utilization. To the extent that indicia of glucose metabolism (i.e., blood insulin, blood glucose) are too high, the compounds and compositions of the invention are administered to a patient to restore normal levels. Conversely, to the extent that indicia of glucose metabolism are too low, the compounds and compositions of the invention are administered to a patient to restore normal levels. Normal indicia of glucose metabolism are reported in medical treatises known to those of skill in the art.

Glucose metabolism disorders which the compounds and compositions of the present invention are useful for preventing or treating include but are not limited to impaired glucose tolerance; insulin resistance; insulin resistance related breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; polycystic ovarian disease; and high levels of blood insulin and/or glucose.

The present invention further provides methods for altering glucose metabolism in a patient, for example to increase insulin sensitivity and/or oxygen consumption of a patient, said methods comprising administering to the patient a compound or a composition comprising a compound of the invention in an amount effective to alter glucose metabolism.

5.3.5. PPAR Associated Disorders

The present invention provides methods for the treatment or prevention of a PPAR-associated disorder, comprising administering to a patient a therapeutically effective amount of a compound or a composition comprising a compound of the invention and a pharmaceutically acceptable vehicle, excipient, or diluent. As used herein, "treatment or prevention of PPAR associated disorders" encompasses treatment or prevention of rheumatoid arthritis; multiple sclerosis; psoriasis; inflammatory bowel diseases; breast; colon or prostate cancer; low levels of blood HDL; low levels of blood, lymph and/or cerebrospinal fluid apo E; low blood, lymph and/or cerebrospinal fluid levels of apo A-I; high levels of blood VLDL; high levels of blood LDL; high levels of blood triglyceride; high levels of blood apo B; high levels of blood apo C-III and reduced ratio of post-heparin hepatic lipase to lipoprotein lipase activity. HDL may be elevated in plasma, lymph, cerebral spinal, and/or cerebral fluid.

5.3.6. Renal Diseases

The present invention provides methods for the treatment or prevention of a renal disease, comprising administering to a patient a therapeutically effective amount of a compound or a composition comprising a compound of the invention and a pharmaceutically acceptable vehicle, excipient, or diluent. Renal diseases that can be treated by the compounds of the present invention include glomerular diseases (including but not limited to acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (including but not limited to acute tubular necrosis and acute renal failure, polycystic renal diseasemedullary sponge kidney, medullary cystic disease, nephrogenic diabetes, and renal tubular acidosis), tubulointerstitial diseases (including but not limited to pyelonephritis, drug and toxin induced tubulointerstitial nephritis, hypercalcemic nephropathy, and hypokalemic nephropathy) acute and rapidly progressive renal failure, chronic renal failure, nephrolithiasis, or tumors (including but not limited to renal cell carcinoma and nephroblastoma). In a most preferred embodiment, renal diseases that are treated by the compounds of the present invention are vascular diseases, including but not limited to hypertension, nephrosclerosis, microangiopathic hemolytic anemia, atheroembolic renal disease, diffuse cortical necrosis, and renal infarcts.

5.3.7. Cancer

The present invention provides methods for the treatment or prevention of cancer, comprising administering to a patient a therapeutically effective amount of a compound or a composition comprising a compound of the invention and a pharmaceutically acceptable vehicle, excipient, or diluent. Cancers that can be treated or prevented by administering the compounds or the compositions of the invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adeno carcinomas, cystadeno carcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In a most preferred embodiment, cancers that are treated or prevented by administering the compounds of the present invention are insulin resistance or Syndrome X related cancers, including but not limited to breast, prostate and colon cancer.

5.3.8. Other Diseases

The present invention provides methods for the treatment or prevention of Alzheimer's Disease, Syndrome X, septicemia, thrombotic disorders, obesity, pancreatitis, hypertension, inflammation, and impotence, comprising administering to a patient a therapeutically effective amount of a compound or a composition comprising a compound of the invention and a pharmaceutically acceptable vehicle, excipient, or diluent.

As used herein, "treatment or prevention of Alzheimer's Disease" encompasses treatment or prevention of lipoprotein abnormalities associated with Alzheimer's Disease.

As used herein, "treatment or prevention of Syndrome X or Metabolic Syndrome" encompasses treatment or prevention of a symptom thereof, including but not limited to impaired glucose tolerance, hypertension and dyslipidemia/dyslipoproteinemia.

As used herein, "treatment or prevention of septicemia" encompasses treatment or prevention of septic shock.

As used herein, "treatment or prevention of thrombotic disorders" encompasses treatment or prevention of high blood levels of fibrinogen and promotion of fibrinolysis.

In addition to treating or preventing obesity, the compounds and compositions of the invention can be administered to an individual to promote weight reduction of the individual.

5.4. Surgical Uses

Cardiovascular diseases such as atherosclerosis often require surgical procedures such as angioplasty. Angioplasty is often accompanied by the placement of a reinforcing a metallic tube-shaped structure known as a "stent" into a damaged coronary artery. For more serious conditions, open heart surgery such as coronary bypass surgery may be required. These surgical procedures entail using invasive surgical devices and/or implants, and are associated with a high risk of restenosis and thrombosis. Accordingly, the compounds and compositions of the invention may be used as coatings on surgical devices (e.g., catheters) and implants (e.g., stents) to reduce the risk of restenosis and thrombosis associated with invasive procedures used in the treatment of cardiovascular diseases.

5.5. Veterinary and Livestock Uses

A composition of the invention can be administered to a non-human animal for a veterinary use for treating or preventing a disease or disorder disclosed herein.

In a specific embodiment, the non-human animal is a household pet. In another specific embodiment, the non-human animal is a livestock animal. In a preferred embodiment, the non-human animal is a mammal, most preferably a cow, horse, sheep, pig, cat, dog, mouse, rat, rabbit, or guinea pig. In another preferred embodiment, the non-human animal is a fowl species, most preferably a chicken, turkey, duck, goose, or quail.

In addition to veterinary uses, the compounds and compositions of the invention can be used to reduce the fat content of livestock to produce leaner meats. Alternatively, the compounds and compositions of the invention can be used to reduce the cholesterol content of eggs by administering the compounds to a chicken, quail, or duck hen. For non-human animal uses, the compounds and compositions of the invention can be administered via the animals' feed or orally as a drench composition.

5.6. Therapeutic/Prophylactic Administration of the Compounds and Compositions of the Invention Due to the activity of the compounds and compositions of the invention, they are useful in veterinary and human medicine. As described above, the compounds and compositions of the invention are useful for the treatment or prevention of cardiovascular diseases, dyslipidemias, dyslipoproteinemias, glucose metabolism disorders, Alzheimer's Disease, Syndrome X, PPAR-associated disorders, septicemia, thrombotic disorders, obesity, pancreatitis, hypertension, renal disease, cancer, inflammation, and impotence.

The invention provides methods of treatment and prophylaxis by administration to a patient of a therapeutically effective amount of a compound or a composition comprising a compound of the invention. The patient is an animal, including, but not limited to, an animal such a cow, horse, sheep, pig, chicken, turkey, quail, cat, dog, mouse, rat, rabbit, guinea pig, etc., and is more preferably a mammal, and most preferably a human.

The compounds and compositions of the invention, are preferably administered orally. The compounds and compositions of the invention may also be administered by any other convenient route, for example, by intravenous infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

In certain embodiments, for example, for the treatment of Alzheimer's Disease, it may be desirable to introduce one or more compounds of the invention into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds and compositions of the invention can be delivered in a vesicle, in particular a liposome (see Langer, 1990, *Science* 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.).

In yet another embodiment, the compounds and compositions of the invention can be delivered in a controlled release system. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled-release system can be placed in proximity of the target area to be treated, e.g., the liver, thus requiring only a fraction of the systemic dose (see, e.g., Goodson, in Medical Applications of Controlled Release, supra, vol. 2, pp. 115–138 (1984)). Other controlled-release systems discussed in the review by Langer, 1990, *Science* 249:1527–1533) maybe used.

The present compounds and compositions will contain a therapeutically effective amount of a compound of the invention, optionally more than one compound of the invention, preferably in purified form, together with a suitable amount of a pharmaceutically acceptable vehicle, excipient, or diluent so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds and compositions of the invention and pharmaceutically acceptable vehicle, excipient, or diluents are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compounds and compositions, if desired, can also contain minor amounts of wetting or emulsifying agents, or pH buffering agents.

The present compounds and compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the compounds and compositions of the invention are formulated in accordance with routine procedures as a pharmaceutical composition adapted for intravenous administration to human beings. Typically, compounds and compositions of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by intravenous infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compounds and compositions of the invention for oral delivery may be in the form of tablets, lozenges, aqueous or oily suspensions, granules, powders, emulsions, capsules, syrups, or elixirs. Compounds and compositions of the invention for oral delivery can also be formulated in foods and food mixes. Orally administered compounds and compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compounds and compositions may be coated to delay disintegration and absorption in the gastrointestinal tract thereby providing a sustained action over an extended period of time. Selectively permeable membranes surrounding an osmotically active driving compound are also suitable for orally administered compounds and compositions of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compounds and compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound of the invention per kilogram body weight. In specific preferred embodiments of the invention, the oral dose is 0.01 milligram to 70 milligrams per kilogram body weight, more preferably 0.1 milligram to 50 milligrams per kilogram body weight, more preferably 0.5 milligram to 20 milligrams per kilogram body weight, and yet more preferably 1 milligram to 10 milligrams per kilogram body weight. In a most preferred embodiment, the oral dose is 5 milligrams of a compound of the invention per kilogram body weight. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a compound of the invention and another lipid-mediating compound, including but not limited to a statin, a thiazolidinedione, or a fibrate.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for lowering fatty acid synthesis. The compounds and compositions of the invention may also be demonstrated to be effective and safe using animal model systems.

Other methods will be known to the skilled artisan and are within the scope of the invention.

5.7. Combination Therapy

In certain embodiments, a compound of the invention is administered to a mammal, preferably, a human concurrently with one or more other biologically active agents, or with one or more other compounds of the invention, or with both. By "concurrently" it is meant that a compound of the invention and the other agent are administered to a mammal in a sequence and within a time interval such that the compound of the invention can act together with the other agent to provide an increased or synergistic benefit than if they were administered otherwise. For example, each component may be administered at the same time or sequentially in any order at different points in time; however, if not administered at the same time, they should be administered sufficiently closely in time so as to provide the desired treatment effect. Preferably, all components are administered at the same time, and if not administered at the same time, preferably, they are all administered from about 6 hours to about 12 hours apart from one another.

The compounds and compositions of the invention can be used in combination therapy with at least one other therapeutic agent. The compound of the invention and the therapeutic agent can act additively or, more preferably, synergistically. In a preferred embodiment, a compound or a composition comprising a compound of the invention is administered concurrently with the administration of another therapeutic agent, which can be part of the same composition as the compound of the invention or a different composition. In another embodiment, a compound or a composition comprising a compound of the invention is administered prior or subsequent to administration of another therapeutic agent. As many of the disorders for which the compounds and compositions of the invention are useful in treating are chronic disorders, in one embodiment combination therapy involves alternating between administering a compound or a composition comprising a compound of the invention and a composition comprising another therapeutic agent, e.g., to minimize the toxicity associated with a particular drug. The duration of administration of each drug or therapeutic agent can be, e.g., one month, three months, six months, or a year. In certain embodiments, when a composition of the invention is administered concurrently with another therapeutic agent that potentially produces adverse side effects including but not limited to toxicity, the therapeutic agent can advantageously be administered at a dose that falls below the threshold at which the adverse side is elicited.

The present compounds and compositions can be administered together with a statin. Statins for use in combination with the compounds and compositions of the invention include but are not limited to atorvastatin, pravastatin, fluvastatin, lovastatin, simvastatin, and cerivastatin.

The present compounds and compositions can also be administered together with a PPAR agonist, for example a thiazolidinedione or a fibrate. Thiazolidinediones for use in combination with the compounds and compositions of the invention include but are not limited to 5-((4-(2-(methyl-2-pyridinylamino)ethoxy)phenyl)methyl)-2,4-thiazolidinedione, troglitazone, pioglitazone, ciglitazone, WAY-120,744, englitazone, AD 5075, darglitazone, and rosiglitazone. Fibrates for use in combination with the compounds and compositions of the invention include but are not limited to gemfibrozil, fenofibrate, clofibrate, or ciprofibrate. As mentioned previously, a therapeutically effective amount of a fibrate or thiazolidinedione often has toxic side effects. Accordingly, in a preferred embodiment of the present invention, when a composition of the invention is administered in combination with a PPAR agonist, the dosage of the PPAR agonist is below that which is accompanied by toxic side effects.

The present compounds and compositions can also be administered together with a bile-acid-binding resin. Bile-acid-binding resins for use in combination with the compounds and compositions of the invention include but are not limited to cholestyramine and colestipol hydrochloride. The present compounds and compositions can also be administered together with niacin or nicotinic acid. The present compounds and compositions can also be administered together with a RXR agonist. RXR agonists for use in combination with the compounds of the invention include but are not limited to LG 100268, LGD 1069, 9-cis retinoic acid, 2-(1-(3,5,5,8,8-pentamethyl-5,6,7,8-tetrahydro-2-naphthyl)-cyclopropyl)-pyridine-5- carboxylic acid, or 4-((3,5,5,8,8-pentamethyl-5,6,7,8-tetrahydro-2-naphthyl)2-carbonyl)-benzoic acid.

The present compounds and compositions can also be administered together with an anti-obesity drug. Anti-obesity drugs for use in combination with the compounds of the invention include but are not limited to β-adrenergic receptor agonists, preferably β-3 receptor agonists, fenfluramine, dexfenfluramine, sibutramine, bupropion, fluoxetine, and phentermine. The present compounds and compositions can also be administered together with a hormone. Hormones for use in combination with the compounds of the invention include but are not limited to thyroid hormone, estrogen and insulin. Preferred insulins include but are not limited to injectable insulin, transdermal insulin, inhaled insulin, or any combination thereof. As an alternative to insulin, an insulin derivative, secretagogue, sensitizer or mimetic may be used. Insulin secretagogues for use in combination with the compounds of the invention include but are not limited to forskolin, dibutryl cAMP or isobutyl-methylxanthine (IBMX). The present compounds and compositions can also be administered together with a tyrphostin or an analog thereof. Tyrphostins for use in combination with the compounds of the invention include but are not limited to tryphostin 51. The present compounds and compositions can also be administered together with sulfonylurea-based drugs. Sulfonylurea-based drugs for use in combination with the compounds of the invention include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide. The present compounds and compositions can also be administered together with a biguanide. Biguanides for use in combination with the compounds of the invention include but are not limited to metformin, phenformin and buformin. The present compounds and compositions can also be administered together with an α-glucosidase inhibitor. α-glucosidase inhibitors for use in combination with the compounds of the invention include but are not limited to acarbose and miglitol.

The present compounds and compositions can also be administered together with an apo A-I agonist. In one embodiment, the apo A-I agonist is the Milano form of apo A-I (apo A-IM). In a preferred mode of the embodiment, the apo A-IM for administration in conjunction with the compounds of the invention is produced by the method of U.S. Pat. No. 5,721,114 to Abrahamsen. In another preferred embodiment, the apo A-I agonist is a peptide agonist. In another preferred embodiment, the apo A-I agonist is proapo A-I. In a preferred mode of the embodiment, the apo A-I peptide agonist for administration in conjunction with the compounds of the invention is a peptide of U.S. Pat. Nos. 6,004,925 or 6,037,323 to Dasseux.

The present compounds and compositions can also be administered together with apolipoprotein E (apo E). In a preferred mode of the embodiment, the apoE for administration in conjunction with the compounds of the invention is produced by the method of U.S. Pat. No. 5,834,596 to Ageland.

The present compounds and compositions can also be administered together with antibiotics, antihypertensives, and antineoplastic agents routinely used for treating cancer, impotence, cardiovascular, and renal diseases.

In yet other embodiments, the present compounds and compositions can be administered together with an HDL-raising drug; an HDL enhancer; or a regulator of the apolipoprotein A-I, apolipoprotein A-IV and/or apolipoprotein genes.

5.8. Combination Therapy with Cardiovascular Drugs

The present compounds and compositions can be administered together with a known cardiovascular drug. Cardiovascular drugs for use in combination with the compounds of the invention to prevent or treat cardiovascular diseases include but are not limited to peripheral antiadrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., amrinone, milrinone, enoximone, fenoximone, imazodan, sulmazole), antidysrhythmic drugs, calcium entry blockers, ranitine, bosentan, and rezulin.

5.9. Combination Therapy for Cancer Treatment

The present compounds and compositions can be administered together with treatment with irradiation or one or more chemotherapeutic agents. For irridiation treatment, the irradiation can be gamma rays or X-rays. For a general overview of radiation therapy, see Hellman, Chapter 12: Principles of Radiation Therapy Cancer, in: Principles and Practice of Oncology, DeVita et al., eds., $2^{nd}$. Ed., J.B. Lippencott Company, Philadelphia. Useful chemotherapeutic agents include methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a specific embodiment, a composition of the invention further comprises one or more chemotherapeutic agents and/or is administered concurrently with radiation therapy. In another specific embodiment, chemotherapy or radiation therapy is administered prior or subsequent to administration of a present composition, preferably at least an hour, five hours, 12 hours, a day, a week, a month, more preferably several months (e.g., up to three onths), subsequent to administration of a composition of the invention.

6. EXAMPLES

6.1. 5-[2-(5-Hydroxy-4,4-dimethyl-pentyloxy-ethoxy]-2,2-dimethyl-pentan-1-ol

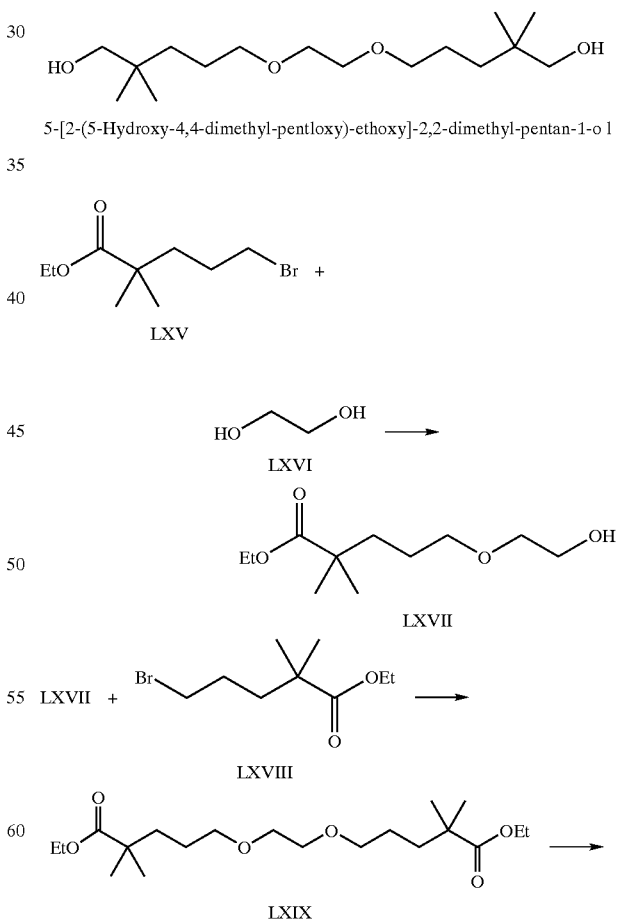

Title Compound

5-Bromo-2,2-dimethyl-1-pentanol

Under argon, a suspension of LiBH$_4$ (14.8 g, 646 mmol) in methylene chloride (600 mL) was stirred as methanol (25.6 mL, 20.2 g, 629 mmol) was added dropwise, taking care to keep the temperature below 30° C. To this mixture, a solution of ethyl 5-bromo-2,2-dimethylpentanoate (100.0 g, 392 mmol; prepared according to Kuwahara et al. *Chem. Pharm. Bull* 1997, 48, 1447) in methylene chloride (200 mL) was added dropwise over 20 minutes, and the solution was heated under reflux for 21 h. After chilling in an ice-bath, the reaction was quenched by adding H$_2$O dropwise (100 mL). After the effervescence stopped, 2 N HCl (125 mL) was added dropwise and the solution was stirred until the effervescence ceased. The procedure was repeated with another portion of 2 N HCl (125 mL). The layers were separated, and the aqueous layer was extracted with an additional methylene chloride (500 mL). The two organic portions were combined and washed with 2 N HCl 9300 mL), then sat. NaHCO$_3$ (300 mL). After drying the organics over Na$_2$SO$_4$, the solution was evaporated to yield the product as a light yellow oil (77.6 g, 91% yield). $^1$H NMR (d6-DMSO), d (ppm): 4.42 (s, 1H); 3.45 (t, 2 H, J=6.6); 3.08 (s, 2H); 1.84–1.69 (m, 2H); 1.27 (t, 2 H, J=8.3); 0.78 (s, 6H). $^{13}$C NMR (d6-DMSO), d (ppm): 69.7, 36.9, 35.7, 34.5, 27.4, 24.0.

5-Bromo-2,2-dimethyl-1-(tetrahydropyranyloxy)-pentane

5-Bromo-2,2-dimethyl-1-pentanol (77.4 g, 357 mmol) was dissolved in dichloromethane (400 mL), andp-toluenesulfonic acid (6.9 g, 36 mmol) was added. The mixture was stirred under argon, chilled in an ice-bath, then was added 3,4-dihydro-2H-pyran (37.2 g, 428 mmol) and stirred, gradually letting warm to rt overnight. The reaction mixture was then filtered through neutral alumina (100 g); the alumina was rinsed with additional dichloromethane (600 mL). After evaporating to about 500 mL, the organic layer was extracted with sat. NaHCO$_3$ (3' 200 mL), then dried over MgSO$_4$. The solution was concentrated under reduced pressure to produce the expected product (107.83 g, 97% yield) as a yellow oil. $^1$H NMR (CDCl3), d (ppm): 4.55 (m, 1H); 3.83 (m, 1H); 3.51 (m, 1H); 3.47 (d, 1 H, J=9.0); 3.38 (t, 2 H, J=6.8); 2.98 (d, 1 H, J=9.0); 1.94–1.75 (m, 2H); 1.75–1.44 (m, 6H); 1.40 (t, 2 H, J=8.5); 0.93–0.87 (m, 6H). $^{13}$C NMR (CDCl3), d (ppm): 99.0, 76.2, 61.9, 37.9, 34.6, 34.0, 30.6, 27.9, 25.6, 24.64, 24.56, 19.4. HRMS calcd. for C$_{12}$H$_{24}$BrO$_2$ (MH$^+$): 279.0960, found 279.0955.

5-(2-Hydroxy-ethoxy)-2,2-dimethyl-pentanoic acid ethyl ester (compound LXVII)

5-Bromo-2,2-dimethyl-pentanoic acid ethyl ester LVX (19 g, 74.5 mmol) was dissolved in ethylene glycol LXVI (150 mL) and stirred under argon. After NaI (1.13 g, 7.5 mmol) was added as a catalyst, NaH as a dispersion in mineral oil (3.0 g, 60%, in mineral oil; 75 mmol) was added slowly in five portions. After stirring for 20 min at rt, the mixture was subjected to gentle heating in an oil-bath to 70° C. After 20 h, the heating was discontinued and the mixture was cooled to rt. The reaction mixture was diluted with H$_2$O (500 mL), then extracted with chloroform (5' 100 mL). The chloroform extract was then washed with 10% aq Na$_2$S$_2$O$_3$ (300 mL), then with H$_2$O (400 mL). After drying over MgSO$_4$, the solvent was evaporated to give crude product (13.1 g), which was further purified by vacuum distillation (80–83 C., 0.11 torr) to give the desired product (3.25 g, 20% yield) as a clear, colorless oil. $^1$H NMR (CDC13), d (ppm): 4.51 (t, 1 H, J=5.5); 4.05 (q, 2 H,J=7.1); 3.48 (m, 2H); 3.40–3.31 (m, 4H); 1.18 (t, 3 H,J=7.1); 1.11 (s, 6H). $^{13}$C NMR (CDCl3), d (ppm): 176.7, 72.0, 70.5, 60.3, 59.8, 41.3, 36.7, 24.88, 24.78, 14.0. HRMS calcd. for C$_{11}$H$_{23}$O$_4$ (MH$^+$): 219.1613, found 219.1605.

5-[2-(4-Ethoxycarbonyl-4-methyl-pentyloxy)-ethoxy]-2,2-dimethyl-pentanoic Acid Ethyl Ester (compound LXIX)

A solution of 3.25 g of LXVII above (3.25 g, 14.4 mmol) and 5-bromo-2,2-dimethyl-pentanoic acid ethyl ester LXVIII (4.40 g, 93% purity, 17.3 mmol) in freshly distilled anhydrous THF (50 mL) was stirred under argon and chilled in an ice-bath. Carefully, NaH (0.88 g, 60%, as a dispersion in mineral oil; 22 mmol) was added, then tetrabutylammonium iodide catalyst (75 mg, 0.2 mmol). The solution was heated to reflux for 4 days, until TLC evaluation (silica, 1:1 hexane/ethyl acetate) showed total product conversion (starting alcohol RF 0.5, product diester 0.9). After cooling to rt, the THF was diluted with H$_2$O (300 mL); the pH was carefully adjusted to 1.0 with concentrated HCl. Extraction with methylene chloride (3'200 mL) gave a combined organic layer which was then washed with sat. NaHCO$_3$ (3'200 mL), then sat. KCl (100 mL). The solution was dried (anh. Na$_2$SO$_4$) and the solvent was evaporated to give the crude product (4.90 g), which was further purified by vacuum distillation (149–151 C/0.10 torr) to give the desired product (2.1 g, 31% yield). $^1$H NMR (CDCl3), d (ppm): 4.11 (q, 4 H, J=7.1); 3.56 (s, 4H); 3.44 (t, 4 H, J=6.1); 1.60–1.46 (m, 8H); 1.24 (t, 6 H, J 7.1); $^{13}$C NMR (CDCl3), d (ppm): 1.17 (s, 12H). 177.8, 71.7, 70.1, 60.3, 42.0, 37.0, 25.25, 25.15, 14.3.

5-[2-(5-Hydroxy-4,4-dimethyl entyloxy)-ethoxy]-2,2-dimethyl-pentan-1-ol

Under argon, a suspension of LiBH$_4$ (406 mg, 17.7 mmol) in methylene chloride (5 mL) was stirred as a solution of methanol (567 mg, 17.7 mmol) in methylene chloride (5 mL) was added slowly. After the effervescence from the addition had ceased, a solution of LXIX (2.9 g, 5.9 mmol) in methylene chloride (5 mL) was added dropwise. Having stirred at rt for 45 min after addition, the solution was heated to reflux for 25 h. Upon cooling to rt, the reaction mixture and precipitated solids were washed into a separatory funnel with methylene chloride(50 mL); the remaining reagent was quenched by slow addition of H$_2$O (25 mL), then 6 N HCl (25 mL). The layers were separated, and the aqueous layer was extracted with methylene chloride (2'100 mL). The combined organic phases were washed with sat. NaHCO$_3$ (100 mL), then sat. KCl (100 mL) and dried (anh. Na$_2$SO$_4$). Removal of the solvent by vacuum distillation gave the product (1.70 g, 85% yield) as a light yellow oil, pure by NMR. $^1$H NMR (d6-DMSO), d (ppm): 4.41 (t, 2 H, J=5.3); 3.45 (s, 4H); 3.34 (t, 4 H, J=6.7); 3.08 (d, 4 H, J=5.3); 1.50–1.36 (m, 4H); 1.22–1.10 (m, 4H); 0.78 (s, 12H). $^{13}$C NMR (d6-DMSO), d (ppm): 71.3, 69.8, 69.5, 34.7, 34.5, 24.0, 23.9. HRMS calcd. for C$_{16}$H$_{35}$O$_4$ (MH$^+$): 291.2533, found 291.2534.

6.2. Synthesis of 3-{3-[3-(2-Carboxy-2-methyl-propyl)-phenoxy]-phenyl}-2,2-dimethyl-propionic Acid Referred to herein as Compound B

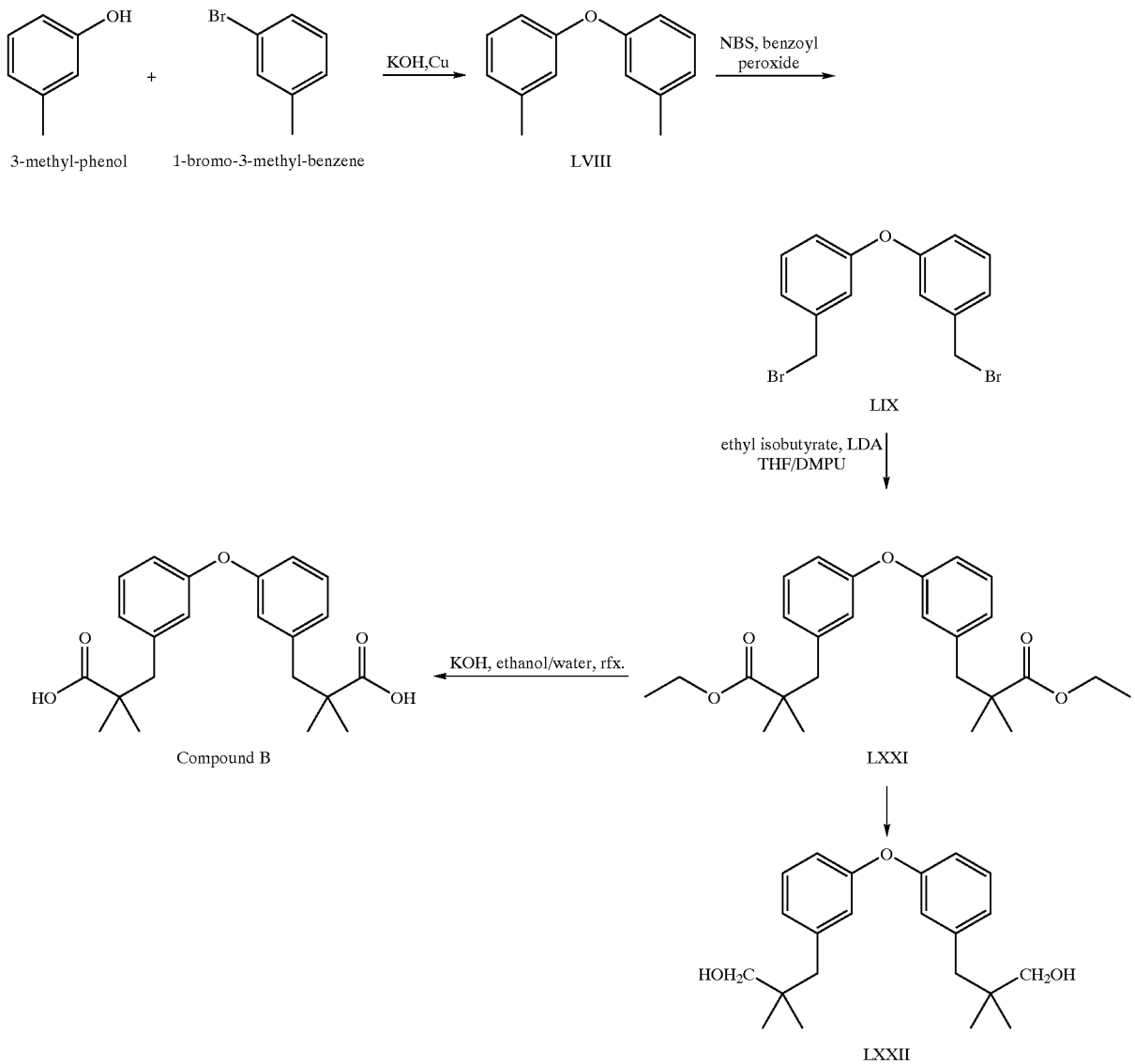

The synthetic sequence leading to the dicarboxylic acid Compound B is shown above. First, Ullmann condensation between 2-methyl-phenol and 1 bromo-3-methyl-benzene gave LVII in 81% yield (Von Schickh 1936, Ber. 69:242–244, incorporated herein by reference). Side chain alkylation with N-bromosuccinimide and benzoyl peroxide as a radical initiator afforded bromoderivative LIX (Bergmann et al., 1969, Tetrahedron Lett. 25:2007–200, incorporated herein by reference), which was used without purification in the enolate alkylation with ethyl lithioisobutyrate, to produce the diester LXXI that was purified by flash chromatography. Saponification of bisester LXXI was performed with potassium hydroxide in ethanol-water at reflux temperature (Breslow et al., 1944, J. Am. Chem. Soc. 66:1287. Compound B was obtained as a white solid after crystallization from hexanes, in a 35% yield.

Compound LXII was synthesized from crude ester LXXI as shown above. The reduction was achieved with lithium aluminum hydride. The crude LXXII was purified by repeated flash chromatography (silica, toluene: ethyl acetate=80:20 as best solvent mixture; 9% yield from LVII) as a colorless, viscous oil.

6.3. LDL-Cholesterol, HDL-Cholesterol and Triglyceride Levels in Male Sprague-Dawley Rats Illustrative compounds of the invention are administered daily at a dose of 100 mg/kg to chow fed male Sprague-Dawley rats for seven days in the morning by oral gavage in 1.5% carboxymethylcellulose/0.2% Tween-20 (dosing vehicle). Animals are weighed daily. Animals are allowed free access to rodent chow and water throughout the study. After the seventh dose, animals are sacrificed in the evening and blood serum is assayed for lipoprotein cholesterol profiles, serum triglycerides, total cholesterol VLDL, LDL, and HDL cholesterol, and the ratio of HDL cholesterol to that of VLDL plus LDL cholesterol, apolipoproteins A-I, C-II, C-III, and E by immunoelectrophoresis, and percent weight gain.

6.4. LDL-Cholesterol, HDL-Cholesterol and Triglyceride Levels in Obese Female Zucker Rats

6.4.1. Experiment A

Dosing vehicle, Compound A (86 mg/kg of body weight) or troglitazone (120 mg/kg of body weight) is administered to eight week old female obese Zucker rats daily for seven days in the morning by oral gavage in 1.5% carboxymethylcellulose/0.2% Tween-20. Troglitazone is obtained commercially. Finely crushed tablets are suspended in vehicle for dosing. Orbital blood samples are obtained following a six-hour fast prior to the initial dose and also following the seventh dose.

Blood serum is assayed for total cholesterol and triglycerides, lipoprotein cholesterol profiles, VLDL plus LDL cholesterol combined (also referred to as apo B containing lipoprotein cholesterol or non-HDL cholesterol), HDL cholesterol, and the ratio of HDL cholesterol to that of VLDL plus LDL cholesterol, serum glucose, and non-esterified fatty acids, and percent weight gain.

6.4.2. Experiments B, C, D, & E

In a number of different experiments, illustrative compounds of the invention and troglitazone are administered daily at various doses to 10-week old chow fed obese female Zucker rats for 14 days in the morning by oral gavage in 1.5% carboxymethylcellulose/0.2% Tween-20 (dosing vehicle). Animals are weighed daily. Animals are allowed free access to rodent chow and water throughout the study. Blood glucose is determined after a 6-hour fast in the afternoon without anesthesia from a tail vein. Serum is also prepared from a blood sample subsequently obtained from the orbital venous plexus (with $O_2/CO_2$ anesthesia) prior to and after one week treatment and used lipid and insulin determinations. At two weeks, blood glucose is again determined after a 6-hour fast without anesthesia from a tail vein. Soon thereafter, animals are sacrificed by $CO_2$ inhalation in the evening and cardiac blood serum is collected and assessed for various lipids and insulin. Body weight is determined daily prior to dosing and at the time of euthanasia. Blood glucose and serum insulin levels are determined from fasted rats just prior to and following one and two weeks of treatment. Percent liver to body weight is determined after two weeks of treatment at the time of sacrifice.

6.5. Lipoprotein Cholesterol Profile in LDL Receptor-deficient Mice

Homozygous familial hypercholesterolemia is a rare human disease (~1/1,000,000) characterized by absent or defective LDL receptors, markedly elevated serum LDL cholesterol levels and very early and severe onset of atherosclerosis. The more common form of this disease in humans, heterozygous familial hypercholesterolemia, occurs in about one in every 500 humans. Patients with the heterozygous form of this disease also present with elevated LDL levels and early onset of atherosclerosis.

The effect of Compound A on LDL levels in a murine model of homozygous familial hypercholesterolemia are studied according to the methods described in Ishibashi et al., 1993, *J. Clin. Invest.* 92:883–893; Ishibashi et al., 1994, *J. Clin. Invest.* 93:1885–1893, incorporated by reference herein. LDL receptor-deficient mice have elevated LDL cholesterol relative to wild type mice when fed a chow diet. When fed cholesterol-enriched diets, these mice develop atherosclerosis.

6.6. Non-saponified and Saponified Lipids in Hepatocyte Cells Isolated from a Male Sprague-dawley Rat Washout buffer containing; 149 mM sodium chloride, 9.2 mM sodium N-2-hyroxyethylpiperazine-N'-2-ethanesulfonic acid, 1.7 mM fructose, 0.5 mM EGTA, 10 U/mL heparin at pH 7.5 and digestion buffer containing; 6.7 mM potassium chloride, 143 mM sodium chloride, 9.2 mM sodium N-2-hyroxyethylpiperazine-N'-2-ethanesulfonic acid, 5 mM calcium chloride-dihydrate, 1.7 mM fructose, 0.2% bovine serum albumin, 100 U/ mL collagenase Type I, 93 U/ mL Hyaluronidase, 160 BAEE/ mL trypsin inhibitor at pH 7.5 were prepared. Solutions were oxygenate prior to perfusion. Wash buffer containing Dulbecco's Modified Eagle Medium (DMEM) containing 4.5 gm/L D-glucose, 2 mM GlutMax-1, 0.2% BSA, 5% fetal bovine serum (FBS), 12 riM insulin, 1.2 mM hydrocortisone and DMEM+HS solution containing DMEM, 2 mM GlutMax-1, 20 nM delta-aminolevulinic acid, 17.4 mM MEM non-essential amino acids, 20% FBS, 12 nM insulin and 1.2 mM hydrocortisone was prepared. DMEM-solution containing DMEM, 2 mM GlutMax-1, 20 mM delta-aminolevulinic acid and 17.4 mM MEM non-essential amino acids were prepared. Male Sprague-Dawley rats weighing 125–250 gms were maintained on a standard rodent chow diet and freely given water. On the evening prior to cell isolation, selected healthy animals were feed restricted. The rat was anesthetized with a 50 mg/kg intraperitoneal administration of sodium pentobarbital. Clotting was minimized with intraperitoneal administer of heparin at 1000 IU/kg body weight. The abdominal cavity was opened and the portal vein was surgical isolated. The angiocatheter was inserted into the portal vein at the general location of the lineal branch and connected to a perfusion pump. The in situ perfusion was performed at (~30 mL/min) with washout buffer, equilibrated with atmosphere gases at a temperature of 37° C. The internal iliac artery was cut to allow pressure equilibration. The caustal area of the diaphragm was excised to provide access to the caudal vena cava and the aorta, using curved forceps both vessels were occluded. About 200 mL of buffer was needed to clear the liver. Digestion buffer was circulated at the same flow rate for about 7 minutes after the initial entry of digestion buffer into the liver. When the liver had significantly increased in size, and consistency, and started to leak perfusate the perfusion was discontinued. The liver was rinsed in situ with sterile saline and surgical removed from the animal to a sterile beaker. Additional digestion solution was dispensed into the beaker and cap with foil. The liver tissue was gently shaken using sterile forceps to free hepatocyte cells. Cells were filtered through presterilized stainless steels mesh sieves of pore sizes 250, 106 and 75 mm. Cells were diluted in with ice-cold wash buffer, pipetted successively to assist the disassociation of the cells and transferred to a 50 mL tube. The cells are centrifuged for about 4 minutes at 50 x g to form a loosely packed pellet. The supernatant is discarded and the pelleted cells were resuspend in ice-cold wash buffer. The washing procedure was repeated twice for a total of three washes. The final pellet was suspended in 50 mL of wash buffer and held on wet-ice. The viability and cell number was checked by diluting duplicate 100 mL aliquots of cell suspension with 400 mL of wash buffer and 500 mL of 0.4% trypan blue in isotonic buffer. The cell concentration was determined in several fields on the hemocytometer. The cell viability (those that exclude die) was 85% or greater. Cells were diluted in DMEM+HS to a final concentration to ensure plating at a density of 150,000 cells/cm$^2$ on collagen coated 6- or 12-well plates. Four hours after plating change the media was changed with DMEM- and culture overnight. Solutions of lovastatin, and compounds A and B were prepared at 30 mM with DMSO. To obtain a compound solution mixtures were vortexed and sonicated.

To evaluate the effect of the reference compound (lovastatin) and compounds A and B on saponified and non-saponifed lipid synthesis, the monolayer cultures were exposed to compounds formulated in DMEM- containing $^{14}$C-acetate. All cells were exposed to 1% DMSO. Metabolic labeling with $^{14}$C-acetate continued for 4 hr at 37° C. After labeling, cells were washed twice with 1 mL of PBS followed by lysing in 1 mL deionized water. Cells were scraped from the dishes and transferred to glass tubes at which point they were sonicated. 2.5 mL of 2:1 chloroform/methanol mixture was added followed by 1.5 mL of Phosphate Buffered Saline (PBS). To correct for extraction efficiency in the upcoming extractions, 3000 dpm of $^3$H-cholesterol was added to each tube. Tubes were shaken for 30 min. to extract lipids into the organic phase followed by centrifugation for 10 minutes at 1000× g to separate the organic and aqueous phases. The lower organic phase containing total lipids was removed and placed in a new tube. The organic solution was evaporated under $N_2$. Resuspend the dry lipid extract in 1 mL of 93% ethanol containing 1M KOH and placed at 70° C. for 2.5 hours. After the reaction and cooling, 2 mL of hexane and 2.5 mL of water was added to each tube followed by rigorous shaking for 10 min. Tubes were centrifuged for 10 min at 1000× g and the organic (top) layer containing the non-saponifed lipids was transferred to a new tube followed by evaporation of the organic solvent under $N_2$. The aqueous phase containing the saponfied lipids was also transferred to a new tube. The non-saponified lipid extract, after drying, was suspended in toluene and an aliquot added to scintillation cocktail followed by radioactive counting. $^{14}$C counts representing the incorporation of $^{14}$C acetate into non-saponified lipids was corrected by the $^3$H counts, which represented the extraction efficiency of the procedure as, noted above by the addition of $^3$H cholesterol. To isolate saponified lipids, 1.5 mL of aqueous phase solution was mixed with 400 ul of 1M HCl and then lipids extracted by the addition of 2.5 mL of 2:1 chloroform:methanol, 1.5 mL of PBS, and 1 mL of water followed by rigorous shaking and isolation of the organic phase. Resuspend the $N_2$ dried organic phase extraction in toluene, and measure radioactivity using liquid scintillant method. The rate of $^{14}$C-acetate incorporation into saponified and non-saponified lipids is reported.

FIG. 1 shows the rates of saponified, non-saponified lipid synthesis following treatment with lovastatin and compounds A and B of the invention. Data are represented as a percent of no compound treatment (Vehicle control). Data are represented as the mean of three measurements +/− one standard deviation. The data indicate that compounds A and B of the invention are useful for inhibition of lipid synthesis. In particular, compound A at 30 mM reduced the rate of saponifiable and non-saponified lipid synthesis by 18 and 7% respectively in the rat hepatocyte cells. Compound B also reduced the rates of saponified and non-saponified lipid synthesis by 25 and 7% respectively. Accordingly, Compounds A and B are useful for inhibiting the synthesis of saponified lipids.

6.7. Cytotoxicity

To evaluate the effects of illustrative compounds of the invention on cytotoxicity, monolayer hepatocyte cultures are exposed to increasing concentrations of up to 250 μM Compound A in DMEM+ for 24 hours. Control cells are exposed to the same media lacking a test compound. All cells are exposed to 0.1% DMSO. The measure of cytotoxicity, release of lactate dehydrogenase (LDH) from the cytosolic compartment of hepatocyte monolayer cultures, reflects damage to the plasma membrane. The assay, is based on the method of Wroblewski and LaDue, 1955, Proc. Soc. Exp. Biol. Med. 90:210–213; see also Ulrich et al., 1995, Toxicol. Lett. 82/83:107–115, describing the use of hepatocytes as models for hepatic toxicity), and measures the LDH activity in tissue culture medium and a cell homogenate. Briefly, all the media are removed from plates and transferred to a separate plate. Following removal of media, attached cells are lysed with a hypotonic Tris/Glycerol/EDTA buffer (0.1 M Tris, 20% glycerol, 1 mM EDTA pH 7.3). Activity of LDH in medium and cells is measured spectrophotometrically by monitoring the rate of pyruvate reduction to lactate, coupled with oxidation of NADH; the rate of absorbance change is measured at 340 nm. Cytotoxicity is expressed as a ratio using the following equation: (LDH in medium/(LDH in medium+LDH in solubilized hepatocytes))=R.

6.8. Insulin Sensitization Effects

The effects of Compound A on rate of differentiation of 3T3-L1 cells from a "committed pre-adipocyte" to an "adipocyte" phenotype in the absence or presence of insulin is tested. The differentiation of 3T3-L1 cells to an adipocyte-like phenotype is highly dependent upon insulin. This insulin-dependent changes in cellular morphology and metabolism, including: expression of adipocyte-specific genes, greatly increased levels of glucose uptake and metabolism, induction of GLUT4 (and increased expression of GLUT1) glucose transporters, greatly increased lipid synthesis and deposition of intracellular lipid droplets. In this assay the degree of differentiation is a reflection of the rate of lipid synthesis, as measured through incorporation of $^{14}$C-acetate over 2 hours. Thus the ability of a compound to stimulate a submaximal insulin response would suggest an insulin-sensitizing activity (Kletzein et al., 1991, Molecular Pharm.41:393–398).

3T3-L1 stem cells are induced to differentiate with dexamethasone, isobutylmethylxanthine and insulin (Green and Kehinde, 1975, Cell 5:19–27). Cells are plated in Dulbecco's modified Eagle medium containing 10% calf serum and grown to confluence. Cells are then refreshed with 10% fetal calf serum, and treated with 0.5 mM isobutylmethylxanthine and 250 riM dexamethasone, but no additional insulin, for 48 hours. This treatment induces the differentiation of 3T3-L1 cells into pre-adipocytes. Conversion of preadipocytes to adipocyte phenotype requires the removal of dexamethasone and the presence of insulin, which stimulates differentiation of preadipocytes into adipocytes in a concentration- and time-dependent manner. A maximal insulin effect occurs at about 100 nM insulin, and leads to nearly complete (95–100%) conversion to adipocytes within 4 days.

The preadipocytes are then treated for 4 days with various concentrations of Compound A in 5% fetal calf serum in Dulbecco's modified Eagles medium, with or without a submaximal concentration of insulin (30 nM). Following this four-day treatment, the predipocytes are pulsed with 0.1 mCi $^{14}$C-acetate per well for 2 hours. Cell are then washed with phosphate buffered saline, lysed with 0.1 N NaOH, and $^{14}$C-acetate incorporation into lipids is determined using phase separation and liquid scintillation counting.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

What is claimed is:

1. A compound of formula III:

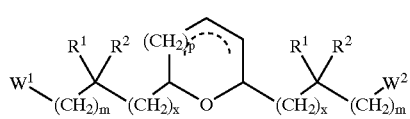

III or a pharmaceutically acceptable salt, hydrate, solvate or a mixture thereof, wherein (a) each occurrence of $R^1$ and $R^2$ is independently $(C_1-C_6)$alkyl, $(C_2-C_6)$alkenyl, $(C_2-C_6)$alkynyl, phenyl, or benzyl; or $R^1$, $R^2$, and the carbon to which they are both attached are taken together to form a $(C_3-C_7)$cycloalkyl group;

(b) each occurrence of m is independently an integer ranging from 0 to 4;

(c) each occurrence of x is independently 2 or 3;

(d) $W^1$ and $W^2$ are independently OH, C(O)OH, CHO, OC(O)$R^7$, C(O)O$R^7$, SO$_3$H,

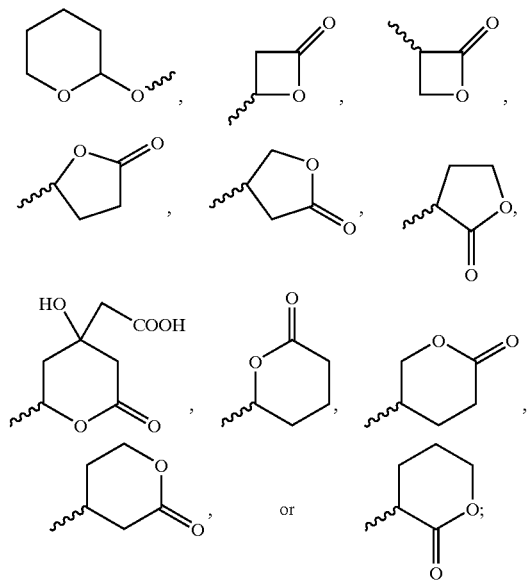

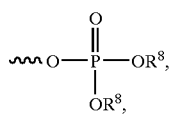

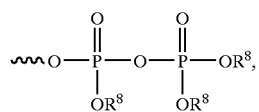

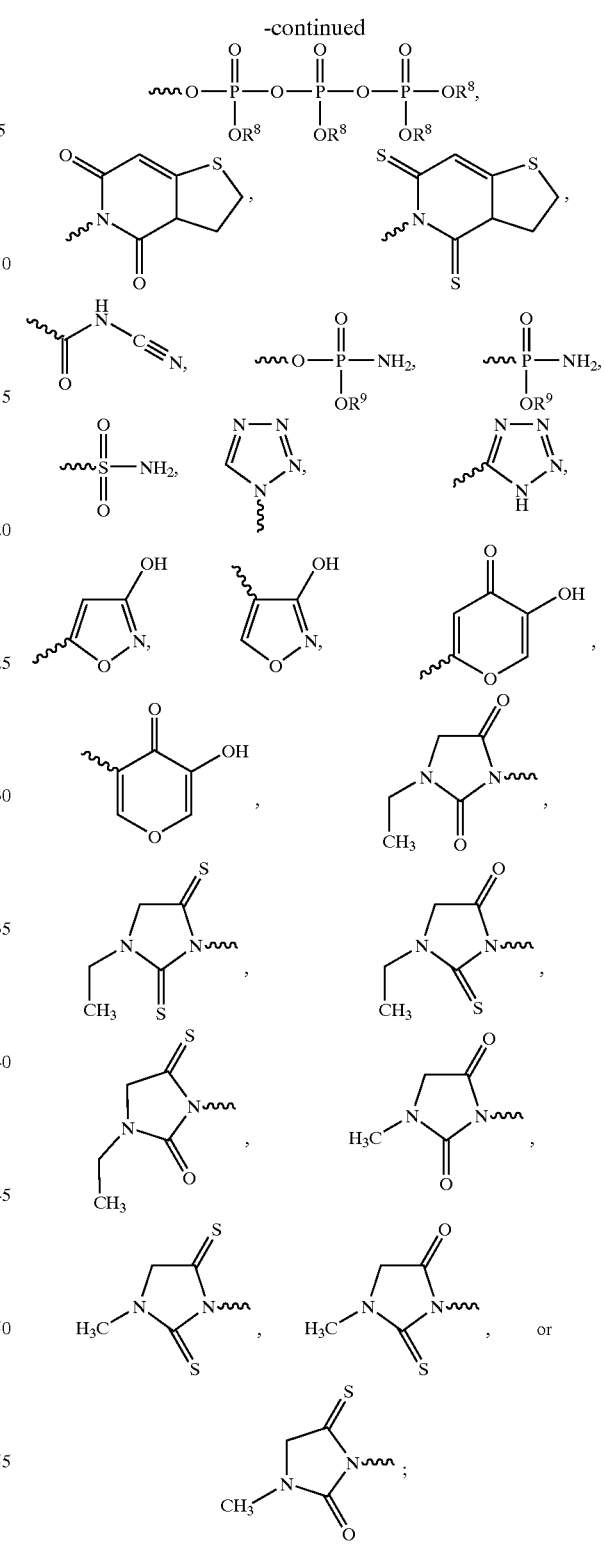

(e) $R^7$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups, (f) each occurrence of $R^8$ is independently H, $(C_1-C_6)$alkyl, $(C_2-C_6)$alkenyl, or $(C_2-C_6)$alkynyl and is unsubstituted or substituted with one or two halo, OH, $(C_1-C_6)$alkoxy, or phenyl groups;

(g) each occurrence of $R^9$ is independently H, $(C_1-C_6)$alkyl, $(C_2-C_6)$alkenyl, or $(C_2-C_6)$alkynyl; and (h) p is 0 or 1 where the broken line represents an optional presence of 1 or 2 additional carbon—carbon bonds that when present complete 1 or 2 carbon—carbon double bonds.

2. The compound of claim 1, wherein $W^1$ and $W^2$ are independently OH, $COOR^7$, or COOH.

3. The compound of claim 1, wherein p is 0.

4. The compound of claim 1, wherein p is 1.

5. The compound of claim 1, wherein the broken line is absent.

6. The compound of claim 1, wherein each occurrence of $R^1$ and $R^2$ is independently $(C_1-C_6)$alkyl, $(C_2-C_6)$alkenyl, $(C_2-C_6)$alkynyl, phenyl, or benzyl.

7. A pharmaceutical composition comprising a compound of claim 1 or a pharmaceutically acceptable salt, hydrate, solvate or a mixture thereof and a pharmaceutically acceptable vehicle, excipient, or diluent.

8. A method of lowering LDL levels, which comprises administering to a patient in need thereof a therapeutically effective amount of a compound of claim 1.

9. A method of increasing HDL levels, which comprises administering to a patient in need thereof a therapeutically effective amount of a compound of claim 1.

10. A method of treating or preventing a disease or disorder that is capable of being treated or prevented by lowering LDL levels, which comprises administering to a patient in need of such treatment or prevention a therapeutically effective amount of a compound of claim 1.

11. The method of claim 10, wherein the disease or disorder is cardiovascular disease.

12. The method of claim 10, wherein the disease or disorder is dyslipidemia.

13. The method of claim 10, wherein the disease or disorder is dyslipidproteinemia.

14. The method of claim 10, wherein the disease or disorder is hypertension.

15. A method of treating or preventing a disease or disorder that is capable of being treated or prevented by increasing HDL levels, which comprises administering to a patient in need of such treatment or prevention a therapeutically effective amount of a compound of claim 1.

16. The method of claim 15, wherein the disease or disorder is cardiovascular disease.

17. The method of claim 15, wherein the disease or disorder is dyslipidemia.

18. The method of claim 15, wherein the disease or disorder is dyslipidproteinemia.

19. The method of claim 15, wherein the disease or disorder is hypertension.

* * * * *